United States Patent
Rao et al.

(10) Patent No.: US 10,736,892 B2
(45) Date of Patent: *Aug. 11, 2020

(54) STEM CELL MODULATION II

(71) Applicant: University of Canberra, Bruce (AU)

(72) Inventors: Sudha Rao, McKellar (AU); Anjurn Zafar, Bruce (AU)

(73) Assignee: EpiAxis Therapeutics Pty Ltd., Herston (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/186,786

(22) Filed: Nov. 12, 2018

(65) Prior Publication Data

US 2019/0192509 A1     Jun. 27, 2019

Related U.S. Application Data

(63) Continuation of application No. 15/023,358, filed as application No. PCT/AU2014/050237 on Sep. 18, 2014, now Pat. No. 10,124,001.

(30) Foreign Application Priority Data

Sep. 18, 2013    (AU) ............................... 2013903589

(51) Int. Cl.

| A61K 31/496 | (2006.01) |
| A61K 45/06 | (2006.01) |
| C12Q 1/6886 | (2018.01) |
| G01N 33/574 | (2006.01) |

(52) U.S. Cl.
CPC .......... *A61K 31/496* (2013.01); *A61K 45/06* (2013.01); *C12Q 1/6886* (2013.01); *G01N 33/57484* (2013.01); *C12Q 2600/158* (2013.01); *G01N 2333/91205* (2013.01)

(58) Field of Classification Search
CPC .... A61K 31/496; A61K 45/06; C12Q 1/6886; C12Q 2600/50; G01N 2333/91205
See application file for complete search history.

(56) References Cited

U.S. PATENT DOCUMENTS

| 2005/0222186 A1 | 10/2005 | Baudler et al. |
| 2009/0093457 A1 | 4/2009 | Himmelsbach et al. |
| 2009/0093475 A1 | 4/2009 | Prien et al. |
| 2009/0149468 A1 | 6/2009 | Cao et al. |
| 2010/0063109 A1 | 3/2010 | Jordan et al. |
| 2012/0136000 A1 | 5/2012 | Jimenez |
| 2013/0053388 A1 | 2/2013 | Jimenez et al. |
| 2013/0157980 A1 | 6/2013 | Cooke et al. |

FOREIGN PATENT DOCUMENTS

| WO | 9212119 A1 | 7/1992 |
| WO | 02090595 A1 | 11/2002 |
| WO | 2009062059 A2 | 5/2009 |
| WO | 2011094273 A1 | 8/2011 |

OTHER PUBLICATIONS

Stapleton et al. Journal of Cell Science 115, 2713-2724 (2002).*
Belguise, K. et al.: "The PKCθ pathway participates in the aberrant accumulation of Fra-1 protein in invasive ER-negative breast cancer cells", Oncogene, vol. 31, pp. 4889-4897 (2012).
Lopez-Sanchez, et al., "Protein Kinase C-theta (PKCO) Phosphorylates and Inhibits the Guanine Exchange Factor, GIV/Girdin," PNAS, vol. 110(14), pp. 5510-5515 (Apr. 2013).
Sparatore, B. et al.: "Human Neuroblastoma Cell Differentiation Requires Protein Kinase CO", Biochemical and Biophysical Research Communications, vol. 279, pp. 589-594 (2000).
Urtreger, A.J., et al., "Contribution of Individual PKC Isoforms to Breast Cancer Progression," IUBMB Life, vol. 64 (1), pp. 18-26 (Jan. 2012).
Van Laere, S., et al., "Is There a Role foe Mammary Stem Cells in Inflammatory Breast Carcinoma," Cancer, pp. 2794-2805 (Jun. 2010).
Villalba, M & Altman, A.: "Protein Kinase C-O (PKCO), A Potential Drug Target for Therapeutic Intervention with Human T Cell Leukemia", Current Cancer Drug Targets, vol. 2, pp. 125-134 (2002).
Visvader, J.E., and G.J. Lindeman, "Cancer Stem Cells: Current Status and Evolving Complexities," Cell Stem Cell, vol. 10, pp. 717-728 (Jun. 2012).
Zafar, A. et al.: "Chromatinized Protein Kinase C-O Directly Regulates Inducible Genes in Epithelial to Mesenchymal Transition and Breast Cancer Stem Cells", Molecular and Cellular Biology, vol. 34(16), pp. 2961-2980 (Jun. 2014).
Zafar, A. et al.: "Chromatinized PKC-θ Directly Regulates Inducible Genes in Epithelial to Mesenchymal Transition and Breast Cancer Stem Cells", Mol. Cell. Biol., pp. 1-70 (Jun. 2014).
Zafar, A, et al., "The Role of Protein Kinase-C theta in Control of Epithelial to Mesenchymal Transition and Cancer Stem Cell Formation," Genomics Data, vol. 3, pp. 28-32 (2015).
International Search Report in International Application No. PCT/AU2014/050237, dated Oct. 15, 2014, 4 pages.

* cited by examiner

*Primary Examiner* — Shirley V Gembeh
(74) *Attorney, Agent, or Firm* — Edell, Shapiro & Finnan, LLC

(57) ABSTRACT

Disclosed are methods and compositions for modulating cancer stem cells. More particularly, the present invention discloses the use of protein kinase C theta inhibitors (PKC-θ) for inhibiting the growth of PKC-θ-overexpressing cells including cancer stem cells, for enhancing the biological effects of chemotherapeutic drugs or irradiation on cancer cells, for treating cancer, including metastatic cancer and/or for preventing cancer recurrence.

11 Claims, 19 Drawing Sheets
Specification includes a Sequence Listing.

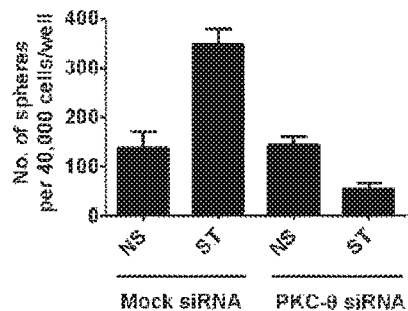
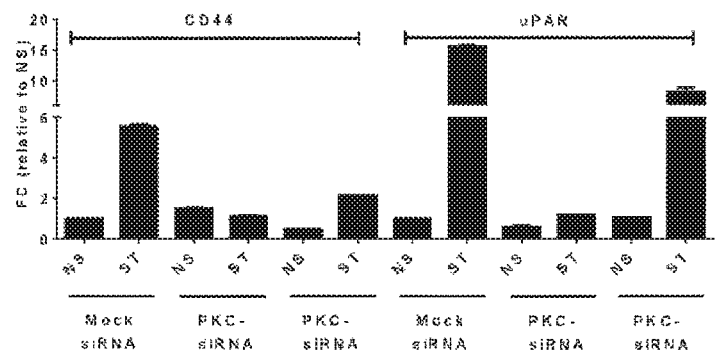
Fig. 3E
Fig. 3F
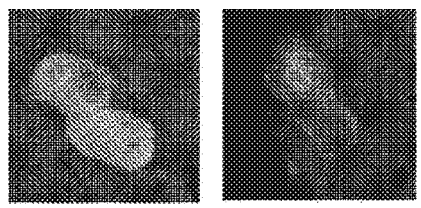
PKC-θ Wild type    PKC-θ NLS mutation
Fig. 3G
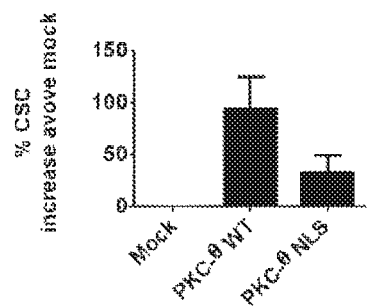
Fig. 3H
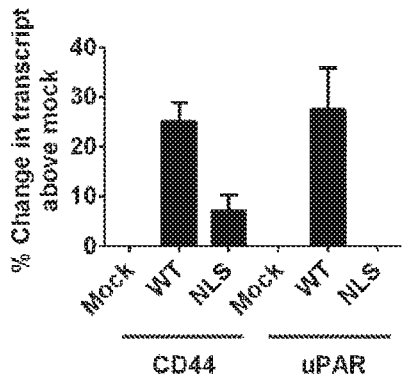
Fig. 3I

STEM CELL MODULATION II

This application is a continuation of U.S. patent application Ser. No. 15/023,358 filed Mar. 18, 2016, which is a U.S. National Stage Application of International Application No. PCT/AU2014/050237 filed Sep. 18, 2014, which claims priority to Australian Provisional Application No. 2013903589 entitled "Stem Cell Modulation II" filed 18 Sep. 2013, the contents of each of which are incorporated herein by reference in their entirety.

FIELD OF THE INVENTION

This invention relates generally to compositions and methods for modulating cancer stem cells. More particularly, the present invention relates to the use of protein kinase C theta inhibitors (PKC-θ) for inhibiting the growth of PKC-θ-overexpressing cells including cancer stem cells, for enhancing the biological effects of chemotherapeutic drugs or irradiation on cancer cells, for treating cancer, including metastatic cancer and/or for preventing cancer recurrence.

BACKGROUND OF THE INVENTION

Epithelial-to-mesenchymal cell transition (EMT) is a key step in cancer progression and metastasis. However, only a small subpopulation of tumor cells referred to as cancer stem cells (CSCs), or 'precursor' metastatic cells, potentially plays a significant role for metastatic tumor initiation and recurrence. CSCs initiate tumors and drive malignant progression by generating and supporting replication of more differentiated non-stem cell progeny (see, for example, Kleffel et al., 2013. *Adv Exp Med Biol.* 734:145-79; Chen et al., 2013. *Acta Pharmacologica Sinica* 34:732-740; Páez et al., 2012, *Clin Cancer Res.* 18(3):645-53). CSCs have been demonstrated to be fundamentally responsible for tumorigenesis, cancer metastasis, tumor relapse, drug resistance, and chemo- and radiotherapy failure. Unfortunately, the mechanisms by which CSCs cause tumor formation and growth and the potential role of CSC-specific differentiation plasticity in tumorigenicity are currently unknown.

Of interest, CSCs share many similar traits with normal stem cells. For example, CSCs have self-renewal capacity, namely, the ability to give rise to additional tumorigenic cancer stem cells, typically at a slower rate than other dividing tumor cells, as opposed to a limited number of divisions. CSCs also have the ability to differentiate into multiple cell types (i.e., they are multipotent), which would explain histological evidence that not only many tumors contain multiple cell types native to the host organ, but also that heterogeneity is commonly retained in tumor metastases.

CSCs express certain cell surface markers as listed for example in Table 1 below:

TABLE 1

CSC markers for distinct solid tumor types

| Breast | Colon | Glioma | Liver | Lung | Melanoma | Ovarian | Pancreatic | Prostate |
|---|---|---|---|---|---|---|---|---|
|  | ABCB5 |  |  |  |  |  |  |  |
| ALDH1 | ALDH1 |  |  |  |  |  | ABCG2 |  |
| CD24 | β-catenin activity | CD15 | CD13 | ALDH1 | ABCB5 |  | ALDH1 | ALDH1 |
| CD44 | CD24 | CD90 | CD24 | ABCG2 | ALDH1 | CD24 | CD24 | CD44 |
| CD90 | CD26 | CD133 | CD44 | CD90 | CD20 | CD44 | CD44 | CD133 |
| CD133 | CD29 | $\alpha_6$ integrin | CD90 | CD117 | CD133 | CD117 | CD133 | $\alpha_2 \beta_1$ integrin |
| Hedgehog-Gli activity | CD44 | Nestin | CD133 | CD133 | CD271 | CD133 | c-Met | $\alpha_6$ integrin |
| $\alpha_6$ integrin | CD133 |  |  |  |  |  | CXCR4 | Trop2 |
|  | CD166 |  |  |  |  |  | Nestin |  |
|  | LGR5 |  |  |  |  |  | Nodal-Activin |  |

Normal somatic stem cells are naturally resistant to chemotherapeutic agents—they have various pumps (such as multi-drug resistance (MDR) proteins) that pump out drugs, and efficient DNA repair mechanisms. Further, they also have a slow rate of cell turnover while chemotherapeutic agents target rapidly replicating cells. CSCs, being the mutated counterparts of normal stem cells, may also have similar mechanisms that allow them to survive drug therapies and radiation treatment. In other words, conventional chemotherapies and radiotherapies kill differentiated or differentiating cells, which form the bulk of the tumor that are unable to regenerate tumors. The population of CSCs that gave rise to the differentiated and differentiating cells, on the other hand, could remain untouched and cause a relapse of the disease. A further danger for the conventional anti-cancer therapy is the possibility that the treatment of, for instance, chemotherapy, leaves only chemotherapy-resistant CSCs, and the ensuing recurrent tumor will likely also be resistant to chemotherapy.

Consequently, there is a pressing need for the identification of novel approaches that target cytotoxic drug-resistant, tumor-initiating CSCs for preventing and/or treating disease recurrence and distant metastatic spread.

SUMMARY OF THE INVENTION

The present invention is based in part on the determination that PKC-θ is overexpressed in CSC and non-CSC tumor cells and is important for controlling EMT as well as the formation and maintenance of CSC and non-CSC tumor cells. The present inventors have also found that it is possible to inhibit EMT, formation and maintenance of CSC and non-CSC tumor cells, as well as inducing mesenchymal-to-epithelial cell transition (MET) by inhibiting the activity of this enzyme. It is proposed, therefore, that PKC-θ inhibitors are useful for reducing or inhibiting proliferation of CSC and non-CSC tumor cells, including inhibiting EMT, stimulating or inducting MET and reducing cancer recurrence, as described hereafter.

Accordingly, in one aspect, the present invention provides methods for altering at least one of: (i) formation; (ii) proliferation; (iii) maintenance; (iv) EMT; or (v) MET of a PKC-θ-overexpressing cell. These methods generally comprise, consist or consist essentially of contacting the PKC- θ-overexpressing cell with a formation-, proliferation-, maintenance-; EMT- or MET-modulating amount of a PKC-θ inhibitor. Suitably, the PKC-θ-overexpressing cell is selected from a CSC and a non-CSC tumor cell, illustrative examples of which include breast, prostate, lung, bladder, pancreatic, colon, melanoma, liver or glioma CSC and non-CSC tumor cells. In some embodiments, the CSC is a breast CSC (e.g., a breast epithelial CSC, including a breast ductal epithelial CSC). In some embodiments, the non-CSC tumor cell is a breast non-CSC tumor cell (e.g., a breast epithelial non-CSC tumor cell, including a breast ductal epithelial non-CSC tumor cell). Suitably, the PKC-θ-overexpressing cell is contacted with one or more of a PKC-θ-overexpressing cell formation-inhibiting, proliferation-inhibiting, maintenance-inhibiting, EMT-inhibiting amount or MET-stimulating/inducing amount of the PKC-θ inhibitor. In some embodiments, overexpression of PKC-θ in the PKC-θ-overexpressing cell comprises presence or an increased amount of PKC-θ in the nucleus of the PKC-θ-overexpressing cell.

In some embodiments in which the PKC-θ-overexpressing cell is a CSC, the CSC expresses one or more (e.g., 1, 2, 3, 4, 5, 6, 7, 8 or more) CSC markers selected from ABCB5, ALDH1, ABCG2, $\alpha_6$ integrin, $\alpha_2$ $\beta_1$ integrin, β-catenin activity, CD15, CD13, CD20, CD24, CD26, CD29, CD44, CD90, CD133, CD166, CD271, c-Met, Hedgehog-Gli, Nestin, CXCR4, LGR5, Trop2 and Nodal-Activin. In some embodiments, the CSC expresses one or more (e.g., 1, 2, 3, 4, 5, 6, 7, 8 or more) CSC markers selected from ALDH1, CD24, CD44, CD90, CD133, Hedgehog-Gli, a integrin. In illustrative examples of this type, the CSC expresses CD24 and CD44 (e.g., $CD44^{high}$, $CD24^{low}$).

Non-limiting examples of suitable PKC-θ inhibitors include nucleic acids, peptides, polypeptides, peptidomimetics, carbohydrates, lipids or other organic (carbon containing) or inorganic molecules. In specific embodiments, the PKC-θ inhibitor is selected from small molecule inhibitors and nucleic acid molecules (e.g., ones that inhibit the transcription or translation of a PKC-θ gene or that mediate RNA interference). In some embodiments, the PKC-θ inhibitor reduces the expression of the PKC-θ gene or the level or functional activity of a PKC-θ expression product (e.g., reduces the level of a PKC-θ polypeptide, reduces PKC-θ-mediated phosphorylation, inhibits binding of PKC-θ to the promoter of CD44 or uPAR, reduces binding of PKC-θ (e.g., active PKC-θ) to chromatin; reduces PKC-θ-mediated inhibition of guanine exchange factor, GIV/Girdin, reduces PKC-θ-mediated inhibition of regulatory T cell function, or reduces PKC-θ-mediated EMT) to less than about $9/10$, $4/5$, $7/10$, $3/5$, $1/2$, $2/5$, $3/10$, $1/5$, $1/10$, $1/20$, $1/50$, $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$ or about $10^{-15}$ of the expression of the PKC-θ gene, or the level or functional activity of a corresponding PKC-θ expression product in the absence of the inhibitor. In some embodiments, the PKC-θ inhibitor is a selective PKC-θ inhibitor. In other embodiments, the PKC-θ inhibitor is a non-selective PKC-θ inhibitor.

In some embodiments, the methods for altering at least one of: (i) formation; (ii) proliferation; (iii) maintenance; (iv) EMT; or (v) MET of the PKC-θ-overexpressing cell further comprise detecting overexpression of PKC-θ (e.g., relative to the expression of PKC-θ in a normal cell (e.g., a normal breast cell)) in the PKC-θ-overexpressing cell prior to contacting the PKC-θ-overexpressing cell with the PKC-θ inhibitor. In non-limiting examples of this type, the methods comprise detecting overexpression of PKC-θ in a CSC. In other non-limiting examples, the methods comprise detecting overexpression of PKC-θ in a non-CSC tumor cell. In still other non-limiting examples, the methods comprise detecting overexpression of PKC-θ in a CSC and a non-CSC tumor cell.

In some embodiments, the methods for altering at least one of: (i) formation; (ii) proliferation; (iii) maintenance; (iv) EMT; or (v) MET of the PKC-θ-overexpressing cell further comprise detecting presence or an increased amount of PKC-θ in the nucleus of the PKC-θ-overexpressing cell (e.g., relative to the amount of PKC-θ in the nucleus of a normal cell (e.g., a normal breast cell)) prior to contacting the PKC-θ-overexpressing cell with the PKC-θ inhibitor. In illustrative examples of this type, the methods comprise detecting presence or an increased amount of PKC-θ in the nucleus of a CSC. In other illustrative examples, the methods comprise detecting presence or an increased amount of PKC-θ in the nucleus of a non-CSC tumor cell. In still other illustrative examples, the methods comprise detecting presence or an increased amount of PKC-θ in the nucleus of a CSC and a non-CSC tumor cell.

In some embodiments, the methods for altering at least one of: (i) formation; (ii) proliferation; (iii) maintenance; (iv) EMT; or (v) MET of the PKC-θ-overexpressing cell further comprise detecting binding of PKC-θ to the promoter of CD44 or uPAR in the PKC-θ-overexpressing cell prior to contacting the PKC-θ-overexpressing cell with the PKC-θ inhibitor. In representative examples of this type, the methods comprise detecting binding of PKC-θ to the promoter of CD44 or uPAR in a CSC. In other representative examples, the methods comprise detecting the methods comprise detecting binding of PKC-θ to the promoter of CD44 or uPAR in a non-CSC tumor cell. In still other representative examples, the methods comprise detecting the methods comprise detecting binding of PKC-θ to the promoter of CD44 or uPAR in a CSC and a non-CSC tumor cell.

In some embodiments, the methods for altering at least one of: (i) formation; (ii) proliferation; (iii) maintenance; (iv) EMT; or (v) MET of the PKC-θ-overexpressing cell further comprise detecting binding of PKC-θ to chromatin in the PKC-θ-overexpressing cell prior to contacting the PKC-θ-overexpressing cell with the PKC-θ inhibitor. In non-limiting examples of this type, the methods comprise detecting binding of PKC-θ to chromatin in a CSC. In other non-limiting examples, the methods comprise detecting binding of PKC-θ to chromatin in a non-CSC tumor cell. In still other non-limiting examples, the methods comprise detecting binding of PKC-θ to chromatin in a CSC and a non-CSC tumor cell.

Suitably, the methods for altering at least one of: (i) formation; (ii) proliferation; (iii) maintenance; (iv) EMT; or (v) MET of the PKC-θ-overexpressing cell further comprise detecting that the PKC-θ-overexpressing cell expresses one or more CSC markers as broadly described above.

In another aspect, the present invention provides methods for treating or preventing a cancer (e.g., a metastatic cancer) in a subject, wherein the cancer comprises at least one PKC-θ-overexpressing cell. These methods generally comprise, consist or consist essentially of administering to the subject a PKC-θ inhibitor in an effective amount to alter at least one of: (i) formation; (ii) proliferation; (iii) maintenance; (iv) EMT; or (v) MET of the at least one PKC-θ-overexpressing cell. Suitably, the PKC-θ inhibitor is administered to the subject in an effective amount to inhibit (i) formation, (ii) proliferation, (iii) maintenance, or (iv) EMT of the at least one PKC-θ-overexpressing cell, or to stimulate or induce (v) MET of the at least one PKC-θ-overexpressing cell. In some embodiments, the PKC-θ inhibitor is a selective PKC-θ inhibitor. In other embodiments, the PKC-θ inhibitor is a non-selective PKC-θ inhibitor. Suitably, the at least one PKC-θ-overexpressing cell is selected from a CSC and a non-CSC tumor cell.

In some embodiments, the cancer is selected from breast, prostate, lung, bladder, pancreatic, colon, melanoma, liver or glioma cancer. Suitably, the cancer is breast cancer. In some embodiments, the CSCs give rise to non-CSC tumor cells that are hormone-resistant.

In some embodiments, the methods for treating or preventing a cancer further comprise detecting overexpression of a PKC-θ gene in a tumor sample obtained from the subject, wherein the tumor sample comprises the at least one PKC-θ-overexpressing cell (e.g., a CSC and/or a non-CSC tumor cell), prior to administering the PKC-θ inhibitor to the subject.

In some embodiments, the methods for treating or preventing a cancer further comprise detecting expression of one or more CSC markers as broadly described above in a tumor sample obtained from the subject, wherein the tumor sample comprises the at least one PKC-θ-overexpressing cell, prior to administering the PKC-θ inhibitor to the subject.

Yet another aspect of the present invention provides methods for treating or preventing a cancer (e.g., a metastatic cancer) in a subject, wherein the cancer comprises a CSC and a non-CSC tumor cell. These methods generally comprise, consist or consist essentially of concurrently administering to the subject (1) a PKC-θ inhibitor in an effective amount to inhibit at least one of: (i) formation, (ii) proliferation, or (iii) maintenance of the CSC and/or the non-CSC tumor cell; and/or to inhibit (iv) EMT of the CSC; and/or to stimulate or induce (v) MET of the CSC, and (2) a cancer therapy or agent that inhibits the proliferation, survival or viability of the non-CSC tumor cell, to thereby treat or prevent the cancer. Suitably, the PKC-θ inhibitor is administered to the subject in an effective amount to inhibit (i) formation, (ii) proliferation or (iii) maintenance of the CSC and/or non-CSC tumor cell, and/or to inhibit (iv) EMT of the CSC, and/or to stimulate or induce (v) MET of the CSC. In some embodiments, the PKC-θ inhibitor is a selective PKC-θ inhibitor. In other embodiments, the PKC-θ inhibitor is a non-selective PKC-θ inhibitor. In some embodiments, the cancer therapy or agent is selected from radiotherapy, surgery, chemotherapy, hormone ablation therapy, pro-apoptosis therapy and immunotherapy. In illustrative examples of this type, the cancer therapy or agent targets rapidly dividing cells or disrupts the cell cycle or cell division.

Suitably, the methods further comprise identifying that the subject has or is at risk of developing a cancer comprising the CSC and the non-CSC tumor cell prior to the co-administration. In some embodiments, the cancer is selected from breast, prostate, lung, bladder, pancreatic, colon, melanoma, liver or glioma cancer. Suitably, the cancer is selected from breast, prostate, lung, bladder, pancreatic, colon, melanoma, liver or brain cancer.

In some embodiments, the methods for treating or preventing a cancer further comprise detecting overexpression of PKC-θ (e.g., relative to the expression of PKC-θ in a normal cell (e.g., a normal breast cell)) in a tumor sample obtained from the subject, wherein the tumor sample comprises the CSC or the non-CSC tumor cell or both, prior to administering the PKC-θ inhibitor to the subject.

In some embodiments, the methods for treating or preventing a cancer further comprise detecting presence or an increased amount of PKC-θ in the nucleus of a CSC and/or a non-CSC tumor cell (e.g., relative to the amount of PKC-θ in the nucleus of a normal cell (e.g., a normal breast cell)) in a tumor sample obtained from the subject, wherein the tumor sample comprises the CSC or the non-CSC tumor cell or both, prior to administering the PKC-θ inhibitor to the subject.

In some embodiments, the methods for treating or preventing a cancer further comprise detecting binding of PKC-θ to the promoter of CD44 or uPAR in a CSC and/or a non-CSC tumor cell of a tumor sample obtained from the subject, wherein the tumor sample comprises the CSC or the non-CSC tumor cell or both, prior to administering the PKC-θ inhibitor to the subject.

In some embodiments, the methods for treating or preventing a cancer further comprise detecting binding of PKC-θ to chromatin in a CSC and/or a non-CSC tumor cell of a tumor sample obtained from the subject, wherein the tumor sample comprises the CSC or the non-CSC tumor cell or both, prior to administering the PKC-θ inhibitor to the subject.

In some embodiments, the methods for treating or preventing a cancer further comprise detecting that the CSC expresses one or more CSC markers as broadly described above prior to administering the PKC-θ inhibitor to the subject.

Suitably, the PKC-θ inhibitor and the cancer therapy agent are administered in synergistically effective amounts.

Typically, one or both of the PKC-θ inhibitor and the cancer therapy or agent are administered on a routine schedule, for example, every day, at least twice a week, at least three times a week, at least four times a week, at least five times a week, at least six times a week, every week, every other week, every third week, every fourth week, every month, every two months, every three months, every four months, and every six months.

In some embodiments, the cancer therapy is likely to expose the subject to a higher risk of infection with a pathogenic organism. Accordingly, in these embodiments, the methods may further comprise administering simultaneously, sequentially or separately with the PKC-θ inhibitor and/or the cancer therapy/agent at least one anti-infective agent that is effective against an infection that develops or that has an increased risk of developing by administration of the cancer therapy or agent, wherein the anti-infective agent is selected from antimicrobials, antibiotics, antivirals, antifungals, anthelmintics, antiprotozoals and nematocides.

In yet another aspect, the invention provides methods for identifying agents that are useful for inhibiting (i) formation, (ii) proliferation, or (iii) maintenance of a PKC-θ-overexpressing cell (e.g., a CSC and/or a non-CSC tumor cell), or for inhibiting (iv) EMT of a PKC-θ-overexpressing cell (e.g., a CSC), or for stimulating or inducing (v) MET of a PKC-θ-overexpressing cell (e.g., a CSC), or for treating or preventing a cancer in a subject, wherein the cancer comprises a PKC-θ-overexpressing cell (e.g., a CSC and/or a non-CSC tumor cell). These methods generally comprise contacting a preparation with a test agent, wherein the preparation comprises (i) a polypeptide comprising an amino acid sequence corresponding to at least a biologically active fragment of a PKC-θ, or to a variant or derivative thereof; or (ii) a polynucleotide comprising a nucleotide sequence from which a transcript of a PKC-θ gene or portion thereof is producible, or (iii) a polynucleotide comprising at least a portion of a genetic sequence (e.g., a transcriptional element) that regulates the expression of a PKC-θ gene, which is operably linked to a reporter gene. A detected reduction in the level and/or functional activity (e.g., as broadly described above) of the polypeptide, transcript or transcript portion or an expression product of the reporter gene, relative to a normal or reference level and/or functional activity in the absence of the test agent, indicates that the agent is useful for inhibiting (i) formation, (ii) proliferation, or (iii) maintenance a PKC-θ-overexpressing cell (e.g., a CSC and/or a non-CSC tumor cell), or for inhibiting (iv) EMT of a PKC-θ-overexpressing cell (e.g., a CSC), or for stimulating or inducing (v) MET of a PKC-θ-overexpressing cell (e.g., a CSC), or for treating or preventing a cancer.

Still another aspect of the present invention provides methods of producing an agent for inhibiting (i) formation, (ii) proliferation, or (iii) maintenance of a PKC-θ-overexpressing cell (e.g., a CSC and/or a non-CSC tumor cell), or for inhibiting (iv) EMT of a PKC-θ-overexpressing cell (e.g., a CSC), or for stimulating or inducing (v) MET of a PKC-θ-overexpressing cell (e.g., a CSC), or for treating or preventing a cancer in a subject, wherein the cancer comprises a PKC-θ-overexpressing cell (e.g., a CSC and/or a non-CSC tumor cell), as broadly described above. These methods generally comprise: testing an agent suspected of inhibiting a PKC-θ as broadly described above; and synthesizing the agent on the basis that it tests positive for the inhibition. Suitably, the method further comprises derivatizing the agent, and optionally formulating the derivatized agent with a pharmaceutically acceptable carrier and/or diluent, to improve the efficacy of the agent for inhibiting (i) formation, (ii) proliferation, or (iii) maintenance of a PKC-θ-overexpressing cell (e.g., a CSC and/or a non-CSC tumor cell), or for inhibiting (iv) EMT of a PKC-θ-overexpressing cell (e.g., a CSC), or for stimulating or inducing (v) MET of a PKC-θ-overexpressing cell (e.g., a CSC), or for treating or preventing a cancer in a subject, wherein the cancer comprises a PKC-θ-overexpressing cell (e.g., a CSC and/or a non-CSC tumor cell).

Another aspect of the present invention provides pharmaceutical compositions for inhibiting at least one of: (i) formation, (ii) proliferation, or (iii) maintenance of a CSC and/or a non-CSC tumor cell; and/or for inhibiting (iv) EMT of a CSC; and/or for stimulating (v) MET of a CSC; and/or for treating or preventing a cancer that comprises a CSC and/or a non-CSC tumor cell, as broadly described above. These compositions generally comprise, consist or consist essentially of a PKC-θ inhibitor and a second/auxiliary agent that inhibits the proliferation, survival or viability of the non-CSC tumor cell. In some embodiments, the PKC-θ inhibitor is a selective PKC-θ inhibitor. In other embodiments, the PKC-θ inhibitor is a non-selective PKC-θ inhibitor.

In a further aspect, the present invention provides the use of a PKC-θ inhibitor for altering at least one of: (i) formation; (ii) proliferation; (iii) maintenance; (iv) EMT; or (v) MET of a PKC-θ-overexpressing cell or for treating or preventing a cancer that comprises a PKC-θ-overexpressing cell (e.g., a CSC or a non-CSC tumor cell), as broadly described above.

Still another aspect of the present invention provides the use of a PKC-θ inhibitor for enhancing the efficacy of a cancer therapy or agent that inhibits the proliferation, survival or viability of a non-CSC tumor cell.

In yet another aspect, the present invention provides the use of PKC-θ inhibitor and a cancer therapy or agent that inhibits the proliferation, survival or viability of a non-CSC tumor cell for treating or preventing a cancer that comprises a CSC and a non-CSC tumor cell, as broadly described above. In some embodiments, the PKC-θ inhibitor and optionally the cancer therapy or agent are prepared or manufactured as medicaments for this purpose.

BRIEF DESCRIPTION OF THE DRAWINGS

FIG. 3E is a graphical representation showing that PKC-θ knockdown reduces mammosphere formation in MCF-IM model. Mammosphere assay was performed with $4 \times 10^4$ MCF-7 cells/well in an ultra low attachment 6 well plates. MCF-7 cells were transfected with either mock siRNA (mock) or PKC-θ siRNA for 48 hrs. and followed by either left untreated, non-stimulation (NS) or PMA stimulation (ST) (0.65 ng/mL for 60 hrs.). Phase contrast microscopic images of mammospheres were taken after 6 days of assay and only mammospheres larger than 60 μm were counted and a bar graph was plotted. Data represent the mean±standard error (SE) of two independent experiments.

FIG. 3F is a graphical representation showing that PKC-θ knockdown results in inhibition of transcription of key inducible EMT/CSC genes in MCF-IM model while PKC-β knockdown does not have this inhibition in n MCF-IM model. MCF-7 cells were transfected with either mock siRNA (mock), PKC-θ siRNA or PKC-β siRNA for 48 hrs. and followed by either left untreated, non-stimulation (NS) or PMA stimulation (ST) (0.65 ng/mL for 60 hrs.). TaqMan® real time PCR analysis for EMT/CSC genes—uPAR and CD44 was performed on cDNA synthesized from total RNA. Threshold cycle (Ct) values generated for each time point were converted to arbitrary copy number and normalized to Cyclophilin A reference levels. mRNA levels are expressed in fold change in comparison to non-stimulated cells. Data represent the mean±standard error (SE) of two independent experiments.

FIG. 3G is a photographic representation showing that over-expression of PKC-θ NLS (Nuclear Localization Signal) mutation reduces entry of PKC-θ in nucleus. Over-expression of PKC-θ WT (Wild Type) or PKC-θ NLS was performed in the MCF-IM model for 72 hrs. before confocal microscopy.

FIG. 3H is a graphical representation showing that over-expression of PKC-θ NLS (Nuclear Localization Signal) mutation reduces the % CSC in the MCF-IM model. Over-expression of Mock vector, PKC-θ WT (Wild Type) or PKC-θ NLS was performed in MCF-IM model for 72 hrs. before cells were stimulated (0.65 ng/mL for 60 hrs.). FACS analysis was subsequently carried out by staining cells with Hoechst, APC-anti-CD44 and PE-anti-CD24 antibodies stain cocktail. Appropriate gating of CSC-like subpopulation was done and % increase in CSC-like subpopulation above the mock was calculated and is shown in a bar graph. Data represent the mean±standard error (SE) of two independent experiments.

FIG. 3I is a graphical representation showing that over-expression of PKC-θ NLS (Nuclear Localization Signal) mutation results in inhibition of transcription of key inducible EMT/CSC genes in the MCF-IM model. Over-expression of Mock vector, PKC-θ WT (Wild Type) or PKC-θ NLS was performed in MCF-IM model for 72 hours before cells were stimulated (0.65 ng/mL for 60 hr). TaqMan® real time PCR analysis for EMT/CSC genes—uPAR and CD44 was performed on cDNA synthesized from total RNA. Threshold cycle (Ct) values generated for each time point were converted to arbitrary copy number and normalized to Cyclophilin A reference levels. mRNA levels are expressed in fold change in comparison to non-stimulated cells. Data represent the mean±standard error (SE) of two independent experiments.

DETAILED DESCRIPTION OF THE INVENTION

1. Definitions

Figure 1A:
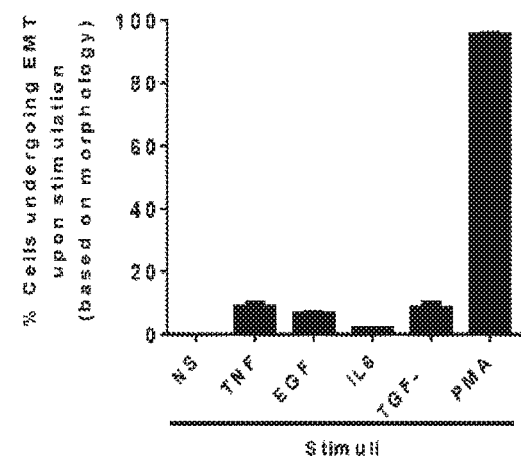
FIG. 1A is a graphical representation showing that stimulation of MCF-7 cells in the MCF-IM model with the PKC inducer, Phorbol 12-Myristate 13-Acetate (PMA) results in maximal EMT. MCF-7 cells were either non-stimulated (NS) or stimulated with TNF-α (20 ng/mL), EGF (50 ng/mL), IL-6 (50 ng/mL), TGF-3 (2.5 ng/mL) or PMA (20 ng/mL) for 60 hr. Three or more phase contrast images were captured for every stimulus using Olympus 17X1 microscope. At least 200 cells were counted in every image and average percentage (%) of the cells undergoing EMT was calculated and subsequently a graph was plotted. Results are shown as average±standard error from two independent experiments.
Figure 1B:
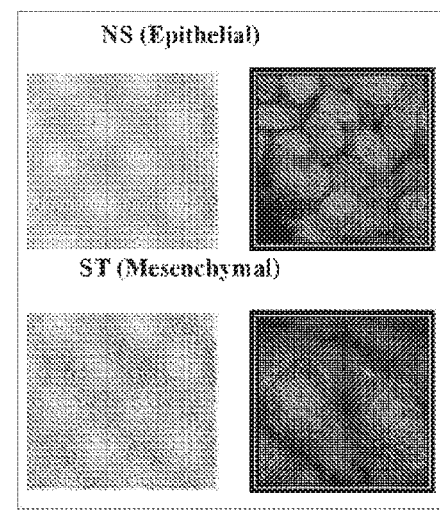
FIG. 1B is a photographic representation showing morphological EMT changes and differential intracellular staining patterns of EMT marker, Laminin-5 in the MCF-IM model. MCF-7 cells were either non-stimulated (NS) or stimulated with PMA (ST) (0.65 ng/mL for 60 hrs.) and subsequently either photographs were taken by phase contrast microscopy or stained with anti-laminin-5 antibody (green color) or DAPI stain (nuclear stain) (blue color) respectively. Confocal microscopic images of MCF-7 were captured using Leica microscope at 60× magnification.
Figure 1C:
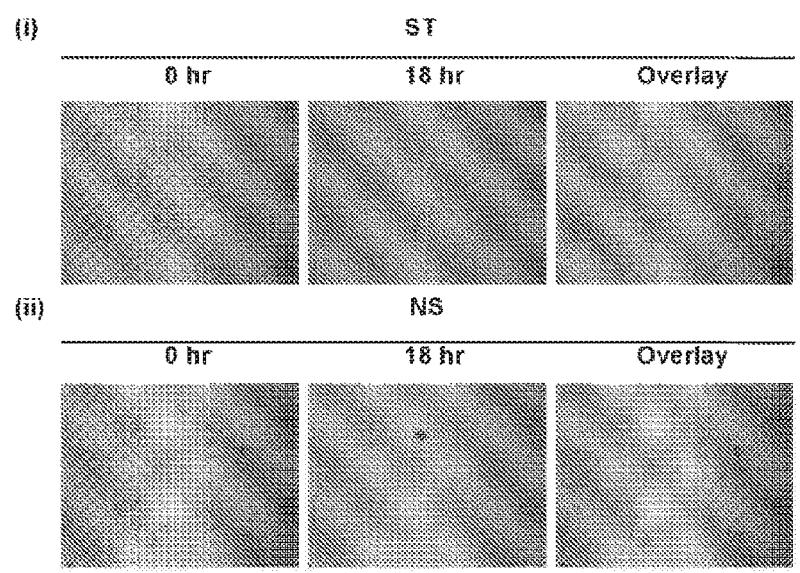
FIG. 1C is a photographic representation showing greater wound healing in the MCF-IM model. MCF-7 cells were stimulated for 18 hrs. with (i) PMA (0.65 ng/mL) or (ii) left untreated, non-stimulated (NS). Phase contrast images of wound healing assay were subsequently captured by Olympus 17X1 using 10× magnification at time points, 0 hr. (red line) and 18 hrs. (green line). An overlaying (red and green line together in one image) of the two images was done to show wound healing ability of the treatment.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "agent" or "modulatory agent" includes a compound that induces a desired pharmacological and/or physiological effect. The term also encompasses pharmaceutically acceptable and pharmacologically active ingredients of those compounds specifically mentioned herein including but not limited to salts, esters, amides, prodrugs, active metabolites, analogs and the like. When the above term is used, then it is to be understood that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and genetic molecules such as RNA, DNA and mimetics and chemical analogs thereof as well as cellular agents. The term "agent" includes a cell that is capable of producing and secreting a polypeptide referred to herein as well as a polynucleotide comprising a nucleotide sequence that encodes that polypeptide. Thus, the term "agent" extends to nucleic acid constructs including vectors such as viral or non-viral vectors, expression vectors and plasmids for expression in and secretion in a range of cells.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

"Antigenic or immunogenic activity" refers to the ability of a polypeptide, fragment, variant or derivative according to the invention to produce an antigenic or immunogenic response in an animal, suitably a mammal, to which it is administered, wherein the response includes the production of elements which specifically bind the polypeptide or fragment thereof.

"Aralkyl" means alkyl as defined above which is substituted with an aryl group as defined above, e.g., —$CH_2$phenyl, —$(CH_2)_2$phenyl, —$(CH_2)_3$phenyl, —$H_2CH$ ($CH_3$)$CH_2$phenyl, and the like and derivatives thereof.

As used herein, "aromatic" or "aryl" is intended to mean any stable monocyclic or bicyclic carbon ring of up to 7 atoms in each ring, wherein at least one ring is aromatic. Examples of such aryl elements include, but are not limited to, phenyl, naphthyl, tetrahydronaphthyl, indanyl, biphenyl, phenanthryl, anthryl or acenaphthyl.

In certain instances, substituents may be defined with a range of carbons that includes zero, such as ($C_0$-$C_6$)alkylene-aryl. If aryl is taken to be phenyl, this definition would include phenyl itself as well as, for example, —$CH_2$Ph, —$CH_2CH_2$Ph, $CH(CH_3)CH_2CH(CH_3)$Ph.

It will also be recognized that the compounds described herein may possess asymmetric centers and are therefore capable of existing in more than one stereoisomeric form. The invention thus also relates to compounds in substantially pure isomeric form at one or more asymmetric centers e.g., greater than about 90% ee, such as about 95% or 97% ee or greater than 99% ee, as well as mixtures, including racemic mixtures, thereof. Such isomers may be naturally occurring or may be prepared by asymmetric synthesis, for example using chiral intermediates, or by chiral resolution.

As used herein, the term "binds specifically," "specifically immuno-interactive" and the like when referring to an antigen-binding molecule refers to a binding reaction which is determinative of the presence of an antigen in the presence of a heterogeneous population of proteins and other biologics. Thus, under designated immunoassay conditions, the specified antigen-binding molecules bind to a particular antigen and do not bind in a significant amount to other proteins or antigens present in the sample. Specific binding to an antigen under such conditions may require an antigen-binding molecule that is selected for its specificity for a particular antigen. For example, antigen-binding molecules can be raised to a selected protein antigen, which bind to that antigen but not to other proteins present in a sample. A variety of immunoassay formats may be used to select antigen-binding molecules specifically immuno-interactive with a particular protein. For example, solid-phase ELISA immunoassays are routinely used to select monoclonal antibodies specifically immuno-interactive with a protein. See Harlow and Lane (1988) Antibodies, A Laboratory Manual, Cold Spring Harbor Publications, New York, for a description of immunoassay formats and conditions that can be used to determine specific immunoreactivity.

The term "cancer stem cell" or CSC refers to a cell that has tumor-initiating and tumor-sustaining capacity, including the ability to extensively proliferate, form new tumors and maintain cancer development, i.e., cells with indefinite proliferative potential that drive the formation and growth of tumors. CSCs are biologically distinct from the bulk tumor cells and possess characteristics associated with stem cells, specifically the ability to self renew and to propagate and give rise to all cell types found in a particular cancer sample. The term "cancer stem cell" or CSC includes both gene alteration in stem cells (SCs) and gene alteration in a cell which becomes a CSC. In specific embodiments, the CSCs breast CSCs, which are suitably $CD24^+CD44^+$, illustrative examples of which include $CD44^{high}CD24^{low}$.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

By "corresponds to" or "corresponding to" is meant a nucleic acid sequence that displays substantial sequence identity to a reference nucleic acid sequence (e.g., at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence identity to all or a portion of the reference nucleic acid sequence) or an amino acid sequence that displays substantial sequence similarity or identity to a reference amino acid sequence (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to all or a portion of the reference amino acid sequence).

The term "derivatize," "derivatizing" and the like refer to producing or obtaining a compound from another substance by chemical reaction, e.g., by adding one or more reactive groups to the compound by reacting the compound with a functional group-adding reagent, etc.

The term "derivative" refers to a compound having a structure derived (e.g., by chemical transformation) from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives of small molecules include salts, esters, amides, salts of esters or amides, and N-oxides of a parent compound. With reference to polypeptides, the term "derivative" refers to a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions or deletions that provide for functional equivalent molecules. The preparation of derivatives can be carried out by methods known in the art.

The term "differentiation" of cancer stem cells as used herein refers to both the change of cancer stem cells into pluripotent tumor progenitors and the change of pluripotent tumor progenitors into unipotent tumor progenitors and/or terminally differentiated tumor cells.

By "effective amount", in the context of treating or preventing a condition is meant the administration of an amount of an agent or composition to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

As used herein, the term "epithelial-to-mesenchymal transition" (EMT) refers to the conversion from an epithelial to a mesenchymal phenotype, which is a normal process of embryonic development. EMT is also the process whereby injured epithelial cells that function as ion and fluid transporters become matrix remodeling mesenchymal cells. In carcinomas, this transformation typically results in altered cell morphology, the expression of mesenchymal proteins and increased invasiveness. The criteria for defining EMT in vitro involve the loss of epithelial cell polarity, the separation into individual cells and subsequent dispersion after the acquisition of cell motility (see, Vincent-Salomon et al., Breast Cancer Res. 2003; 5(2): 101-106). Classes of molecules that change in expression, distribution, and/or function during EMT, and that are causally involved, include growth factors (e.g., transforming growth factor (TGF)-β, wnts), transcription factors (e.g., Snail, SMAD, LEF, and nuclear β-catenin), molecules of the cell-to-cell adhesion axis (cadherins, catenins), cytoskeletal modulators (Rho family), and extracellular proteases (matrix metalloproteinases, plasminogen activators) (see, Thompson et al., Cancer Research 65, 5991-5995, Jul. 15, 2005).

As used herein, the term "mesenchymal-to-epithelial transition" (MET) is a reversible biological process that involves the transition from motile, multipolar or spindle-shaped mesenchymal cells to planar arrays of polarized cells called epithelia. MET is the reverse process of EMT. METs occur in normal development, cancer metastasis, and induced pluripotent stem cell reprogramming.

As used herein, the term "epithelium" refers to the covering of internal and external surfaces of the body, including the lining of vessels and other small cavities. It consists of a collection of epithelial cells forming a relatively thin sheet or layer due to the constituent cells being mutually and extensively adherent laterally by cell-to-cell junctions. The layer is polarized and has apical and basal sides. Despite the tight regimentation of the epithelial cells the epithelium does have some plasticity and cells in an epithelial layer can alter shape, such as change from flat to columnar, or pinch in at one end and expand at the other. However, these tend to occur in cell groups rather than individually (see, Thompson et al., 2005, supra).

As used herein, the term "mesenchyme" refers to the part of the embryonic mesoderm, consisting of loosely packed, unspecialized cells set in a gelatinous ground substance, from which connective tissue, bone, cartilage, and the circulatory and lymphatic systems develop. Mesenchyme is a collection of cells which form a relatively diffuse tissue network. Mesenchyme is not a complete cellular layer and the cells typically have only points on their surface engaged in adhesion to their neighbors. These adhesions may also involve cadherin associations (see, Thompson et al., 2005, supra).

The term "expression" refers the biosynthesis of a gene product. For example, in the case of a coding sequence, expression involves transcription of the coding sequence into mRNA and translation of mRNA into one or more polypeptides. Conversely, expression of a non-coding sequence involves transcription of the non-coding sequence into a transcript only.

By "expression vector" is meant any genetic element capable of directing the transcription of a polynucleotide contained within the vector and suitably the synthesis of a peptide or polypeptide encoded by the polynucleotide. Such expression vectors are known to practitioners in the art.

As used herein, the term "function" refers to a biological, enzymatic, or therapeutic function.

The term "gene" as used herein refers to any and all discrete coding regions of the cell's genome, as well as associated non-coding and regulatory regions. The term is intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

The term "group" as applied to chemical species refers to a set of atoms that forms a portion of a molecule. In some instances, a group can include two or more atoms that are bonded to one another to form a portion of a molecule. A group can be monovalent or polyvalent (e.g., bivalent) to allow bonding to one or more additional groups of a molecule. For example, a monovalent group can be envisioned as a molecule with one of its hydrogen atoms removed to allow bonding to another group of a molecule. A group can be positively or negatively charged. For example, a positively charged group can be envisioned as a neutral group with one or more protons (i.e., H+) added, and a negatively charged group can be envisioned as a neutral group with one or more protons removed. Non-limiting examples of groups include, but are not limited to, alkyl groups, alkylene groups, alkenyl groups, alkenylene groups, alkynyl groups, alkynylene groups, aryl groups, arylene groups, iminyl groups, iminylene groups, hydride groups, halo groups, hydroxy groups, alkoxy groups, carboxy groups, thio groups, alkylthio groups, disulfide groups, cyano groups, nitro groups, amino groups, alkylamino groups, dialkylamino groups, silyl groups, and siloxy groups. Groups such as alkyl, alkenyl, alkynyl, aryl, and heterocyclyl, whether used alone or in a compound word or in the definition of a group may be optionally substituted by one or more substituents. "Optionally substituted," as used herein, refers to a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, phenylamino, diphenylamino, benzylamino, dibenzylamino, hydrazino, acyl, acylamino, diacylamino, acyloxy, heterocyclyl, heterocycloxy, heterocyclamino, haloheterocyclyl, carboxy ester, carboxy, carboxy amide, mercapto, alkylthio, benzylthio, acylthio and phosphorus-containing groups. As used herein, the term "optionally substituted" may also refer to the replacement of a $CH_2$ group with a carbonyl (C=O) group. Non-limiting examples of optional substituents include alkyl, preferably $C_{1-8}$ alkyl (e.g., $C_{1-6}$ alkyl such as methyl, ethyl, propyl, butyl, cyclopropyl, cyclobutyl, cyclopentyl or cyclohexyl), hydroxy $C_{1-8}$ alkyl (e.g., hydroxymethyl, hydroxyethyl, hydroxypropyl), alkoxyalkyl (e.g., methoxymethyl, methoxyethyl, methoxypropyl, ethoxymethyl, ethoxyethyl, ethoxypropyl etc.) $C_{1-8}$ alkoxy, (e.g., $C_{1-6}$ alkoxy such as methoxy, ethoxy, propoxy, butoxy, cyclopropoxy, cyclobutoxy), halo (fluoro, chloro, bromo, iodo), trifluoromethyl, trichloromethyl, tribromomethyl, hydroxy, phenyl (which itself may be further substituted, by an optional substituent as described herein, e.g., hydroxy, halo, methyl, ethyl, propyl, butyl, methoxy, ethoxy, acetoxy, amino), benzyl (wherein the $CH_2$ and/or phenyl group may be further substituted as described herein), phenoxy (wherein the $CH_2$ and/or phenyl group may be further substituted as described herein), benzyloxy (wherein the $CH_2$ and/or phenyl group may be further substituted as described herein), amino, $C_{1-8}$ alkylamino (e.g., $C_{1-6}$ alkyl, such as methylamino, ethylamino, propylamino), di $C_{1-8}$ alkylamino (e.g., $C_{1-6}$ alkyl, such as dimethylamino, diethylamino, dipropylamino), acylamino (e.g., $NHC(O)CH_3$), phenylamino (wherein phenyl itself may be further substituted as described herein), nitro, formyl, —C(O)—$C_{1-8}$ alkyl (e.g., $C_{1-6}$ alkyl, such as acetyl), O—C(O)— alkyl (e.g., $C_{1-6}$ alkyl, such as acetyloxy), benzoyl (wherein the $CH_2$ and/or phenyl group itself may be further substituted), replacement of $CH_2$ with C=O, $CO_2H$, $CO_2C_{1-8}$ alkyl (e.g., $C_{1-6}$ alkyl such as methyl ester, ethyl ester, propyl ester, butyl ester), $CO_2$phenyl (wherein phenyl itself may be further substituted), $CONH_2$, CONHphenyl (wherein phenyl itself may be further substituted as described herein), CONHbenzyl (wherein the $CH_2$ and/or phenyl group may be further substituted as described herein), CONH $C_{1-8}$ alkyl (e.g., $C_{1-6}$ alkyl such as methyl amide, ethyl amide, propyl amide, butyl amide), CONHdi $C_{1-8}$ alkyl (e.g., $C_{1-6}$ alkyl).

"Heteroaralkyl" group means alkyl as defined above which is substituted with a heteroaryl group, e.g., —$CH_2$pyridinyl, —$(CH_2)_2$pyrimidinyl, —$(CH_2)_3$imidazolyl, and the like, and derivatives thereof.

The term "heteroaryl" or "heteroaromatic", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl.

Further examples of "heterocyclyl" and "heteroaryl" include, but are not limited to, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazoyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As used herein, "heteroarylene" refers to a bivalent monocyclic or multicyclic ring system, preferably of about 3 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, suitably 1 to 3, aryl group substituents. Exemplary heteroarylene groups include, for example, 1,4-imidazolylene.

The term "heterocycle", "heteroaliphatic" or "heterocyclyl" as used herein is intended to mean a 5- to 10-membered nonaromatic heterocycle containing from 1 to 4 heteroatoms selected from the group consisting of O, N and S, and includes bicyclic groups.

"Heterocyclylalkyl" group means alkyl as defined above which is substituted with a heterocycle group, e.g., —CH$_2$pyrrolidin-1-yl, —(CH$_2$)$_2$piperidin-1-yl, and the like, and derivatives thereof.

The term "high," as used herein, refers to a measure that is greater than normal, greater than a standard such as a predetermined measure or a subgroup measure or that is relatively greater than another subgroup measure. For example, CD44$^{high}$ refers to a measure of CD44 that is greater than a normal CD44 measure. Consequently, "CD44$^{high}$" always corresponds to, at the least, detectable CD44 in a relevant part of a subject's body or a relevant sample from a subject's body. A normal measure may be determined according to any method available to one skilled in the art. The term "high" may also refer to a measure that is equal to or greater than a predetermined measure, such as a predetermined cutoff. If a subject is not "high" for a particular marker, it is "low" for that marker. In general, the cut-off used for determining whether a subject is "high" or "low" should be selected such that the division becomes clinically relevant.

"Homolog" is used herein to denote a gene or its product, which is related to another gene or product by decent from a common ancestral DNA sequence.

The term "homology" is used herein as equivalent to "sequence identity" or "sequence similarity" and is not intended to require identity by descent or phylogenetic relatedness.

The term "hormone receptor negative (HR−) tumor" means a tumor that does not express a receptor for a hormone that stimulates the proliferation, survival or viability of the tumor above a certain threshold as determined by standard methods (e.g., immunohistochemical staining of nuclei in the patients biological samples. The threshold may be measured, for example, using an Allred score or gene expression. See, e.g., Harvey et al. (1999. *J Clin Oncol* 17:1474-1481) and Badve et al. (2008. *J Clin Oncol* 26(15): 2473-2481). In some embodiments, the tumor does not express an estrogen receptor (ER−) and/or a progesterone receptor (PR−).

The term "hormone receptor positive (HR+) tumor" means a tumor that expresses a receptor for a hormone that stimulates the proliferation, survival or viability of the tumor above a certain threshold as determined by standard methods (e.g., immunohistochemical staining of nuclei in the patients biological samples. The threshold may be measured, for example, using an Allred score or gene expression. See, e.g., Harvey et al. (1999. *J Clin Oncol* 17:1474-1481) and Badve et al. (2008. *J Clin Oncol* 26(15):2473-2481). a tumor expressing either estrogen receptor (ER) or progesterone receptor (PR) as determined by standard methods (e.g., immunohistochemical staining of nuclei in the patients biological samples).

The term "hormone-resistant cancer" as used herein refers to a cancer that has a decreased or eliminated response to a hormone therapy or endocrine therapy when compared to a non-hormone-resistant cancer. From a biological and clinical standpoint, several patterns of resistance can be distinguished: A) tumors that are inherently insensitive to endocrine therapy (e.g., estrogen receptor) targeting despite endocrine receptor expression (pan-endocrine therapy resistance or de novo resistance); B) tumors that are hormone dependent but resistant to one or more specific endocrine therapies (agent-selective resistance; for example responded to tamoxifen but not aromatase inhibitor); and C) tumors that initially respond to endocrine therapy but subsequently progress (acquired resistance). All types of resistance are included herein. In some embodiments, the hormone-resistant cancer is a cancer that is hormone-resistant prior to the administration of a hormone or endocrine therapy (i.e., it is de novo hormone-resistant). In other embodiments, the hormone-resistant cancer is a cancer that is initially not hormone-resistant, but becomes hormone-resistant after at least one treatment of a hormone or endocrine therapy.

The term "hormone therapy" or "endocrine therapy" as used herein is defined as a treatment pertaining to blocking or removing hormones. The treatment may remove the gland that synthesizes the hormone or the prohormone, block or inhibit hormone synthesis, or prevent or inhibit the hormone from binding to its receptor, or down-regulate or degrade the hormone receptor.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances as known to those of skill in the art.

The phrase "hybridizing specifically to" and the like refer to the binding, duplexing, or hybridizing of a molecule only to a particular nucleotide sequence under stringent conditions when that sequence is present in a complex mixture (e.g., total cellular) DNA or RNA.

The term "hydrocarbyl" as used herein includes any radical containing carbon and hydrogen including saturated, unsaturated, aromatic, straight or branched chain or cyclic including polycyclic groups. Hydrocarbyl includes but is not limited to $C_1$-$C_8$alkyl, $C_2$-$C_8$alkenyl, $C_2$-$C_8$alkynyl, $C_3$-$C_{10}$cycloalkyl, aryl such as phenyl and naphthyl, Ar($C_1$-$C_8$)alkyl such as benzyl, any of which may be optionally substituted.

Reference herein to "immuno-interactive" includes reference to any interaction, reaction, or other form of association between molecules and in particular where one of the molecules is, or mimics, a component of the immune system.

As used herein, the term "inhibitor" means an agent that decreases or inhibits the function or biological activity of a PKC-θ polypeptide, or the expression of a PKC-θ gene (e.g., PRKCQ—also known as, PRKCT, PKCT, MGC126514, MGC141919, nPKC-theta).

By "isolated" is meant material that is substantially or essentially free from components that normally accompany it in its native state.

The term "low," as used herein, refers to a measure that is lower than normal, lower than a standard such as a predetermined measure or a subgroup measure or that is relatively lower than another subgroup measure. For example, $CD24^{low}$ refers to a measure of CD24 that is lower than a normal CD24 measure. A normal measure may be determined according to any method available to one skilled in the art. The term "low" may also refer to a measure that is equal to or lower than a predetermined measure, such as a predetermined cutoff.

The term "lower alkyl" refers to straight and branched chain alkyl groups having from 1 to 6 carbon atoms, such as methyl, ethyl, n-propyl, iso-propyl, n-butyl, tert-butyl, sec-butyl, n-pentyl, n-hexyl, 2-methylpentyl, and the like. In some embodiments, the lower alkyl group is methyl or ethyl.

The term "lower alkoxy" refers to straight and branched chain alkoxy groups having from 1 to 6 carbon atoms, such as methoxy, ethoxy, n-propoxy, iso-propoxy, n-butoxy, tert-butoxy, sec-butoxy, n-pentoxy, n-hexoxy, 2-methyl-pentoxy, and the like. Usually, the lower alkoxy group is methoxy or ethoxy.

By "modulating" is meant increasing or decreasing, either directly or indirectly, the level or functional activity of a target molecule. For example, an agent may indirectly modulate the level/activity by interacting with a molecule other than the target molecule. In this regard, indirect modulation of a gene encoding a target polypeptide includes within its scope modulation of the expression of a first nucleic acid molecule, wherein an expression product of the first nucleic acid molecule modulates the expression of a nucleic acid molecule encoding the target polypeptide.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "operably connected" or "operably linked" as used herein means placing a structural gene under the regulatory control of a regulatory element including but not limited to a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e., the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The terms "overexpress," "overexpression," or "overexpressed" interchangeably refer to a gene (e.g., a PKC-θ gene) that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Overexpression can also be by 10%, 20%, 30%, 40%, 50%, 60%, 70%, 80%, 90% or more in comparison to a normal cell or comparison cell (e.g., a breast cell).

The terms "patient," "subject," "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars etc.), marine mammals (e.g., dolphins, whales), reptiles (snakes, frogs, lizards etc.), and fish. In specific embodiments, the subject is a primate such as a human. However, it will be understood that the aforementioned terms do not imply that symptoms are present.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, coloring agents, wetting or emulsifying agents, pH buffering agents, preservatives, transfection agents and the like.

Similarly, a "pharmacologically acceptable" salt, ester, amide, prodrug or derivative of a compound as provided herein is a salt, ester, amide, prodrug or derivative that this not biologically or otherwise undesirable.

The terms "polynucleotide," "genetic material," "genetic forms," "nucleic acids" and "nucleotide sequence" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art.

"Phenylalkyl" means alkyl as defined above which is substituted with phenyl, e.g., —$CH_2$phenyl, —$(CH_2)_2$phenyl, —$(CH_2)_3$phenyl, $CH_3CH(CH_3)CH_2$phenyl, and the like and derivatives thereof. Phenylalkyl is a subset of the aralkyl group.

The terms "polynucleotide variant" and "variant" refer to polynucleotides displaying substantial sequence identity with a reference polynucleotide sequence or polynucleotides that hybridize with a reference sequence under stringent conditions as known in the art (see for example Sambrook et al., Molecular Cloning. A Laboratory Manual", Cold Spring Harbor Press, 1989). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally occurring allelic variants.

The terms "polypeptide," "proteinaceous molecule," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject proteinaceous molecules are particularly useful. Included within the definition are, for example, polypeptides containing one or more analogs of an amino acid including, for example, unnatural amino acids or polypeptides with substituted linkages.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative.

As used herein, the terms "prevent," "prevented," or "preventing," refer to a prophylactic treatment which increases the resistance of a subject to developing the disease or condition or, in other words, decreases the likelihood that the subject will develop the disease or condition as well as a treatment after the disease or condition has begun in order to reduce or eliminate it altogether or prevent it from becoming worse. These terms also include within their scope preventing the disease or condition from occurring in a subject which may be predisposed to the disease or condition but has not yet been diagnosed as having it.

As used herein, "racemate" refers to a mixture of enantiomers.

The terms "salts" and "prodrugs" include any pharmaceutically acceptable salt, ester, hydrate, or any other compound which, upon administration to the recipient, is capable of providing (directly or indirectly) a compound of the invention, or an active metabolite or residue thereof. Suitable pharmaceutically acceptable salts include salts of pharmaceutically acceptable inorganic acids such as hydrochloric, sulfuric, phosphoric, nitric, carbonic, boric, sulfamic and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, toluenesulfonic, benzenesulfonic, salicyclic, sulfanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkylammonium. Also, basic nitrogen-containing groups may be quaternized with such agents as lower alkyl halides, such as methyl, ethyl, propyl, and butyl chlorides, bromides and iodides; dialkyl sulfates like dimethyl and diethyl sulfate; and others. However, it will be appreciated that non-pharmaceutically acceptable salts also fall within the scope of the invention since these may be useful in the preparation of pharmaceutically acceptable salts. The preparation of salts and prodrugs can be carried out by methods known in the art. For example, metal salts can be prepared by reaction of a compound of the invention with a metal hydroxide. An acid salt can be prepared by reacting an appropriate acid with a compound of the invention.

The term "selective" refers to compounds that inhibit or display antagonism towards PKC-θ without substantial inhibiting or antagonizing the function of another PKC enzyme such as PKC-α, PKC-β, PKC-γ, PKC-δ, PKC-ε, PKC-ζ, PKC-η, PKC-λ, PKC-μ, or PKC-ν. By contrast, the term "non-selective" refers to compounds that inhibit or display antagonism towards PKC-θ and that also substantially inhibit or antagonize the function of at least one other PKC enzyme such as PKC-α, PKC-β, PKC-γ, PKC-δ, PKC-ε, PKC-ζ, PKC-η, PKC-λ, PKC-μ, or PKC-ν. Generally, a compound that is selective for PKC-θ exhibits PKC-θ selectivity of greater than about 2-fold, 5-fold, 10-fold, 20-fold, 50-fold or greater than about 100-fold with respect to inhibition or antagonism of another PKC (i.e., a PKC other than PKC-θ such as PKC-α, PKC-β, PKC-γ, PKC-δ, PKC-ε, PKC-ζ, PKC-η, PKC-λ, PKC-μ, or PKC-ν). In some embodiments, selective compounds display at least 50-fold greater inhibition or antagonism towards PKC-θ than towards another PKC (i.e., a PKC other than PKC-θ such as PKC-α, PKC-β, PKC-γ, PKC-δ, PKC-ε, PKC-ζ, PKC-η, PKC-λ, PKC-μ, or PKC-ν). In still other embodiments, selective compounds inhibit or display at least 100-fold greater inhibition or antagonism towards PKC-θ than towards another PKC (i.e., a PKC other than PKC-θ such as PKC-α, PKC-β, PKC-γ, PKC-δ, PKC-ε, PKC-ζ, PKC-η, PKC-λ, PKC-μ, or PKC-ν). In still other embodiments, selective compounds display at least 500-fold greater inhibition or antagonism towards PKC-θ than towards another PKC (i.e., PKC other than PKC-θ such as a PKC-α, PKC-β, PKC-γ, PKC-δ, PKC-ε, PKC-ζ, PKC-η, PKC-λ, PKC-μ, or PKC-ν). In still other embodiments, selective compounds display at least 1000-fold greater inhibition or antagonism towards PKC-θ than towards another PKC (i.e., a PKC other than PKC-θ such as PKC-α, PKC-β, PKC-γ, PKC-δ, PKC-ε, PKC-ζ, PKC-η, PKC-λ, PKC-μ, or PKC-ν).

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by an appropriate method. For example, sequence identity analysis may be carried out using the DNASIS computer program (Version 2.5 for windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in Table 2.

TABLE 2

| ORIGINAL RESIDUE | EXEMPLARY SUBSTITUTIONS |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology," John Wiley & Sons Inc, 1994-1998, Chapter 15.

As used herein a "small molecule" refers to a composition that has a molecular weight of less than 3 kilodaltons (kDa), and typically less than 1.5 kilodaltons, and more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kilodaltons, less than 1.5 kilodaltons, or even less than about 1 kDa.

"Stringency" as used herein refers to the temperature and ionic strength conditions, and presence or absence of certain organic solvents, during hybridization. The higher the stringency, the higher will be the observed degree of complementarity between sequences. "Stringent conditions" as used herein refers to temperature and ionic conditions under which only polynucleotides having a high proportion of complementary bases, preferably having exact complementarity, will hybridize. The stringency required is nucleotide sequence dependent and depends upon the various components present during hybridization, and is greatly changed when nucleotide analogues are used. Generally, stringent conditions are selected to be about 10° C. to 20° C. less than the thermal melting point (Tm) for the specific sequence at a defined ionic strength and pH. The Tm is the temperature (under defined ionic strength and pH) at which 50% of a target sequence hybridizes to a complementary probe. It will be understood that a polynucleotide will hybridize to a target sequence under at least low stringency conditions, preferably under at least medium stringency conditions and more preferably under high stringency conditions. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at room temperature. Medium stringency conditions include and encompass from at least about 16% v/v to at least about 30% v/v formamide and from at least about 0.5 M to at least about 0.9 M salt for hybridization at 42° C., and at least about 0.5 M to at least about 0.9 M salt for washing at 42° C. Medium stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at 42° C. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 mM EDTA, 0.5 M NaHPO4 (pH 7.2), 7% SDS for hybridization at 65° C., and (i) 0.2×SSC, 0.1% SDS; or (ii) 0.5% BSA, 1 mM EDTA, 40 mM NaHPO4 (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing 0.5 M sodium phosphate, 7% SDS at 65° C., followed by one or more washes at 0.2×SSC, 1% SDS at 65° C. Other stringent conditions are well known in the art. A skilled addressee will recognize that various factors can be manipulated to optimize the specificity of the hybridization. Optimization of the stringency of the final washes can serve to ensure a high degree of hybridization. For detailed examples, see CURRENT PROTOCOLS IN MOLECULAR BIOLOGY (supra) at pages 2.10.1 to 2.10.16 and MOLECULAR CLONING. A LABORATORY MANUAL (Sambrook, et al., eds.) (Cold Spring Harbor Press 1989) at sections 1.101 to 1.104.

By "substantially complementary" it is meant that an oligonucleotide or a subsequence thereof is sufficiently complementary to hybridize with a target sequence. Accordingly, the nucleotide sequence of the oligonucleotide or subsequence need not reflect the exact complementary sequence of the target sequence. In a preferred embodiment, the oligonucleotide contains no mismatches and with the target sequence.

As used herein, the term "synergistic" means that the therapeutic effect of a PKC-θ inhibitor when administered in combination with a cancer therapy or agent (or vice-versa) is greater than the predicted additive therapeutic effects of the PKC-θ inhibitor and the cancer therapy or agent when administered alone. The term "synergistically effective amount" as applied to a PKC-θ inhibitor and a cancer therapy agent refers to the amount of each component in a composition (generally a pharmaceutical composition), which is effective for inhibiting (i) formation, (ii) proliferation, (iii) maintenance, or (iv) EMT of a PKC-θ-overexpressing cell (e.g., a CSC), or for stimulating or inducing (v) MET of a PKC-θ-overexpressing cell (e.g., a CSC) and inhibiting proliferation, survival or viability of a non-CSC tumor cell, to thereby treat or prevent the cancer, and which produces an effect which does not intersect, in a dose-response plot of the dose of PKC-θ inhibitor versus a dose of the cancer therapy agent versus inhibiting the (i) formation, (ii) proliferation, (iii) maintenance, or (iv) EMT of a PKC-θ-overexpressing cell (e.g., a CSC), or stimulating or inducing (v) MET of a PKC-θ-overexpressing cell (e.g., a CSC), and inhibiting the proliferation, survival or viability of a non-CSC tumor cell, either the dose PKC-θ inhibitor axis or the dose cancer therapy agent axis. The dose response curve used to determine synergy in the art is described for example by Sande et al. (see, p. 1080-1105 in A. Goodman et al., ed., the Pharmacological Basis of Therapeutics, MacMillan Publishing Co., Inc., New York (1980)). The optimum synergistic amounts can be determined, using a 95% confidence limit, by varying factors such as dose level, schedule and response, and using a computer-generated model that generates isobolograms from the dose response curves for various combinations of the PKC-θ inhibitor and the cancer therapy agent. The highest inhibition of proliferation, survival or viability of CSCs and non-CSC tumor cells on the dose response curve correlates with the optimum dosage levels.

As used herein, the terms "treatment," "treating," and the like, refer to obtaining a desired pharmacologic and/or physiologic effect. The effect may be therapeutic in terms of a partial or complete cure for a disease or condition (e.g., a cancer including a metastatic cancer) and/or adverse effect attributable to the disease or condition. These terms also cover any treatment of a condition or disease in a mammal, particularly in a human, and include: (a) inhibiting the disease or condition, i.e., arresting its development; or (b) relieving the disease or condition, i.e., causing regression of the disease or condition.

The term "tumor," as used herein, refers to any neoplastic cell growth and proliferation, whether malignant or benign, and all pre-cancerous and cancerous cells and tissues. The terms "cancer" and "cancerous" refer to or describe the physiological condition in mammals that is typically characterized in part by unregulated cell growth. As used herein, the term "cancer" refers to non-metastatic and metastatic cancers, including early stage and late stage cancers. The term "precancerous" refers to a condition or a growth that typically precedes or develops into a cancer. By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer. By "early stage cancer" is meant a cancer that is not invasive or metastatic or is classified as a Stage 0, I, or II cancer. The term "late stage cancer" generally refers to a Stage III or Stage IV cancer, but can also refer to a Stage II cancer or a substage of a Stage II cancer. One skilled in the art will appreciate that the classification of a Stage II cancer as either an early stage cancer or a late stage cancer depends on the particular type of cancer. Illustrative examples of cancer include, but are not limited to, breast cancer, prostate cancer, ovarian cancer, cervical cancer, pancreatic cancer, colorectal cancer, lung cancer, hepatocellular cancer, gastric cancer, liver cancer, bladder cancer, cancer of the urinary tract, thyroid cancer, renal cancer, carcinoma, melanoma, brain cancer, non-small cell lung cancer, squamous cell cancer of the head and neck, endometrial cancer, multiple myeloma, rectal cancer, and esophageal cancer. In an exemplary embodiment, the cancer is breast cancer.

The term "tumor sample" as used herein means a sample comprising tumor material obtained from a cancerous patient. The term encompasses clinical samples, for example tissue obtained by surgical resection and tissue obtained by biopsy, such as for example a core biopsy or a fine needle biopsy. The term also encompasses samples comprising tumor cells obtained from sites other than the primary tumor, e.g., circulating tumor cells, as well as well as preserved tumor samples, such as formalin-fixed, paraffin-embedded tumor samples or frozen tumor samples. The term encompasses cells that are the progeny of the patient's tumor cells, e.g., cell culture samples derived from primary tumor cells or circulating tumor cells. The term encompasses samples that may comprise protein or nucleic acid material shed from tumor cells in vivo, e.g., bone marrow, blood, plasma, serum, and the like. The term also encompasses samples that have been enriched for tumor cells or otherwise manipulated after their procurement and samples comprising polynucleotides and/or polypeptides that are obtained from a patient's tumor material.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene, which confers resistance to the antibiotic hygromycin B.

As used herein, underscoring or italicizing the name of a gene shall indicate the gene, in contrast to its protein product, which is indicated by the name of the gene in the absence of any underscoring or italicizing. For example, "PKC-θ" shall mean the PKC-θ gene, whereas "PKC-θ" shall indicate the protein product or products generated from transcription and translation and/or alternative splicing of the PKC-θ gene.

Each embodiment described herein is to be applied mutatis mutandis to each and every embodiment unless specifically stated otherwise.

2. Compositions and Methods for Reducing or Abrogating the Proliferation or Viability of Cancer Stem Cells The present invention is based in part on the determination that breast cancers are enriched for CSC and that PKC-θ is overexpressed in those CSC as well as in non-CSC tumor cells. Based on these findings, the present inventors treated breast cells, breast CSC and breast non-CSC tumor cells with PKC-θ inhibitors and found that they specifically inhibited formation, proliferation or maintenance of breast CSC and non-CSC tumor cells, inhibited EMT of breast CSC, and/or stimulated/induced MET in breast CSC. Without wishing to be bound by any theory or mode of operation, it is proposed that PKC-θ is important at both the level of its signaling and epigenetic roles for the functioning of breast CSC and that overexpression of this enzyme stimulates not only the production and maintenance of breast CSC and non-CSC tumor cells but also the production of CSC and non-CSC tumor cells generally.

Based on the above observations, the present inventors propose that PKC-θ inhibition will result in reduced formation, proliferation or maintenance of CSC and/or non-CSC tumor cells, and/or in reduced EMT of CSC, and/or in increased MET of CSC, which will in turn result in fewer non-CSC tumor cells differentiating therefrom and in more effective treatment of non-CSC tumor cells with a cancer therapy or agent.

Thus, in accordance with the present invention, methods and compositions are provided that take advantage of a PKC-θ inhibitor to reduce or abrogate formation, proliferation or maintenance of CSC and/or non-CSC tumor cells, and/or to reduce or abrogate EMT of CSC, and/or to stimulate or induce MET of CSC for the treatment or prophylaxis of a cancer (e.g., a metastatic cancer). In specific embodiments, the PKC-θ inhibitor is used in combination with a cancer therapy or agent that reduces the proliferation, survival or viability of non-CSC tumor cell progeny of those cells. The methods and compositions of the present invention are thus particularly useful in the treatment or prophylaxis of cancers, including metastatic cancers, as described hereafter.

2.1 PKC-θ Inhibitors

The PKC-θ inhibitor includes and encompasses any active agent that reduces the accumulation, function or stability of a PKC-0; or decreases expression of a PKC-θ gene, and such inhibitors include without limitation, small molecules and macromolecules such as nucleic acids, peptides, polypeptides, peptidomimetics, carbohydrates, poly-saccharides, lipopolysaccharides, lipids or other organic (carbon containing) or inorganic molecules.

In some embodiments, the PKC-θ inhibitor is an antagonistic nucleic acid molecule that functions to inhibit the transcription or translation of PKC-θ transcripts. Representative transcripts of this type include nucleotide sequences corresponding to any one the following sequences: (1) human PKC-θ nucleotide sequences as set forth for example in GenBank Accession Nos. XM_005252496, XM_005252497, XM_005252498, and XM_005252499, (2) nucleotide sequences that share at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with any one of the sequences referred to in (1); (3) nucleotide sequences that hybridize under at least low, medium or high stringency conditions to the sequences referred to in (1); (4) nucleotide sequences that encode any one of the following amino acid sequences: human PKC-θ amino acid sequences as set forth for example in GenPept Accession Nos. XP_005252553, XP_005252554, XP_005252555 and XP_005252556; (5) nucleotide sequences that encode an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence similarity with any one of the sequences referred to in (4); and nucleotide sequences that encode an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with any one of the sequences referred to in (4).

Illustrative antagonist nucleic acid molecules include antisense molecules, aptamers, ribozymes and triplex forming molecules, RNAi and external guide sequences. The nucleic acid molecules can act as effectors, inhibitors, modulators, and stimulators of a specific activity possessed by a target molecule, or the functional nucleic acid molecules can possess a de novo activity independent of any other molecules.

Antagonist nucleic acid molecules can interact with any macromolecule, such as DNA, RNA, polypeptides, or carbohydrate chains. Thus, antagonist nucleic acid molecules can interact with PKC-θ mRNA or the genomic DNA of PKC-θ or they can interact with a PKC-θ polypeptide. Often antagonist nucleic acid molecules are designed to interact with other nucleic acids based on sequence homology between the target molecule and the antagonist nucleic acid molecule. In other situations, the specific recognition between the antagonist nucleic acid molecule and the target molecule is not based on sequence homology between the antagonist nucleic acid molecule and the target molecule, but rather is based on the formation of tertiary structure that allows specific recognition to take place.

In some embodiments, anti-sense RNA or DNA molecules are used to directly block the translation of PKC-θ by binding to targeted mRNA and preventing protein translation. Antisense molecules are designed to interact with a target nucleic acid molecule through either canonical or non-canonical base pairing. The interaction of the antisense molecule and the target molecule may be designed to promote the destruction of the target molecule through, for example, RNAseH mediated RNA-DNA hybrid degradation.

Alternatively the antisense molecule may be designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Non-limiting methods include in vitro selection experiments and DNA modification studies using DMS and DEPC. In specific examples, the antisense molecules bind the target molecule with a dissociation constant ($K_d$) less than or equal to $10^{-6}$, $10^{-8}$, $10^{-10}$, or $10^{-12}$. In specific embodiments, antisense oligodeoxyribonucleotides derived from the translation initiation site, e.g., between −10 and +10 regions are employed.

Aptamers are molecules that interact with a target molecule, suitably in a specific way. Aptamers are generally small nucleic acids ranging from 15-50 bases in length that fold into defined secondary and tertiary structures, such as stem-loops or G-quartets. Aptamers can bind small molecules, such as ATP and theophylline, as well as large molecules, such as reverse transcriptase and thrombin. Aptamers can bind very tightly with Kds from the target molecule of less than $10^{-12}$ M. Suitably, the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is desirable that an aptamer have a $K_d$ with the target molecule at least 10-, 100-, 1000-, 10,000-, or 100,000-fold lower than the $K_d$ with a background-binding molecule. A suitable method for generating an aptamer to a target of interest (e.g., PKC-θ) is the "Systematic Evolution of Ligands by EXponential Enrichment" (SELEX™). The SELEX™ method is described in U.S. Pat. Nos. 5,475,096 and 5,270,163 (see also WO 91/19813). Briefly, a mixture of nucleic acids is contacted with the target molecule under conditions favorable for binding. The unbound nucleic acids are partitioned from the bound nucleic acids, and the nucleic acid-target complexes are dissociated. Then the dissociated nucleic acids are amplified to yield a ligand-enriched mixture of nucleic acids, which is subjected to repeated cycles of binding, partitioning, dissociating and amplifying as desired to yield highly specific high affinity nucleic acid ligands to the target molecule.

In other embodiments, anti-PKC-θ ribozymes are used for catalyzing the specific cleavage of PKC-θ RNA. The mechanism of ribozyme action involves sequence specific hybridization of the ribozyme molecule to complementary target RNA, followed by a endonucleolytic cleavage. There are several different types of ribozymes that catalyze nuclease or nucleic acid polymerase type reactions, which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Representative ribozymes cleave RNA or DNA substrates. In some embodiments, ribozymes that cleave RNA substrates are employed. Specific ribozyme cleavage sites within potential RNA targets are initially identified by scanning the target molecule for ribozyme cleavage sites, which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base pairing. Triplex molecules are preferred because they can bind target regions with high affinity and specificity. It is generally desirable that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, and this complex is recognized by RNAse P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells.

In other embodiments, RNA molecules that mediate RNA interference (RNAi) of a PKC-θ gene or PKC-θ transcript can be used to reduce or abrogate gene expression. RNAi refers to interference with or destruction of the product of a target gene by introducing a single-stranded or usually a double-stranded RNA (dsRNA) that is homologous to the transcript of a target gene. RNAi methods, including double-stranded RNA interference (dsRNAi) or small interfering RNA (siRNA), have been extensively documented in a number of organisms, including mammalian cells and the nematode *C. elegans* (Fire et al., 1998. *Nature* 391, 806-811). In mammalian cells, RNAi can be triggered by 21- to 23-nucleotide (nt) duplexes of small interfering RNA (siRNA) (Chiu et al., 2002 *Mol. Cell*. 10:549-561; Elbashir et al., 2001. *Nature* 411:494-498), or by micro-RNAs (miRNA), functional small-hairpin RNA (shRNA), or other dsRNAs which are expressed in vivo using DNA templates with RNA polymerase III promoters (Zeng et al., 2002. *Mol. Cell* 9:1327-1333; Paddison et al., 2002. *Genes Dev*. 16:948-958; Lee et al., 2002. *Nature Biotechnol*. 20:500-505; Paul et al., 2002. *Nature Biotechnol*. 20:505-508; Tuschl, T., 2002. *Nature Biotechnol*. 20:440-448; Yu et al., 2002. *Proc. Natl. Acad. Sci. USA* 99(9):6047-6052; McManus et al., 2002. *RNA* 8:842-850; Sui et al., 2002. *Proc. Natl. Acad. Sci. USA* 99(6):5515-5520).

In specific embodiments, dsRNA per se and especially dsRNA-producing constructs corresponding to at least a portion of a PKC-θ gene are used to reduce or abrogate its expression. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for a PKC-θ gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts, which then anneal to form a dsRNA having homology to a target gene.

Absolute homology is not required for RNAi, with a lower threshold being described at about 85% homology for a dsRNA of about 200 base pairs (Plasterk and Ketting, 2000, *Current Opinion in Genetics and Dev.* 10: 562-67). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene. RNA-encoding constructs that express a single RNA transcript designed to anneal to a separately expressed RNA, or single constructs expressing separate transcripts from convergent promoters, are suitably at least about 100 nucleotides in length. RNA-encoding constructs that express a single RNA designed to form a dsRNA via internal folding are usually at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In some embodiments, RNA molecules of about 21 to about 23 nucleotides, which direct cleavage of specific mRNA to which they correspond, as for example described by Tuschl et al. in U.S. 2002/0086356, can be utilized for mediating RNAi. Such 21- to 23-nt RNA molecules can comprise a 3' hydroxyl group, can be single-stranded or double stranded (as two 21- to 23-nt RNAs) wherein the dsRNA molecules can be blunt ended or comprise overhanging ends (e.g., 5',3').

In some embodiments, the antagonist nucleic acid molecule is a siRNA. siRNAs can be prepared by any suitable method. For example, reference may be made to International Publication WO 02/44321, which discloses siRNAs capable of sequence-specific degradation of target mRNAs when base-paired with 3' overhanging ends, which is incorporated by reference herein. Sequence specific gene silencing can be achieved in mammalian cells using synthetic, short double-stranded RNAs that mimic the siRNAs produced by the enzyme dicer. siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER™ siRNA Construction Kit.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US 2002/0120129, each of which is incorporated herein by reference.

Illustrative RNAi molecules (e.g., PKC-θ siRNA and shRNA) are described in the art (e.g., Ma et al., 2013. BMC Biochem. 14: 20; and Kim et al., 2013. Immune Netw. 13(2):55-62) or available commercially from Santa Cruz Biotechnology, Inc. (Santa Cruz, Calif., USA), OriGene Technologies, Inc. (Rockville, Md., USA), Sigma-Aldrich Pty Ltd (Castle Hill, NSW, Australia).

The present invention further contemplates peptide or polypeptide based inhibitor compounds. For example, various PKC-θ isozyme- and variable region-specific peptides are known, illustrative examples of which include:

(a) θV1 derived peptides θV1-1 and θV1-2, having the amino acid sequence GLSNFDCG [SEQ ID NO: 1] (PKC-θ residues 8-15) or YVESENGQMYI [SEQ ID NO:2](PKC-θ residues 36-46), respectively, as disclosed for example in U.S. Pat. No. 5,783,405, which is hereby incorporated by reference herein in its entirety;

(b) θV5 derived peptides having the amino acid sequence VKSPFDCS [SEQ ID NO:3] (PKC-θ residues 655-662) or DRALINS [SEQ ID NO:4], or modified peptide VrSPFDCS [SEQ ID NO:5], as disclosed for example in US 2004/0009922, which is hereby incorporated by reference herein in its entirety; and (c) Ψθ RACK derived peptides having the amino acid sequence KGDNVDLI [SEQ ID NO:6], KGENVDLI [SEQ ID NO:7], KGKEVDLI [SEQ ID NO:8], KGKNVDLI [SEQ ID NO:9], RGKNVELA [SEQ ID NO: 10], RGENVELA [SEQ ID NO: 11], KGKQVNLI [SEQ ID NO: 12], KGKQVNLI [SEQ ID NO: 13], KGDQVNLI [SEQ ID NO: 14], or KGEQVNLI [SEQ ID NO: 15] as disclosed for example in US 2010/0311644, which is hereby incorporated by reference herein in its entirety.

PKC-θ inhibitory peptides, as described for example above may be modified by being part of a fusion protein. The fusion protein may include a transport protein or peptide that functions to increase the cellular uptake of the peptide inhibitors, has another desired biological effect, such as a therapeutic effect, or may have both of these functions. The fusion protein may be produced by methods known to the skilled artisan. The inhibitor peptide may be bound, or otherwise conjugated, to another peptide in a variety of ways known to the art. For example, the inhibitor peptide may be bound to a carrier peptide or other peptide described herein via cross-linking wherein both peptides of the fusion protein retain their activity. As a further example, the peptides may be linked or otherwise conjugated to each other by an amide bond from the C-terminal of one peptide to the N-terminal of the other peptide. The linkage between the inhibitor peptide and the other member of the fusion protein may be non-cleavable, with a peptide bond, or cleavable with, for example, an ester or other cleavable bond known to the art.

In some embodiments, the transport protein or peptide may be, for example, a *Drosophila* Antennapedia homeodomain-derived sequence comprising the amino acid sequence CRQIKIWFQNRRMKWKK [SEQ ID NO: 16], and may be attached to the inhibitor by cross-linking via an N-terminal Cys-Cys bond (as discussed, for example, in Theodore et al., 1995. J. Neurosci. 15:7158-7167; Johnson et al., 1996. Circ. Res 79:1086). Alternatively, the inhibitor may be modified by a transactivating regulatory protein (Tat)-derived transport polypeptide (such as from amino acids 47-57 of Tat shown in SEQ ID NO: 17; YGRKKRRQRRR) from the human immunodeficiency virus, Type 1, as described in Vives et al., 1997. J. Biol. Chem, 272:16010-16017, U.S. Pat. No. 5,804,604 and GenBank Accession No. AAT48070; or with polyarginine as described in Mitchell et al., 2000. J. Peptide Res. 56:318-325 and Rolhbard et al., 2000. Nature Med. 6:1253-1257). The inhibitors may be modified by other methods known to the skilled artisan in order to increase the cellular uptake of the inhibitors.

A PKC-θ inhibitory peptide can also be introduced into a cell by introducing into the cell a nucleic acid comprising a nucleotide sequence that encodes a PKC-θ inhibitory peptide. The nucleic acid can be in the form of a recombinant expression vector. The PKC-θ inhibitory peptide-encoding sequence can be operably linked to a transcriptional control element(s), e.g., a promoter, in the expression vector. Suitable vectors include, e.g., recombinant retroviruses, lentiviruses, and adenoviruses; retroviral expression vectors, lentiviral expression vectors, nucleic acid expression vectors, and plasmid expression vectors. In some cases, the expression vector is integrated into the genome of a cell. In other cases, the expression vector persists in an episomal state in a cell.

Suitable expression vectors include, but are not limited to, viral vectors (e.g., viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet. 5:591 594, 1996; Srivastava in WO 93/09239, Samulski et al., J. Vir. 63:3822-3828, 1989; Mendelson et al., Virol. 166:154-165, 1988; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., murine leukemia virus, spleen necrosis virus, and vectors derived from retroviruses such as Rous sarcoma virus, Harvey sarcoma virus, avian leucosis virus, a lentivirus, human immunodeficiency virus, myeloproliferative sarcoma virus, and mammary tumor virus); and the like.

The present invention also contemplates small molecule agents that reduce the functional activity of PKC-θ (e.g., reduce PKC-θ-mediated phosphorylation, inhibit binding of PKC-θ to the promoter of CD44 or uPAR, reduce binding of PKC-θ (e.g., active PKC-θ) to chromatin; reduce PKC-θ-mediated inhibition of guanine exchange factor, GIV/Girdin, reduce PKC-θ-mediated inhibition of regulatory T cell function, reduce PKC-θ-mediated EMT etc.).

Small molecule agents that reduce functional activity of PKC-θ that are suitable for use in the present invention include pyridine derivatives that inhibit PKC-θ functional activity; purine compounds that inhibit PKC-θ functional activity, pyrimidine derivatives that inhibit PKC-θ functional activity; aniline compounds that inhibit PKC-θ functional activity, indole derivatives that inhibit PKC-θ functional activity, and the like.

In some embodiments, small molecule PKC-θ inhibitors are selected from substituted indole derivatives as described for example by Cooke et al. in US Publication No. 2013/0157980, which is incorporated herein by reference in its entirety. Illustrative derivatives of this type include compounds according to formula (I):

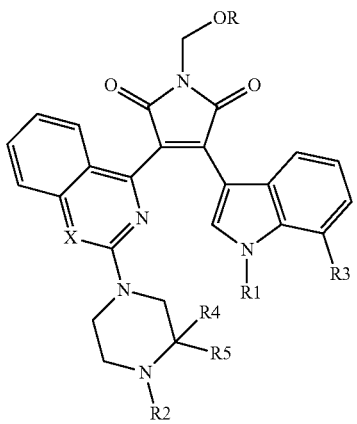

(I)

or a pharmaceutically acceptable salt, or hydrate thereof.

In some embodiments of the compounds according to formula (I):

X is CH or N;
R is H or PO$_3$H$_2$;
R1 is H; or C$_{1-4}$alkyl; R2 is H; or C$_{1-4}$alkyl; R3 is H; C$_{1-4}$alkyl; CN; Hal; or OH; and R4 and R5 are independently from each other H, or C$_{1-4}$alkyl; or R4 and R5 form together with the carbon atom to which they are attached a 3-6 membered cycloalkyl group.

In other embodiments of the compounds according to formula (I):

X is CH;
R is PO$_3$H$_2$;
R1 is H;
R2 is H; or C$_{1-4}$alkyl; R3 is H; or C$_{1-4}$alkyl; and R4 and R5 are independently from each other H; or R4 and R5 form together with the carbon atom to which they are attached a 3-6 membered cycloalkyl group.

In still other embodiments of the compounds according to formula (I):

X is CH;
R is H;
R1 is H;
R2 is H; or C$_{1-4}$alkyl; R3 is H; or C$_{1-4}$alkyl; and R4 and R5 are independently from each other H; or R4 and R5 form together with the carbon atom to which they are attached a 3-6 membered cycloalkyl group.

In still other embodiments of the compounds according to formula (I):

X is N;
R is PO$_3$H$_2$;
R1 is H;
R2 is H; or C$_{1-4}$alkyl;
R3 is H; and
R4 and R5 are independently from each other H; or R4 and R5 form together with the carbon atom to which they are attached a 3-6 membered cycloalkyl group.

In still other embodiments of the compounds according to formula (I):

X is N;
R is PO$_3$H$_2$;
R1 is H;
R2 is H; or C$_{1-4}$alkyl;
R3 is H; and
R4 and R5 are independently from each other H; or C$_{1-4}$alkyl.

In some embodiments, the substituted indole derivatives that inhibit PKC-θ functional activity include compounds according to formula (II):

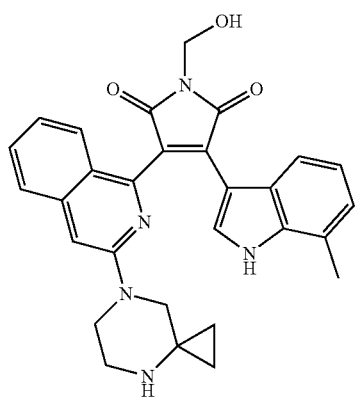

(II)

or a pharmaceutically acceptable salt thereof.

In other embodiments, the substituted indole derivatives that inhibit PKC-θ functional activity include compounds according to formula (III):

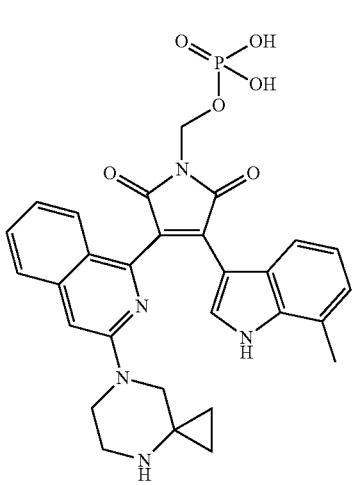

(III)

or a pharmaceutically acceptable salt or hydrate thereof.

In still other embodiments, the substituted indole derivatives that inhibit PKC-θ functional activity include compounds according to formula (IV):

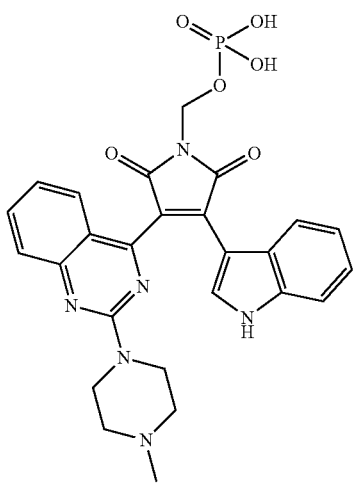

(IV)

or a pharmaceutically acceptable salt thereof.

Representative examples of compounds according to formula (I) include: phosphoric acid mono-[3-[3-(4,7-diaza-spiro[2.5]oct-7-yl)-isoquinolin-1-yl]-4-(7-methyl-1-H-indol-3-yl)-2,5-dioxo-2,5-dihydro-pyrrol-1-ylmethyl]ester, mono-hydrate; 3-[3-(4,7-diaza-spiro[2.5]oct-7-yl)-isoquinolin-1-yl]-1-hydroxymethyl-4-(-7-methyl-1H-indol-3-yl)-pyrrole-2,5-dione or a pharmaceutically acceptable salt thereof; and phosphoric acid mono-{3-(1H-indol-3-yl)-4-[2-(4-methyl-piperazin-1-yl)-quinazolin-4-yl]-2,5-dioxo-2,5-dihydro-pyrrol-1-ylmethyl}ester or a pharmaceutically acceptable salt thereof.

In other embodiments, small molecule PKC-θ inhibitors are selected from pyrimidine diamine derivatives as described for example by Zhao et al. in US Publication No. 2013/0143875, which is incorporated herein by reference in its entirety. Representative derivatives of this type include compounds according to formula (V):

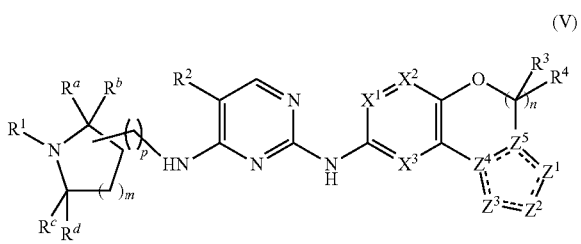

(V)

wherein:

$R^1$ is selected from hydrogen, alkyl, alkenyl, alkynyl, cycloalkyl, —C(O)OR$^{1a}$, —S(O)R$^{1b}$, and —S(O)$_2$R$^{1c}$; wherein each of R$^{1a}$, R$^{1b}$, and R$^{1c}$ is independently hydrogen, alkyl or phenyl-alkyl;

$R^a$, $R^b$, $R^c$ and $R^d$ independently are selected from hydrogen and alkyl;

m is an integer from one to five;

p is an integer from zero to six;

$R^2$ is selected from acyloxy, hydroxy, thiol, acyl, alkyl, alkoxy, substituted alkyl, substituted alkoxy, amino, substituted amino, aminoacyl, acylamino, azido, carboxyl, carboxylalkyl, cyano, halogen, nitro, aminoacyloxy, oxyacylamino, thioalkoxy, substituted thioalkoxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and trihalomethyl;

$X^1$, $X^2$, and $X^3$ are CR$^5$ or one of $X^1$, $X^2$, and $X^3$ is N and rest are CR$^5$;

$R^5$ is selected from hydrogen, halogen, alkyl and substituted alkyl;

$R^3$ and $R^4$ are, for each occurrence, independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO— heteroaryl, —SO$_2$-alkyl, —SO$_2$-substituted alkyl, —SO$_2$-aryl and —SO$_2$-heteroaryl; or $R^3$ and $R^4$ together with the carbon atom to which they are attached form a carbocyclic or heterocyclic 4 to 8-membered ring;

n is an integer from one to three;

$Z^1$, $Z^2$, and $Z^3$ are selected from CR$^6$R$^{6a}$, N, O, and S;

$Z^4$ and $Z^5$ are selected from N, C, and CR$^6$;

$R^6$ is selected from hydrogen, halogen, alkyl and substituted alkyl;

$R^{6a}$ is selected from hydrogen, halogen, alkyl and substituted alkyl or is absent to satisfy valence requirements; and the dashed lines represent a single bond or double bond;

or a salt or solvate or stereoisomer thereof.

In some embodiments of compounds according formula (V), $R^a$, $R^b$, $R^c$ and $R^d$ represent lower alkyl groups. Illustrative examples of such compounds include those wherein $R^a$, $R^b$, $R^c$ and $R^d$ are methyl groups and have formula (VI):

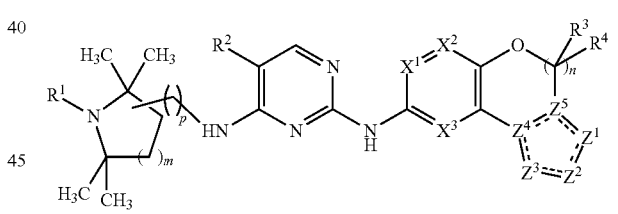

(VI)

In other embodiments of compounds according formula (V), $X^1$, $X^2$, and $X^3$ are each CH. These compounds have the following formula (VII):

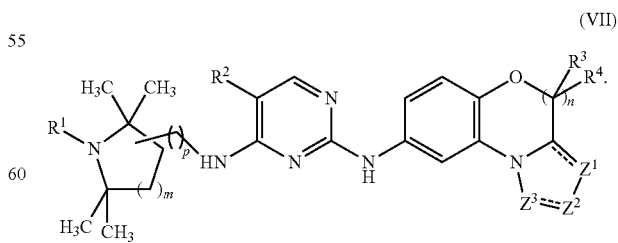

(VII)

In other embodiments of compounds according formula (V), $X^1$, $X^2$, and $X^3$ are each CH; and m is 2. These compounds have the following formula (VIII):

(VIII)

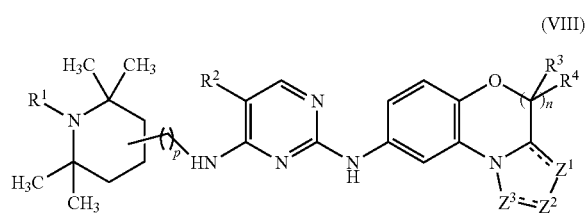

In still other embodiments of compounds according formula (V), $X^1$, $X^2$, and $X^3$ are each CH; and m is one. These compounds have the following formula (IX):

(IX)

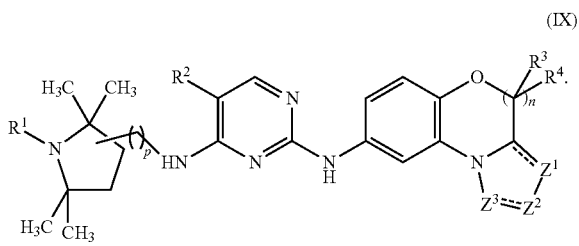

In still other embodiments of compounds according formula (V), $X^1$, $X^2$, and $X^3$ are each CH; n is 2; and one set of $R^1$ and $R^4$ is hydrogen. These compounds have the following formula (X):

(X)

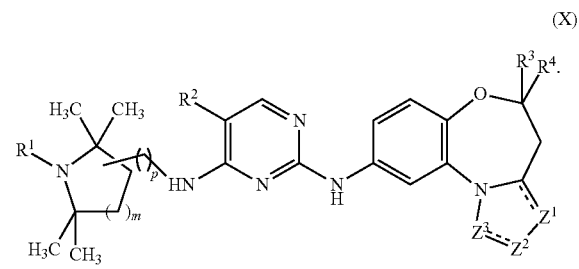

In still other embodiments of compounds according formula (V), $X^2$ is N and $X^1$ and $X^3$ are each CH. These compounds have the following formula (XI):

(XI)

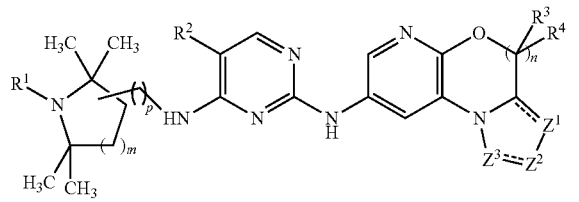

In still other embodiments of compounds according formula (V), $X^3$ is N and $X^1$ and $X^2$ are each CH. These compounds have the following formula (XII):

(XII)

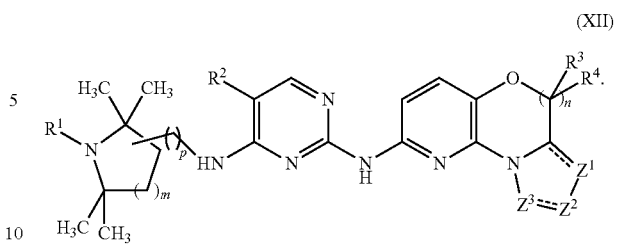

In other embodiments of compounds according formula (V), $Z^4$ is C and $Z^5$ is N. Such compounds have the following formula (XIII):

(XIII)

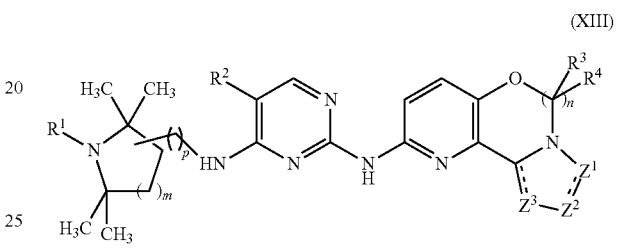

Exemplary compounds of formula V include: N2-(4H-benzo[b]tetrazolo[1,5-d][1,4]oxazin-8-yl)-5-fluoro-N4-(2,2,6,6-tetramethylpiperidin-4-yl)pyrimidine-2,4-diamine; N2-(4H-benzo[b]tetrazolo[1,5-d][1,4]oxazin-8-yl)-5-fluoro-N4-(1,2,2,6,6-p-entamethylpiperidin-4-yl)pyrimidine-2,4-diamine; N2-(4H-benzo[b]pyrrolo[1,2-d][1,4]oxazin-8-yl)-5-fluoro-N4-(2,2,6,6-tetra-methylpiperidin-4-yl)pyrimidine-2,4-diamine; N2-(4H-benzo[b]pyrrolo[1,2-d][1,4]oxazin-8-yl)-5-fluoro-N4-(1,2,2,6,6-pentamethylpiperidin-4-yl)pyrimidine-2,4-diamine; N2-(4,4-difluoro-4H-benzo[b]tetrazolo[1,5-d][1,4]oxazin-8-yl)-5-fluoro-N4-(2,2,6,6-tetramethylpiperidin-4-yl)pyrimidine-2,4-diamine; N2-(4,4-difluoro-4H-benzo[b]tetrazolo[1,5-d][1,4]oxazin-8-yl)-5-fluoro-N4-(1,2,2,6,6-pentamethylpiperidin-4-yl)pyrimidine-2,4-diamine; N2-(4,4-dimethyl-4H-benzo[b]tetrazolo[1,5-d][1,4]oxazin-8-yl)-5-fluoro-N4-(1,2,2,6,6-pentamethylpiperidin-4-yl)pyrimidine-2,4-diamine; N2-(4,4-dimethyl-4H-benzo[b]tetrazolo[1,5-d][1,4]oxazin-8-yl)-5-fluoro-N4-(2,2,6,6-tetramethylpiperidin-4-yl)pyrimidine-2,4-diamine; N2-(5,5-dimethyl-5H-benzo[e]tetrazolo[1,5-c][1,3]oxazin-9-yl)-5-fluoro-N4-(2,2,6,6-tetramethylpiperidin-4-yl)pyrimidine-2,4-diamine; N2-(5,5-dimethyl-5H-benzo[e]tetrazolo[1,5-c][1,3]oxazin-9-yl)-5-fluoro-N4-(1,2,2,6,6-pentamethylpiperidin-4-yl)pyrimidine-2,4-diamine; N2-(8,9-dihydrospiro[benzo[b]tetrazolo[1,5-d][1,4]oxazine-4,1'-cyclobutan-e]-8-yl)-5-fluoro-N4-(2,2,6,6-tetramethylpiperidin-4-yl)pyrimidine-2,4-diamine; N2-(8,9-dihydrospiro[benzo[b]tetrazolo[1,5-d][1,4]oxazine-4,1'-cyclobutane]-[1,5-d][1,4]oxazine-4,1'-cyclobutane]-8-yl)-5-fluoro-N4-(1,2,2,6,6-pentamethylpiperidin-4-yl)pyrimidine-2,4-diamine; 5-fluoro-N2-(4-methyl-8,9-dihydro-4H-benzo[b]tetrazolo[1,5-d][1,4]oxazin-8-yl)-N4-(2,2,6,6-tetramethylpiperidin-4-yl)pyrimidine-2,4-diamine; 5-fluoro-N2-(4-methyl-8,9-dihydro-4H-benzo[b]tetrazolo[1,5-d][1,4]oxazin-8-yl)-N4-(1,2,2,6,6-pentamethylpiperidin-4-yl)pyrimidine-2,4-diamine; N2-(4H-benzo[b]tetrazolo[1,5-d][1,4]oxazin-8-yl)-5-fluoro-N4-((1,2,2,5,5-pentamethylpyrrolidin-3-yl)methyl)pyrimidine-2,4-diamine; N2-(4H-benzo[b]tetrazolo[1,5-d][1,4]oxazin-8- yl)-5-fluoro-N4-((2,2,5,5-tetramethylpyrrolidin-3-yl)methyl)pyrimidine-2,4-diamine; N2-(4,4-dimethyl-4H-benzo[b]tetrazolo[1,5-d][1,4]oxazin-8-yl)-5-fluoro-N4-((1,2,2,5,5-pentamethylpyrrolidin-3-yl)methyl)pyrimidine-2,4-diamine; N2-(4,4-dimethyl-4H-benzo[b]tetrazolo[1,5-d][1,4]oxazin-8-yl)-5-fluoro-N4-((2,2,5,5-tetramethylpyrrolidin-3-yl)methyl)pyrimidine-2,4-diamine-; N2-(4,4-dimethyl-4H-benzo[b]tetrazolo[1,5-d][1,4]oxazin-8-yl)-5-fluoro-N4-(((3S)-2,2,5-trimethylpyrrolidin-3-yl)methyl)pyrimidine-2,4-diamine; and N2-(4,4-dimethyl-4H-benzo[b]tetrazolo[1,5-d][1,4]oxazin-8-yl)-5-fluoro-N4-(((3R)-2,2,5-trimethylpyrrolidin-3-yl)methyl)pyrimidine-2,4-diamine, or salts or solvates or stereoisomers thereof.

Alternative small molecule PKC-θ inhibitors compounds may be selected from aminopyridine compounds as described for example by Maltais et al. in US Publication No. 2013/0137703, which is incorporated herein by reference in its entirety. Non-limiting compounds of this type have the formula (XIV):

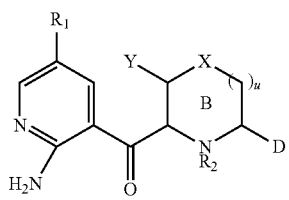

(XIV)

or a pharmaceutically acceptable salt thereof
wherein:
$R_1$ is —H, C1-C3 aliphatic, F, or Cl. Ring B is a 5- or 6-membered monocyclic heteroaromatic ring. X is —CH—, —S—, or —NR$_2$—. R$_2$ is absent or —H. Y is —Y1 or -Q1. Y1 a C1-10 aliphatic group optionally and independently substituted with one or more F.

Q1 is phenyl or a 5-6 membered monocyclic heteroaryl ring having 0-3 heteroatoms independently selected from nitrogen, oxygen, and sulfur; and Q1 is optionally and independently substituted with one or more $J_a$.

D is ring C or -Q-R3.

Ring C is a 6-8-membered non-aromatic monocyclic ring having 1-2 nitrogen atoms, or an 8-12 membered non-aromatic bridged bicyclic ring system having 1-3 heteroatoms selected from nitrogen and oxygen; and ring C is optionally and independently substituted with one or more $J_b$.

O is —NH—, or —O—.

$R_3$ is a C1-10 alkyl substituted with —OH, or —NH$_2$; wherein three to six methylene units in R3 may optionally form a C3-C6 membered cycloalkyl ring; and $R_3$ is further independently optionally and independently substituted with one or more $J_c$.

Each $J_a$ is independently F or C1-C6 alkyl.

$J_b$ is C1-C10 alkyl wherein up to three methylene units are optionally replaced —O—; and wherein the C1-C10 alkyl is optionally and independently substituted with or more $J_c$; or $J_b$ is C3-C6 cycloalkyl, or C5-C6 heteroaryl; or $J_b$ is phenyl optionally and independently substituted with $J_d$; or two $J_b$ on the same carbon atom form =O or spiro C3-C6 cycloalkyl.

Each $J_c$ is independently F, —OH, or C3-C6 cycloalkyl.

Each $J_d$ is independently F or Cl.

Each $J_e$ is independently phenyl, a 5-6-membered monocyclic aromatic or non-aromatic ring having 1-3 heteroatoms independently selected from nitrogen, oxygen, and sulfur, or two $J_e$ on the same carbon atom form a spiro C3-C6 cycloalkyl.

u is 0 or 1.

In some embodiments, ring B is pyridyl; ring C is selected from the group consisting of piperidinyl, piperizinyl, diazepanyl, triazepanyl, azocanyl, diazocanyl, triazocanyl, indolyl, indazolyl, or diazabicyclooctyl; and ring C is optionally and independently substituted with one or more $J_b$, and the remainder of the variables are as described above.

Representative compounds according to formula (XIV) include:

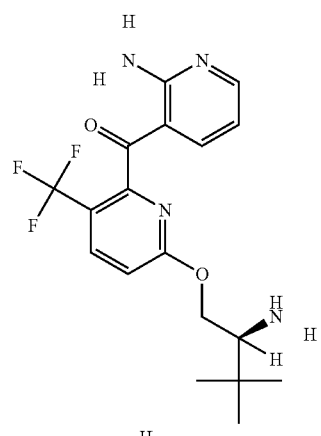

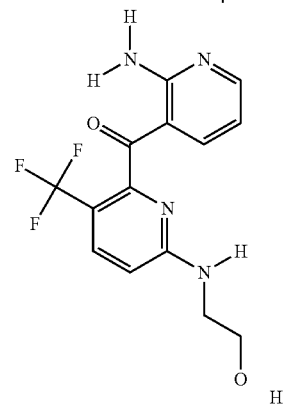

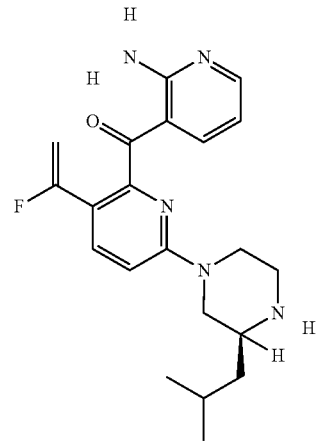

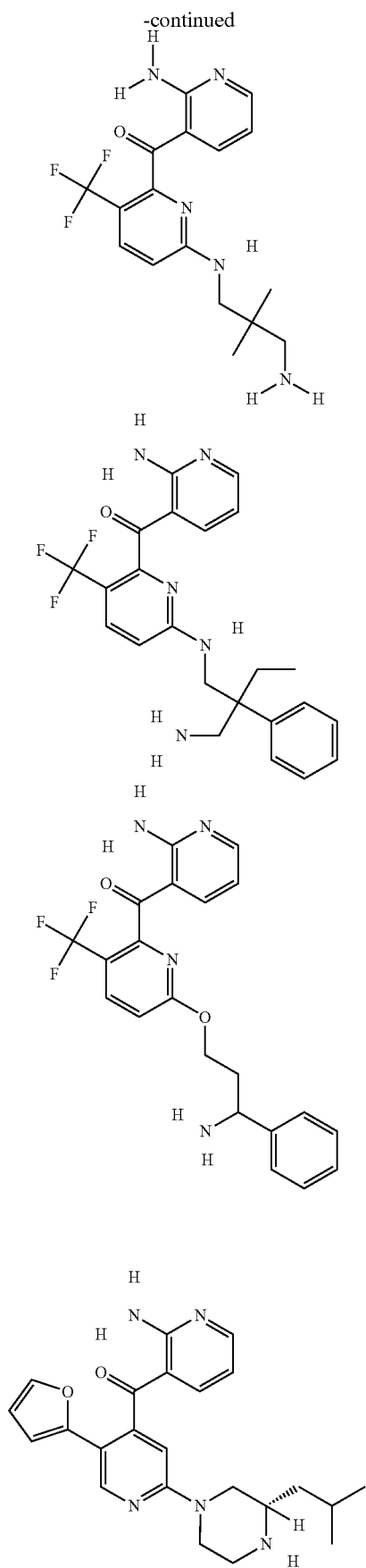
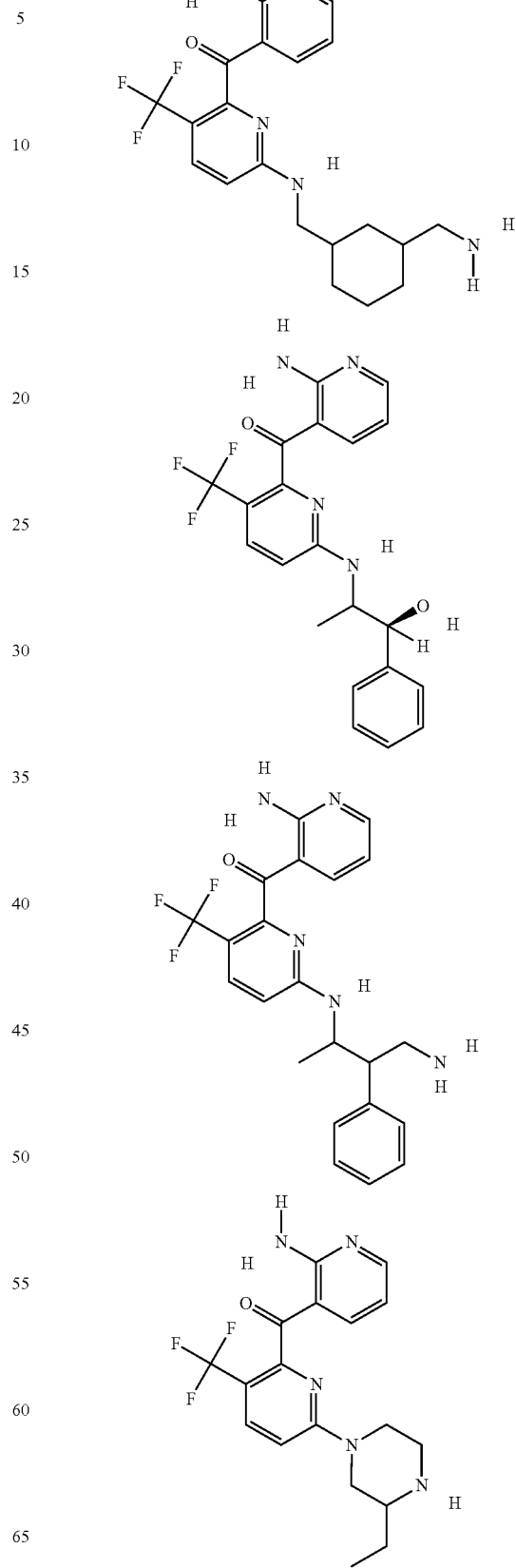

-continued
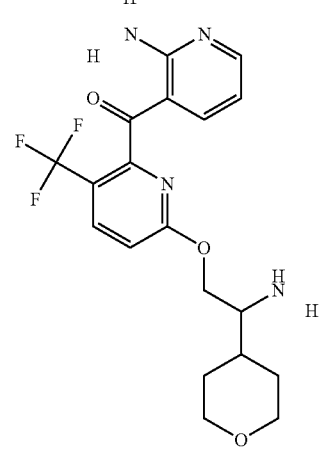
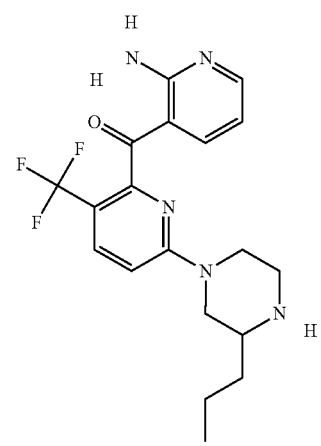
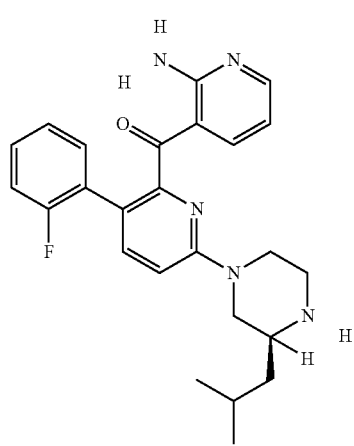
-continued
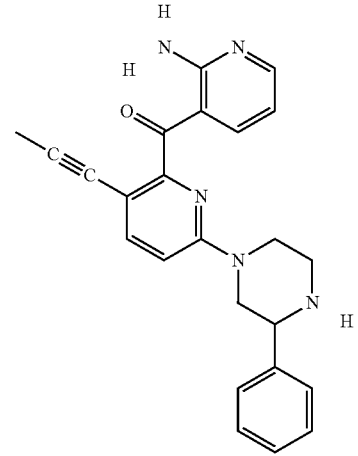
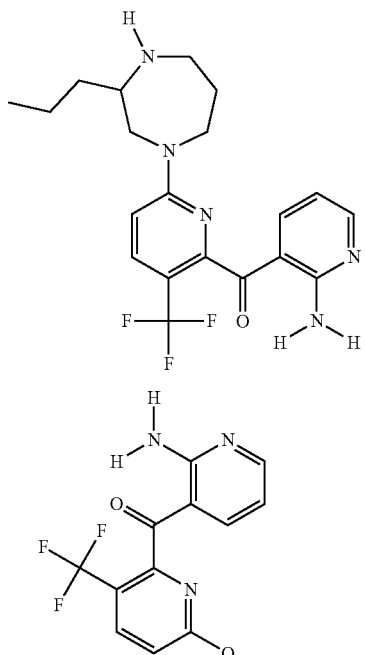
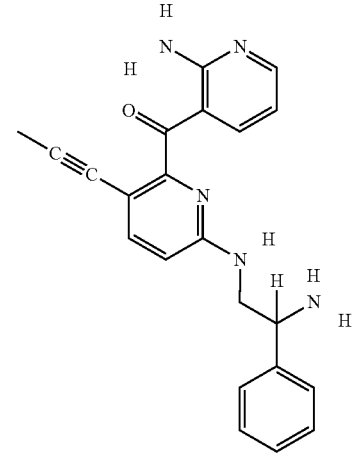

51
-continued

52
-continued

53
-continued
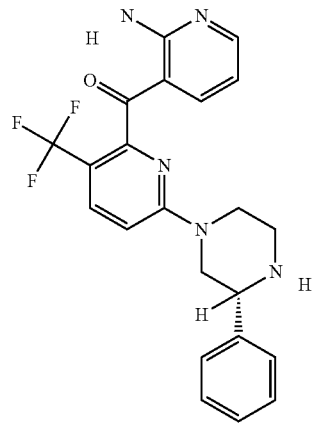
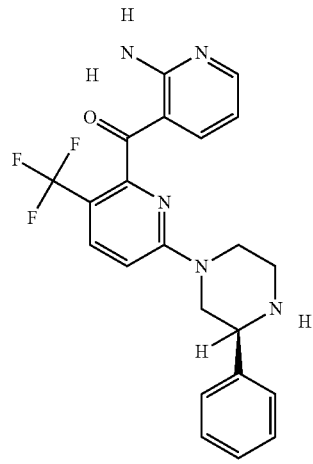
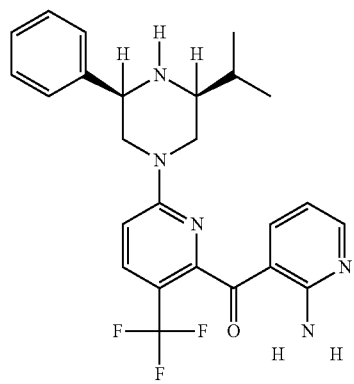
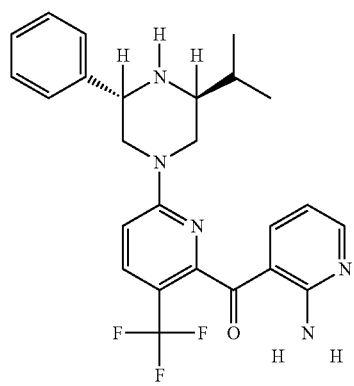
54
-continued
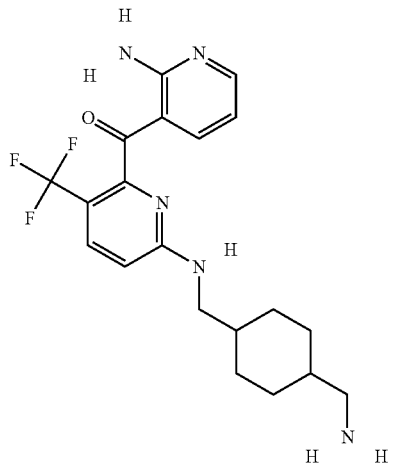
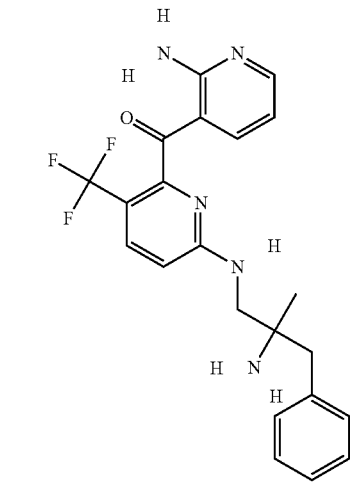
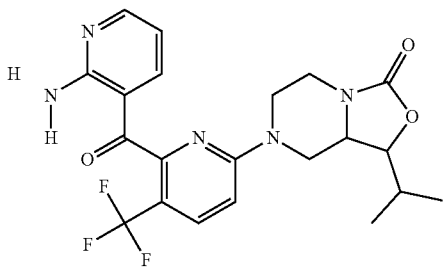
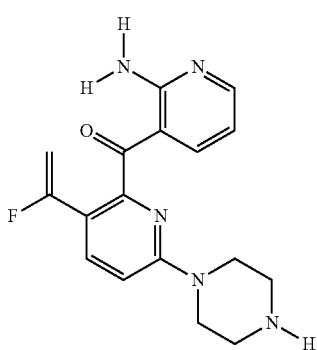

-continued
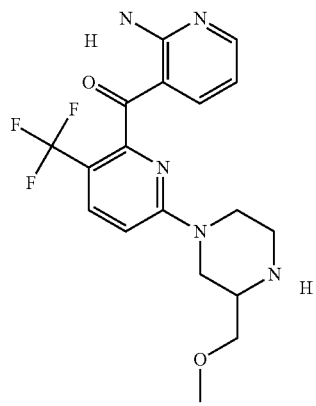
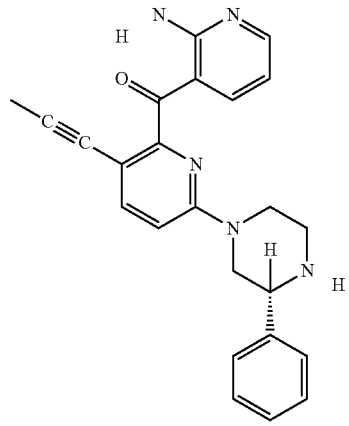
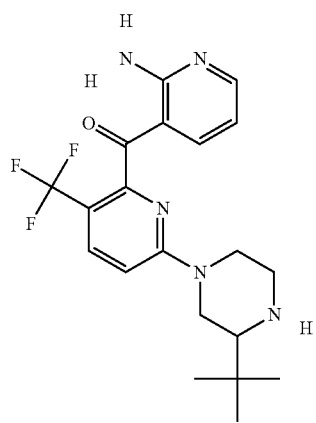
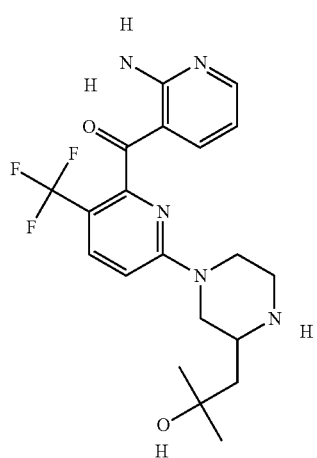
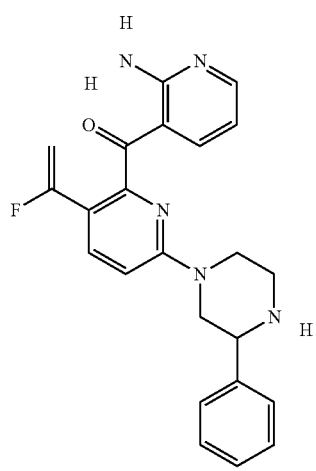
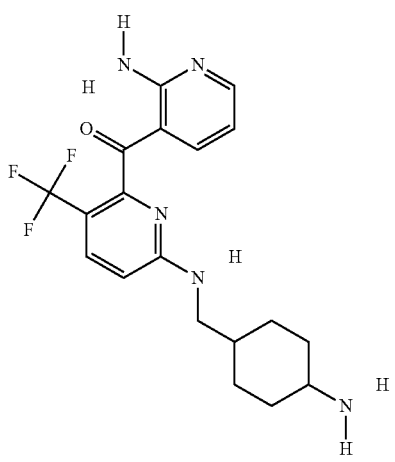

-continued
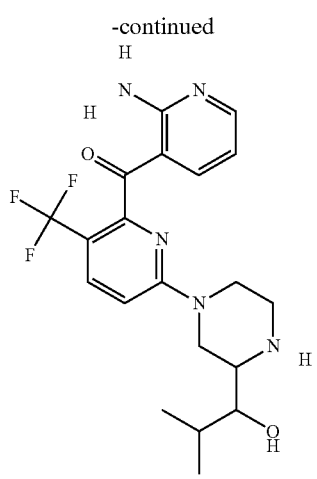
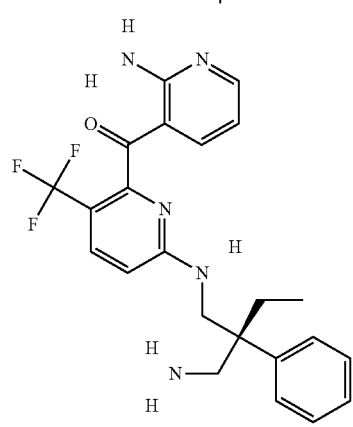
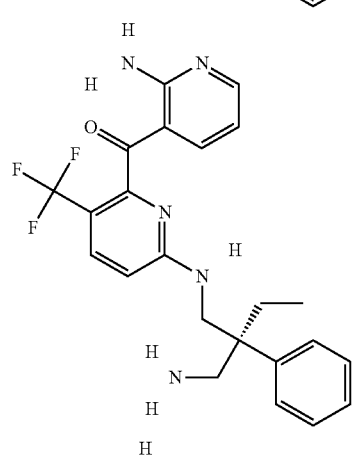
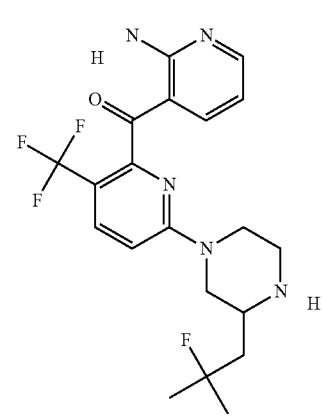
-continued
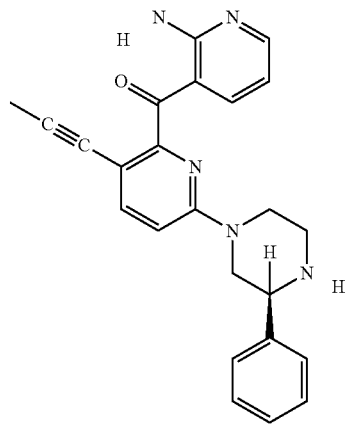
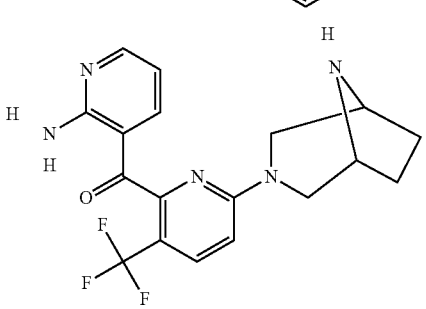
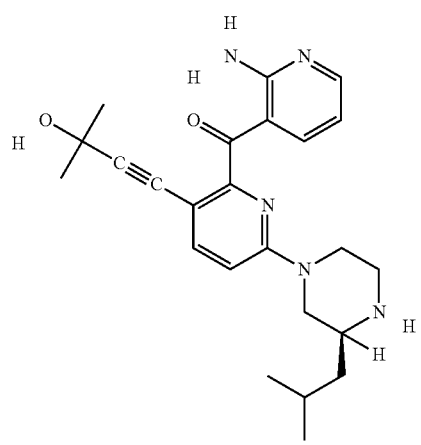
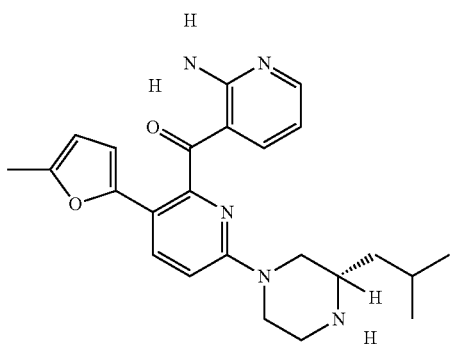

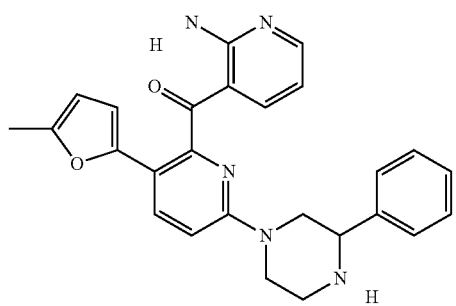
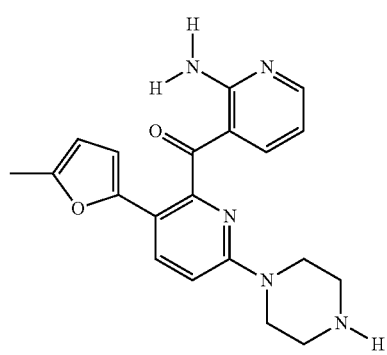
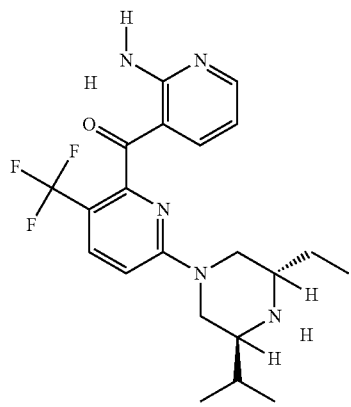
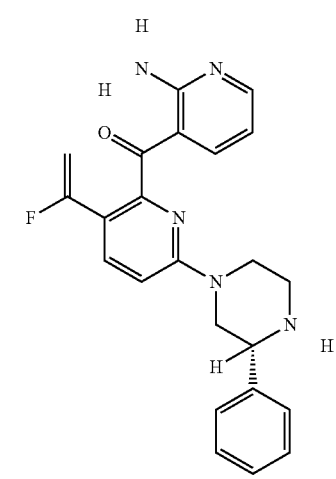
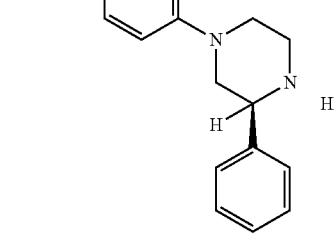

-continued
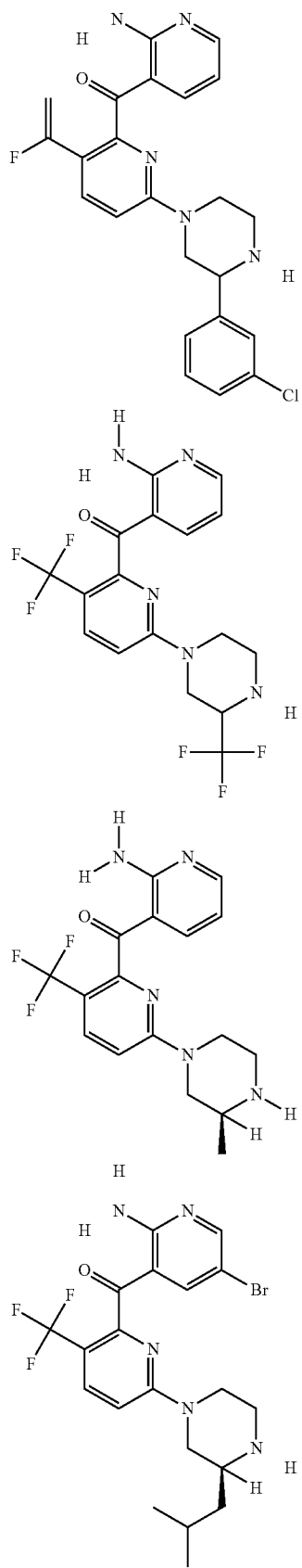
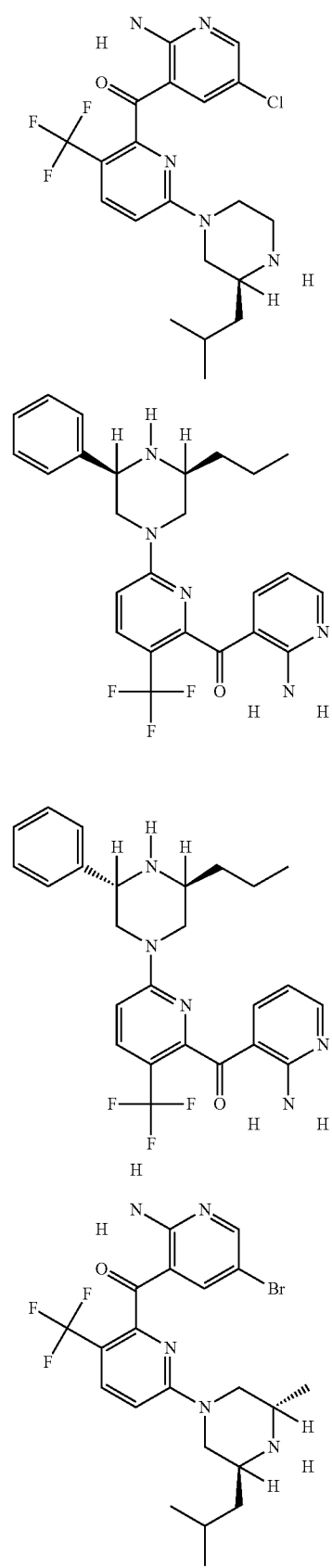

63
-continued
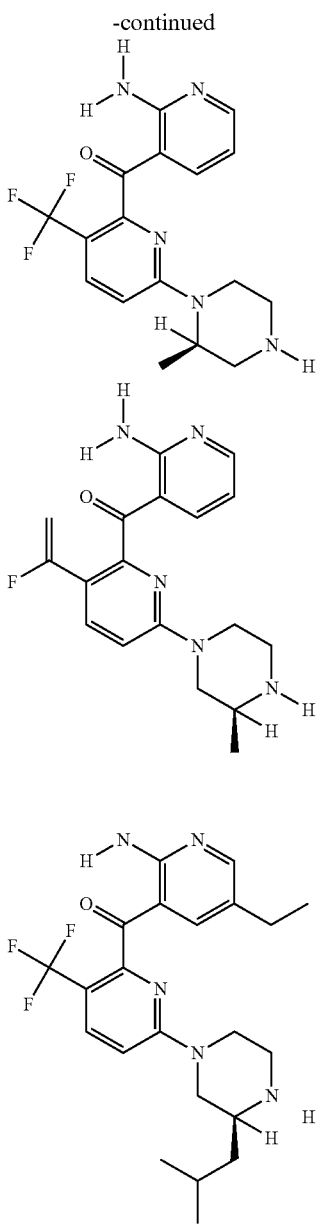
64
-continued
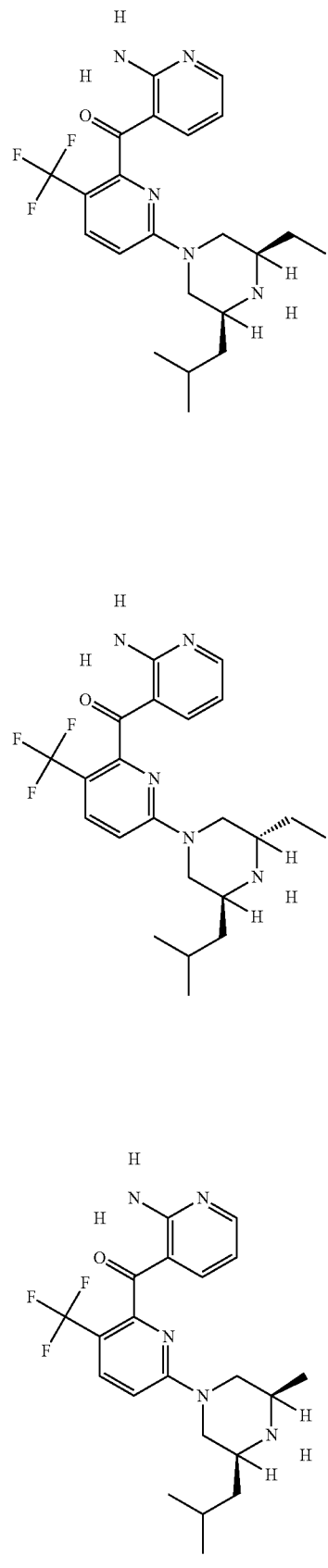

-continued
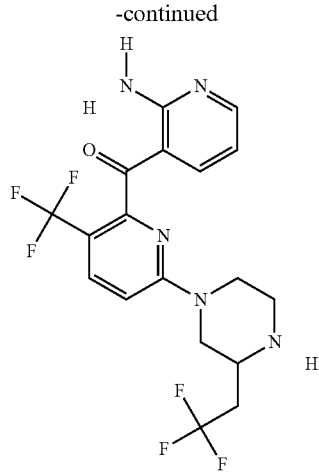
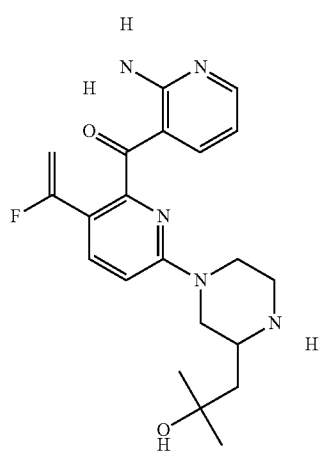
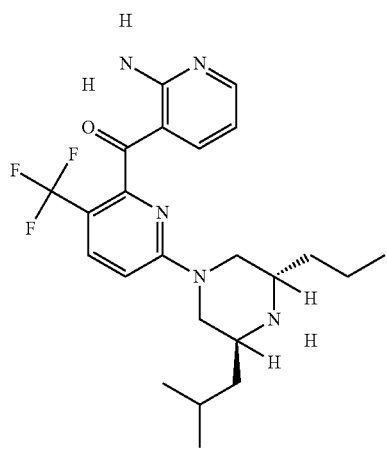
-continued
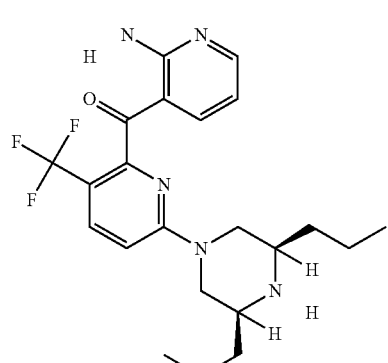
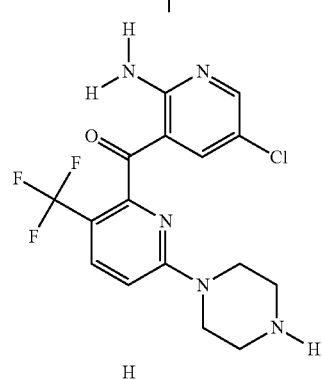
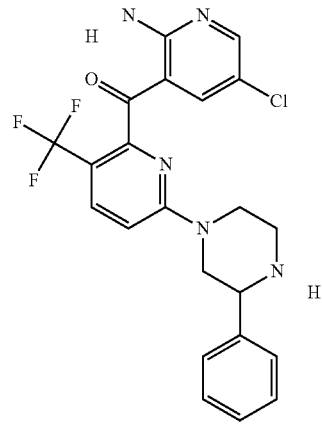
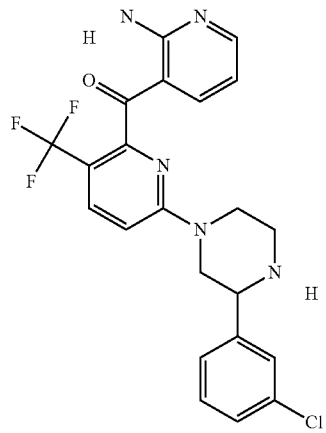

-continued
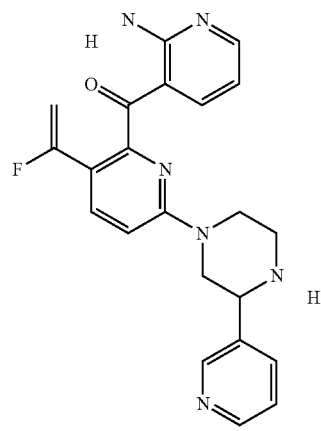
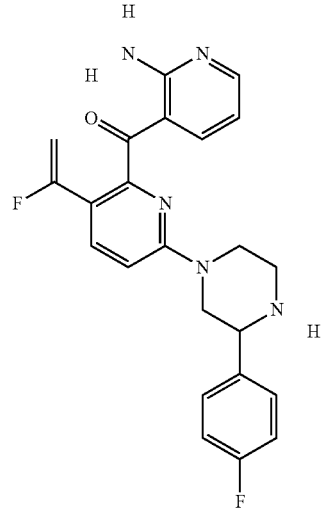
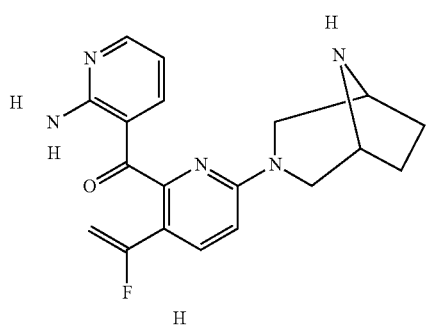
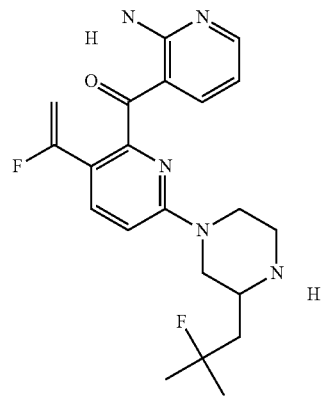
-continued
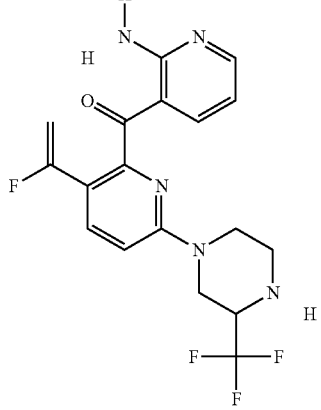
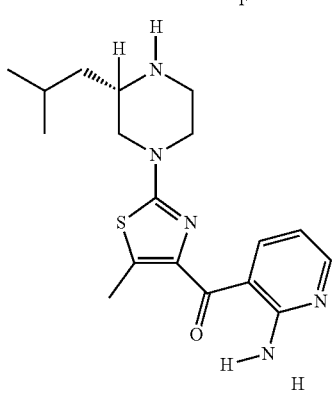
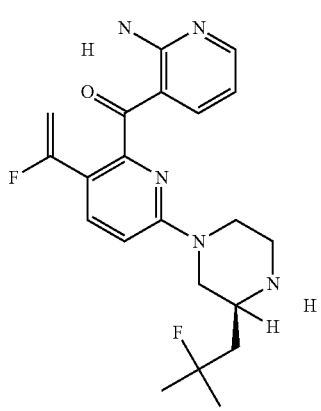
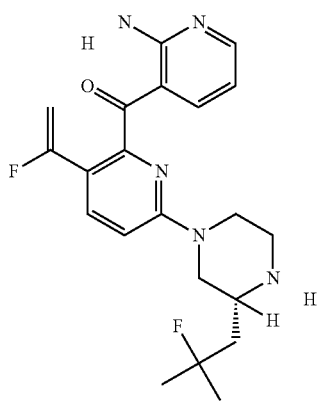

69
-continued
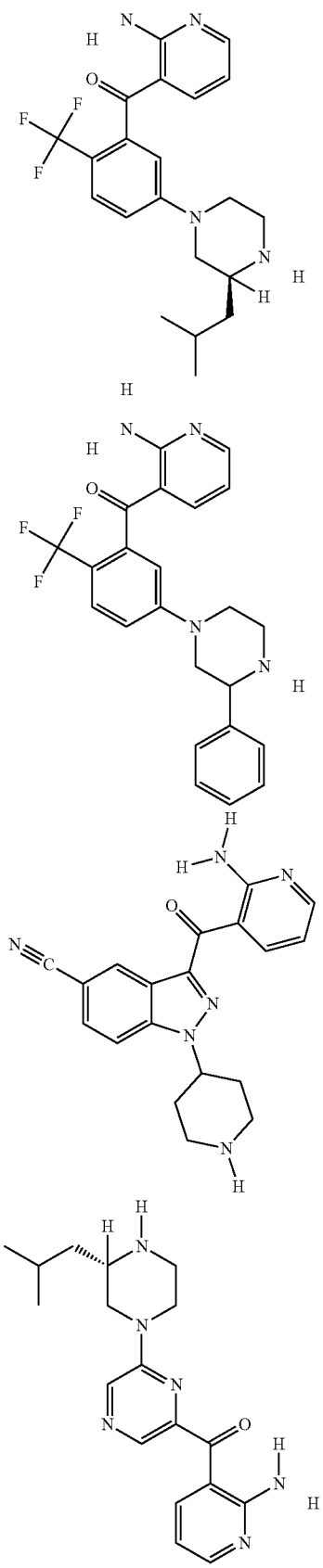
70
-continued
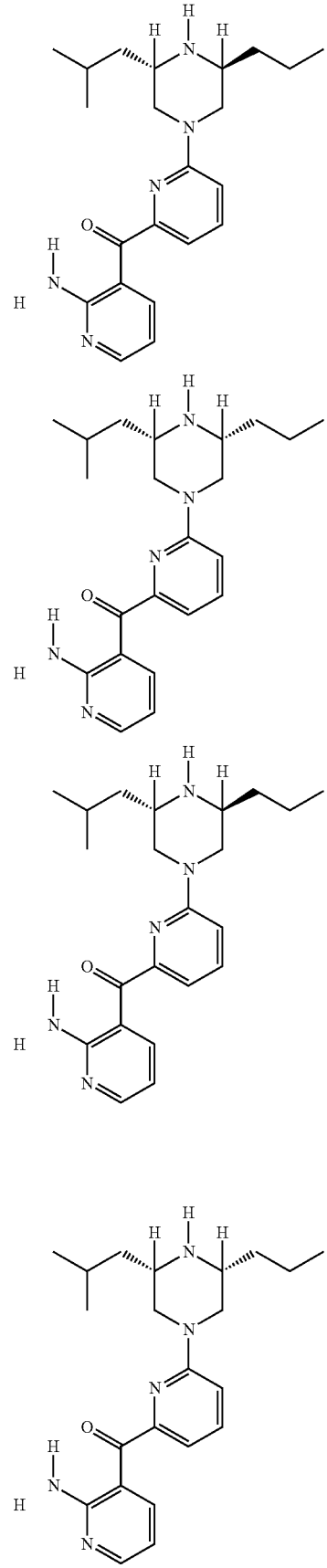

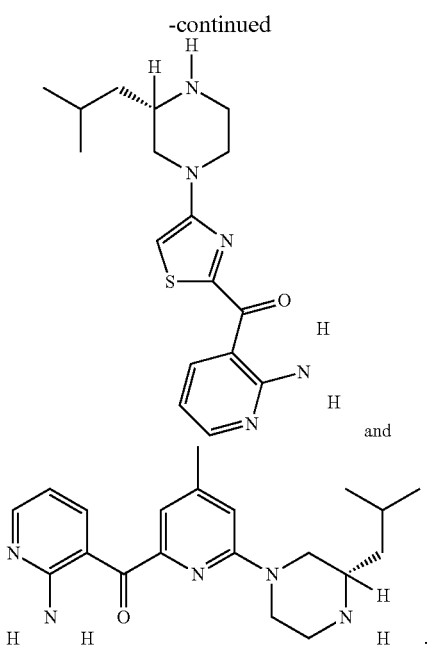

and

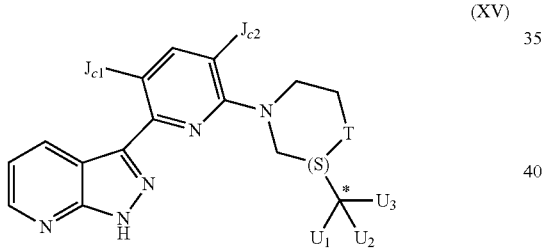

The present invention also contemplates pyrazolopyridine compounds as described for example Jimenez et al. in US Publication 2013/0053395, which is incorporated herein by reference in its entirety, Illustrative derivatives of this type include compounds according to formula (XV):

(XV)

or a pharmaceutically acceptable salt thereof, wherein:

T is —NH— or absent;

each $J_{c1}$ and $J_{c2}$ is independently —CN, —F, —Cl, —OR, —CH$_2$OR, or —CF$_3$;

each $U_1$, $U_2$, and $U_3$ is independently —H, Z, or $J_b$ wherein no more than one of $U_1$, $U_2$, and $U_3$ is —H; or two of $U_1$, $U_2$, and $U_3$ join together to form a $C_{1-6}$ cycloalkyl ring having 0-1 heteroatoms optionally and independently substituted with one or more $J_e$;

Z is Y2-Q2;

Y2 is absent or $C_{1-6}$ alkyl optionally and independently substituted with one or more $J_d$.

Q2 is absent or $C_{3-8}$ cycloalkyl having 0-1 heteroatoms optionally and independently substituted with one or more $J_e$, wherein Y2 and Q2 are not both absent;

each $J_b$ is independently —F, —OR, —CN, —CF$_3$, —N(R)$_2$, —C(O)N(R)$_2$, $C_{1-6}$ alkyl optionally and independently substituted with one or more $J_a$;

each $J_a$ is independently —F, —OR, —N(R)$_2$, or —C(O)N(R)$_2$;

each $J_d$ is independently —OR, —CN, —C(O)N(R)$_2$, —N(R)$_2$ or F;

each $J_e$ is independently $C_{1-6}$ alkyl, —OR, —N(R)$_2$, —CF$_3$, or F; and each R is —H or $C_{1-6}$ alkyl.

In some embodiments there is an achiral center at the carbon indicated by * Non-limiting examples of compounds according to formula (XV) include

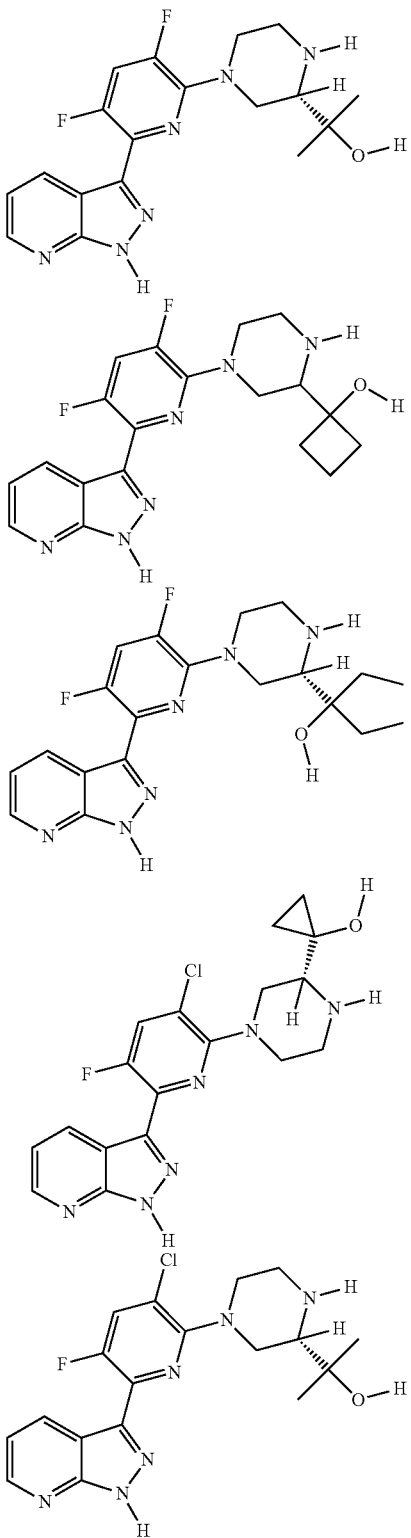

-continued

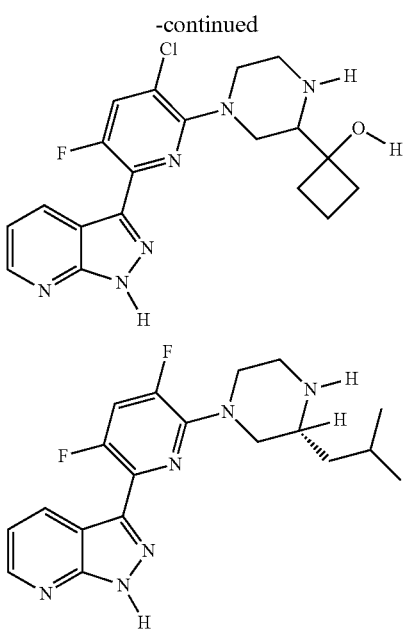

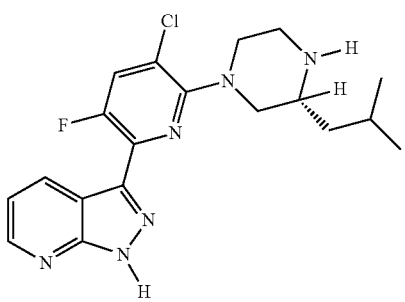

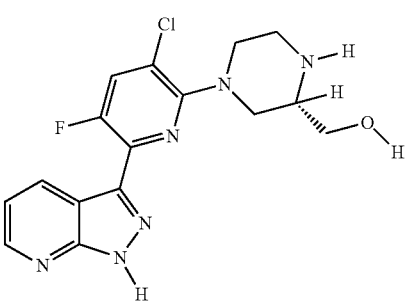

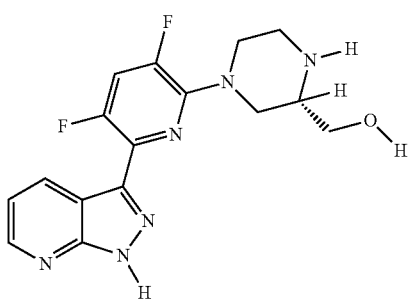

and

-continued

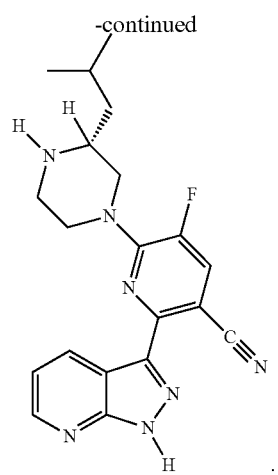

In still other embodiments, small molecule PKC-θ inhibitors are selected from pyrazolopyridine compounds as described for example by Boyall et al. in US Publication No. 2012/0071494, which is incorporated herein by reference in its entirety. Non-limiting compounds of this type are represented by formula (XVa):

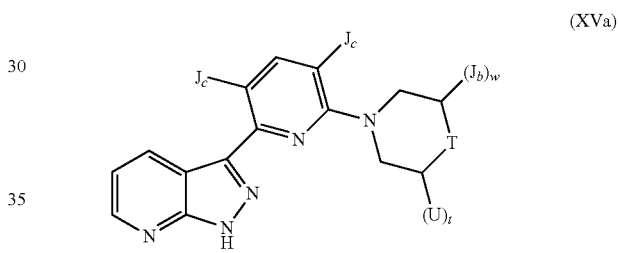

(XVa)

or a pharmaceutically acceptable salt thereof,
wherein:
t is 0, 1, or 2;
w is 0 or 1;
each $J_c$ is independently —CN, —F, —Cl, —OR, —CH$_2$OR, or —CF$_3$;
U is Z or $J_b$;
Z is Y2-Q2;
Y2 is absent or $C_{1-6}$ alkyl optionally and independently substituted with one or more $J_d$;
Q2 is absent or $C_{3-8}$ cycloalkyl having 0-1 heteroatoms optionally and independently substituted with one or more $J_e$, wherein Y2 and Q2 are not both absent;
each $J_b$ is independently —F, —OR, —CN, —CF$_3$, —N(R)$_2$, —C(O)N(R)$_2$, $C_{1-6}$ alkyl optionally and independently substituted with one or more $J_a$;
each $J_a$ is independently —F, —OR, —N(R)$_2$, or —C(O)N(R)$_2$;
each $J_d$ is independently —OR, —CN, —C(O)N(R)$_2$, —N(R)$_2$ or F;
each $J_e$ is independently —OR, —CF$_3$, —N(R)$_2$, or F;
T is —CH$_2$—, —CH(J$_b$)-, —C(J$_b$)$_2$-, —NH— or —N(J$_b$)-; and
each R is —H or $C_{1-6}$ alkyl.

In specific embodiments, compounds according to formula XVa are represented by formula XVa1, as disclosed for example by Jimenez et al. (2013, *J. Med. Chem.* 56 1799-180), which is incorporated herein by reference in its entirety:

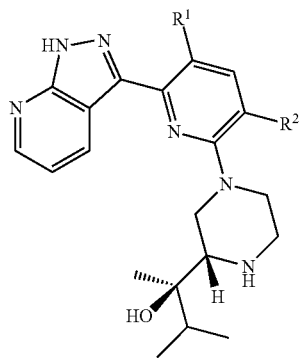

(XVa1)

wherein:
R¹ is independently F, Cl or CF₃; and
R² is independently H, F, Cl, OH, CN or CH₂OH.

In specific embodiments, the pyrazolopyridine compound is represented by formula (XVa2):

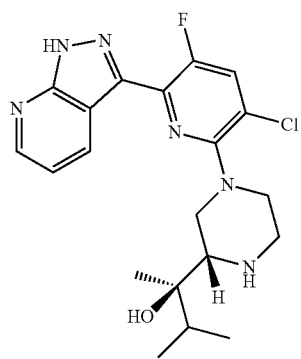

(XVa2)

This compound is designated in Jimenez et al. (2013, *J. Med. Chem.* 56 1799-180) as (R)-2-(S)-4-(3-chloro-5-fluoro-6-(1H-pyrazolo[3,4-b]pyridin-3-yl)pyridin-2-yl)piperazin-2-yl)-3-methylbutan-2-ol or Compound 27 (also referred to herein as "C27").

In still other embodiments, small molecule PKC-θ inhibitors are selected from tri-cyclic pyrazolopyridine compounds as described for example by Brenchley et al. in US Publication No. 2012/0184534, which is incorporated herein by reference in its entirety. Non-limiting compounds of this type are represented by formula (XVI):

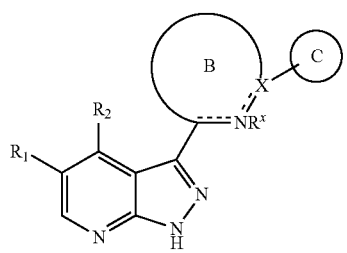

(XVI)

or a pharmaceutically acceptable salt thereof,
wherein:
$R_1$ is —H, halogen, —OR', —N(R')₂, —C(O)OR', —C(O)N(R')₂, —NR'C(O)R', NR'C(O)OR', —CN, —NO₂, $C_{1-10}$ aliphatic optionally and independently substituted with one or more $J_a$, or $C_{3-8}$ cycloaliphatic optionally and independently substituted with one or more $J_b$.

$R_2$ is —H, halogen, —CN, —NO₂, —OR', —N(R')₂, —C(O)OR', —C(O)N(R')₂, —NR'C(O)R', —NR'C(O)OR', $C_{1-10}$ aliphatic optionally and independently substituted with one or more $J_a$, or $C_{3-8}$ cycloaliphatic optionally and independently substituted with one or more $J_b$.

X is —C— or —N—.

$R^x$ is absent or —H.

Ring B is a 5-membered monocyclic heteroaromatic ring optionally fused to an aromatic or non-aromatic ring; and ring B is optionally substituted with one Y and independently further optionally and independently substituted with one or more $J_c$.

Y is —Y1-Q1.

Y1 is absent, or $C_{1-10}$ aliphatic, wherein up to three methylene units of Y1 are optionally and independently replaced with G' wherein G' is —O—, —C(O)—, —N(R')—, or —S(O)$_p$—; and Y1 is optionally and independently substituted with one or more $J_d$.

Q1 is absent, or a $C_{3-8}$ membered saturated, partially unsaturated, or fully unsaturated monocyclic ring having 0-3 heteroatoms independently selected from nitrogen, oxygen, and sulfur; and Q1 is optionally and independently substituted with one or more $J_b$; wherein Y1 and Q1 are not both absent.

Ring C is a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur; and ring C is optionally substituted with one Z and independently further optionally and independently substituted with one or more $J_b$.

Z is —Y2-Q2.

Y2 is absent, or $C_{1-10}$ aliphatic, wherein up to three methylene units of Y2 are optionally and independently replaced with G' wherein G' is —O—, —C(O)—, —N(R')—, or —S(O)$_p$—; and Y2 is optionally and independently substituted with one or more $J_d$.

Q2 is absent, $C_{3-8}$ membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur; and Q2 is optionally and independently substituted with one or more $J_e$; wherein Y2 and Q2 are not both absent.

Each R' is independently —H, or C1-6 alkyl optionally and independently substituted with one or more $J_a$.

Each $J_a$ is independently halogen, —OR, —N(R)₂, —C(O)OR, —C(O)N(R)₂, —NRC(O)R, —NRC(O)OR, —CN, —NO₂, or oxo.

Each $J_b$ is independently halogen, —OR, —N(R)₂, —C(O)OR, —C(O)N(R)₂, —NRC(O)R, —NRC(O)OR, —CN, —NO₂, oxo, or C1-C6 alkyl optionally and independently substituted with $J_a$.

Each $J_c$ is independently halogen, —OR', —N(R')₂, —C(O)OR', —C(O)N(R')₂, —NR'C(O)R', —NR'C(O)OR', —CN, —NO₂, or C1-C10 aliphatic optionally and independently substituted with one or more $J_a$, or C3-C8 cycloaliphatic optionally and independently substituted with one or more $J_b$.

Each $J_d$ is independently halogen, —CN, or —NO$_2$. Each $J_e$ is independently halogen, —CN, —NO$_2$, oxo, C1-10 aliphatic, wherein up to three methylene units are optionally and independently replaced with G' wherein G' is —O—, —C(O)—, —N(R')—, or —S(O)$_p$— and the aliphatic group is optionally and independently substituted with one or more $J_d$, or $J_e$ is C3-s cycloaliphatic optionally and independently substituted with one or more $J_b$.

Each R is independently —H or C$_{1-6}$ alkyl.

Each p is independently 0, 1, or 2.

Representative examples of compounds according to formula (XVI) include:

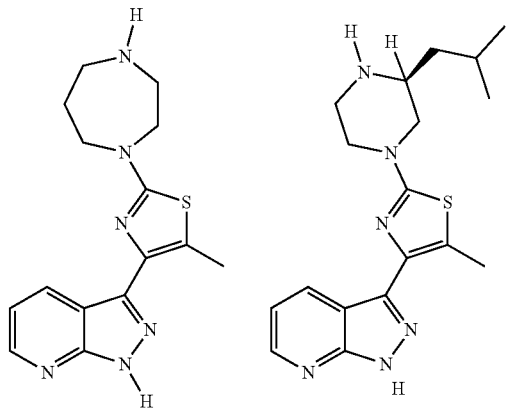
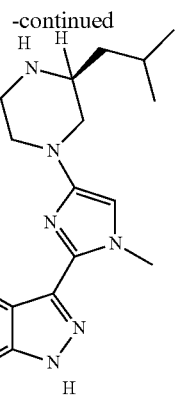
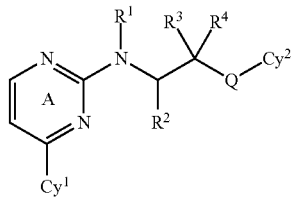

and

Still other embodiments of small molecule PKC-θ inhibitors include 2-(amino-substituted)-4-aryl pyrimidine compounds as described for example by Fleming et al. in US Publication No. 2011/0071134, which is incorporated herein by reference in its entirety. Representative compounds of this type are represented by formula (XVII):

(XVII)

or a pharmaceutically acceptable salt thereof, wherein:

$R^1$ and $R^2$ are each independently H, C$_{1-3}$ alkyl or C$_{3-5}$cycloalkyl;

$R^3$ is H or F;

$R^4$ is H, F, —OR$^a$, —C(O)R$^a$, —C(O)OR$^a$ or —N(R$^a$)$_2$; or $R^3$ and $R^4$ together with the carbon atom to which they are attached form a carbonyl group; wherein each occurrence of $R^a$ is independently H, C$_{1-3}$alkyl or C$_{3-5}$cycloalkyl;

Ring A is optionally substituted with 1 or 2 independent occurrences of $R^5$, wherein each $R^5$ is independently selected from halo, C$_{1-4}$ aliphatic, —CN, —OR$^b$, —SR$^C$, —N(R$^b$)$_2$, —NR$^b$C(O)R$^b$, —NR$^b$C(O)N(R$^b$)$_2$, —NR$^b$CO$_2$R$^C$, —CO$_2$R$^b$, —C(O)R$^b$, —C(O)N(R$^b$)$_2$, —OC(O)N(R$^b$)$_2$, —S(O)$_2$R$^C$, —SO$_2$N(R$^b$)$_2$, —S(O)R$^C$, —NR$^b$SO$_2$N(R$^b$)$_2$, —NR$^b$SO$_2$R$^C$, or C$_{1-4}$aliphatic optionally substituted with halo, —CN, —OR$^b$, —SR$^C$, —N(R$^b$)$_2$, —NR$^b$C(O)R$^b$, —NR$^b$C(O)N(R$^b$)$_2$, —NR$^b$CO$_2$R$^C$, —CO$_2$R$^b$, —C(O)R$^b$, —C(O)N(R$^b$)$_2$, —OC(O)N(R$^b$)$_2$, —S(O)$_2$R$^C$, —SO$_2$N(R$^b$)$_2$, —S(O)R$^C$, —NR$^b$SO$_2$N(R$^b$)$_2$, or —NR$^b$SO$_2$R$^C$, wherein each occurrence of R$_b$ is independently H or C$_{1-4}$aliphatic; or two R$^b$ on the same nitrogen atom taken together with the nitrogen atom form a 5-8 membered aromatic or non-aromatic ring having in addition to the nitrogen atom 0-2 ring heteroatoms selected from N, O or S; and each occurrence of R$^C$ is independently C$_{1-4}$ aliphatic;

Cy$^1$ is selected from: a) a 6-membered aryl or heteroaryl ring substituted by one occurrence of W at the meta or para position of the ring; or b) a 5-membered heteroaryl ring substituted by one occurrence of W;

wherein Cy¹ is optionally further substituted by one to three independent occurrences of $R^6$, wherein each occurrence of $R^6$ is independently selected from -halo, $C_{1-8}$aliphatic, —CN, —OR$^b$, —SR$^D$, —N(R$^E$)$_2$, —NR$^E$C(O)R$^b$, —NR$^E$C(O)N(R$^E$)$_2$, —NR$^E$CO$_2$R$^D$, —CO$_2$R$^b$, —C(O)R$^b$, —C(O)N(R$^E$)$_2$, —OC(O)N(R$^E$)$_2$, —S(O)$_2$R$^D$, —SO$_2$N(R$^E$)$_2$, —S(O)R$^D$, —NR$^E$SO$_2$N(R$^E$)$_2$, —NR$^E$SO$_2$R$^D$, —C(=NH)—N(R$^E$)$_2$, or $C_{1-8}$ aliphatic optionally substituted with halo, —CN, —OR$^b$, —SR$^D$, —N(R$^E$)$_2$, —NR$^E$C(O)R$^b$, —NR$^E$C(O)N(R$^E$)$_2$, —NR$^E$CO$_2$R$^D$, —CO$_2$R$^b$, —C(O)R$^b$, —C(O)N(R$^E$)$_2$, —OC(O)N(R$^E$)$_2$, —S(O)$_2$R$^D$, —SO$_2$N(R$^E$)$_2$, —S(O)R$^D$, —NR$^E$SO$_2$N(R$^E$)$_2$, —NR$^E$SO$_2$R$^D$, or —C(=NH)—N(R$^E$)$_2$, wherein each occurrence of $R^D$ is $C_{1-6}$ aliphatic and each occurrence of $R^E$ is independently H, $C_{1-6}$ aliphatic, —C(=O)R$^b$, —C(O)OR$^b$ or —SO$_2$R$^b$; or two $R^E$ on the same nitrogen atom taken together with the nitrogen atom form a 5-8 membered aromatic or non-aromatic ring having in addition to the nitrogen atom 0-2 ring heteroatoms selected from N, O or S;

W is —R$^8$, V—R$^8$, $L_1$-R$^7$, V-$L_1$-R$^7$, $L_1$-V—R$^8$, or $L_1$-V-$L_2$-R$^7$; wherein: $L_1$ and $L_2$ are each independently an optionally substituted $C_{1-6}$ alkylene chain; V is —CH$_2$—, —O—, —S—, —S(O)—, —S(O)$_2$—, —C(O)—, —CO$_2$—, —NR$^E$—NR$^E$C(O)—, —NR$^E$CO$_2$—, —NR$^E$SO$_2$—, —C(O)N(R$^b$), —SO$_2$N(R$^b$)—, —NR$^E$C(O)N(R$^b$)— or —OC(O)—; $R^7$ is H, halo, —OH, —N(R$^F$)$_2$, —CN, —OR$^G$, —C(O)R$^G$, —CO$_2$H, —CO$_2$R$^G$, —SR$^G$, —S(O)R$^G$, —S(O)$_2$R$^G$, —N(R$^E$)C(O)R$^G$, —N(R$^E$)CO$_2$R$^G$, —N(R$^E$)SO$_2$R$^G$, —C(O)N(R$^F$)$_2$, —SO$_2$N(R$^F$)$_2$, —N(R$^E$)C(O)N(R$^F$)$_2$, —OC(O)R$^F$ or an optionally substituted group selected from $C_{1-10}$ aliphatic, $C_{6-10}$aryl, 3-14 membered heterocyclyl or 5-14 membered heteroaryl, wherein each occurrence of $R^F$ is independently H, $C_{1-6}$ aliphatic, $C_{6-10}$aryl, 3-14 membered heterocyclyl, 5-14 membered heteroaryl, —C(=O)R$^b$, C(O)OR$^b$ or —SO$_2$R$^b$; or two $R^F$ on the same nitrogen atom taken together with the nitrogen atom form an optionally substituted 5-8 membered aromatic or non-aromatic ring having in addition to the nitrogen atom 0-2 ring heteroatoms selected from N, O or S; and each occurrence of $R^G$ is $C_{1-6}$ aliphatic, $C_{6-10}$aryl, 3-14 membered heterocyclyl, or 5-14 membered heteroaryl; $R^8$ is an optionally substituted group selected from $C_{1-10}$ aliphatic, $C_{6-10}$ aryl, 3-14 membered heterocyclyl or 5-14 membered heteroaryl;

Q is a bond, CH$_2$ or C(=O);

Cy² is a $C_{6-10}$ aryl, a 5-10 membered heteroaryl, or a 5-10 membered heterocyclyl ring, wherein each ring is optionally substituted by one to three independent occurrences of $R^9$ and one occurrence of $R^{10}$, wherein each occurrence of $R^9$ is independently selected from $C_{1-4}$aliphatic, —N(R$^b$)$_2$, halo, NO$_2$, —CN, —OR$^b$, —C(O)R$^a$, —CO$_2$R$^a$, —SR$^C$, —S(O)R$^C$, —S(O)$_2$R$^C$, —OS(O)$_2$R$^C$, N(R$^b$)C(O)R$^a$, —N(R$^b$)CO$_2$R$^a$, —N(R$^b$)SO$_2$R$^a$, —C(O)N(R$^b$)$_2$, —SO$_2$N(R$^b$)$_2$, —N(R$^b$)C(O)N(R$^b$)$_2$, —OC(O)R$^a$, or $C_{1-4}$ aliphatic optionally substituted by —N(R$^b$)$_2$, halo, NO$_2$, —CN, —OR$^b$, —C(O)R$^a$, —CO$_2$R$^a$, —SR$^C$, —S(O)R$^C$, —OS(O)$_2$R$^C$, —S(O)$_2$R$^C$, —N(R$^b$)C(O)R$^a$, —N(R$^b$)CO$_2$R$^a$, —N(R$^b$)SO$_2$R$^a$, —C(O)N(R$^b$)$_2$, —SO$_2$N(R$^b$)$_2$, —N(R$^b$)C(O)N(R$^b$)$_2$, or —OC(O)R$^a$, and $R^{10}$ is selected from phenyl, or a 5-6 membered heterocyclyl or heteroaryl ring.

In certain embodiments, compounds of formula XVII are subject to one or more, or all of, the following limitations:

1) when Cy¹ is phenyl substituted in the meta position with W then:

a) when W is —OMe, $R^1$, $R^2$, $R^3$, and $R^4$ are each hydrogen, and Q is a bond, then when ring A is further substituted with $R^5$, $R^5$ is a group other than —CF$_3$ or —C(O)N(R$^b$)$_2$; and b) when W is —OMe, $R^1$, $R^2$, $R^3$, and $R^4$ are each hydrogen, and Q is —CH$_2$—, then Cy² is other than 1H-benzimidazol-1-yl;

2) when Cy¹ is phenyl substituted in the para position with W, and $R^1$, $R^2$, $R^3$, and $R^4$ are each hydrogen then:

a) when Q is a bond, W is other than: i) —CONH$_2$; ii) —CONHR$^8$, where $R^8$ is an optionally substituted group selected from phenyl, -alkylphenyl, alkyl, or -alkylheterocycle; iii) —CF$_3$; iv) —SO$_2$Me; v) —NH$_2$; vi) -tBu; vii) —CO$_2$H when Cy² is morpholine; viii) —O(phenyl) when Cy² is indole; and ix) —OMe;

b) when Q is —CH$_2$—, W is other than: i) —CONH$_2$, when Cy² is optionally substituted imidazole or benzimidazole; ii) —CONHR$^8$, where $R^8$ is an optionally substituted group selected from phenyl, -alkylphenyl, or -alkylheterocycle; iii) —CF$_3$; iv) —SO$_2$Me; v) —OH, where Cy² is a 5-10 membered heterocyclyl ring; vi) tBu, when Cy² is a 5-10 membered heterocyclyl ring; and vii) —OMe; and 3) when Cy¹ is a 5-membered heteroaryl ring then:

a) when Cy¹ is isoxazole, $R^1$, $R^2$, $R^3$, and $R^4$ are each hydrogen, Q is a bond, and W is p-fluoro-phenyl, then Cy² is a group other than pyridyl or N-pyrrolidinyl;

b) when Cy¹ is triazolyl, $R^1$, $R^2$, $R^3$, and $R^4$ are each hydrogen, Q is a bond, and W is —(CH$_2$)$_2$N(cyclopentyl)C(O)CH$_2$(naphthyl), then Cy² is a group other than N-piperidinyl;

c) when Cy¹ is imidazolyl, $R^1$, $R^2$, $R^3$, and $R^4$ are each hydrogen, Q is a bond, and W is meta-CF$_3$-phenyl, then $R^6$ is a group other than C(O)OCH$_2$CH$_3$; and d) when Cy¹ is imidazol-5-yl and W is para-fluoro-phenyl, then $R^6$ is a group other than cyclohexyl.

Non-limiting compounds of this type are represented by the following structures:

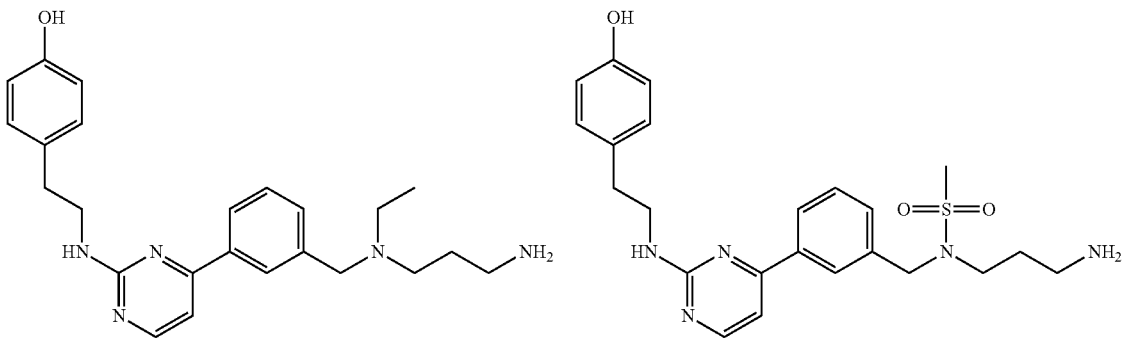

-continued
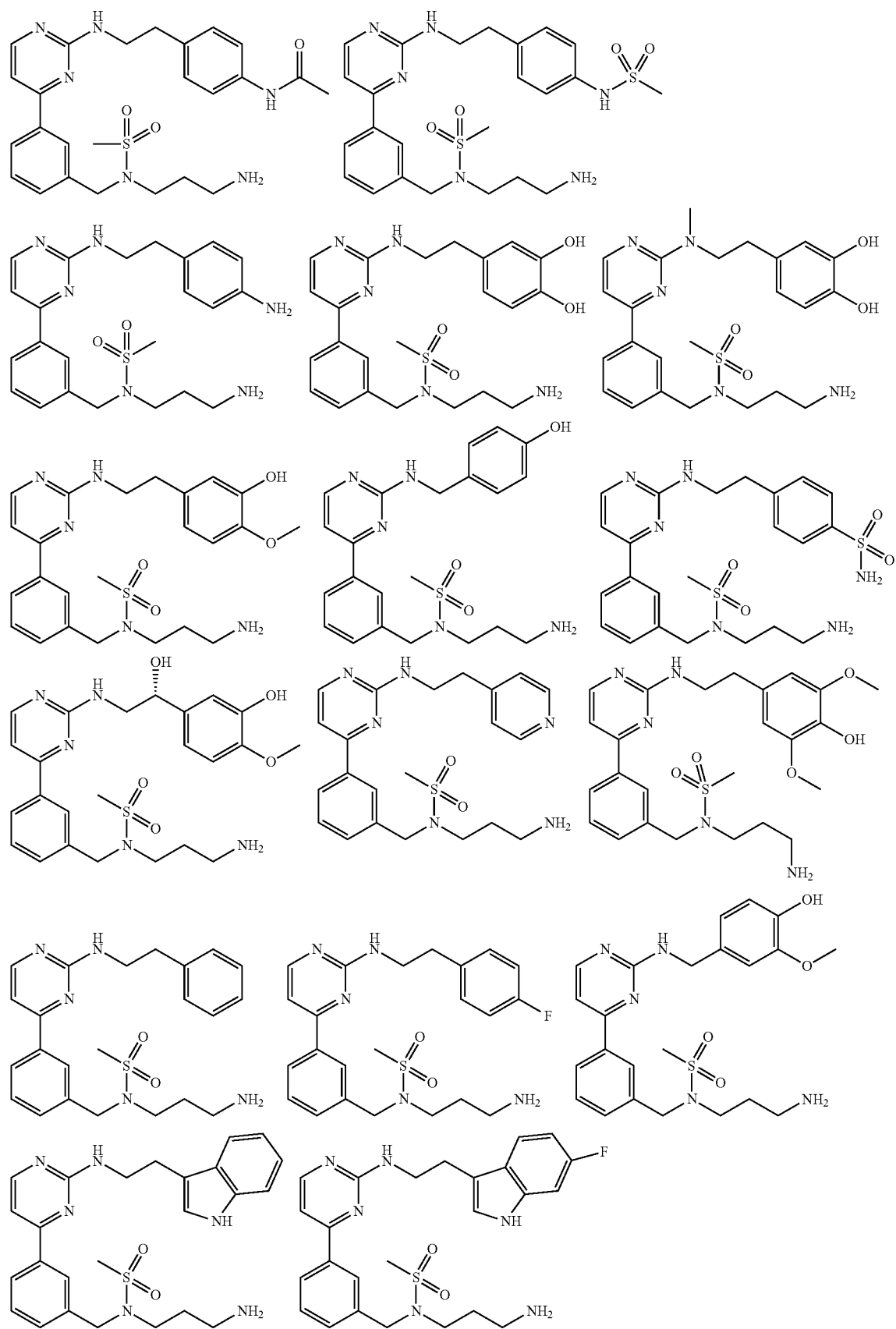

83                                              84
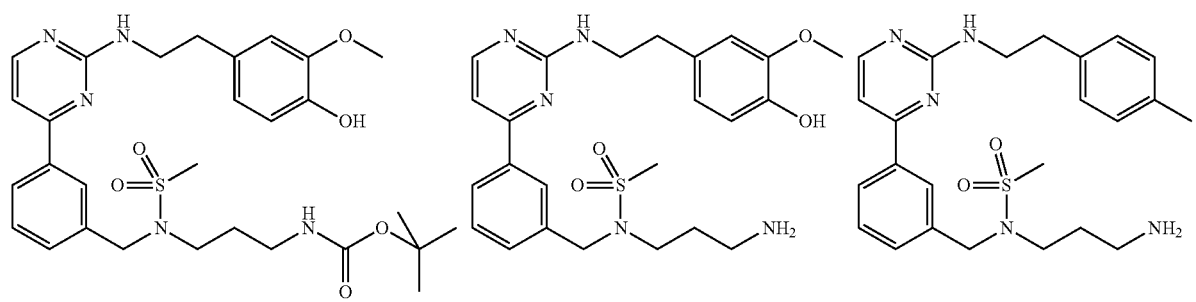
-continued
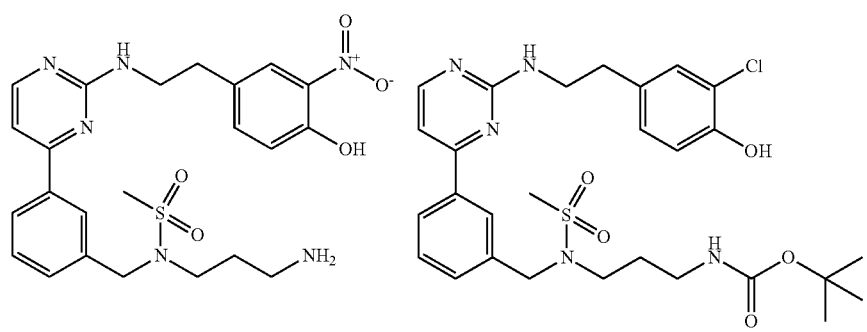
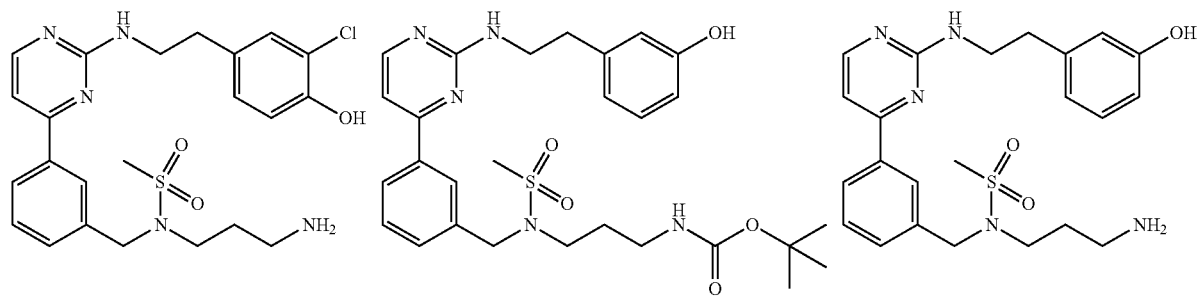
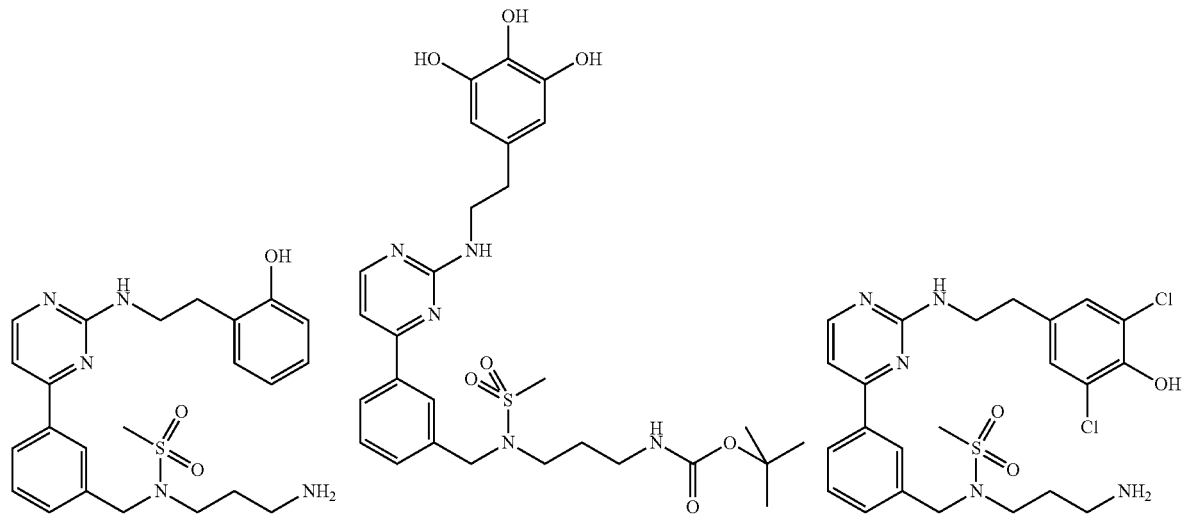

-continued
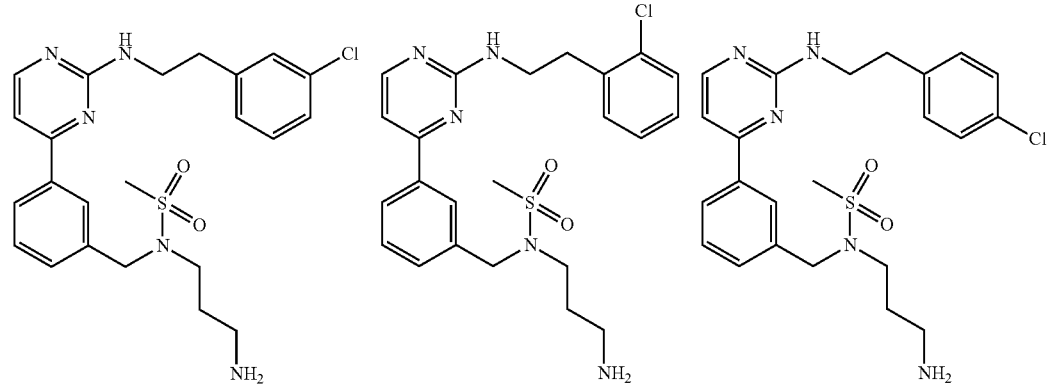
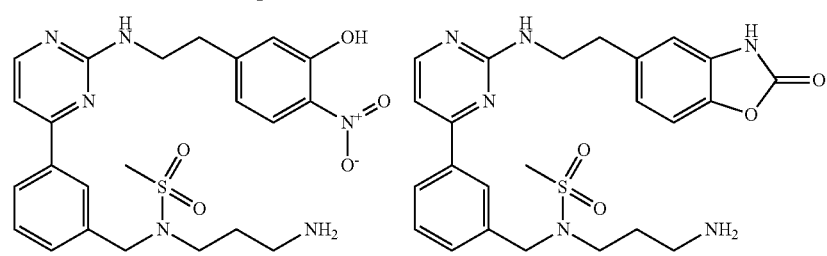
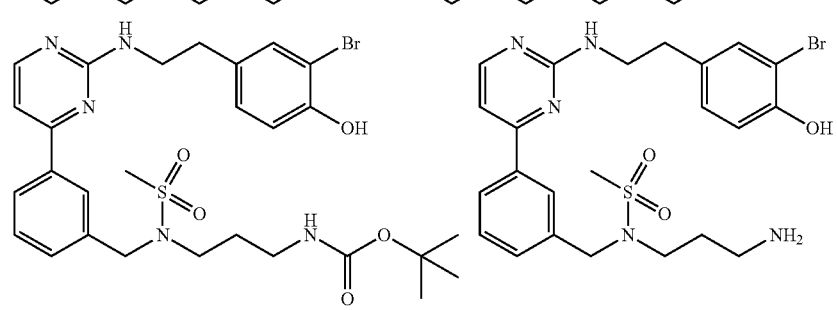
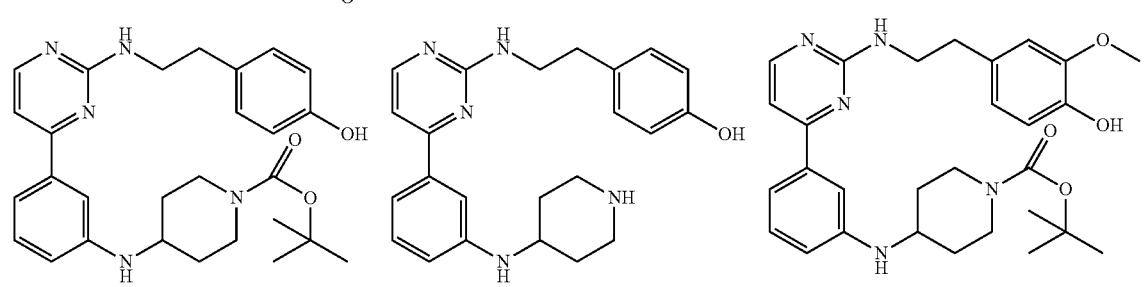
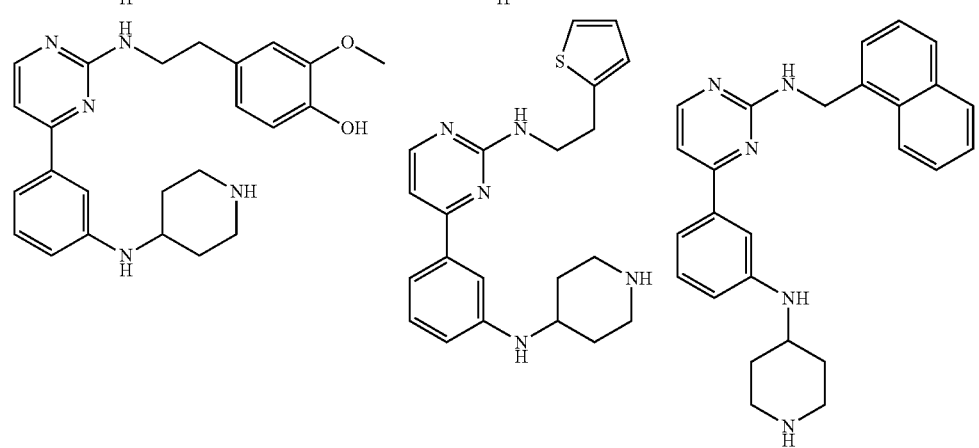

87 88
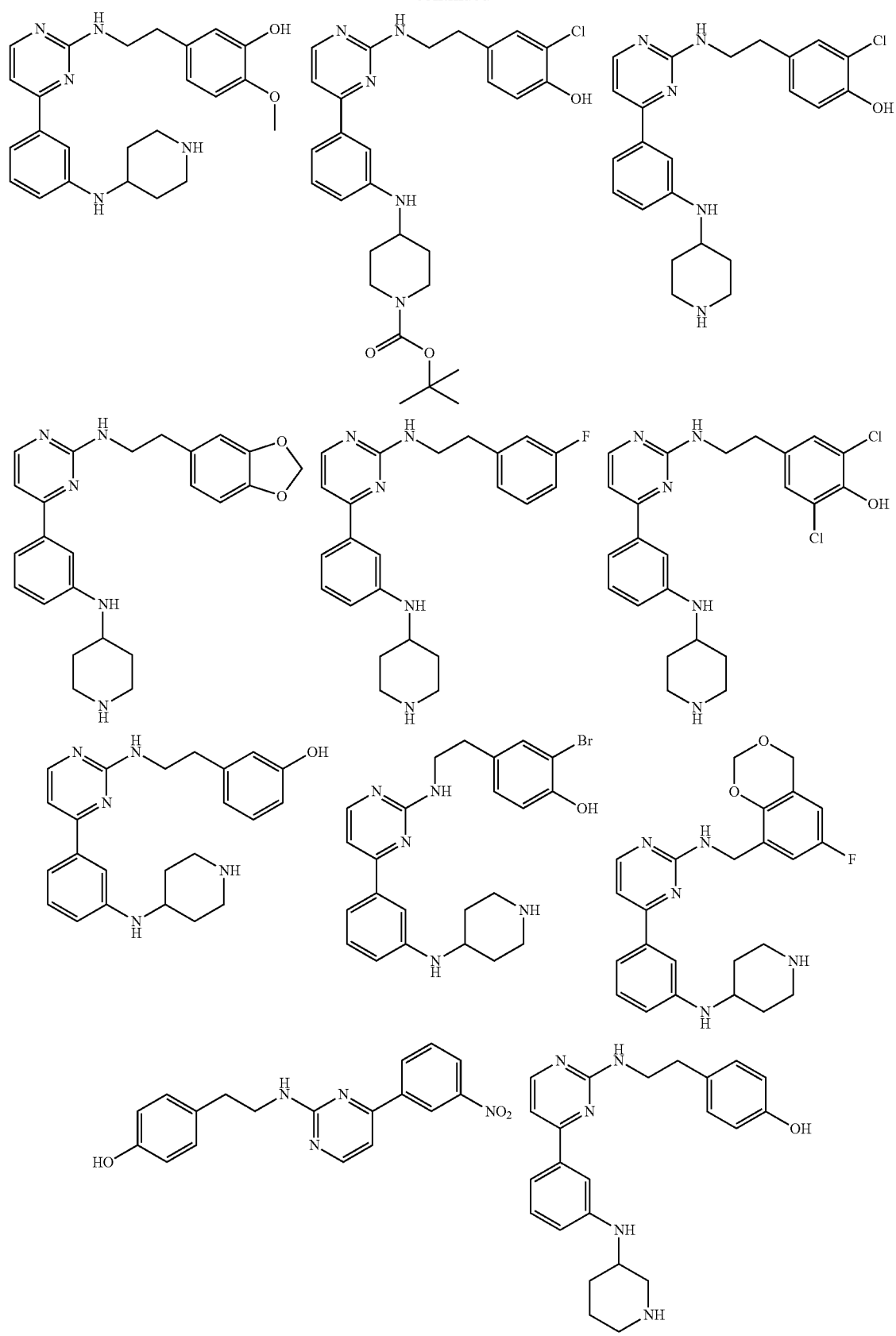
-continued

-continued
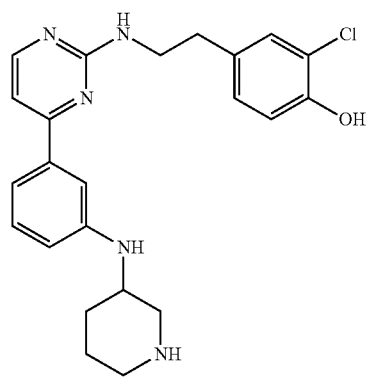
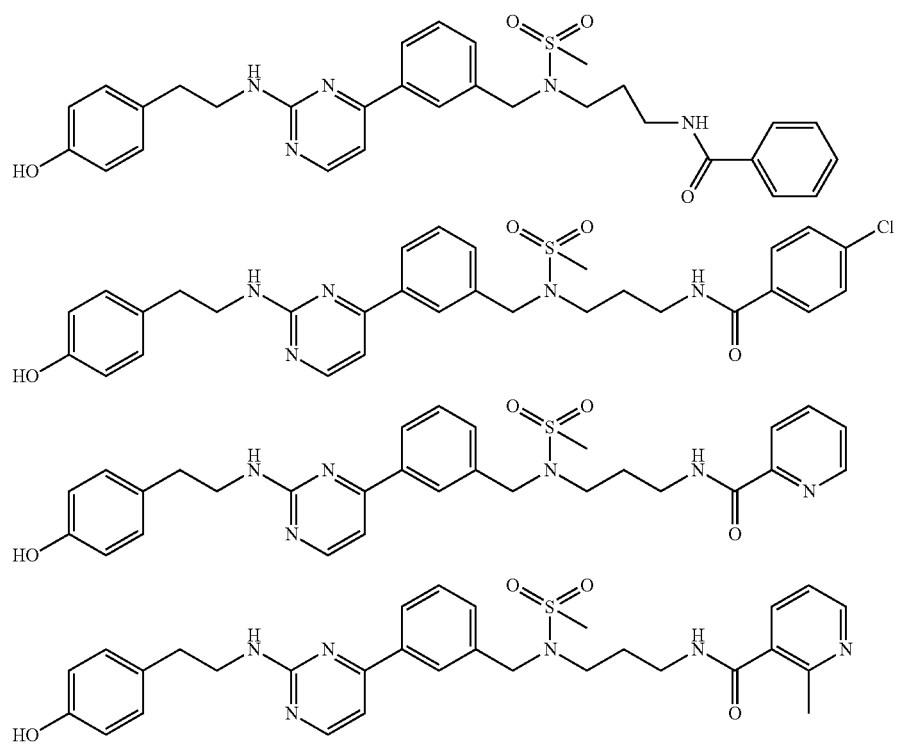
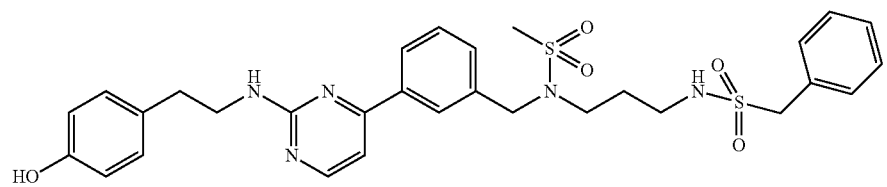
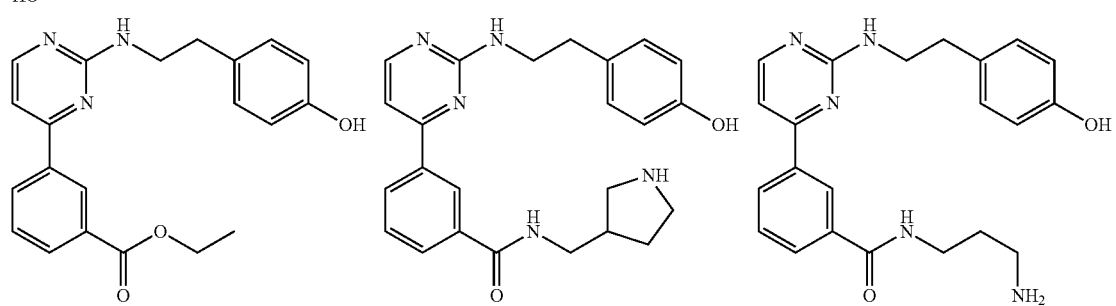

91 92
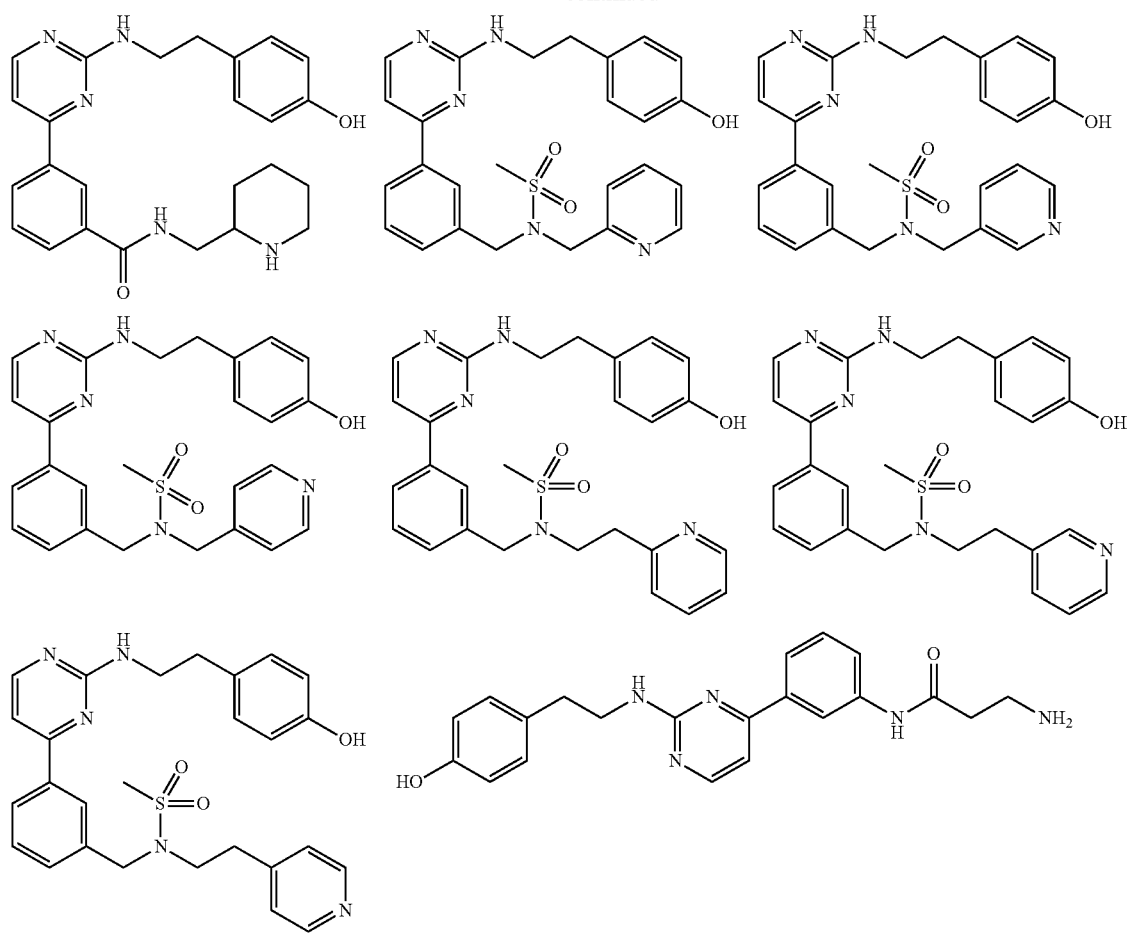
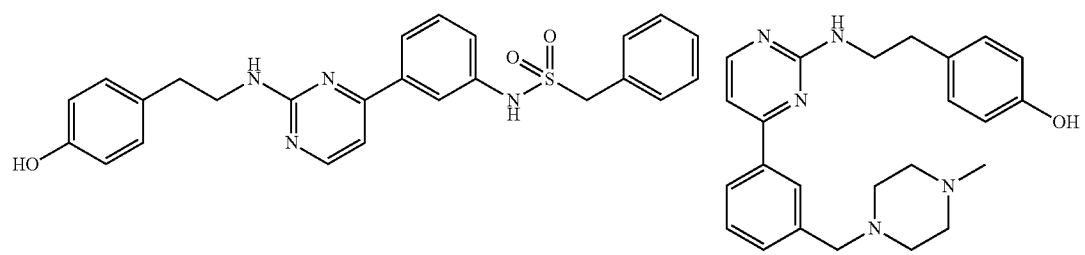
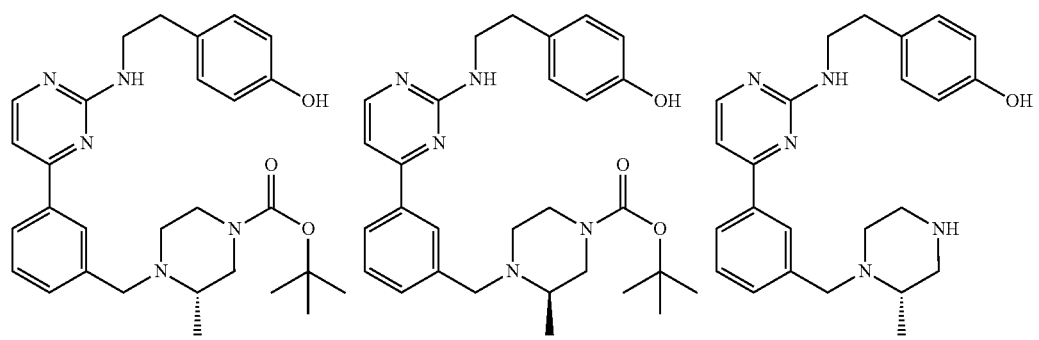

93
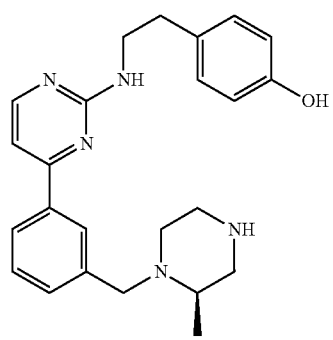
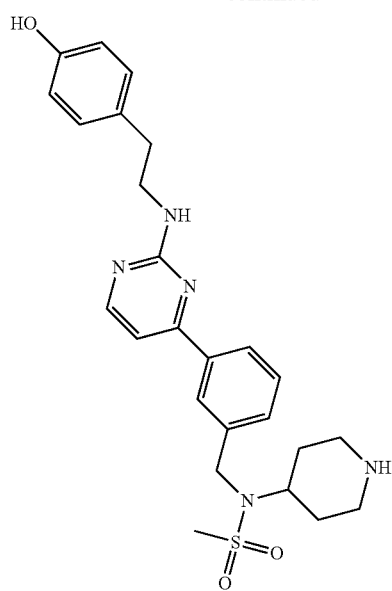
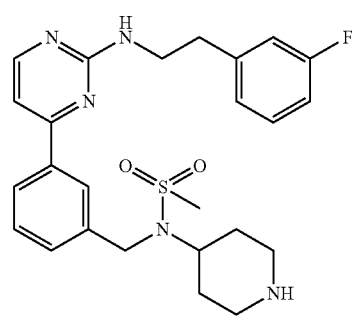
94
-continued
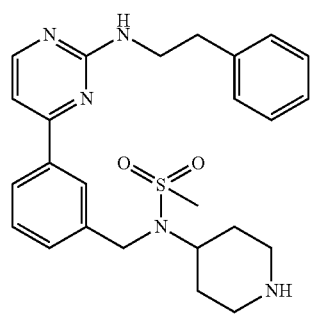
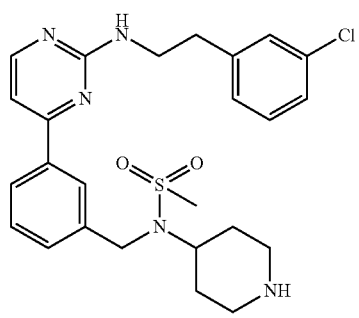
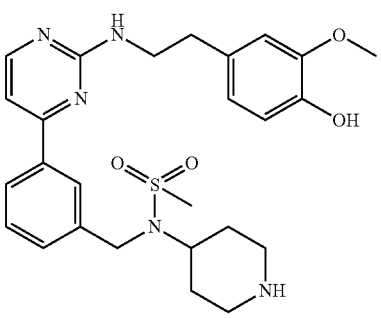
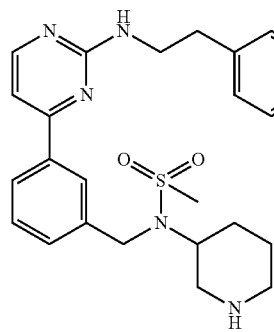
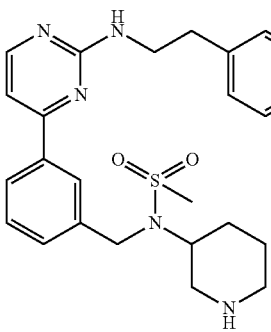
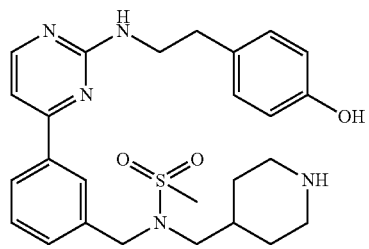
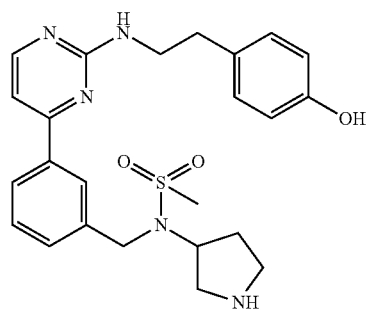
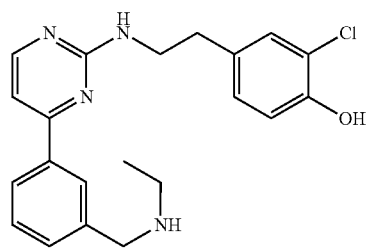
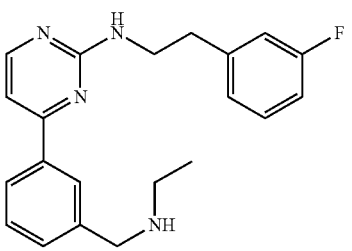

95
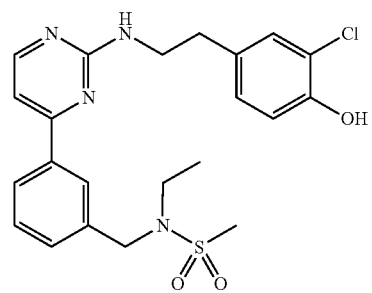 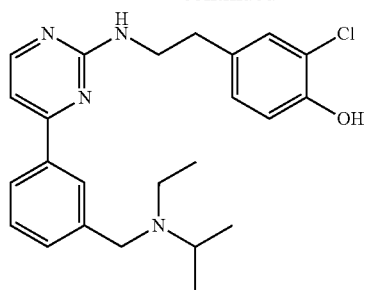
-continued
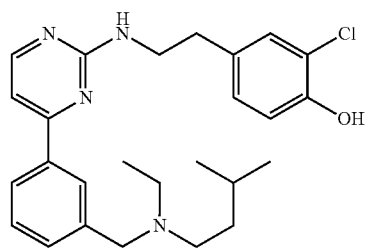
96
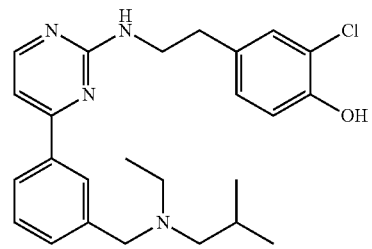 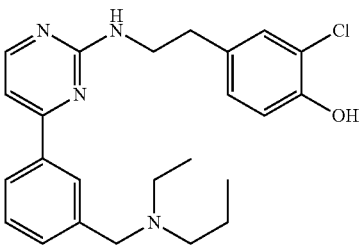 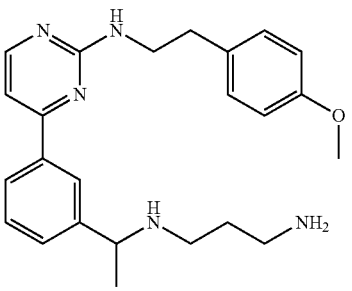
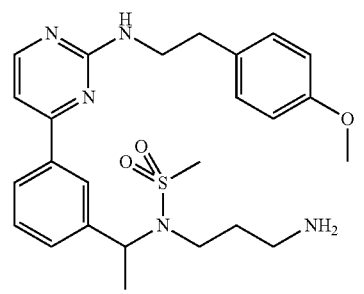 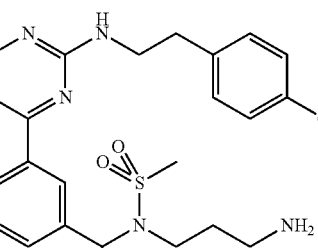 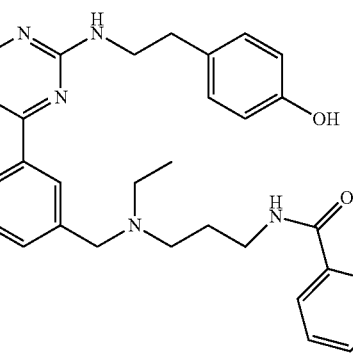
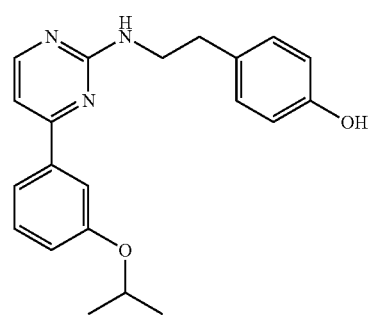 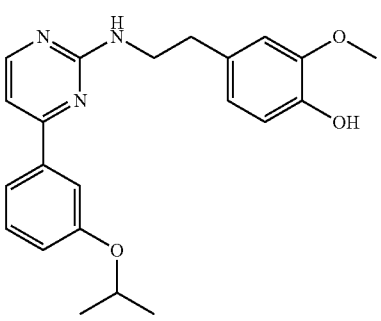 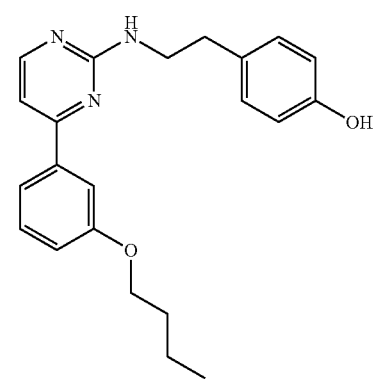
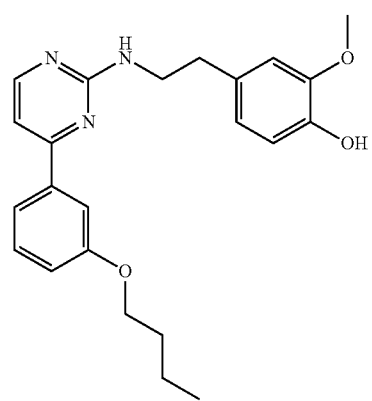 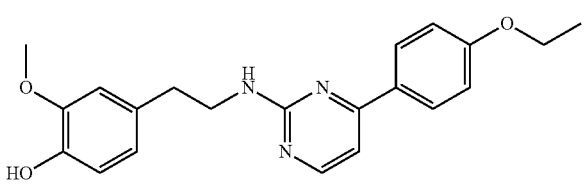

-continued
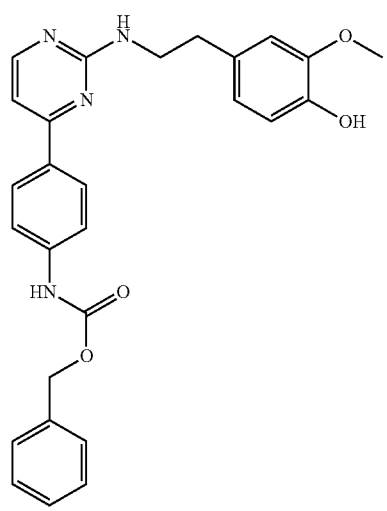
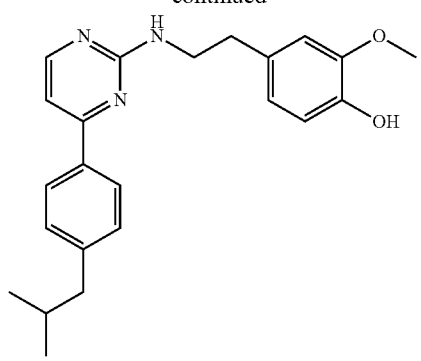
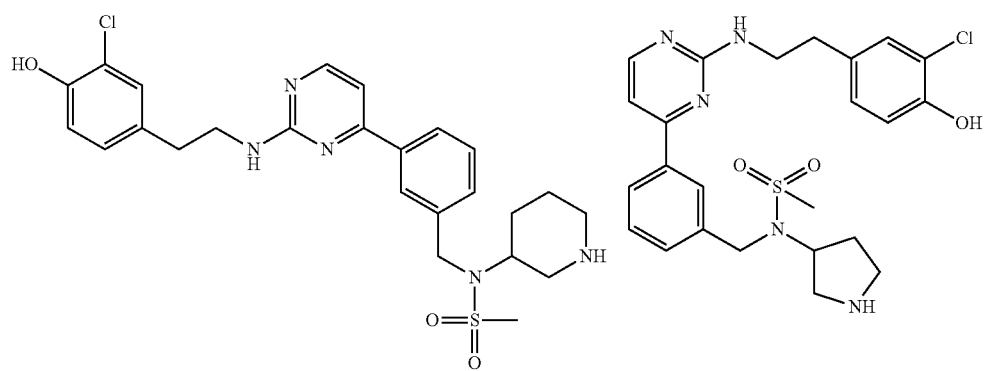
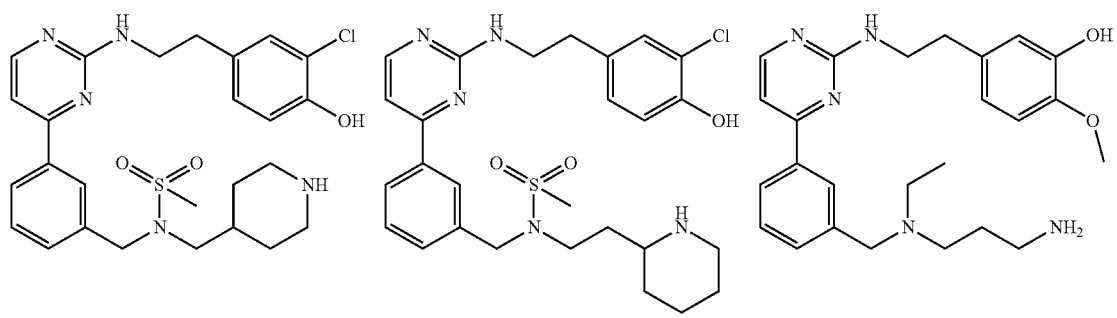
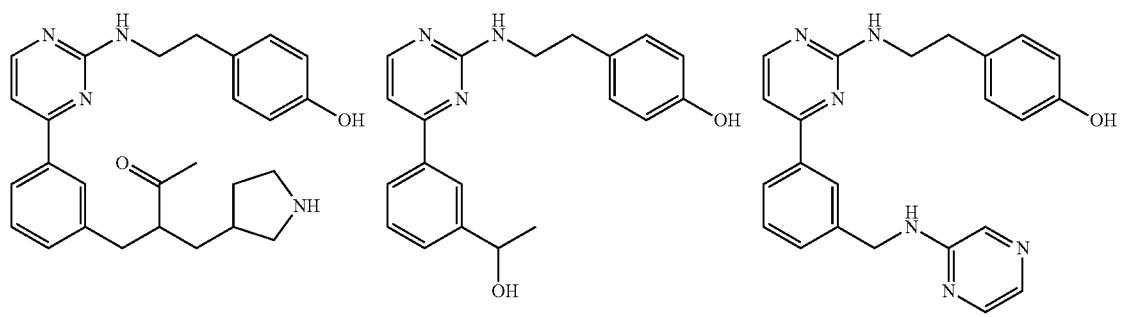

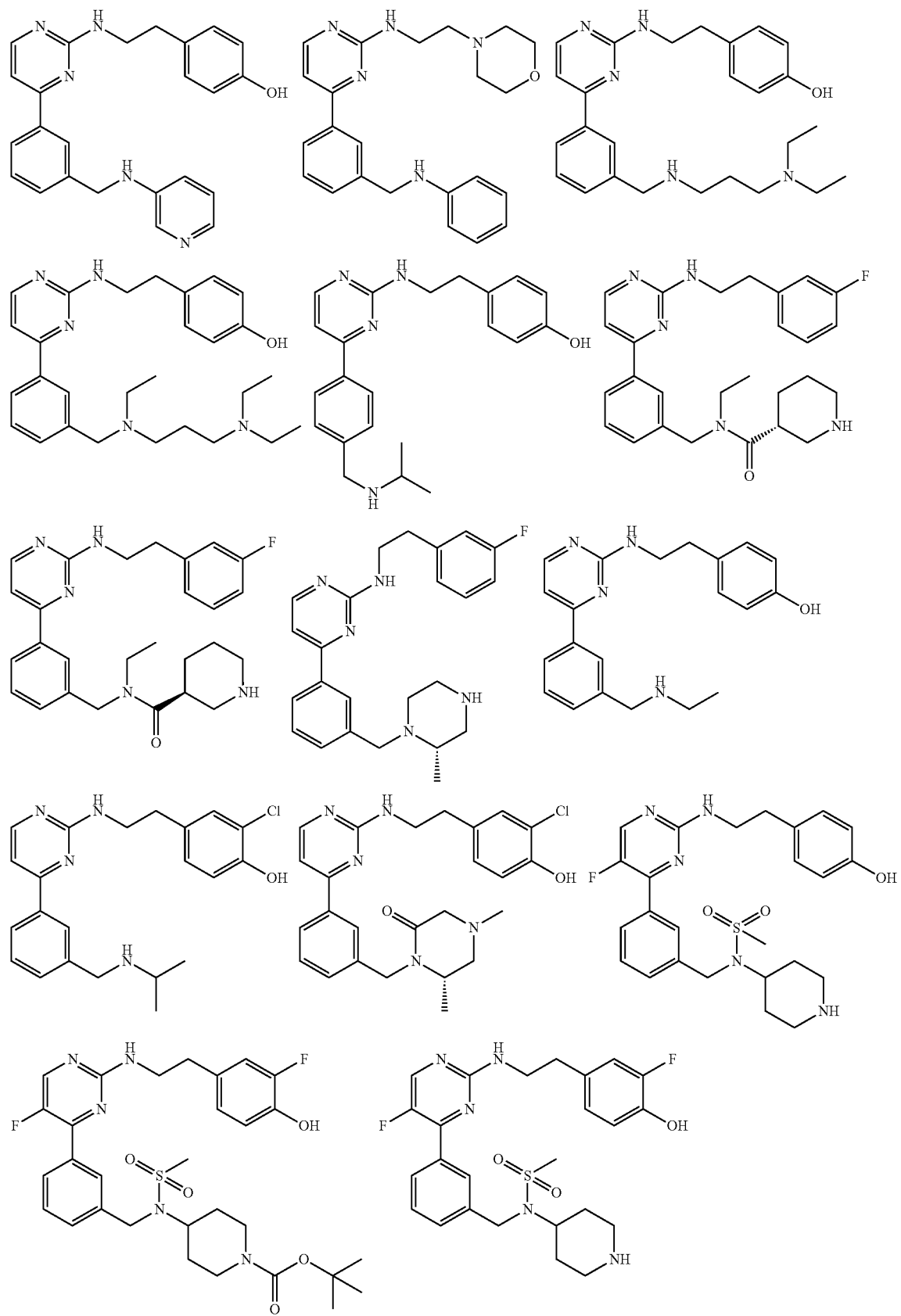

-continued
101
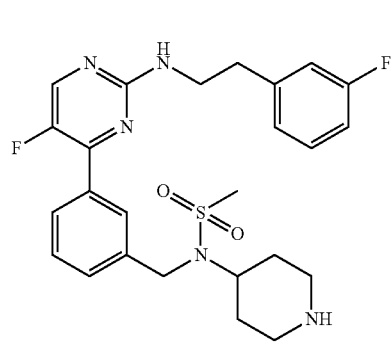
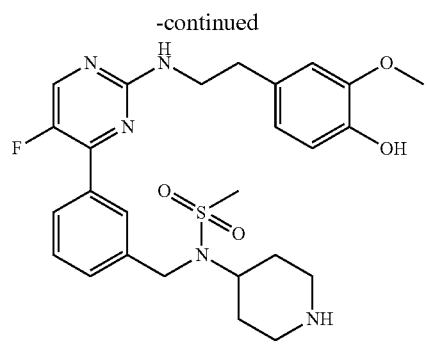
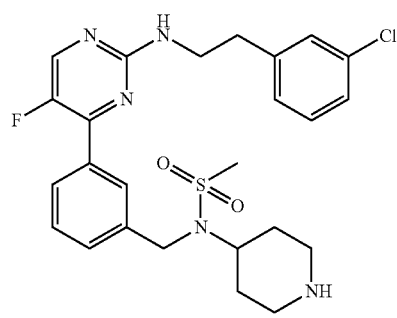
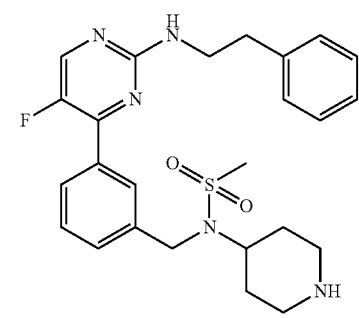
102
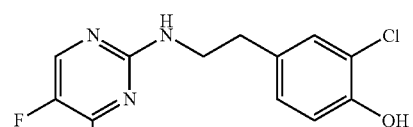
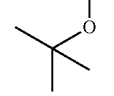
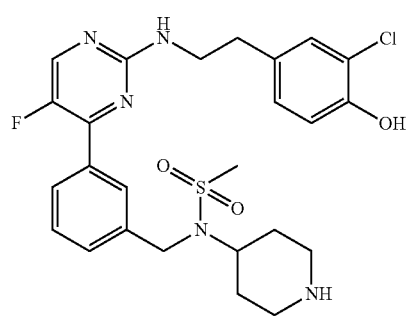
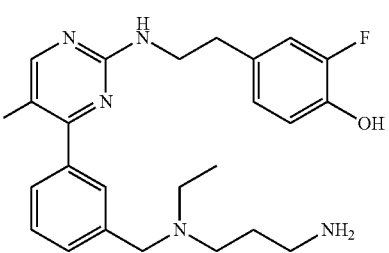
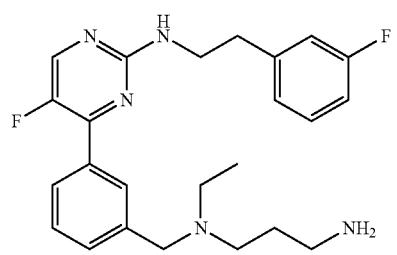
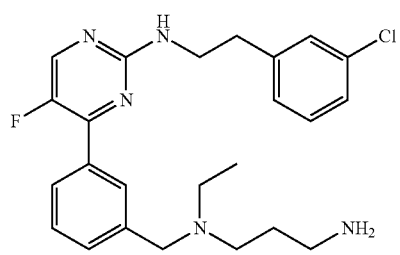
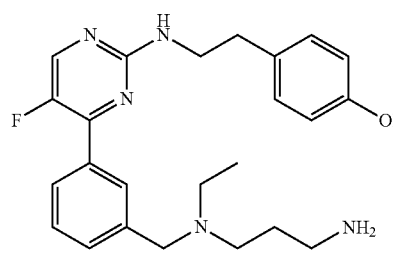
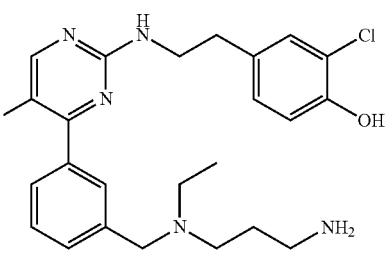

103
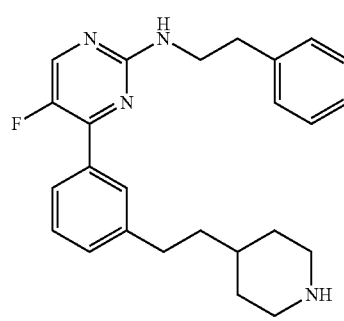
104
-continued
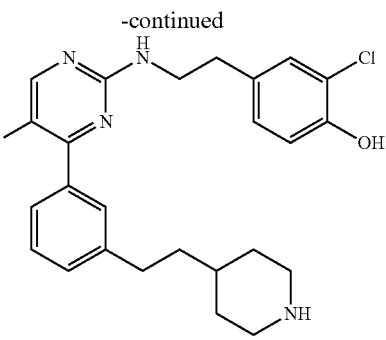
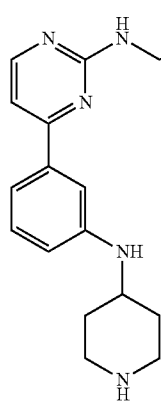
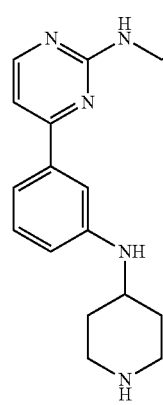
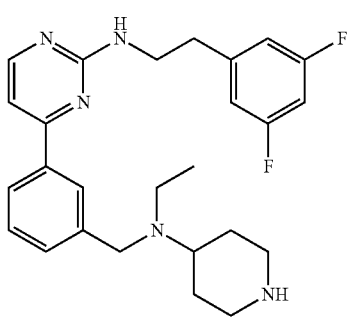
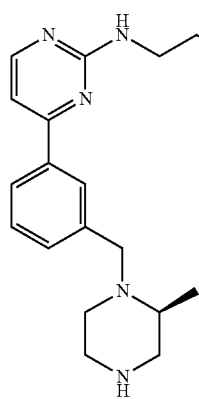
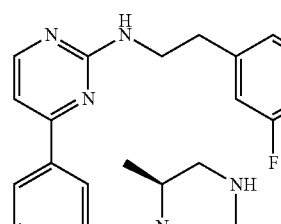
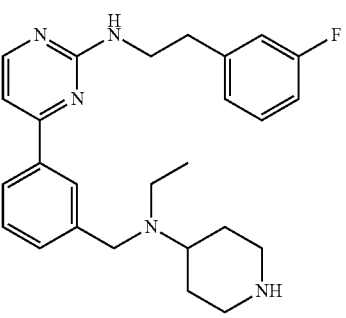
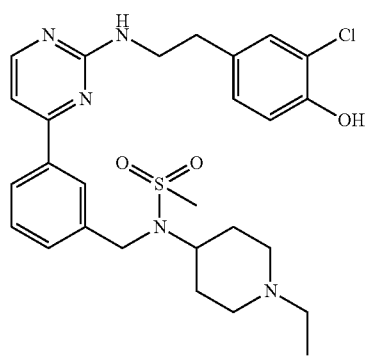
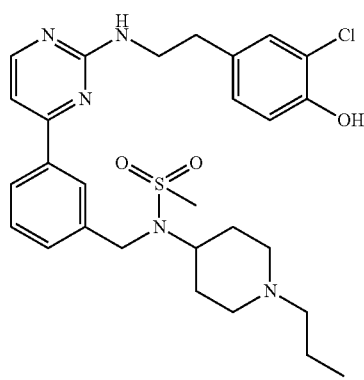
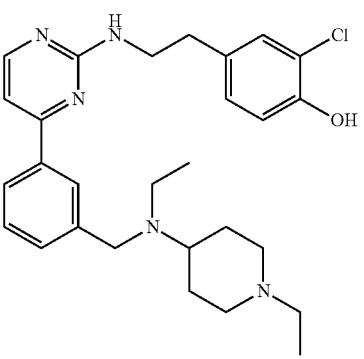

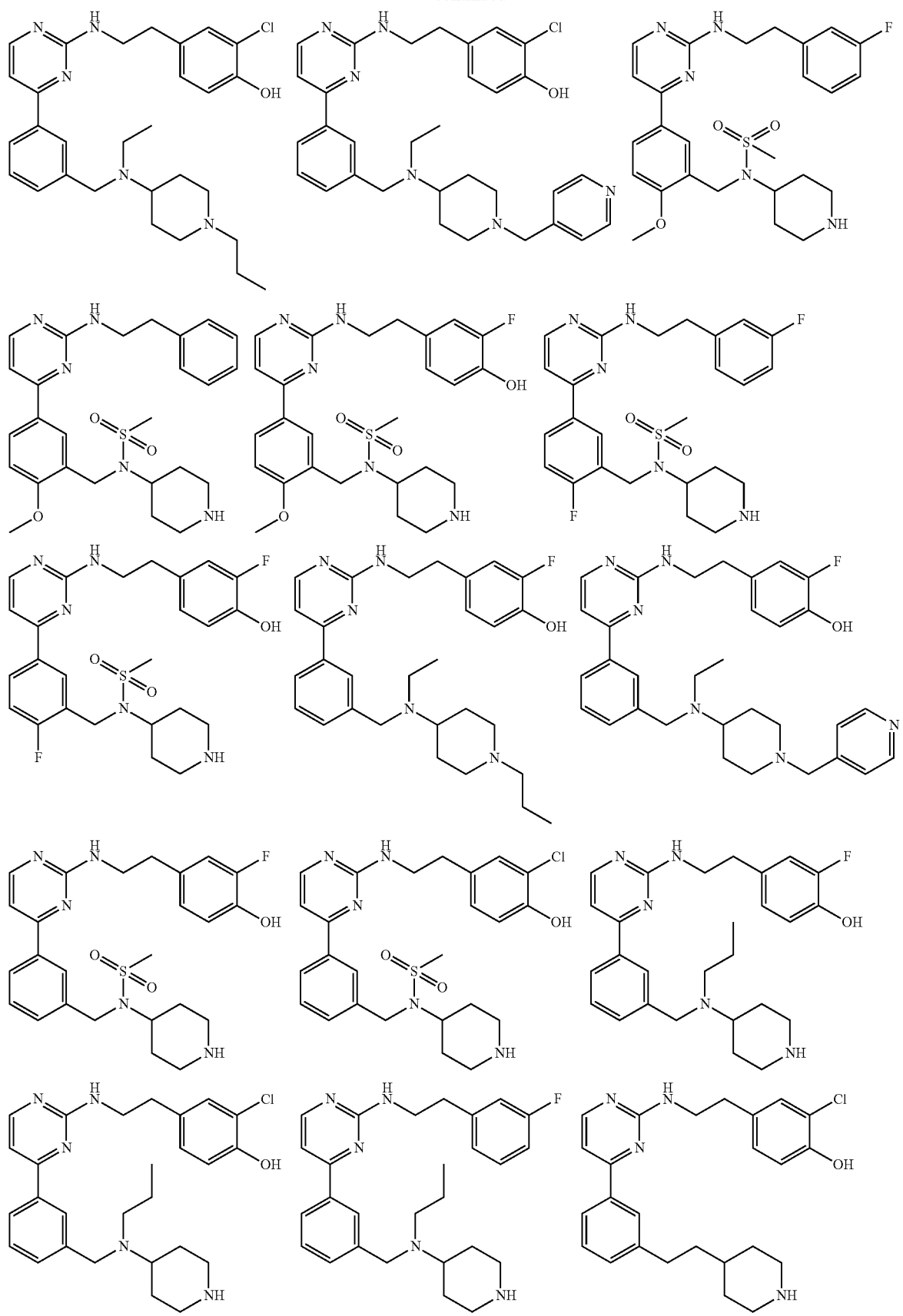

107
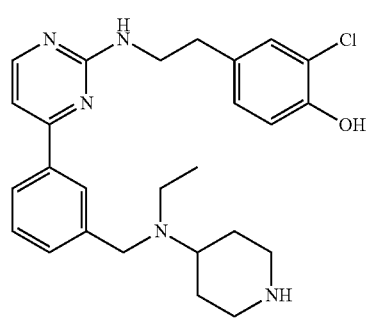
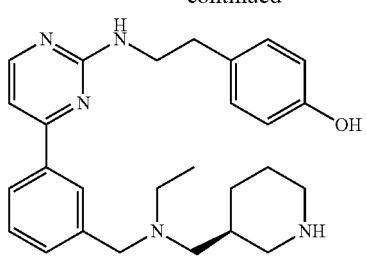
108
-continued
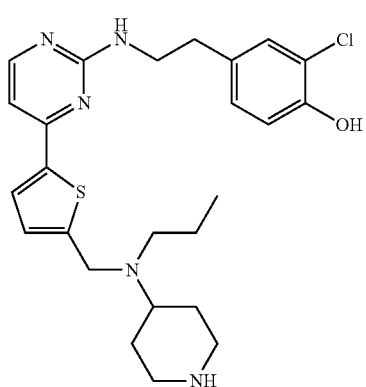
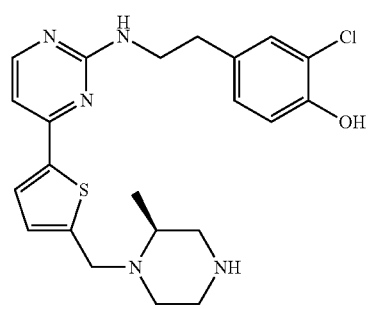
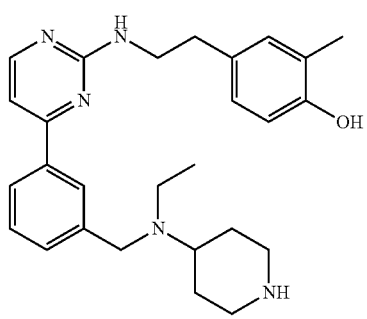
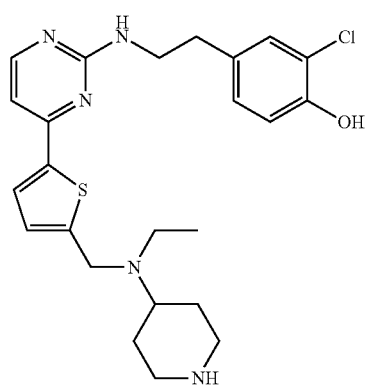
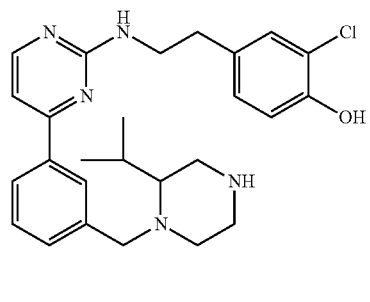
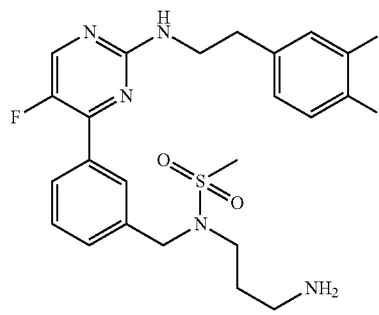
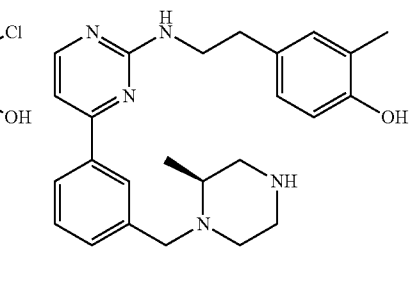
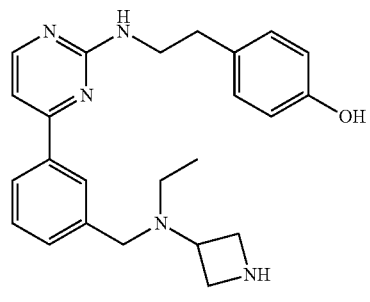
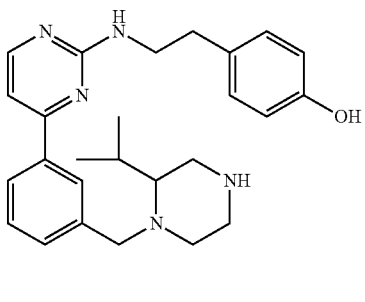
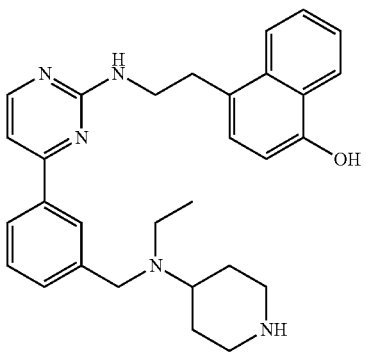

109 110
-continued
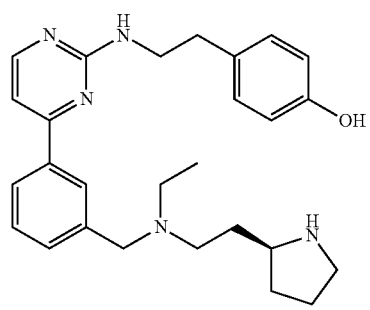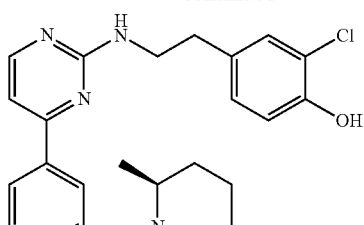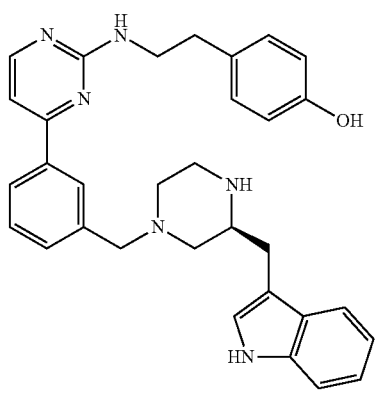
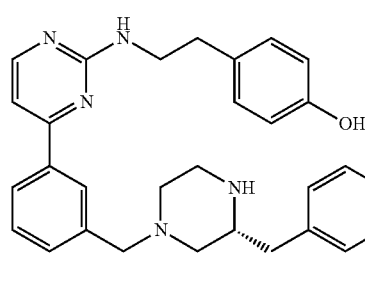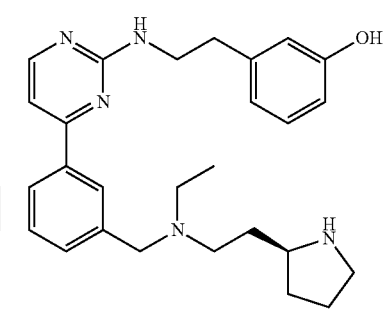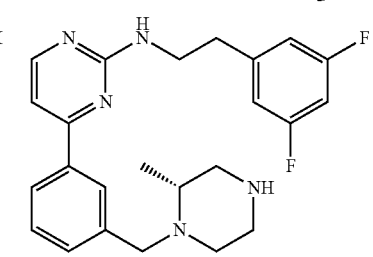
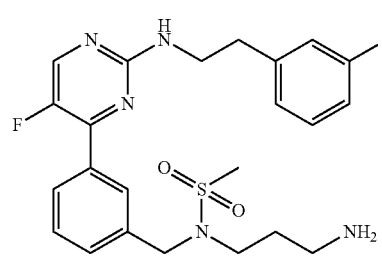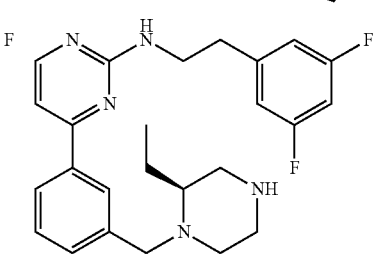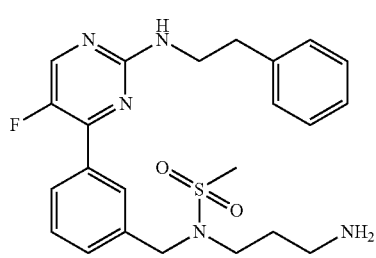
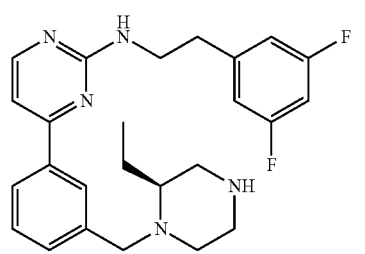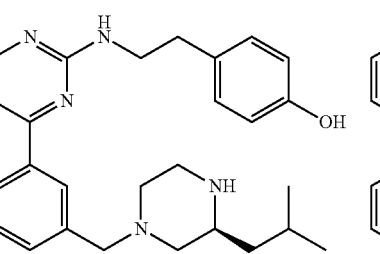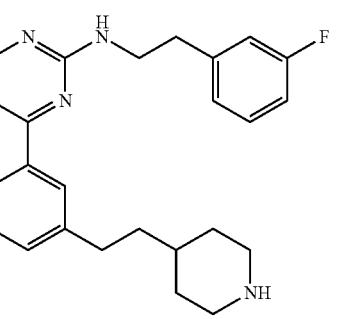
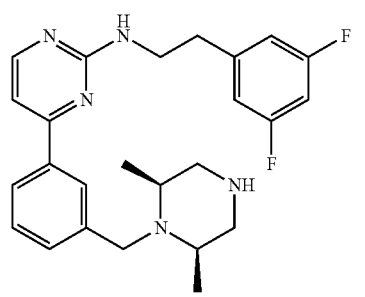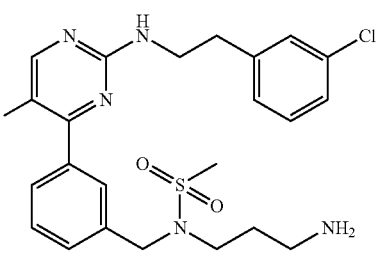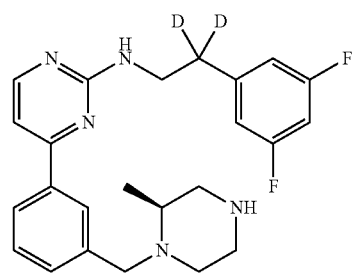

111
112
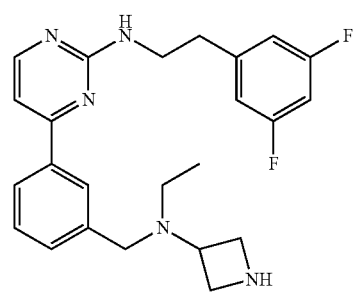 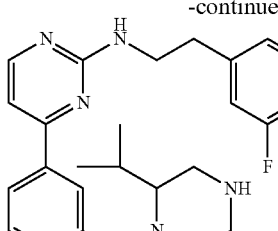 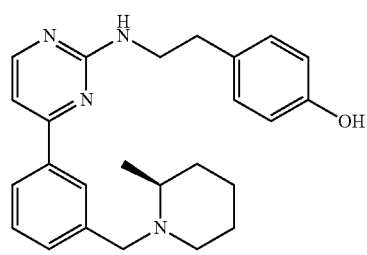
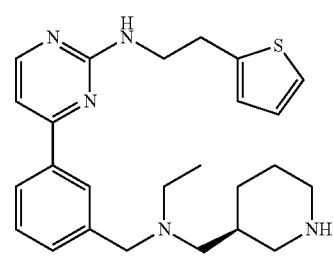 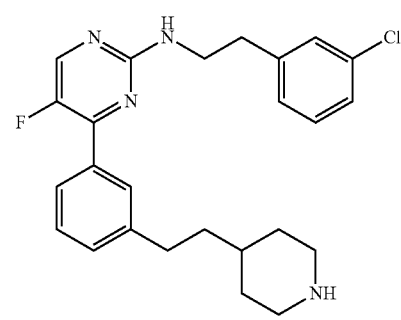
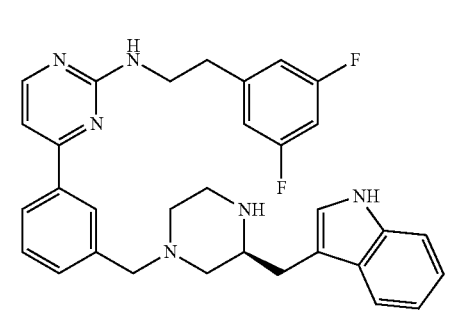 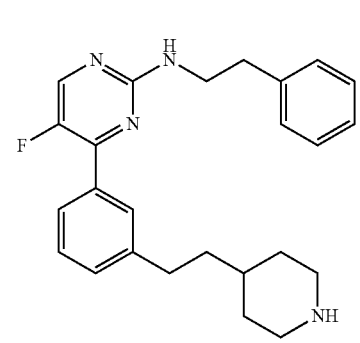
-continued
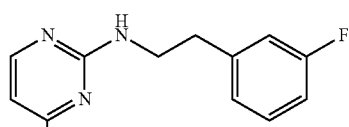
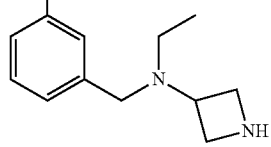
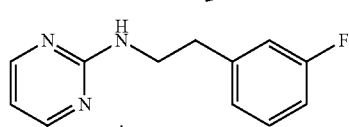
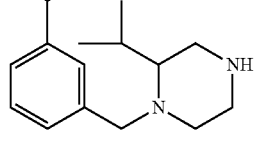
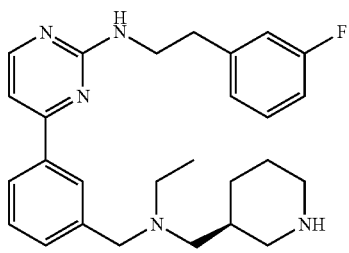
-continued
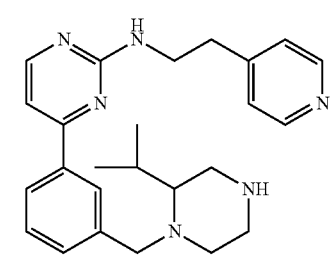

113
-continued
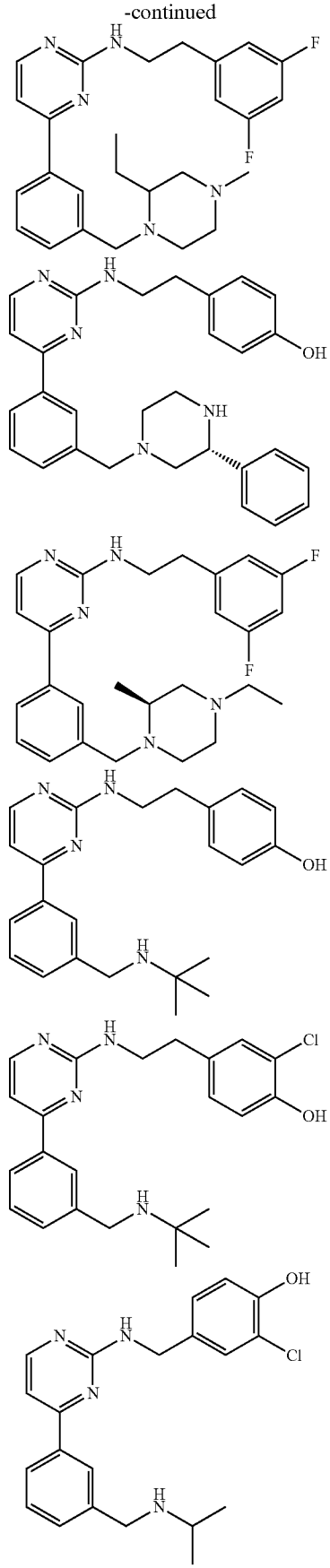
114
-continued
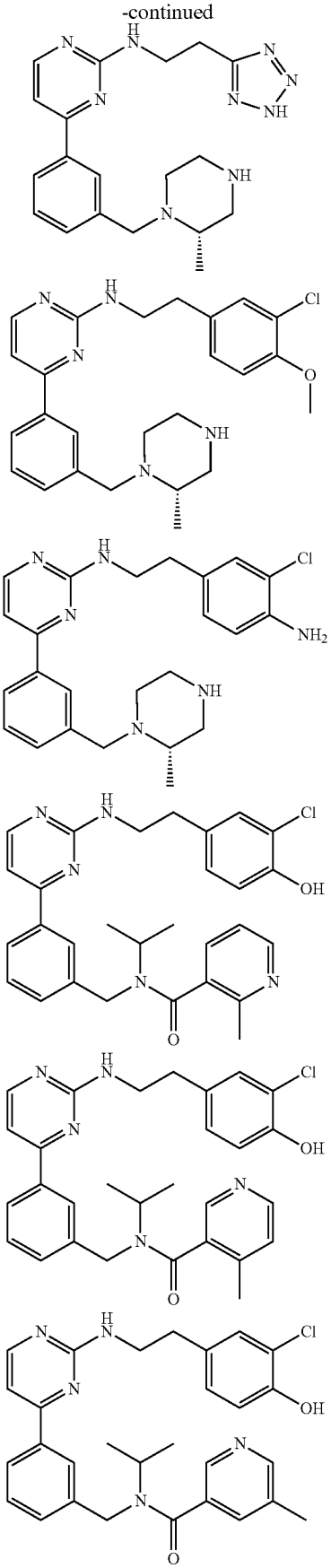

115
-continued
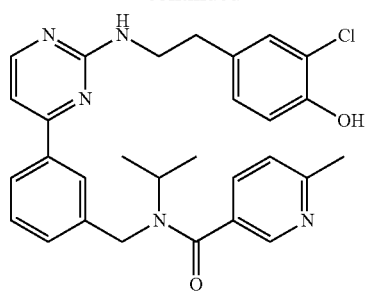
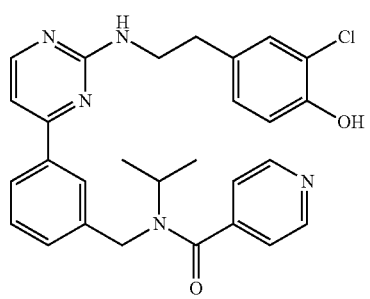
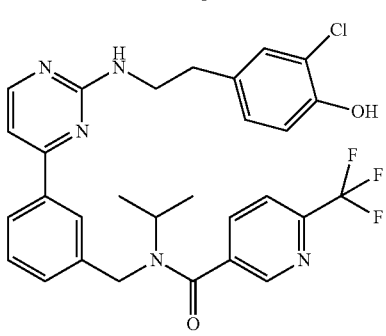
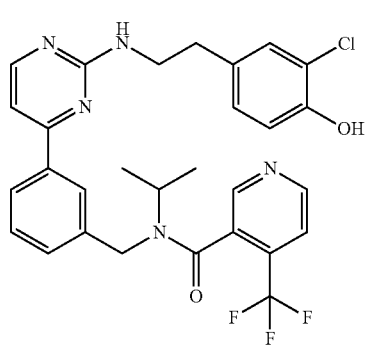
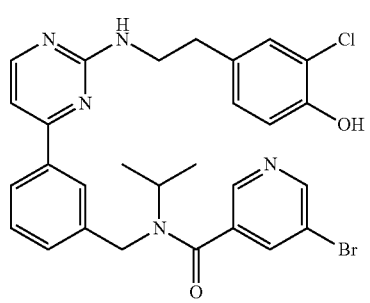
116
-continued
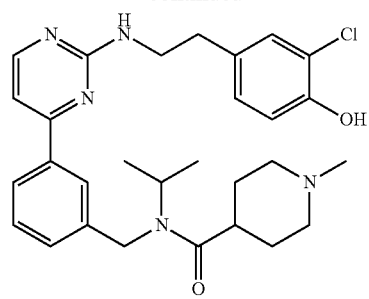
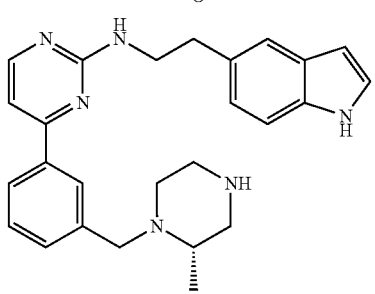
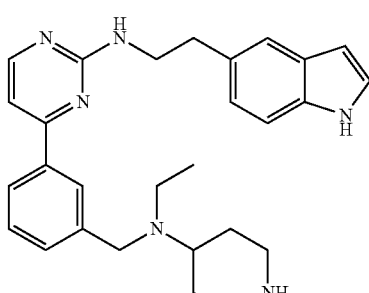
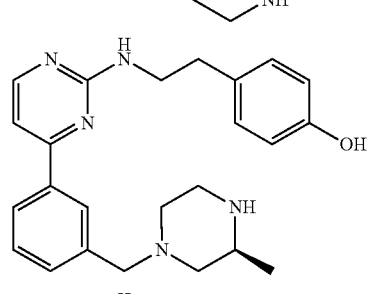
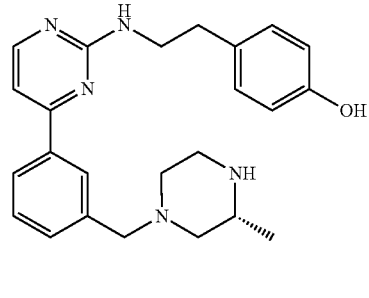
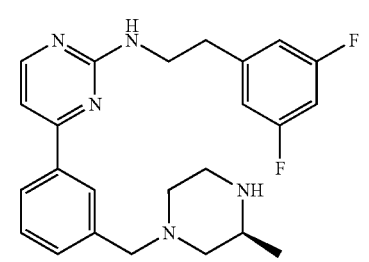

117
-continued
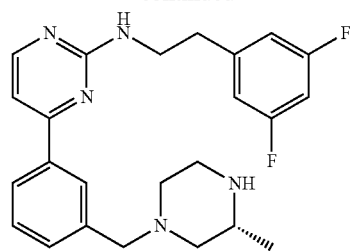
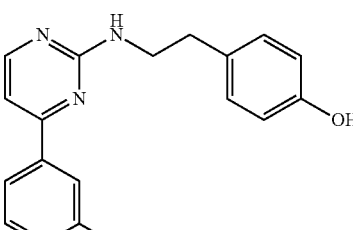
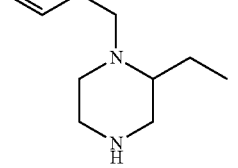
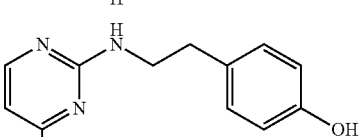
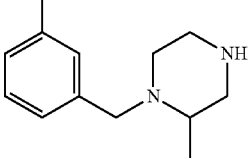
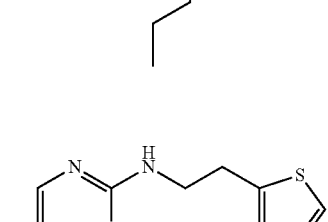
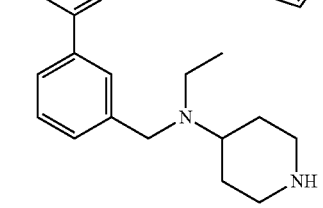
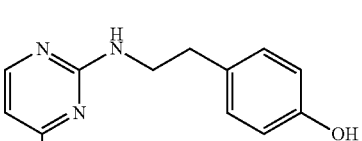
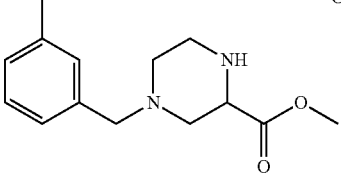
118
-continued
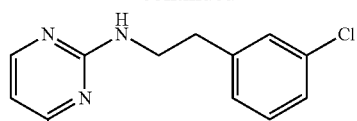
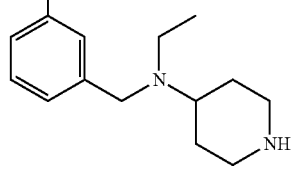
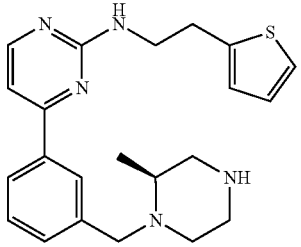
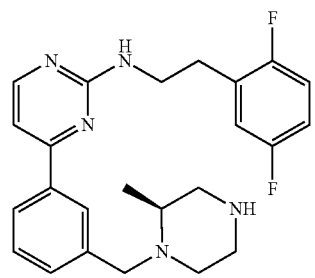
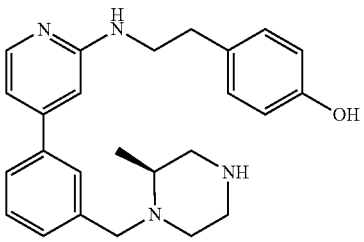
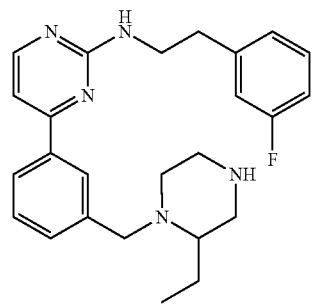
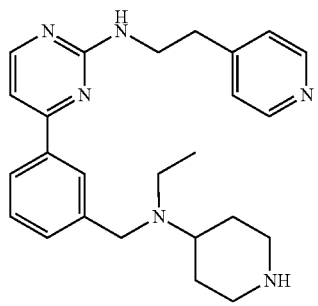

119
-continued
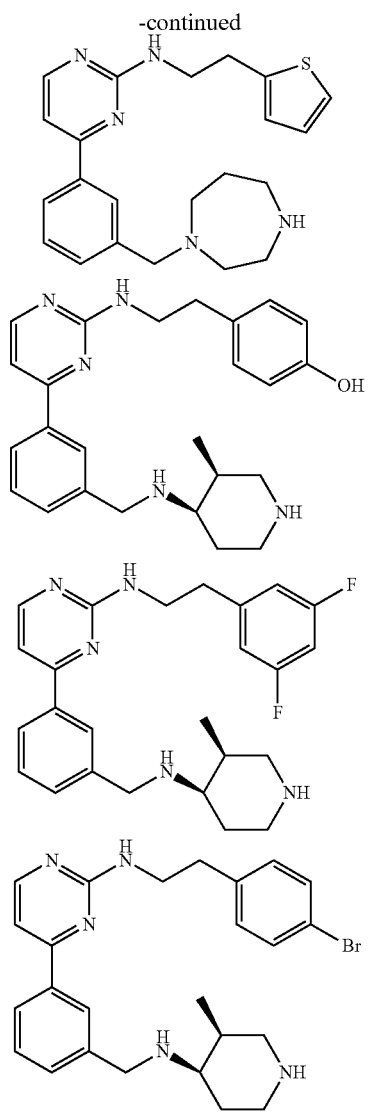
120
-continued
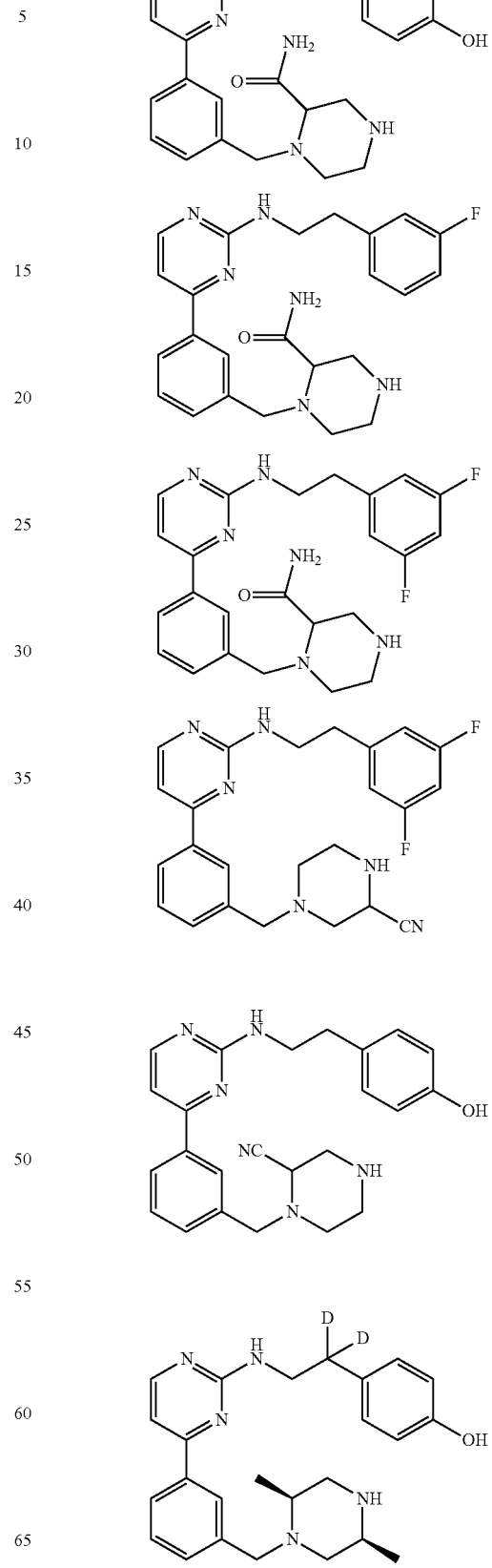

121
-continued
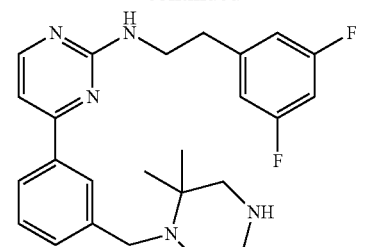
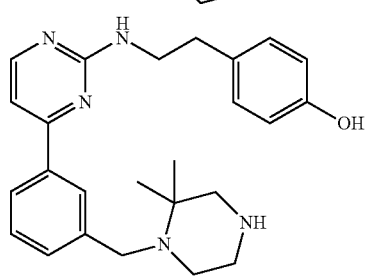
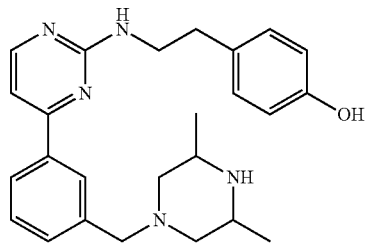
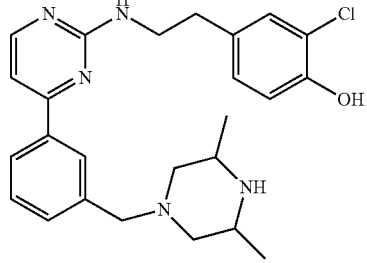
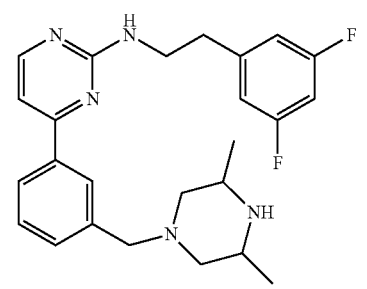
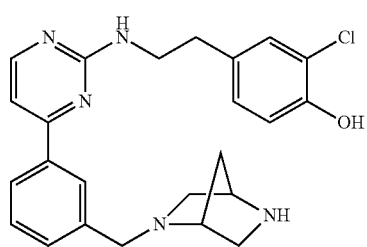
122
-continued
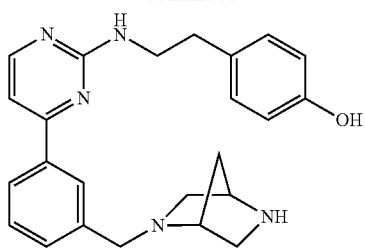
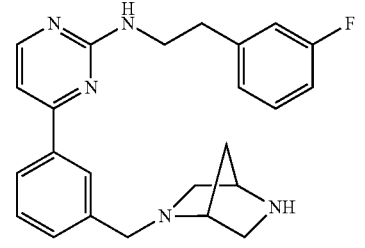
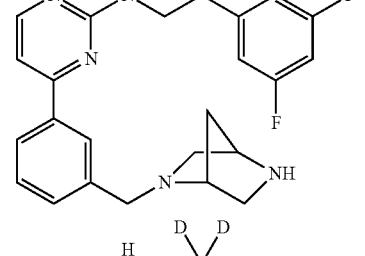
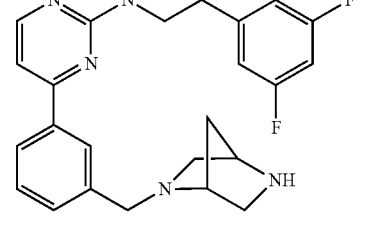
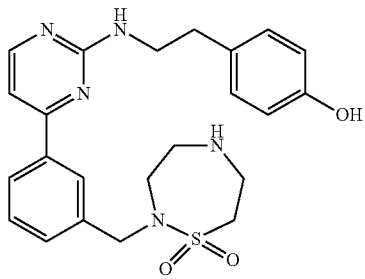
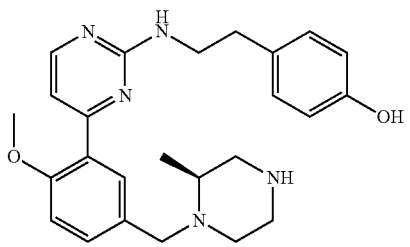

123
-continued
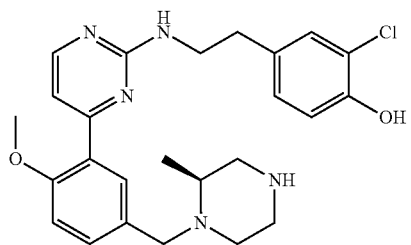
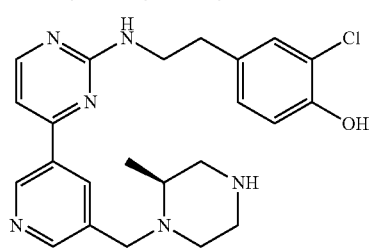
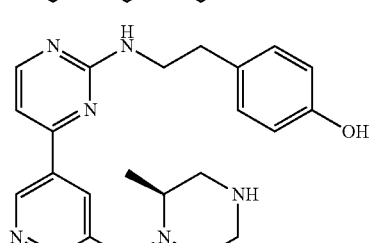
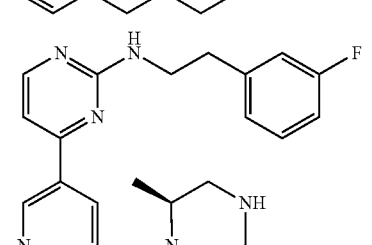
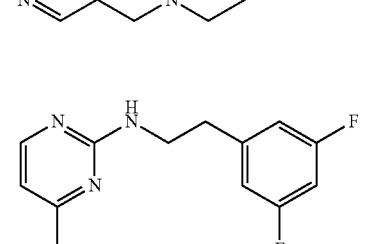
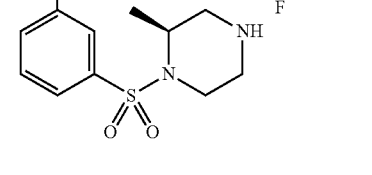
124
-continued
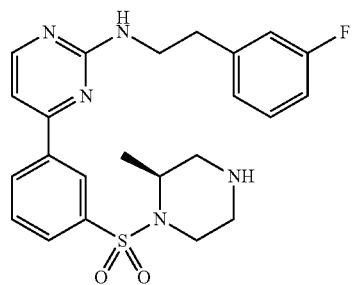
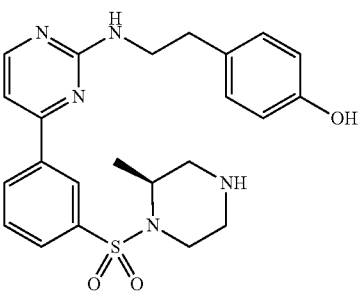
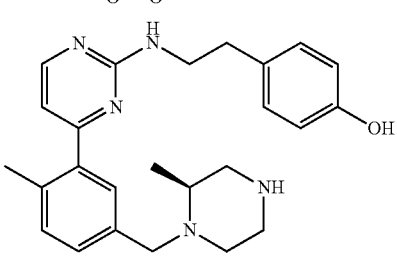
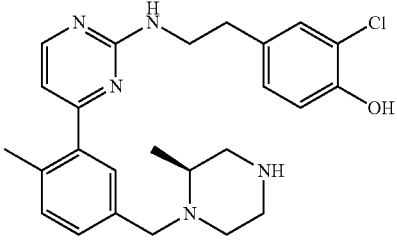
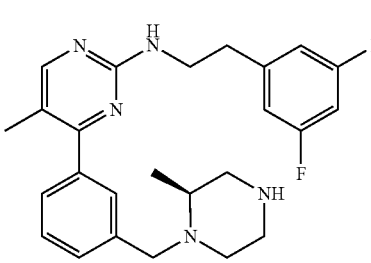
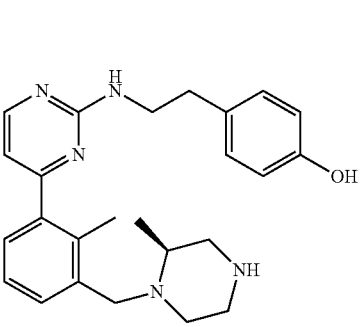

125
-continued
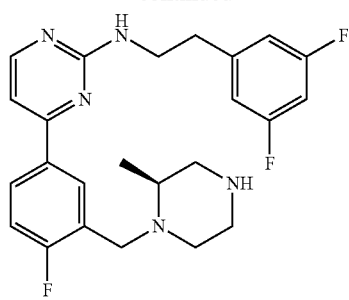
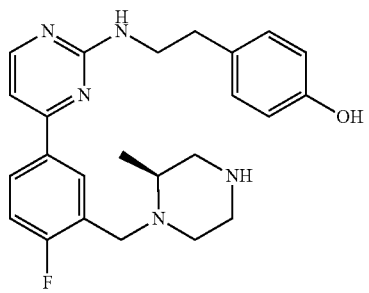
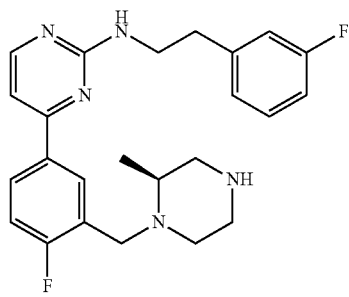
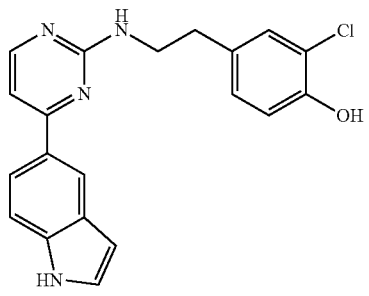
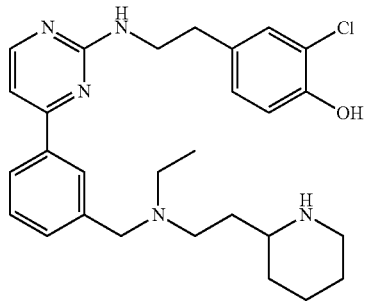
126
-continued
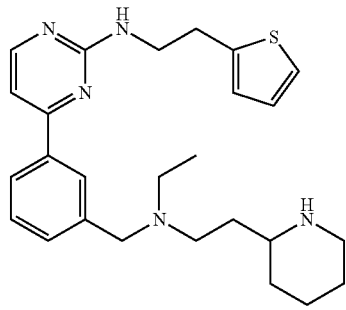
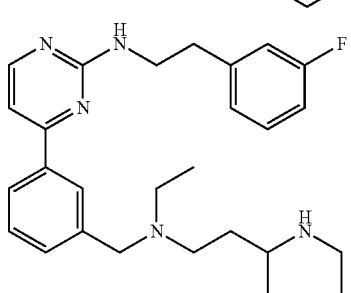
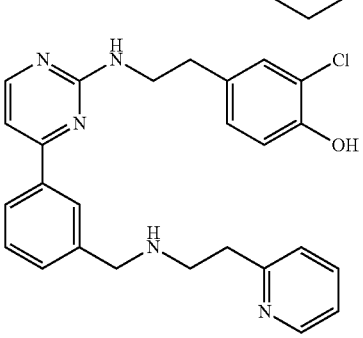
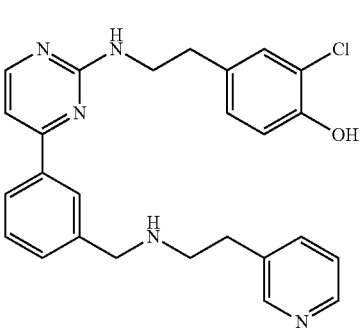
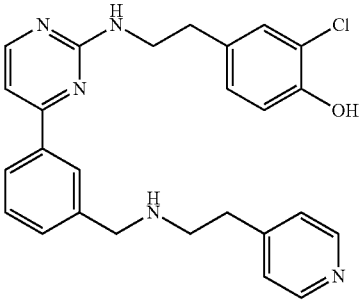

127
-continued
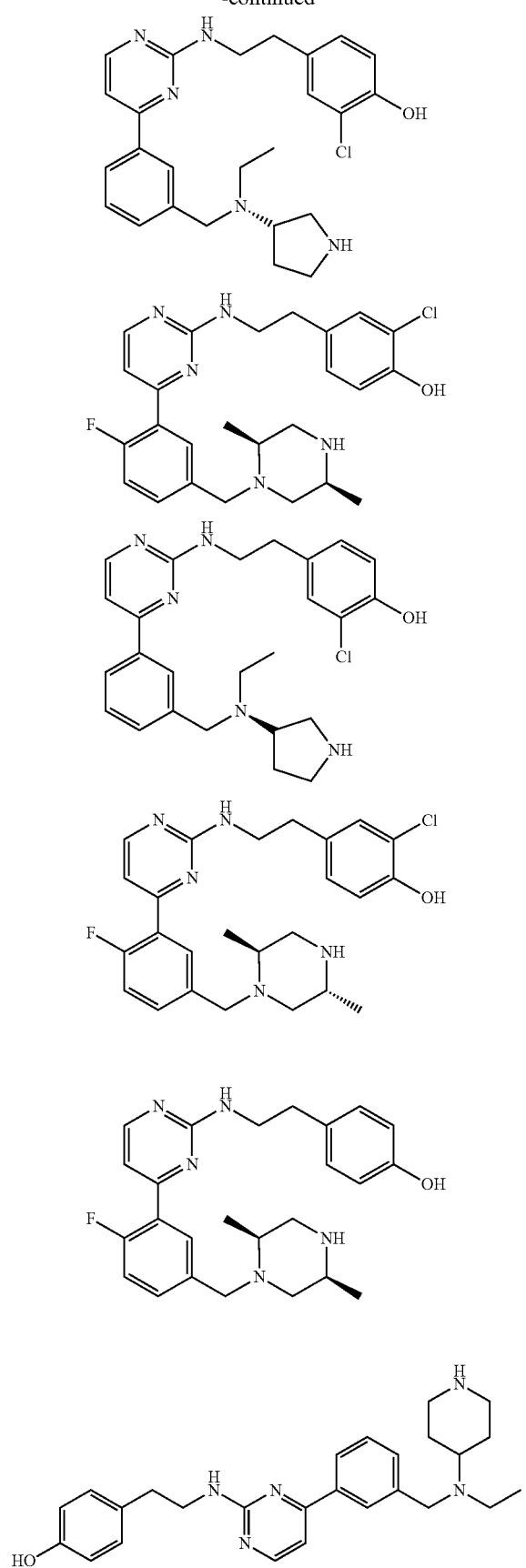
128
-continued
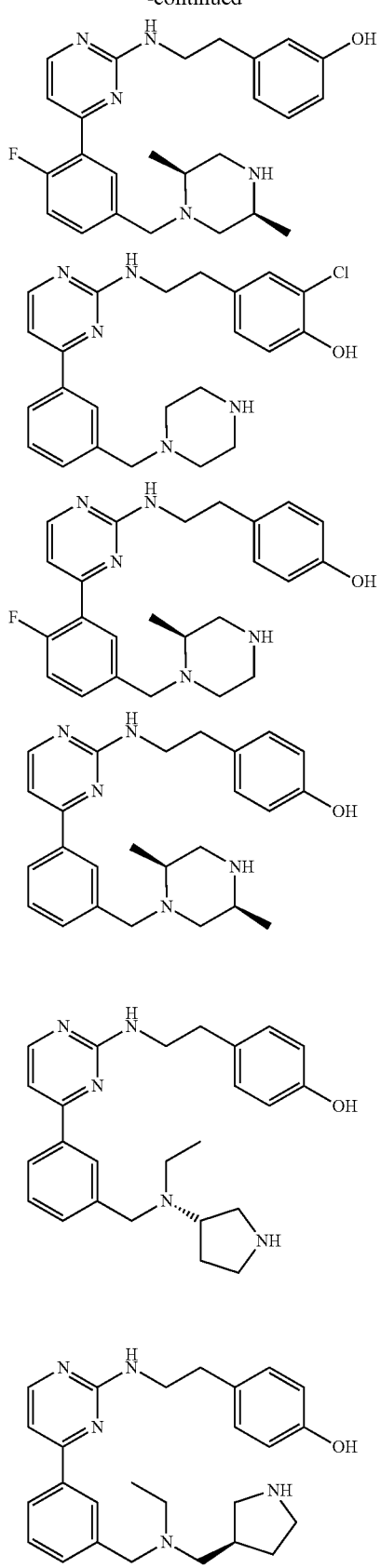

129
-continued
130
-continued
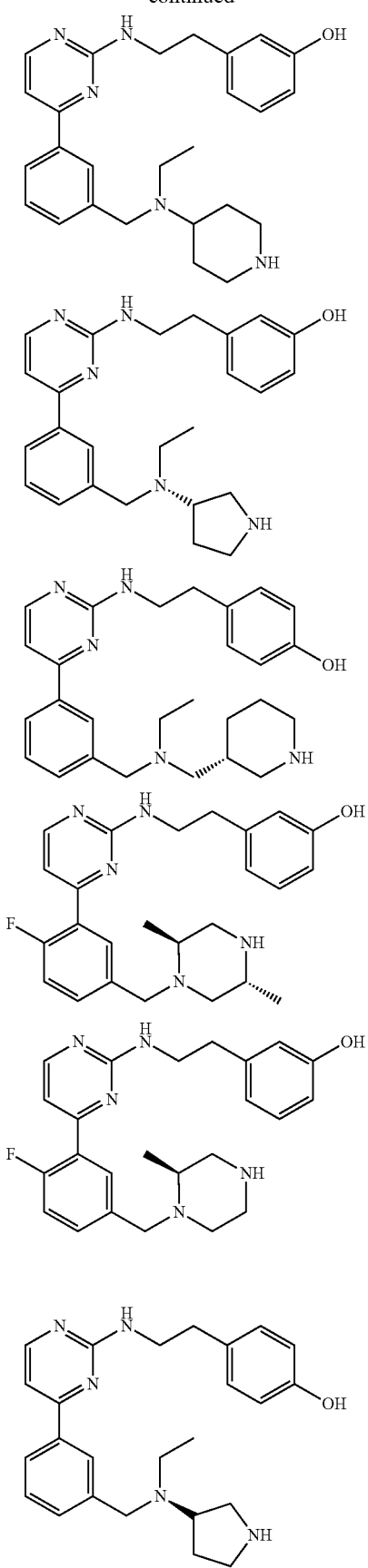
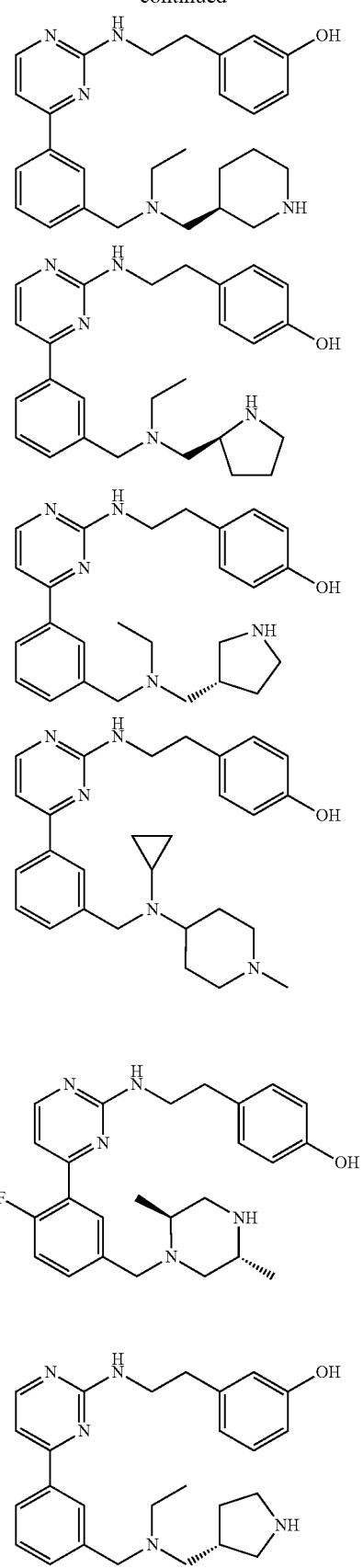

131
-continued
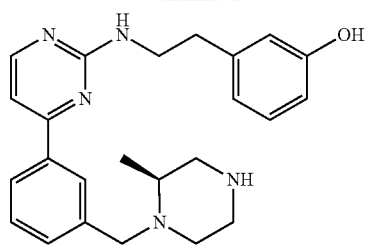
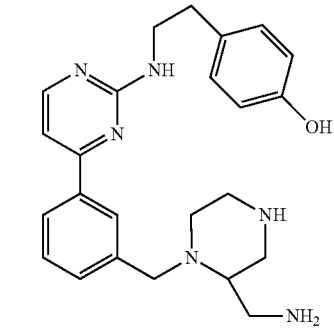
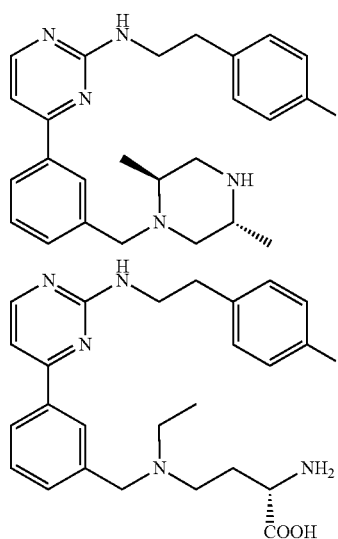
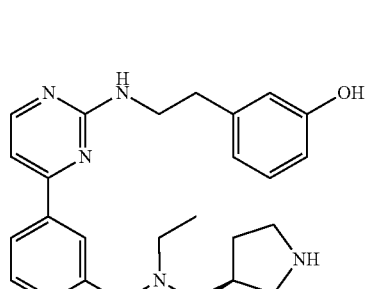
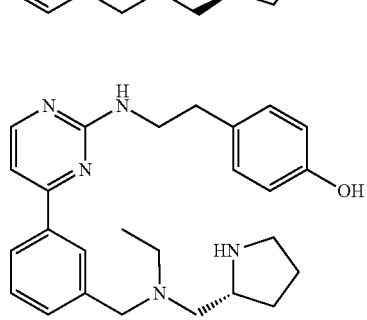
132
-continued
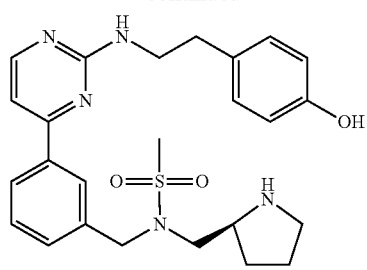
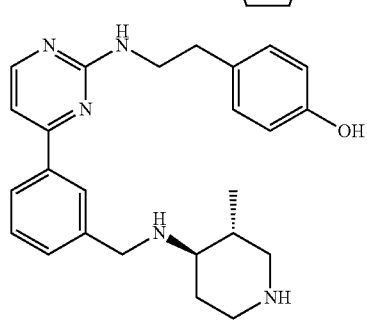
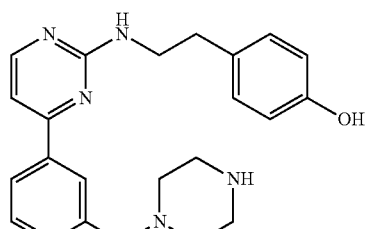
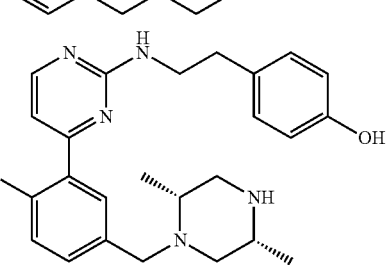
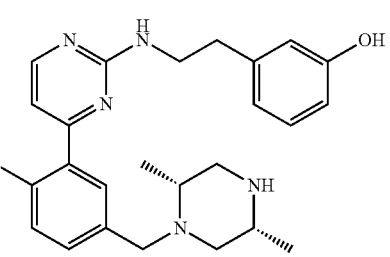
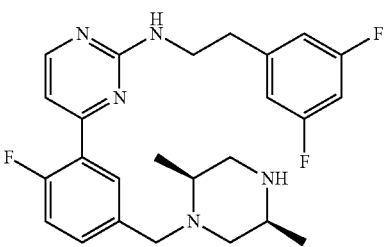

133
-continued
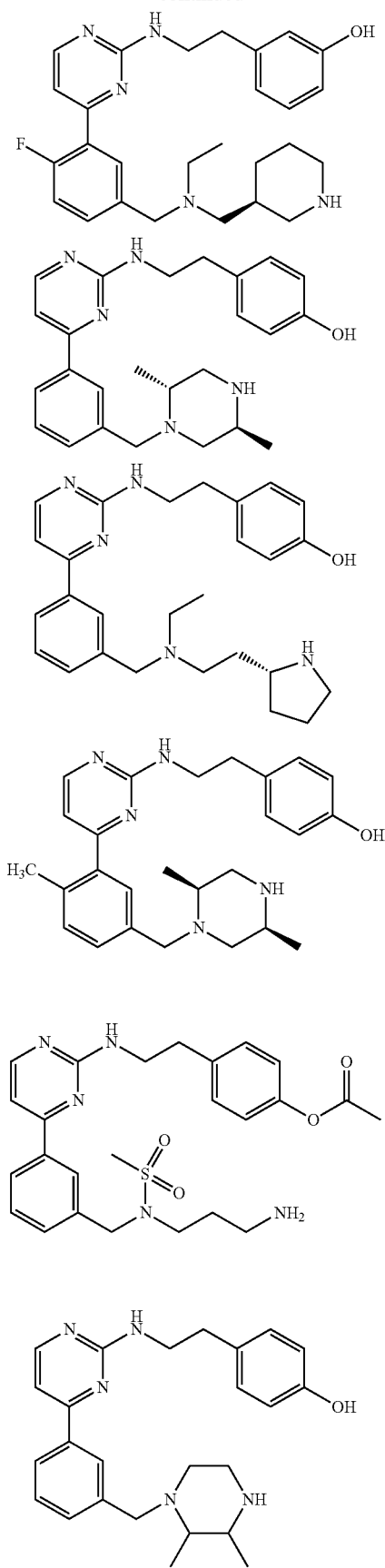
134
-continued
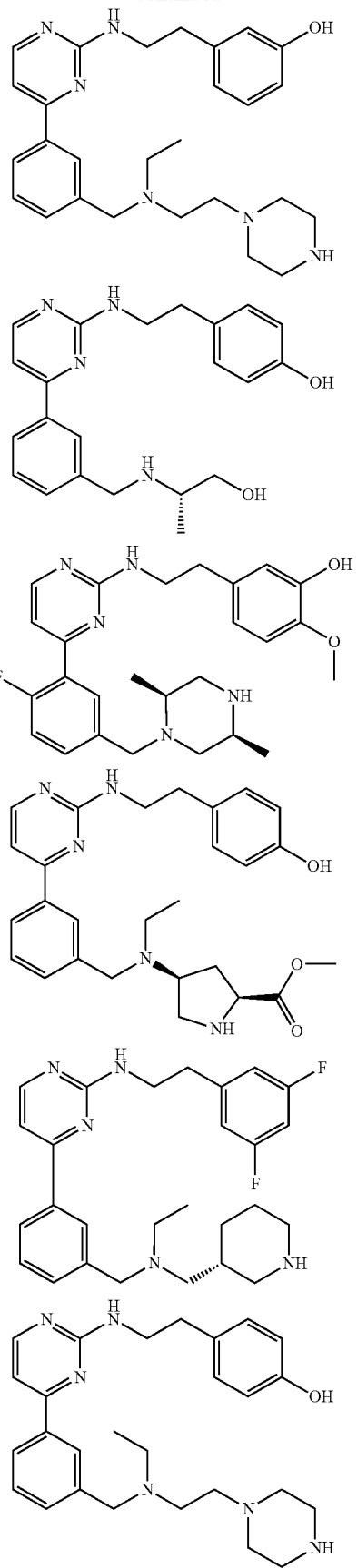

135
-continued
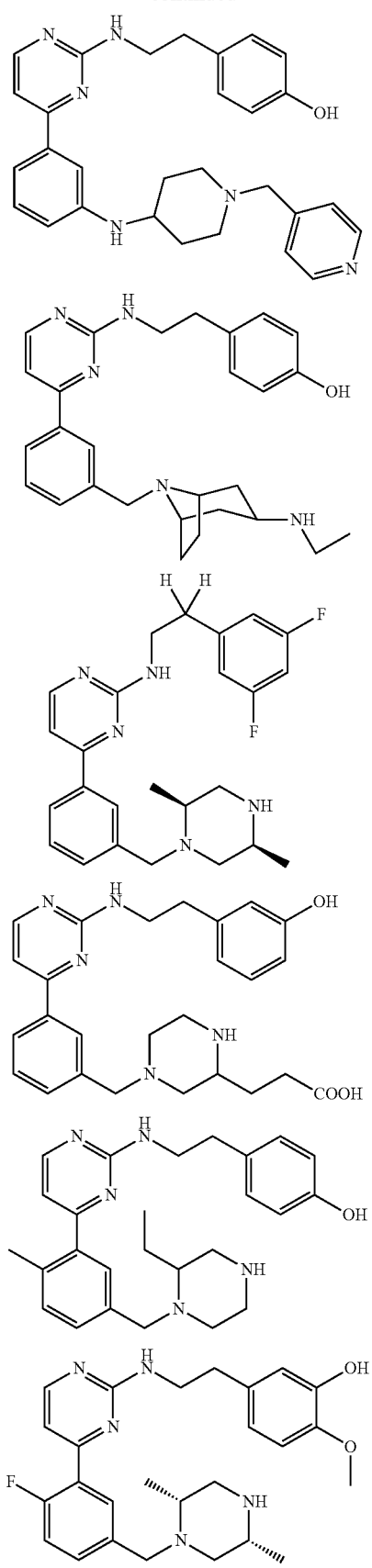
136
-continued
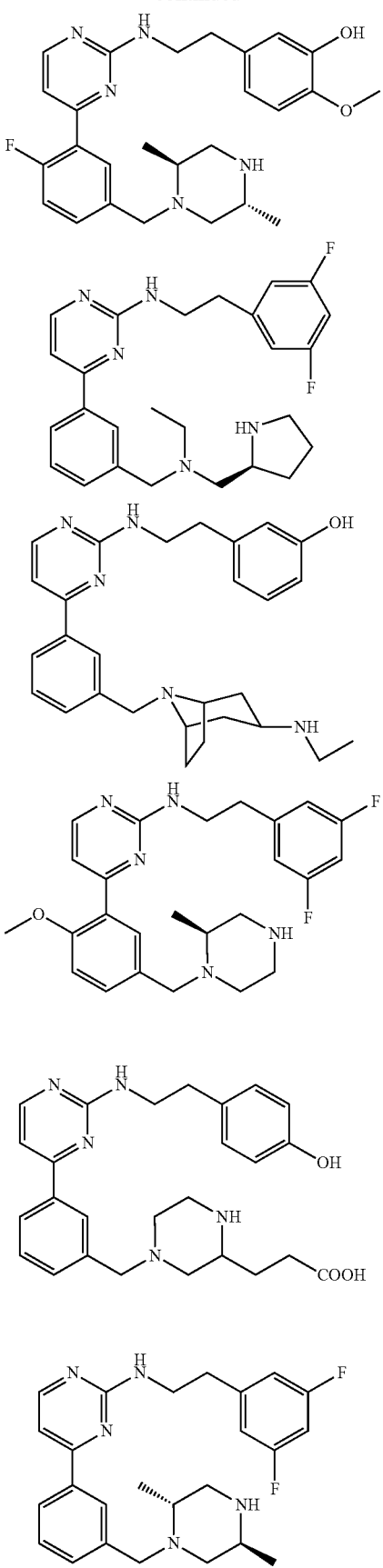

137
-continued
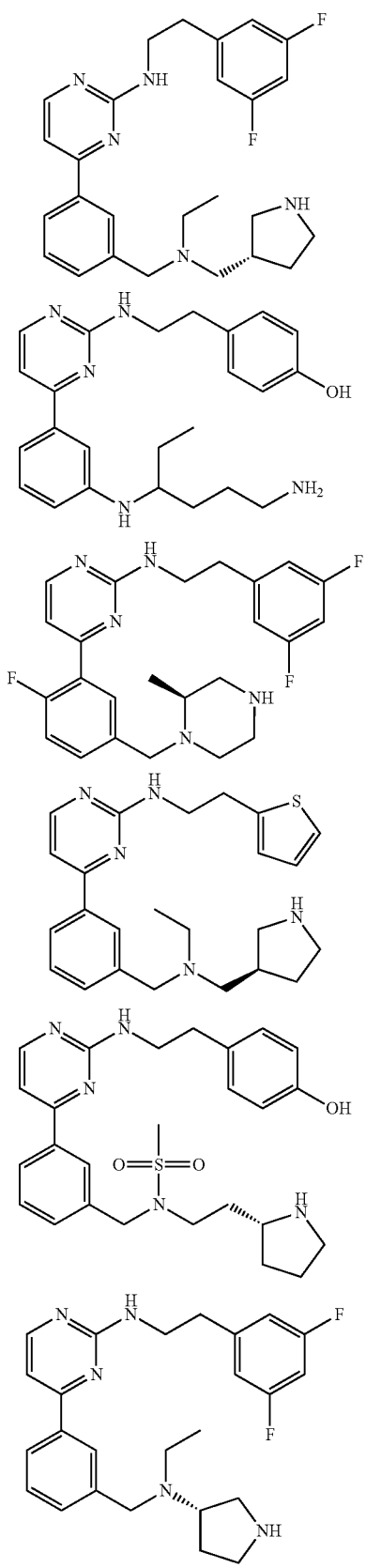
138
-continued
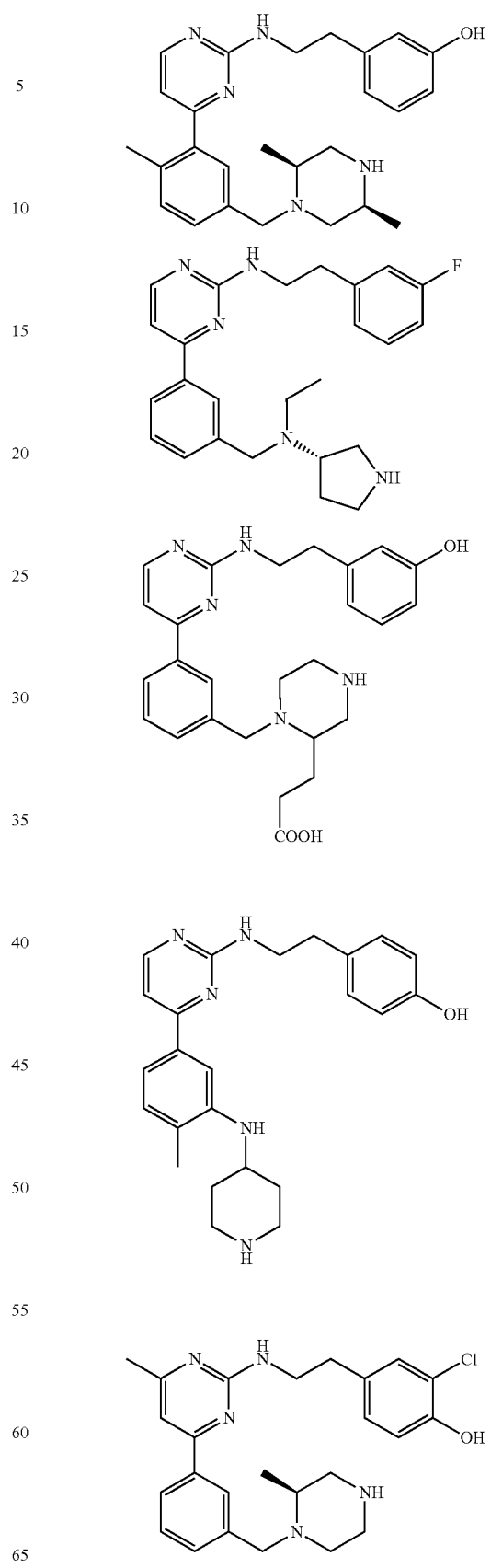

139
-continued
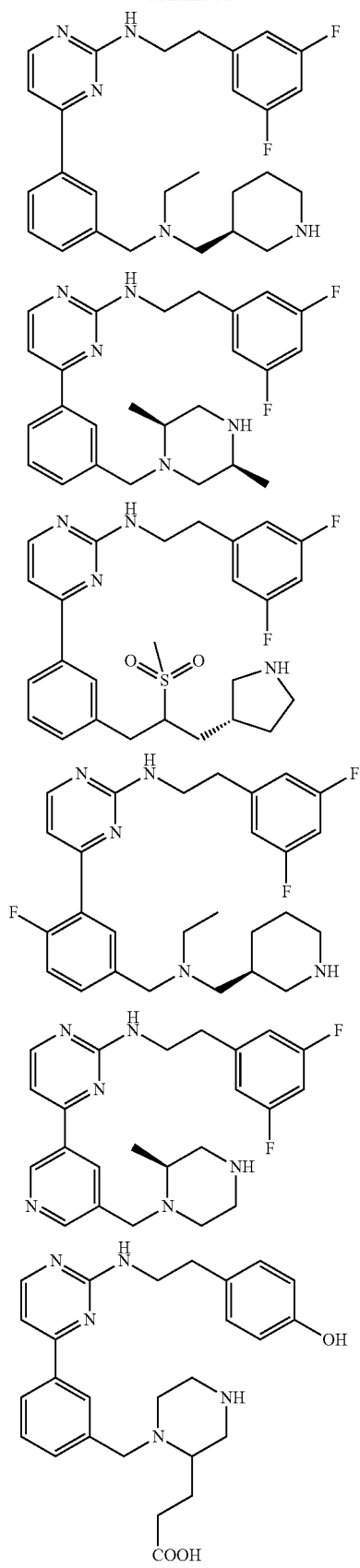
140
-continued
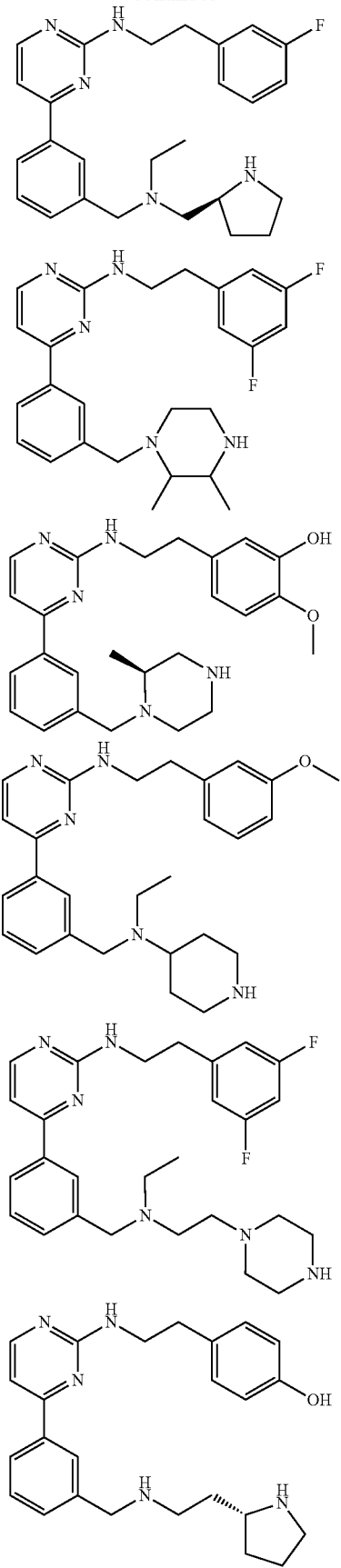

141
-continued
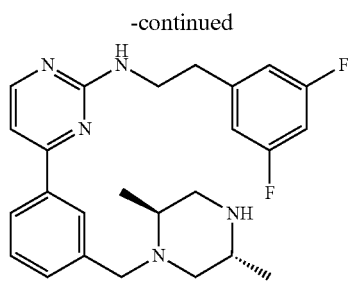
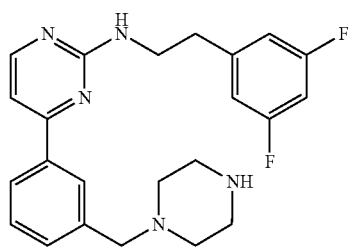
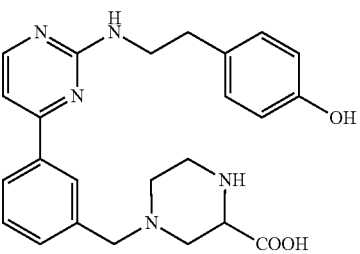
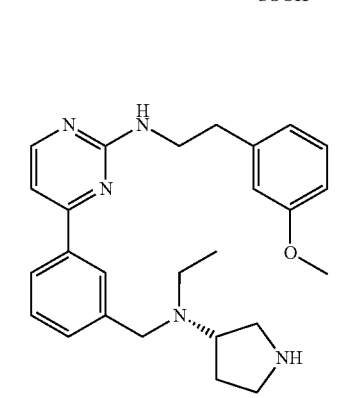
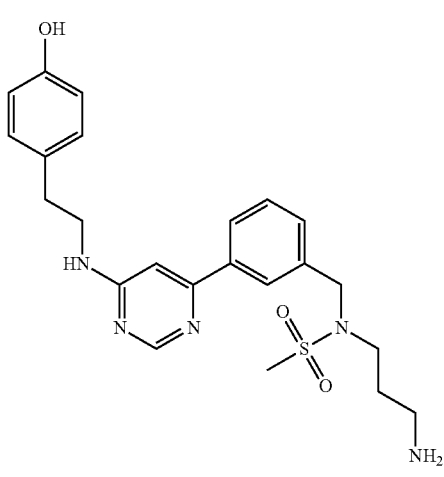
142
-continued
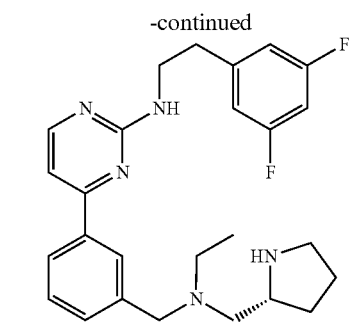
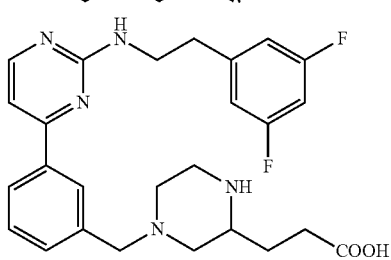
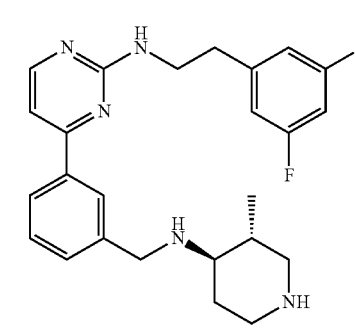
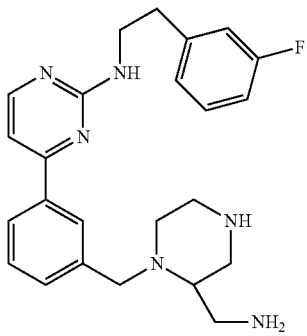
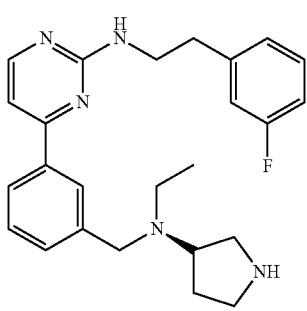

143
-continued
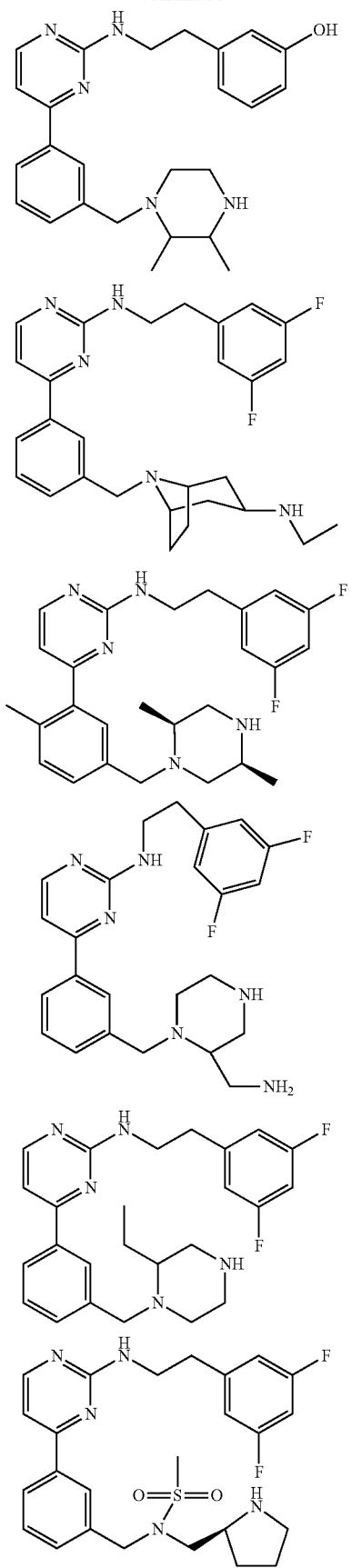
144
-continued
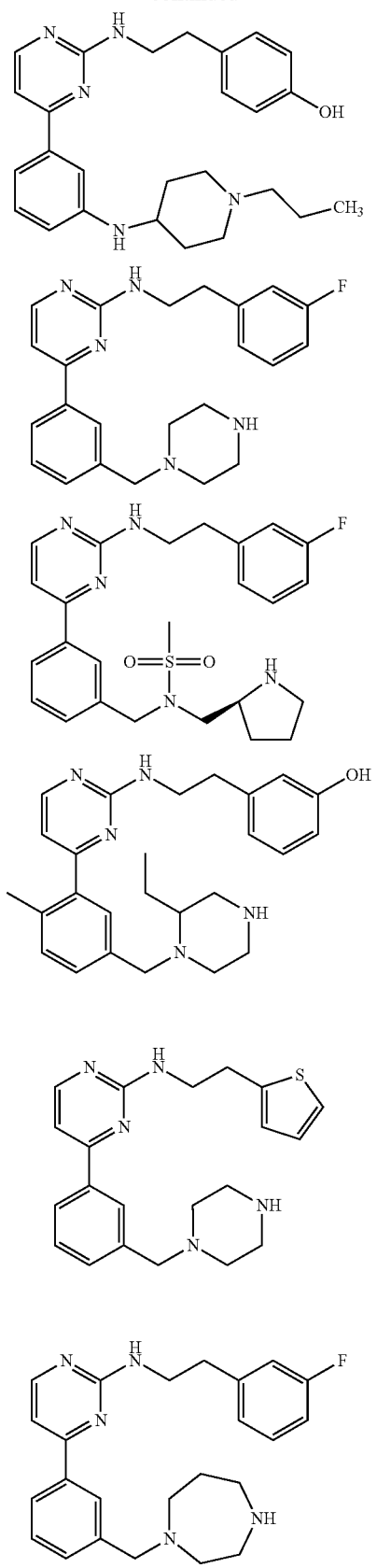

145
-continued
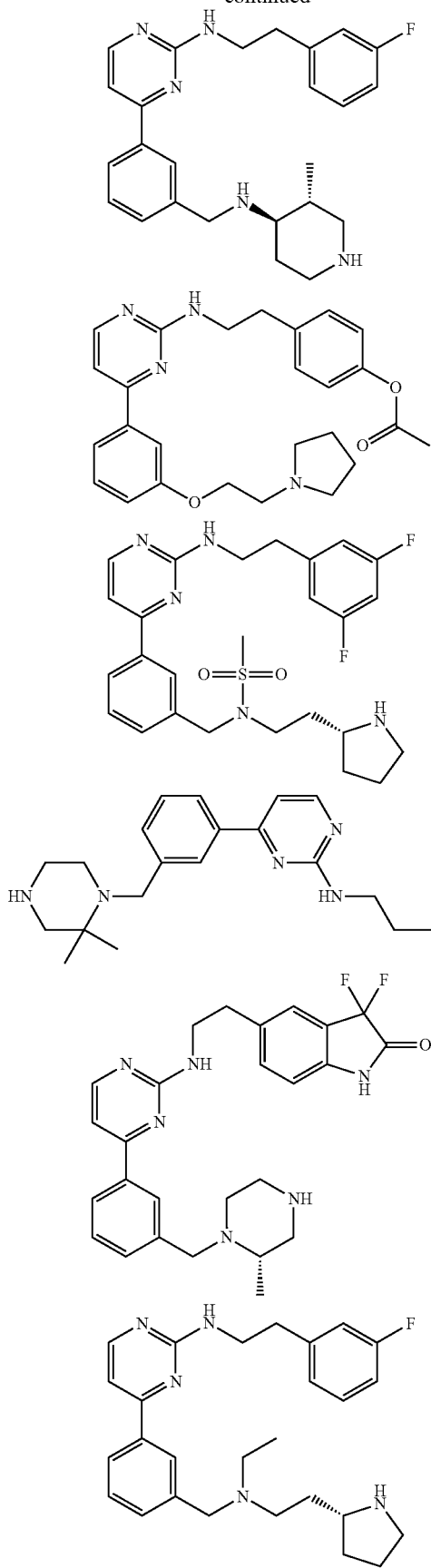
146
-continued
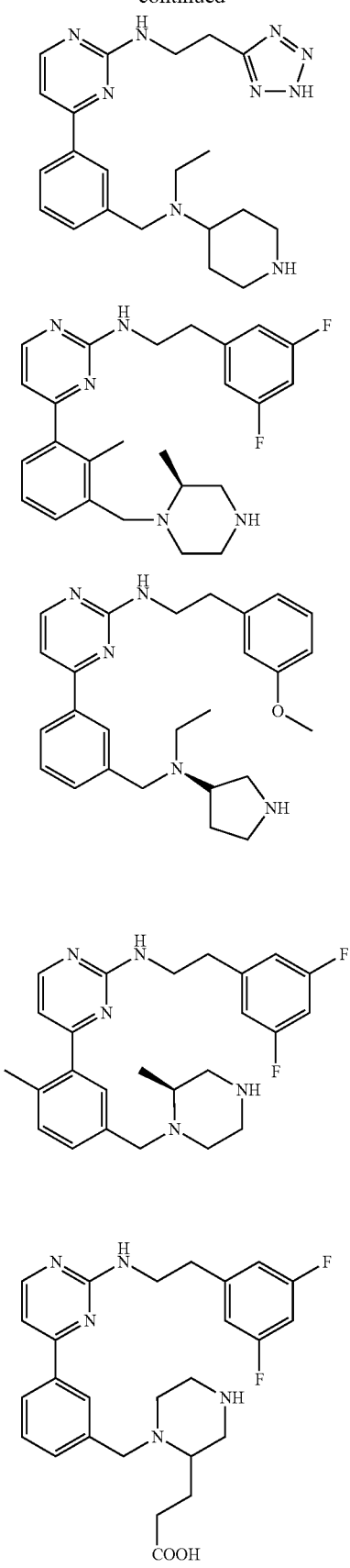

147
-continued
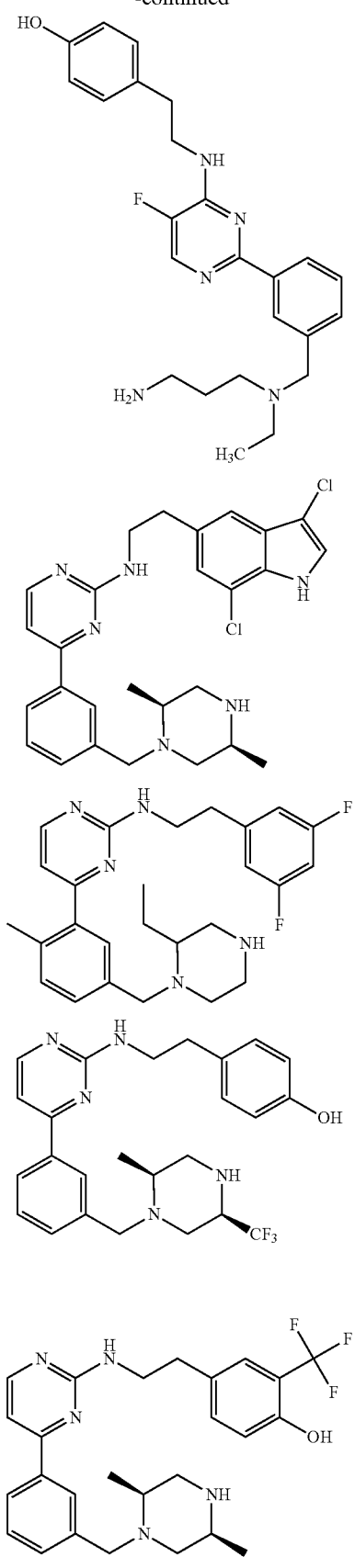
148
-continued
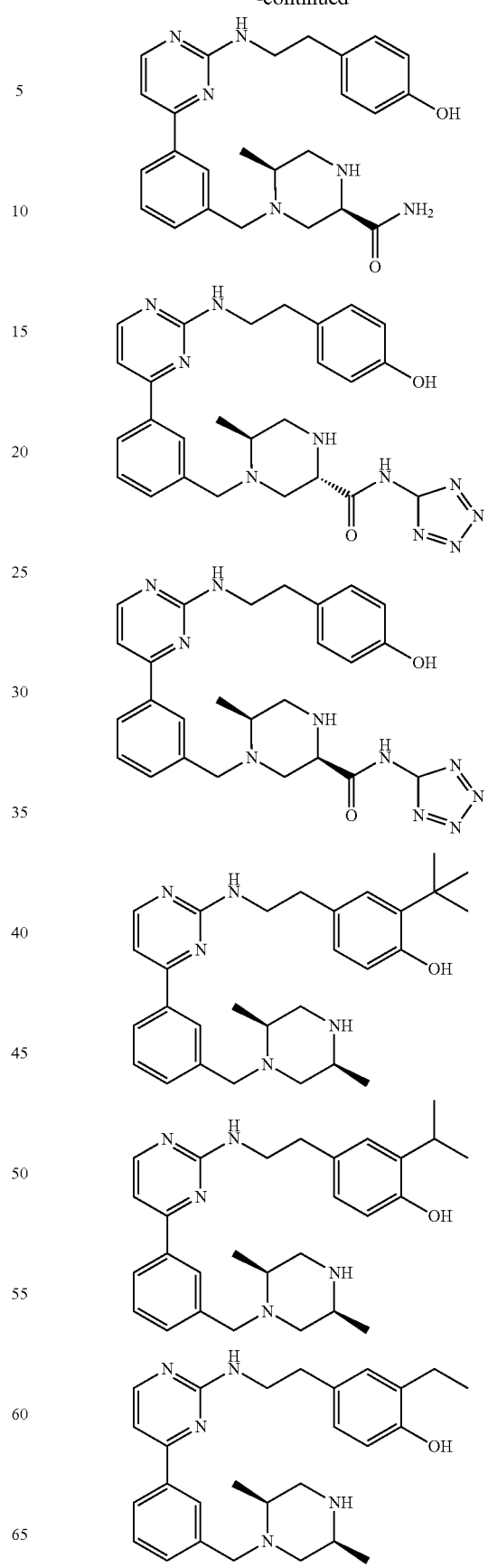

149
-continued
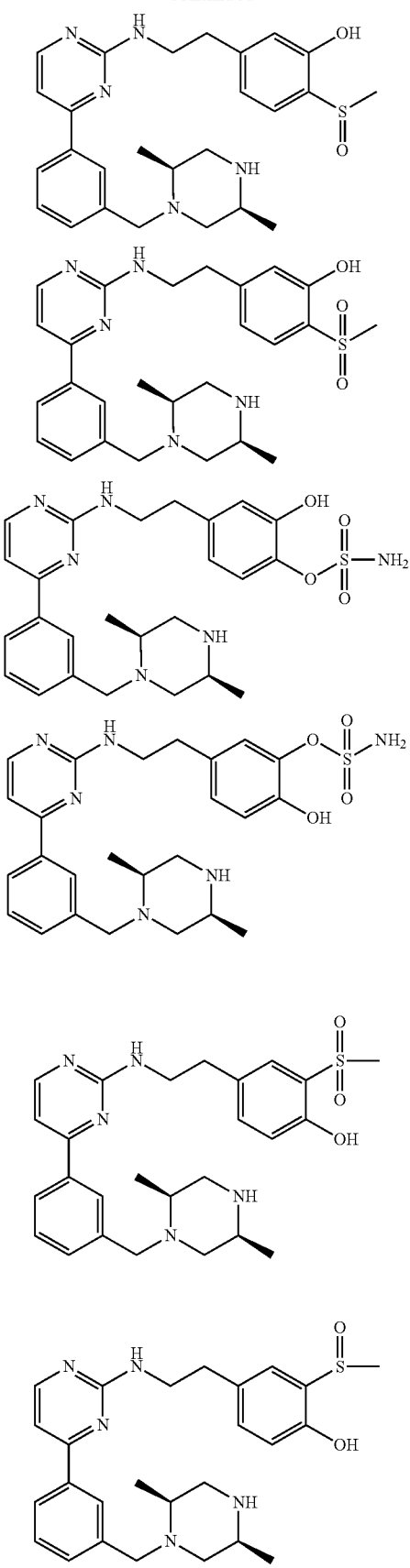
150
-continued
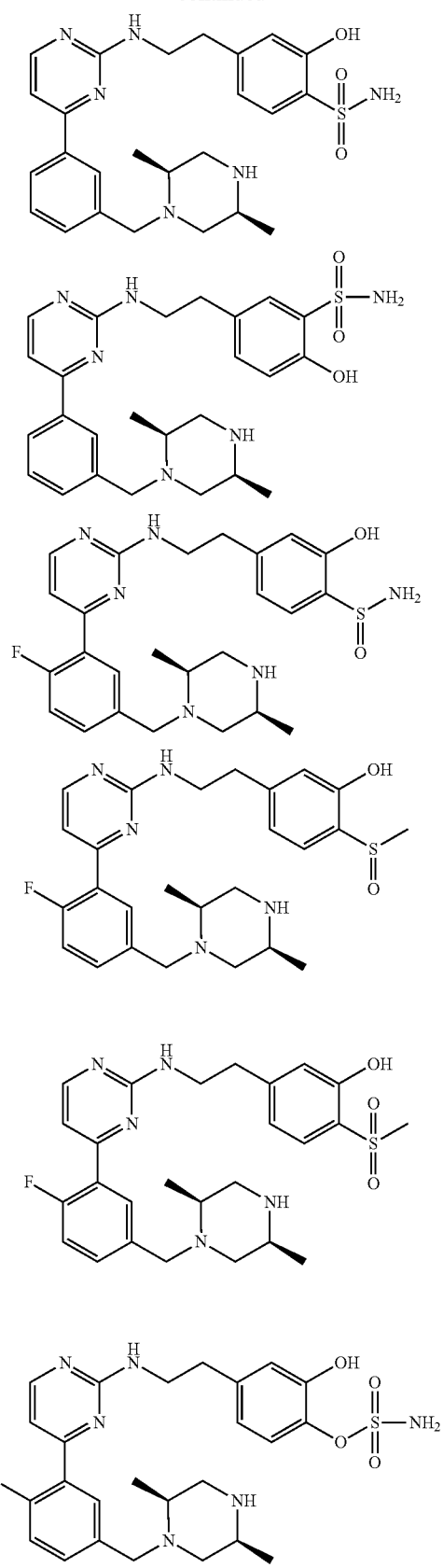

-continued

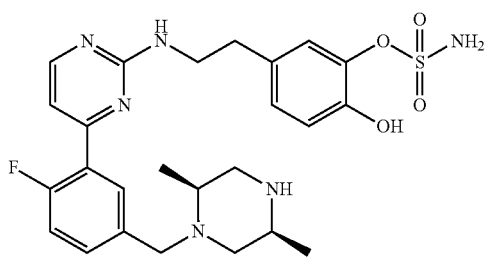

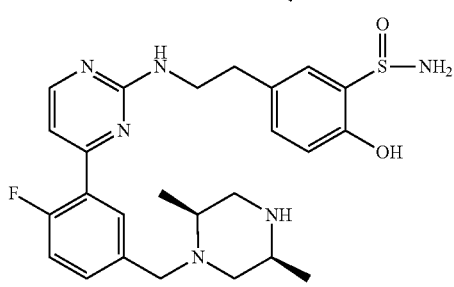

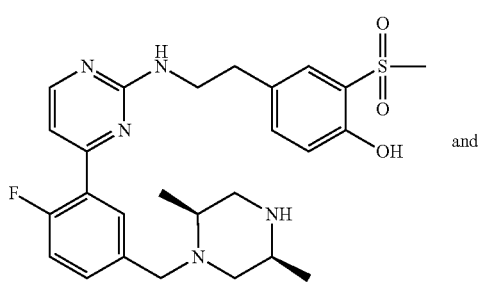

and

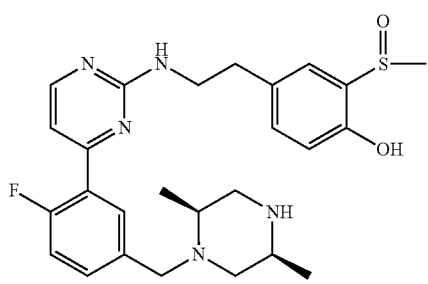

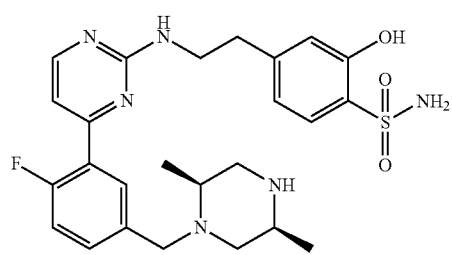

In yet other embodiments, small molecule PKC-θ inhibitors include pyrimidine derivatives as described for example by Cardozo et al. in US Publication No. 2005/0124640, which is incorporated herein by reference in its entirety. Representative compounds of this type are represented by formula (XVIII):

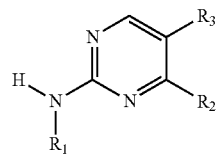

wherein:

$R_1$ is $C_{1-8}$alkyl, $C_{3-7}$cycloalkyl, $C_{3-7}$cycloalkyl-$C_{1-8}$alkyl, naphthyl, quinolinyl, aryl-$C_{1-8}$alkyl, or heteroaryl-$C_{1-8}$alkyl, wherein in each of the $C_{1-8}$alkyl groups a methylene group may optionally be replaced by —NHC(O)— or —C(O)NH—, and wherein each of the $C_{1-8}$alkyl groups is optionally substituted by an oxo group or one or more $C_{1-3}$alkyl groups wherein two alkyl substituents on the same carbon atom of a $C_{1-8}$alkyl group may optionally be combined to form a $C_{2-5}$ alkylene bridge, and wherein the aryl group is optionally substituted on adjacent carbon atoms by a $C_{3-6}$ alkylene bridge group wherein a methylene group is optionally replaced by an oxygen, —S—, —S(O)—, —SO$_2$— or —N(R$_6$)—;

or $R_1$ has the following structure:

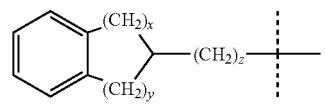

wherein x and y are independently 0, 1, 2, 3 or 4, provided that x+y is 2 to 4, z is 0, 1 or 2, and one or two CH$_2$ groups in the ring may optionally be replaced by —O—, —S—, —S(O)—, —SO$_2$— or —N(R$_6$);

wherein each $R_1$ group is optionally substituted by one or more of the following groups: $C_{1-6}$alkyl, $C_{3-6}$cycloalkyl, halogen, nitro, hydroxy, $C_{1-6}$alkyloxy, $C_{1-6}$alkylthio, aryl, aryl$C_{1-6}$alkyl, aryloxy, arylthio, aminosulfonyl, or amino optionally substituted by one or two $C_{1-6}$alkyl groups, wherein each aryl group is optionally substituted by one or more $C_{1-6}$alkyl, halogen, nitro, hydroxy or amino optionally substituted by one or two $C_{1-6}$alkyl groups, and wherein in each of the $C_{1-6}$alkyl groups a methylene group may optionally be replaced by —NHC(O)— or —C(O)NH—, and wherein each of the $C_{1-6}$alkyl groups is optionally substituted by one or more halogens;

$R_2$ is selected from the following groups:

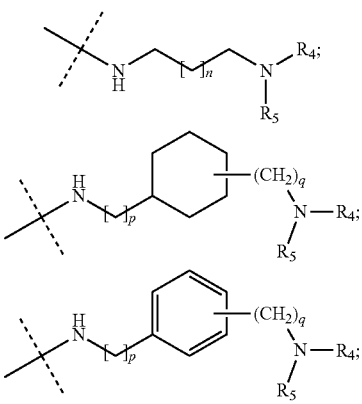

-continued

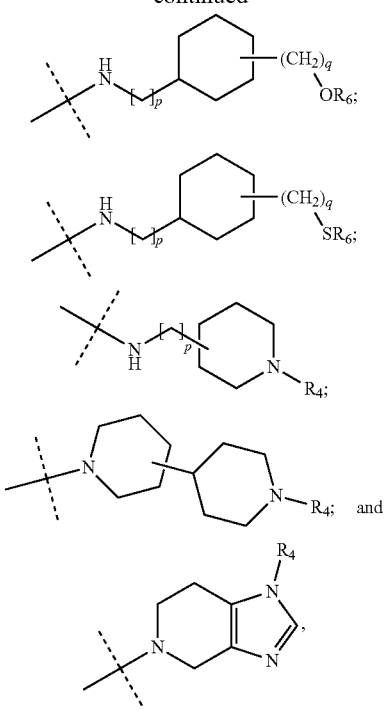

wherein:

n is an integer from 3 to 8;

p is an integer from 1 to 3;

q is an integer from 0 to 3;

$R_4$ and $R_5$ are each independently selected from hydrogen, $C_{1-6}$alkyl, aryl$C_{1-6}$alkyl, or amidino, wherein each aryl group is optionally substituted by one or more $C_{1-6}$alkyl, halogen, nitro, hydroxy or amino optionally substituted by one or two $C_{1-6}$alkyl groups, and wherein each of the $C_{1-6}$alkyl groups is optionally substituted by one or more halogens, and wherein the amidino is optionally substituted by one to three $C_{1-6}$alkyl;

$R_6$ is hydrogen or $C_{1-6}$alkyl;

wherein each R2 group is optionally substituted by one or more $C_{1-6}$alkyl, $C_{1-6}$alkoxy, CN, —OH, —NH$_2$ or halogen;

R3 is halogen, cyano, nitro, $C_{1-6}$alkyl, $C_{1-6}$alkyloxycarbonyl or aminocarbonyl, wherein each of the $C_{1-6}$alkyl groups is optionally substituted by one or more halogens;

or a tautomer, pharmaceutically acceptable salt, solvate, or amino-protected derivative thereof, In some embodiments of the pyrimidine derivative compounds of formula (XVIII):

$R_1$ is aryl-$C_{1-4}$alkyl or heteroaryl-$C_{1-4}$alkyl, wherein in each of the $C_{1-4}$alkyl groups a methylene group may optionally be replaced by —NHC(O)— or —C(O)NH—, and wherein each of the $C_{1-4}$alkyl groups is optionally substituted by an oxo group or one or more $C_{1-3}$alkyl groups wherein two alkyl substituents on the same carbon atom of a $C_{1-4}$alkyl group may optionally be combined to form a $C_{2-5}$ alkylene bridge, and wherein the aryl group is optionally substituted on adjacent carbon atoms by a $C_{3-6}$alkylene bridge group wherein a methylene group is optionally replaced by an oxygen, sulfur or —N($R_6$)—;

or $R_1$ has the following structure:

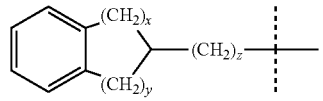

wherein x and y are independently 0, 1, 2 or 3, provided that x+y is 2 to 3, and z is 0 or 1;

wherein "heteroaryl" is defined as pyridyl, furyl, thienyl, pyrrolyl, imidazolyl, or indolyl;

wherein each $R_1$ group is optionally substituted by one or more of the following groups: $C_{1-6}$alkyl, Cl, Br, F, nitro, hydroxy, CF$_3$, —OCF$_3$, —OCF$_2$H, —SCF$_3$, $C_{1-4}$alkyloxy, $C_{1-4}$alkylthio, phenyl, benzyl, phenyloxy, phenylthio, aminosulfonyl, or amino optionally substituted by one or two $C_{1-3}$alkyl groups;

$R_2$ is selected from the following groups:

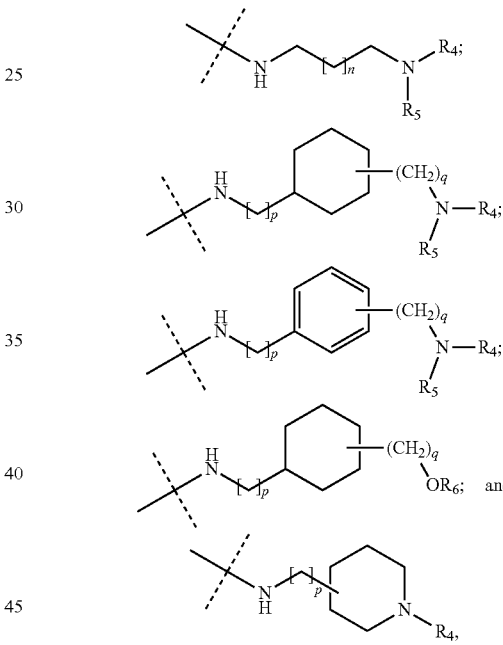

wherein:

n is an integer from 5 to 7;

p is an integer from 1 to 2;

q is an integer from 1 to 2;

$R_4$ and $R_5$ are each independently selected from hydrogen, $C_{1-6}$alkyl, aryl$C_{1-6}$alkyl, or amidino;

$R_6$ is hydrogen;

$R_3$ is Br, Cl, F, cyano or nitro;

or a tautomer, pharmaceutically acceptable salt, solvate, or amino-protected derivative thereof;

In other embodiments of the pyrimidine derivative compounds of formula (XVIII):

$R_1$ is phenyl-$C_{1-4}$alkyl or naphthyl$C_{1-2}$alkyl, wherein each $R_1$ group is optionally substituted by one or more of the following groups: methyl, Cl, Br, F, nitro, hydroxy, CF$_3$, —OCF$_3$, —SCF$_3$, $C_{1-4}$alkyloxy or $C_{1-4}$alkylthio;

$R_2$ is selected from the following groups:

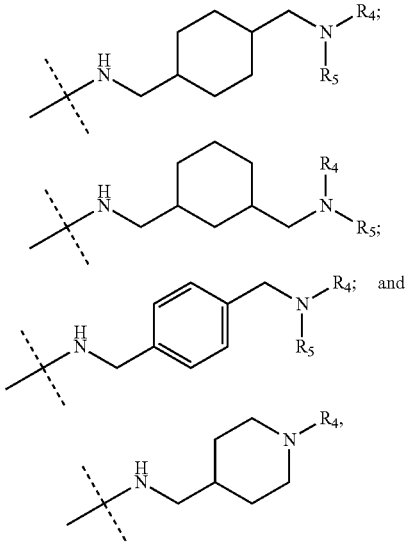

wherein:

$R_4$ and $R_5$ are each independently selected from hydrogen, $C_{1-3}$ alkyl, or amidino;

$R_3$ is Br, Cl, cyano or nitro;

or a tautomer, pharmaceutically acceptable salt, solvate, or amino-protected derivative thereof;

In still other embodiments of the pyrimidine derivative compounds of formula (XVIII):

$R_1$ is phenyl$CH_2$— wherein the phenyl group is optionally substituted by one or more of the following groups: methyl, Cl, Br, F, nitro, hydroxy, $CF_3$, —$OCF_3$, —$SCF_3$, $C_{1-4}$alkyloxy or $C_{1-4}$alkylthio;

$R_2$ is selected from the following groups:

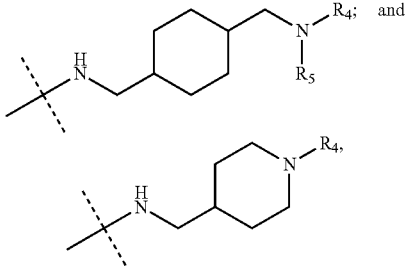

$R_3$ is nitro;

$R_4$ and $R_5$ are each independently selected from hydrogen, methyl, or amidino;

or a tautomer, pharmaceutically acceptable salt, solvate, or amino-protected derivative thereof.

Non-limiting examples of the pyrimidine derivative compounds of formula (XVIII) are selected from:

ethyl 4-({[4-(aminomethyl)cyclohexyl]methyl}amino)-2-[(2-chlorobenzyl)amino]pyrimidine-5-carboxylate; $N^4$-{[4-(aminomethyl)cyclohexyl]-methyl}-5-nitro-$N^2$-[(2R)-1,2,3,4-tetrahydronaphthal-en-2-yl]pyrimidine-2,4-diamine; $N^4$-{[4-(aminomethyl)cyclohexyl]methyl}-5-nitro-$N^2$-[(2S)-1,2,3,4-tetrahydronaphthalen-2-yl]pyrimidine-2,4-diamine; $N^4$-{[4-(aminomethyl)cyclohexyl]methyl}-5-nitro-$N^2$-[(1R)-1,2,3,4-tetrahydronaphthalen-1-yl]pyrimidine-2,4-diamine; $N^4$-{[4-(aminomethyl)cyclohexyl]-methyl}-5-nitro-$N^2$-[(1S)-1,2,3,4-tetrahydronaphthal-en-1-yl]pyrimidine-2,4-diamine; $N^4$-{[4-(aminomethyl)cyclohexyl]methyl}-$N^2$-[2-(4-chlorophenyl)ethyl]-5-nitropynmidine-2,4-diamine; $N^4$-{[4-(aminomethyl)cyclohexyl]methyl}-$N^2$-[2-(2-methylphenyl)ethyl]-5-nitropyrimidine-2,4-diamine; $N^4$-{[4-(aminomethyl)cyclohexyl]methyl}-$N^2$-[2-(3-methylphenyl)ethyl]-5-nitropyrimidine-2,4-diamine; $N^4$-{[4-(aminomethyl)cyclohexyl]methyl}-$N^2$-[2-(4-methylphenyl)ethyl]-5-nitropyrimidine-2,4-diamine; $N^4$-{[4-(aminomethyl)cyclohexyl]methyl}-$N^2$-[2-(2-fluorophenyl)ethyl]-5-nitropyrimidine-2,4-diamine; $N^4$-{[4-(aminomethyl)cyclohexyl]-methyl}-$N^2$-[2-(3-fluorophenyl)ethyl]-5-nitropyrimidine-2,4-diamine; $N^4$-{[4-(aminomethyl)cyclohexyl]methyl}-$N^2$-[2-(4-fluorophenyl)ethyl]-5-nitropyrimidine-2,4-diamine; $N^2$-(2-aminobenzyl)-$N^4$-{[4-(aminomethyl)cyclohexyl]methyl}-5-nitropyrimidine-2,4-diamine; $N^4$-{[4-(aminomethyl)cyclohexyl]m-ethyl}-$N^2$-(3,5-dimethoxybenzyl)-5-nitropyrimidine-2-,4-diamine; $N^4$-{[4-(aminomethyl)cyclohexthyl]methyl}-$N^2$-[3,5-bis(trifluoromethyl)benzyl]-5-nitropyrimidine-2,4-diamine; {3-[({2-[(2-chlorobenzyl)amino]-5-nitropyrimidin-4-yl}amino)methyl]phenyl}methane amine; 2-({[4-({[4-(aminomethyl)cyclohexyl]methyl}amino)-5-nitropyrimidin-2-yl]amino}methyl)phenol; $N^2$-(5-amino-2-chlorobenzyl)-$N^4$-{[4-(aminomethyl)cyclohexyl]methyl}-5-nitropynmidine-2,4-diamine; 4-({[4-(aminomethyl)cyclohexyl]methyl}amino)-2-[(2-chlorobenzyl)amino]pyrimidine-5-carboxamide; $N^4$-{[4-(aminomethyl)cyclohexyl]methyl}-$N^2$-(2-chlorobenzyl)-5-fluoropyrimidine-2,4-diamine; 3-({[4-({[4-(aminomethyl)cyclohexyl]methyl}amino)-5-nitropyrimidin-2-yl]amino}methyl)-N-[2-(2-methylphenyl)ethyl]benzamide; (1 S,2R)-2-({[4-({[4-(aminomethyl)cyclohexyl]methyl}amino)-5-nitropyrimidin-2-yl]amino}methyl)cyclohexanol; (1R,2R)-2-({[4-({[4-(aminomethyl)cyclohexyl]methyl}amino)-5-nitropyrimidin-2-yl]amino}methyl)cyclohexanol; methyl 4-({[4-(aminomethyl)cyclohexyl]methyl}amino)-2-[(2-chlorobenzyl)amino]pyrimidine-5-carboxylate; 4-{[4-({[4-(aminomethyl)cyclohexyl]methyl}amino)-5-nitropyrimidin-2-yl]amino}-N-[2-(2-methylphenyl)ethyl]butanamide; 5-{[4-({[4-(aminomethyl)cyclohexyl]methyl}amino)-5-nitropyrimidin-2-yl]amino}-N-[2-(2-methylphenyl)ethyl]pentanamide; 6-{[4-({[4-(aminomethyl)cyclohexyl]methyl}amino)-5-nitropyrimidin-2-yl]amino}-N-[2-(2-methylphenyl)ethyl]hexanamide; (1R,3R)-3-({[4-({[4-(aminomethyl)cyclohexyl]methyl}amino)-5-nitropyrimidin-2-yl]amino}methyl)-4,4-dimethylcyclohexanol; $N^4$-({4-cis-[(dimethyl-amino)methyl]cyclohexyl}methyl)-$N^2$-(1-naphthylmethyl)-5-nitropyrimidine-2,4-diamine; $N^2$-[2-(methylthio)benzyl]-5-nitro-$N^4$-(piperidin-4-ylmethyl)pyrimidine-2,4-diamine; 5-nitro-$N^4$-(piperidin-4-ylmethyl)-$N^2$-{2-[(trifluoromethyl)thio]benzyl}pyrimidine-2,4-diamine; $N^2$-(1-naphthylmethyl)-5-nitro-$N^4$-(piperidin-4-ylmethyl)pyrimidine-2,4-diamine; $N^4$-({4-[(dimethylamino)methyl]cyclohexyl}methyl)-$N^2$-[2-(methylthio)benzyl]-5-nitropyrimidine-2,4-diamine; $N^4$-({4-[(dimethylamino)methyl]cyclohexyl}methyl)-5-nitro-$N^2$-{2-[(trifluoromethyl)thio]benzyl}pyrimidine-2,4-diamine; $N^4$-({4-[(dimethylamino)methyl]cyclohexyl}methyl)-$N^2$-(1-naphthylmethyl)-5-nitropyrimidine-2,4-diamine; $N^4$-{4-[(dimethylamino)methyl]benzyl}-$N^2$-[2-(methylthio)benzyl]-5-nitropyrimidine-2,4-diamine; $N^4$-{4-[(dimethylamino)methyl]benzyl}-5-nitro-$N^2$-{2-

[(trifluoromethyl)thio]benzyl}pyrimidine-2,4-diamine; $N^4$-{4-[(dimethylamino)methyl]benzyl}-$N^2$-(1-naphtylmethyl)-5-nitropyrimidine-2,4-diamine; $N^4$-[(1-methylpiperidin-4-yl)methyl]-$N^2$-[2-(methylthio)benzyl]-5-nitropyrimidine-2-,4-diamine; $N^4$-[(1-methylpiperidin-4-yl)methyl]-5-nitro-$N^2$-{2-[(trifluoromethyl)thio]benzyl}pyrimidine-2,4-diamine; $N^4$-[(l-methylpiperidin-4-yl)methyl]-$N^2$-(1-naphtylmethyl)-5-nitropynmidine-2,4-diamine; $N^2$-(2-chlorobenzyl)-$N^4$-[(1-m-ethylpiperidin-4-yl)methyl]-5-nitropynmidine-2,4-diamine; $N^2$-(2-methoxybenzyl)-$N^4$-[(1-methylpiperidin-4-yl)methyl]-5-nitropyrimidine-2,4-diamine; $N^4$-{[4-(aminomethyl)cyclohexyl]methyl}-$N^2$-(2-methoxy benzyl)-5-nitropyrim-idine-2,4-diamine; $N^4$-{[4-(aminomethyl)cyclohexyl]methyl}-5-nitro-$N^2$-[2-(trifluoromethyl)benzyl]pyrimidine-2,4-diamine; $N^4$-{[4-(aminomethyl)cyclohexyl]methyl}-$N^2$-(2,4-dichlorobenzyl)-5-nitropyrimidine-2,4-diamine; $N^4$-{[4-(aminomethyl)cyclohexyl]methyl}-$N^2$-(3-methoxybenzyl)-5-nitropyrimidine-2,4-diamine; $N^4$-{[4-(aminomethyl)cyclohexyl]methyl}-$N^2$-[4-fluoro-2-(trifluoromethyl)benzyl]-5-nitropyrimidine-2,4-diamine; $N^4$-{[4-(aminomethyl)cyclohexyl]methyl}-$N^2$-(3-methylbenzyl)-5-nitropyrimidine-2,4-diamine; $N^4$-{[4-(aminomethyl)cyclohexyl]methyl}-5-nitro-$N^2$-(pyridin-2-ylmethyl)pyrimidine-2,4-diamine; $N^4$-{[4-(aminomethyl)cyclohexyl]methyl}-$N^2$-(3-chlorobenzyl)-5-nitropyrimidine-2,4-diamine; $N^4$-{[4-(aminomethyl)cyclohexyl]methyl}-$N^2$-(4-chlorobenzyl)-5-nitropyrimidine-2,4-diamine; $N^4$-{[4-(aminomethyl)cyclohexyl]methyl}-N-(4-bromobenzyl)-5-nitropyrimidine-2,4-diamine; $N^4$-{[4-(aminomethyl)cyclohexyl]methyl}-$N^2$-(2,4-dimethoxybenzyl)-5-nitropyrimidine-2,4-diamine; $N^4$-{[4-(aminomethyl)cyclohexyl]methyl}-N.s-up.2-[2-chloro-5-(trifluoromethyl)benzyl]-5-nitropyrimidine-2,4-diamine; $N^4$-{[4-(aminomethyl)cyclohexyl]methyl}-$N^2$-(2,5-dichlorobenzyl)-5-nitropyrimidine-2,4-diamine; $N^4$-{[4-(aminomethyl)cyclohexyl]methyl}-5-nitro-$N^2$-[2-(trifluoromethoxy)benzyl]pyrimidine-2,4-diamine; $N^4$-{[4-(aminomethyl)cyclohexyl]methyl}-$N^2$-(2-chloro-6-methylbenzyl)-5-nitropyrimidine-2,4-diamine; $N^4$-{[4-(aminomethyl)cyclohexyl]methyl}-$N^2$-(2,3-dichlorobenzyl)-5-nitropyrimidine-2,4-diamine; $N^4$-{[4-(aminomethyl)cyclohexyl]-methyl}-$N^2$-(2-furylmethyl)-5-nitropyrimidine-2,4-diamine; $N^4$-{[4-(aminomethyl)cyclohexyl]methyl}-5-nitro-$N^2$-(thien-2-ylmethyl)pyrimidine-2,4-diamine; $N^4$-{[4-(aminomethyl)cyclohexyl]methyl}-$N^2$-(2-chlorobenzyl)-5-methylpyrimidine-2,4-diamine; $N^4$-(6-aminohexyl)-$N^2$-(2-chlorobenzyl)-5-nitropyrimidine-2,4-diamine; N-[4-(aminomethyl)benzyl]-$N^2$-(2-chlorobenzyl)-5-nitropyrimidine-2,4-diamine; $N^4$-(7-aminoheptyl)-$N^2$-(2-chlorobenzyl)-5-nitropyrimidine-2,4-diamine; $N^4$-{[3-(aminomethyl)cyclohexyl]methyl}-$N^2$-(2-chlorobenzyl)-5-nitropyrimidine-2,4-diamine; $N^4$-{[4-(aminomethyl)cyclohexyl]methyl}-$N^2$-(1-methyl-1-phenylethyl)-5-nitropyrimidine-2,4-diamine; 4-(4,4'-bipiperidin-1-yl)-N-(2-chlorobenzyl)-5-nitropyrimidin-2-amine; $N^2$-(2-chlorobenzyl)-$N^4$-({4-[(dimethylamino)methyl]cyclohexyl}methyl)-5-nitropyri; $N^4$-{[4-(aminomethyl)cyclohexyl]m-ethyl}-$N^2$-(2,5-difluorobenzyl)-5-nitropyrimidine-2,-4-diamine; $N^4$-{[4-(aminomethyl-)cyclohexyl]methyl}-$N^2$-[4-(difluoromethoxy)benzyl]-5-nitropyrimidine-2,4-diamine; $N^4$-{[4-(aminomethyl)cyclohexyl]methyl}-$N^2$-(2-ethoxybenzyl)-5-nitropyrimidine-2,4-diamine; $N^4$-{[4-(aminomethyl)cyclohexyl]methyl}-5-nitro-$N^2$-[(1S)-1-phenylethyl]pyrimidine-2,4-diamine; $N^4$-{[4-(aminomethyl)cyclohexyl]methyl}-N.s-up.2-(2-methylbenzyl)-5-nitropyrimidine-2,4-diamine; $N^4$-{[4-(aminomethyl)cyclohexyl]methyl}-$N^2$-(2-fluorobenzyl)-5-nitropyrimidine-2,4-diamine; $N^4$-{[4-(aminomethyl)cyclohexyl]methyl}-$N^2$-(3-chloro-2-fluorobenzyl)-5-nitropyrimidine-2,4-diamine; $N^4$-{[4-(aminomethyl)cyclohexyl]methyl}-5-nitro-$N^2$-(4-pentylbenzyl)pyrimidine-2,4-diamine; $N^4$-{[4-(aminomethyl)cyclohexyl]methyl}-$N^2$-(4-butoxybenzyl)-5-nitropyrimidine-2,4-diamine; $N^4$-{[4-(aminomethyl)cyclohexyl]methyl}-$N^2$-(2,3-dimethoxybenzyl)-5-nitropynmidine-2,4-diamine; $N^4$-{[4-(aminomethyl)cyclohexyl]methyl}-$N^2$-(2,5-dimethoxybenzyl)-5-nitropyrimidine-2,4-diamine; $N^2$-(2-chlorobenzyl)-$N^4$-[7-(dimethylamino)heptyl]-5-nitropyrimidine-2,4-diamine; $N^4$-{[4-(aminomethyl)cyclohexyl]methyl}-$N^2$-(1,1'-biphenyl-2-ylmethyl)-5-nitropyrimidine-2,4-diamine; $N^4$-{[4-(aminomethyl)cyclohexyl]methyl}-$N^2$-(4-fluorobenzyl)-5-nitropyrimidine-2,4-diamine; $N^4$-{[4-(aminomethyl)cyclohexyl]methyl}-$N^2$-(2,4-difluorobenzyl)-5-nitropyrimidine-2,-4-diamine; $N^4$-{[4-(aminomethyl-)cyclohexyl]methyl}-$N^2$-(3-fluoro-4-methylbenzyl)-5-nitropyrimidine-2,4-diamine; $N^4$-{[4-(aminomethyl)cyclohexyl]methyl}-$N^2$-(2,3-difluorobenzyl)-5-nitropyrimidine-2,4-diamine; $N^4$-{[4-(aminomethyl)cyclohexyl]methyl}-5-bromo-$N^2$-(2-chlorobenzyl)pyrimidine-2,4-diamine; $N^4$-{[4-(aminomethyl)cyclohexyl]-methyl}-$N^2$-(2,6-dimethoxybenzyl)-5-nitropyrimidine-2,4-diamine; $N^4$-{[4-(aminomethyl)cyclohexyl]methyl}-$N^2$-(2,6-difluorobenzyl)-5-nitropyrimidine-2,4-diamine; $N^4$-{[4-(aminomethyl)cyclohexyl]methyl}-$N^2$-[2-fluor-o-3-(trifluoromethyl)benzyl]-5-nitropyrimidine-2,4-diamine; $N^4$-{[4-(aminomethyl)cyclohexyl]methyl}-$N^2$-(4-chloro-2-fluorobenzyl)-5-nitropyrimidine-2,4-diamine; $N^4$-{[4-(aminomethyl)cyclohexyl]methyl}-5-nitro-$N^2$-(1-phenylcyclopropyl)pyrimidine-2,4-diamine; $N^4$-{[4-(aminomethyl)cyclohexyl]methyl}-$N^2$-[l-(2-chlorophenyl)-1-methylethyl]-5-nitropyrimidine-2-,4-diamine; $N^4$-{[4-(aminomethyl)cyclohexyl]methyl}-$N^2$-(2,3-dihydro-1-benzofuran-5-ylmethyl)-5-nitropyrimidine-2,4-diamine; $N^4$-{[4-(aminomethyl)cyclohexyl]methyl}-$N^2$-[(1,5-dimethyl-1H-pyrrol-2-yl)methy l]-5-nitropyrimidine-2,4-diamine; $N^4$-{[4-(aminomethyl)cyclohexyl]methyl}-$N^2$-(2-bromobenzyl)-5-nitropyrimidine-2,4-diamine; $N^4$-{[4-(aminomethyl)cyclohexyl]methyl}-$N^2$-(2,3-dimethylbenzyl)-5-nitropyrimidine-2,4-diamine; $N^4$-{[4-(aminomethyl)cyclohexyl]methyl}-$N^2$-(2,4-dimethylbenzyl)-5-nitropyrimidine-2-,4-diamine; $N^4$-{[4-(aminomethyl)cyclohexyl]methyl}-$N^2$-(2,5-dimethylbenzyl)-5-nitropyrimidine-2,4-diamine; $2N^4$-{[4-(aminomethyl)cyclohexyl]methyl}-N2-[2-fluoro-5-(trifluoromethyl)benzyl[-5-nitropyrimidine-2,4-diamine; $N^4$-{[4-(aminomethyl)cyclohexyl]methyl}-N2-[2-(methylthio)benzyl]-5-nitropyrimidine-2,4-diamine; $N^4$-{[4-(aminomethyl)cyclohexyl]methyl}-5-nitro-$N^2$-{2-[(trifluoromethyl)thio]-benzyl}pyrimidine-2,4-diamine; $N^4$-{[4-(aminomethyl)cyclohexyl]methyl}-$N^2$-(3-fluorobenzyl)-5-nitropyrimidine-2,4-diamine; $N^4$-{[4-(aminomethyl)cyclohexyl]methyl}-$N^2$-(6-chloro-2-fluoro-3-methylbenzyl)-5-nitropyrimidine-2,4-diamine; $N^4$-{[4-(aminomethyl)cyclohexyl]methyl}-$N^2$-(2-chloro-6-fluoro-3-methylbenzyl)-5-nitropyrimidine-2,4-diamine; $N^4$-{[4-(aminomethyl)cyclohexyl]methyl}-$N^2$-2-naphthyl-5-nitropyrimidine-2,4-diamine; $N^4$-{[4-(aminomethyl)cyclohexyl]methyl}-$N^2$-(1-naphthylmethyl)-5-nitropyrimidine-2,4-diamine; $N^4$-{[4-(aminomethyl)cyclohexyl]methyl}-N $N^2$-[2-fluoro-4-(trifluoromethyl)benzyl]-5-nitropyrimidine-2,4-diamine; $N^4$-{[4-

(aminomethyl)cyclohexyl]methyl}-N$^2$-(4-chloro-2-methylbenzyl)-5-nitropyrimidine-2,4-diamine; N$^4$-{[4-(aminomethyl)cyclohexyl]meth-yl}-N$^2$-(5-chloro-2-)methylbenzyl)-5-nitropyrimidine-2,4-diamine; N$^4$-{[4-(aminomethyl)cyclohexyl]methyl}-N$^2$-(3-chloro-2-methylbenzyl)-5-nitropyrimidine-2,4-diamine; N$^4$-{[4-(aminomethyl)cyclohexyl]-methyl}-N$^2$-[5-fluoro-2-(trifluoromethyl)benzyl]-5-nitropyrimidine-2,4-diamine; N$^4$-{[4-(aminomethyl)cyclohexyl]methyl}-N$^2$-(-5-chloro-2-fluorobenzyl)-5-nitropyrimidin-e-2,4-diamine; N$^4$-{[4-(aminomethyl-)cyclohexyl]methyl}-N$^2$-(2,3-difluoro-4-methylbenzyl)-5-nitropyrimidine-2,4-diamine; N$^4$-{[4-(aminomethyl)cyclohexyl]methyl}-N$^2$-(-5-fluoro-2-methylbenzyl)-5-nitropyrimidin-e-2,4-diamine; N$^4$-{[4-(aminomethyl-)cyclohexyl]methyl}-N$^2$-1-naphthyl-5-nitropyrimidine-2,4-diamine; {4-trans-[({2-[(2-chlorobenzyl)amino]-5-nitropyrimidin-4-yl}amino)methyl]cyclohexyl}methanol; N$^4$-{[4-(aminomethyl)cyclohexyl]methyl}-5-bromo-N$^2$-(2,5-dichlorobenzyl)pyrimidine-2,4-diamine; N$^4$-{[4-(aminomethyl)cyclohexyl]methyl}-5-bromo-N$^2$-(2,4-dichlorobenzyl)pyrimidine-2,4-diamine; N$^4$-{[4-(aminomethyl)cyclohexyl]methyl}-5-bromo-N$^2$-(2-bromobenzyl)pyrimidine-2,4-diamine; N$^4$-{[4-(aminomethyl)cyclohexyl]methyl}-N.su-p.2-(cyclohexylmethyl)-5-nitropyrimidine-2,4-diamine; N$^4$-{[4-(aminomethyl)cyclohexyl]methyl}-N$^2$-(2-naphthylmethyl)-5-nitropyrimidine-2,4-diamine; N$^4$-{[4-(aminomethyl)cyclohexyl]methyl}-5-bromo-N$^2$-[2-(trifluoromethoxy)benzyl]pyrimidine-2,4-diamine; N$^4$-{[4-(aminomethyl)cyclohexyl]methyl}-5-bromo-N$^2$-[2-(trifluoromethyl)benzyl]pyrimidine-2,4-diamine; N$^4$-{[4-(aminomethyl)cyclohexyl]methyl}-N$^2$-[2-(difluoromethoxy)benzyl]-5-nitropyrimidine-2,4-diamine; N$^4$-{[4-(aminomethyl)cyclohexyl-]methyl}-N$^2$-[3-(difluoromethoxy)benzyl]-5-nitropyrimidine-2,4-diamine; N$^4$-{[4-(aminomethyl)cyclohexyl]methyl}-N$^2$-(-2-chloro-4-fluorobenzyl)-5-nitropyrimidine-2,4-diamine; N$^4$-{[4-(aminomethyl)-cyclohexyl]methyl}-N$^2$-(2-chloro-3,6-difluorobenzyl)-5-nitropyrimidine-2,4-diamine; N$^4$-{[4-(aminomethyl)cyclohexyl]methyl}-5-nitro-N$^2$-(2,3,5-trifluorobenzyl)pyrimidine-2,4-diamine; N$^4$-{[4-(aminomethyl)cyclohexyl]methyl}-5-nitro-N$^2$-(2,3,4,5-tetrafluorobenzyl)pyrimidine-2,4-diamine; N$^4$-{[4-(aminomethyl)cyclohexyl]methyl}-5-nitro-N$^2$-[(1R)-1-phenylethyl]pyrimidine-2,4-diamine; N$^4$-{[4-(aminomethyl)cyclohexyl]m-ethyl}-N$^2$-2,3-dihydro-1H-inden-2-yl-5-nitropyrimidine-2,4-diamine; N$^4$-{[4-(aminomethyl)cyclohexyl]methyl}-N$^2$-[(1 S)-2,3-dihydro-1H-inden-1-yl]-5-nitropyrimidine-2,4-diamine; N$^4$-{[4-(aminomethyl)cyclohexyl]methyl}-N$^2$-[(1R)-2,3-dihydro-1H-inden-1-yl]-5-nitropyrimidine-2,4-diamine; N$^4$-{[4-(aminomethyl)cyclohexyl]methyl}-N$^2$-(4-chloro-1-naphthyl)-5-nitropyrimidine-2,4-diamine; N$^4$-{[4-(aminomethyl)cyclohexyl]methyl}-N$^2$-(4-methoxy-2-naphthyl)-5-nitropyrimidine-2,4-diamine; N$^4$-{[4-(aminomethyl)cyclohexyl]methyl}-5-nitro-N$^2$-quinohn-6-ylpyrimidine-2,4-diamine; N$^4$-{[4-trans-(aminomethyl)cyclohexyl]methyl}-N$^2$-(2,5-dichlorobenzyl)-5-nitropyrimidine-2,4-diamine; N$^4$-{[4-trans-(aminomethyl)cyclohexyl]methyl}-N$^2$-(2,3-dichlorobenzyl)-5-nitropyrimidine-2,4-diamine; N$^4$-{[4-(aminomethyl)cyclohexyl]methyl}-N$^2$-[2-(2-chlorophenyl)ethyl]-5-nitropyrimidine-2,4-diamine; N$^4$-{[4-(aminomethyl)cyclohexyl]methyl}-N$^2$-[2-(3-chlorophenyl)ethyl]-5-nitropyrimidine-2,4-diamine; N$^4$-{[4-(aminomethyl)cyclohexyl]methyl}-N$^2$-(2-chloro-6-phenoxybenzyl)-5-nitropyrimidine-2,4-di-amine; N$^4$-{[4-(aminomethyl)cyclohexyl]methyl}-5-bromo-N$^2$-2-naphthylpyrimidine-2,4-diamine; N$^4$-{[4-(aminomethyl)cyclohexyl]methyl}-5-bromo-N$^2$-(1-naphthylmethyl)pyrimidine-2,4-diamine; N$^4$-{[4-(aminomethyl)cyclohexyl]methyl}-5-nitro-N$^2$-(pyridin-3-ylmethyl)pyrimidine-2,4-diamine; 4-({[4-(aminomethyl)cyclohexyl]methyl}amino)-2-[(2-chlorobenzyl)amino]pyrimidine-5-carbonitrile; N$^4$-{[4-(aminomethyl)cyclohexyl]methyl}-N$^2$-[4-(dimethylamino)benzyl]-5-nitropyrimidine-2,4-diamine; N$^4$-{[4-trans-(aminomethyl)cyclohexyl]methyl}-N$^2$-(2-bromobenzyl)-5-nitropyrimidine-2,4-diamine; N$^4$-(7-aminoheptyl)-N$^2$-(2-bromobenzyl-)-5-nitropyrimidine-2,4-diamine; N$^4$-(7-aminoheptyl)-N$^2$-(2,5-dichlorobenzyl)-5-nitropyrimidine-2,4-diamine; N-({4-[({2-[(2-chlorobenzyl)amino]-5-nitropyrimidin-4-yl}amino)methyl]cyclohexyl}methyl-)guanidine; N$^2$-(3-aminobenzyl)-M-{-[4-(aminomethyl)cyclohexyl]methyl}-5-nitro-pyrimidine-2,4-diamine; N$^4$-{[4-(aminomethyl)cyclohexyl]methyl}-5-nitro-N$^2$-(2-nitrobenzyl)pyrimidine-2,4-diamine; N$^4$-{[4-(aminomethyl)cyclohexyl]methyl}-N$^2$-[-2-(2-bromophenyl)ethyl]-5-nitropyrimidine-2,4-diamine; N$^4$-{[4-(aminomethyl)cyclohexyl]methyl}-N$^2$-(2-bromobenzyl)-5-chloropyrimidine-2,4-diamine; (4-{[(2-{[2-(1H-indol-3-yl)ethyl]amino}-5-nitropyrimidin-)4-yl)amino]methyl}cyclohexyl)methanaminium chloride; N-({3-[({2-[(2-chlorobenzyl)amino]-5-nitropyrimidin-4-yl}aminomethyl]cyclohexyl}methylguanidine; 3-({[4-({[4-(aminomethyl)cyclohexyl]methyl}amino)-5-nitropyrimidin-2-yl]amino}methy 1)phenol; (4-{[(2-{[2-(1H-imidazol-4-yl)ethyl]amino}-5-nitropyrimidin-4-yl)amino]methyl}cyclohexyl)-methanaminium chloride; N$^2$-(2-chlorobenzyl)-M-({4-cis-[(dimethylamino)methyl]cyclohexyl}methyl)-5-nitropyrimidine-2,4-diamine; N$^4$-{[4-(aminomethyl)cyclohexyl]methyl}-5-chloro-N$^2$-(2-chlorobenzyl)pyrimidine-2,4-diamine; N$^2$-(2-chlorobenzyl)-5-nitro-N$^4$-(piperidin-4-ylmethyl)pyrimidine-2,4-diamine; N$^4$-{[4-(aminomethyl)cyclohexyl]meth-yl}-5-nitro-N$^2$-(2-phenylethyl)pyrimidine-2,4-diamine; N$^4$-{[4-(aminomethyl)cyclohexyl]methyl}-5-nitro-N$^2$-(3-phenylpropyl)pyrimidine-2,4-diamine; N$^4$-{[4-(aminomethyl)cyclohexyl]methyl}-5-nitro-N-$^2$-(4-phenylbutyl)pyrimidine-2,4-diamine; N$^4$-{[4-(aminomethyl)(cyclohexyl-]methyl}-5-nitro-N$^2$-(2-phenylpropyl)pyrimidine-2,4-diamine; N$^4$-{[4-(aminomethyl)cyclohexyl]methyl}-N$^2$-[2-(4-methoxyphenyl)ethyl]-5-nitropyrimidine-2,4-diamine; N$^4$-{[4-(aminomethyl)cyclohexyl]methyl}-N$^2$-[2-(3-methoxyphenyl)ethyl]-5-nitropyrimidine-2,4-diamine; N$^4$-{[4-(aminomethyl)cyclohexyl]methyl}-N$^2$-[2-(2-methoxyphenyl)ethyl]-5-nitropyrimidine-2,4-diamine; 4-[({2-[(2-chlorobenzyl)amino]-5-nitropyrimidin-4-yl}amino)methyl]piperidine-1-carboximidamide; N$^4$-{[4-(aminomethyl)cyclohexyl]methyl}-N$^2$-(3,5-dichlorobenzyl)-5-nitropyrimidine-2,4-diamine; N$^4$-(5-aminopentyl)-N2-(2-chlorobenzyl)-5-nitropyrimidine-2,4-diamine; 2-(benzylamino)-4-(1,4,6,7-tetrahydro-imidazo[4,5-c]pyridin-5-yl)-5-trifluoromethyl-pyrimidine; 2-(4-chlorobenzylamino)-4-(1,4,6,7-tetrahydro-imidazo[4,5-c]pyridin-5-yl)-5-nitro-pyrimidine; 2-(2-chlorobenzylamino)-4-(1,4,6,7-tetrahydro-imidazo[4,5-c]pyridin-5-yl)-5-nitro-pyrimidine; 2-(benzylamino)-4-(1,4,6,7-tetrahydro-imidazo[4,5-c]pyridin-5-yl)-5-nitro-pyrimidine; or N$^4$-{[trans-4-(aminomethyl)cyclohexyl]methyl}-5-nitro-N$^2$-[2-(trifluoromethoxy)benzyl]pyrimidine-2,4-diamine.

In some embodiments, the pyrimidine derivative compounds of formula (XVIII) is selected from:

N$^4$-{[4-(aminomethyl)cyclohexyl]methyl}-5-nitro-N$^2$-[(2R)-1,2,3,4-tetrahydronaphthalen-2-yl]pyrimidine-2,4-diamine; N⁴-{[4-(aminomethyl)cyclohexyl]methyl}-N²-[2-(4-chlorophenyl)ethyl]-5-nitropyrimidine-2,4-diamine; N⁴-{[4-(aminomethyl)cyclohexyl]methyl}-N²-[2-(3-methylphenyl)ethyl]-5-nitropyrimidine-2,4-diamine; N⁴-{[4-(aminomethyl-)cyclohexyl[methyl]-N²-[2-(4-methylphenyl)ethyl]-5-nitropyrimidine-2,4-diamine; N⁴-{[4-(aminomethyl)cyclohexyl]methyl}-N²-[2-(3-fluorophenyl)ethyl]-5-nitropyrimidine-2,4-diamine; N⁴-{[4-(aminomethyl)cyclohexyl]methyl}-N²-[2-(4-fluorophenyl)ethyl]-5-nitropyrimidine-2,4-diamine; (1R,3R)-3-({[4-({[4-(aminomethyl)cyclohexyl]methyl}amino)-5-nitropyrimidin-2-yl]amino}methyl)-4,4-dimethylcyclohexanol; N⁴-({4-cis-[(dimethylamino)methyl]cyclohexyl}methyl)-N²-(1-naphthylmethyl)-5-nitropyrimidine-2,4-diamine; N²-[2-(methylthio)benzyl]-5-nitro-N⁴-(piperidin-4-ylmethyl)pyrimidine-2,4-diamine; 5-nitro-N⁴-(piperidin-4-ylmethyl)-N²-{-2-[(trifluoromethyl)thio]benzyl}pyrimidine-2,4-diamine; N²-(1-naphthylmethyl)-5-nitro-N⁴-(piperidin-4-ylmethyl)pyrimidine-2,4-diamine; N⁴-({4-[(dimethylamino)methyl]cyclohexyl}methyl-)-N²-[2-(methylthio)benzyl]-5-nitropyrimidine-2,4-diamine; N⁴-({4-[(dimethylamino)methyl]cyclohexyl}methyl)-5-nitro-N²-{2-[(trifluoromethyl)thio]benzyl}pyrimidine-2,4-diamine; N⁴-({4-[(dimethylamino)methyl]cyclohexyl}methyl)-N²-(1-naphthyl-methyl)-5-nitropyrimidine-2,4-diamine; N⁴-{4-[(dimethylamino)methyl]benzyl}-N²-[2-(methylthio)benzyl]-5-nitropyrimidine-2,4-diamine; N⁴-{4-[(dimethylamino)methyl]benzyl}-5-nitro-N²-{2-[(trifluoromethyl)thio]benzyl}pyrimidine-2,4-diamine; N⁴-[(1-methylpiperidin-4-yl)methyl]-N²-[2-(methylthio)benzyl]-5-nitropyrimidine-2,4-diamine; N⁴-[(1-methylpiperidin-4-yl)methyl]-5-nitro-N²-{2-[(trifluoromethyl)thio]benzyl}pyrimidine-2,4-diamine; N⁴-{[4-(aminomethyl)cyclohexyl]methyl}-N²-(2-methoxybenzyl)-5-nitropyrimidine-2,4-diamine; N⁴-{[4-(aminomethyl)cyclohexyl]methyl}-5-nitro-N²-[2-(trifluoromethyl)benzyl]pyrimidine-2,4-diamine; N⁴-{[4-(aminomethyl)cyclohexyl]methyl}-N²-(2,-dichlorobenzyl)-5-nitropyrimidine-2,4-diamine; N⁴-{[4-(aminomethyl)cyclohexyl]methyl}-N²-[4-fluoro-2-(trifluoromethyl)benzyl]-5-nitropyrimidine-2,4-diamine; N⁴-{[4-(aminomethyl)cyclohexyl]methyl}-N²-(3-methylbenzyl)-5-nitropyrimidine-2,4-diamine; N⁴-{[4-(aminomethyl)cyclohexyl]methyl}-N²-(3-chlorobenzyl)-5-nitropyrimidine-2,4-diamine; N⁴-{[4-(aminomethyl)cyclohexyl]methyl}-N²-(4-bromobenzyl-)-5-nitropyrimidine-2,4-diamine; N⁴-{[4-(aminomethyl)cyclohexyl]methyl}-N²-[2-chloro-5-(trifluoromethyl)benzyl]-5-nitropyrimidine-2,4-diamine; N⁴-{[4-(aminomethyl)cyclohexyl]methyl}-N²-(2,5-dichlorobenzyl)-5-nitropyrimidine-2,4-diamine; N⁴-{[4-(aminomethyl)cyclohexyl]methyl}-5-nitro-N²-[2-(trifluoromethoxy)benzyl]pyrimidine-2,4-diamine; N⁴-{[4-(aminomethyl)cyclohexyl]methyl}-N²-(2-chloro-6-methylbenzyl)-5-nitropyrimidine-2,4-diamine; N⁴-{[4-(aminomethyl-)cyclohexyl]methyl}-N²-(2,3-dichlorobenzyl)-5-nitropyrimidine-2,4-diamine; N⁴-{[3-(aminomethyl)cyclohexyl]methyl}-N²-(2-chlorobenzyl)-5-nitropyrimidine-2,4-diamine; N²-(2-chlorobenzyl)-N⁴-({4-[(dimethylamino)methyl]cyclohexyl}methyl)-5-nitropyrimidine-2,4-diamine; N⁴-{[4-(aminomethyl)cyclohexyl]methyl}-N²-(2,5-difluorobenzyl)-5-nitropyrimidine-2,4-diamine; N⁴-{[4-(aminomethyl)cyclohexyl]methyl}-N²-(-2-ethoxy benzyl)-5-nitropyrimidine-2,4-diamine; N⁴-{[4-(aminomethyl)cyclohexyl]methyl}-N²-(2-methylbenzyl)-5-nitropyrimidine-2,4-diamine; N⁴-{[4-(aminomethyl)cyclohexyl]methyl}-N²-(2-fluorobenzyl)-5-nitropyrimidine-2,4-diamine; N⁴-{[4-(aminomethyl)cyclohexyl]methyl}-N²-(3-chloro-2-fluorobenzyl)-5-nitropyrimidine-2,4-diamine; N⁴-{[4-(aminomethyl)cyclohexyl]methyl}-N²-(1,1'-biphenyl-2-yl methyl)-5-nitropyrimidine-2,4-diamine; N⁴-{[4-(aminomethyl)cyclohexyl]methyl}-N²-(2,4-difluorobenzyl)-5-nitropyrimidine-2,4-diamine; N⁴-{[4-(aminomethyl)cyclohexyl]methyl}-N²-(-2,3-difluorobenzyl)-5-nitropyrimidine-2,4-diamine; N⁴-{[4-(aminomethyl)cyclohexyl]methyl}-N²-(2,6-difluorobenzyl)-5-nitropyrimidine-2,4-diamine; N⁴-{[4-(aminomethyl)cyclohexyl]methyl}-N²-[2-fluoro-3-(trifluoromethyl)benzyl]-5-nitropyrimidine-2,4-diamine; N⁴-{[4-(aminomethyl)cyclohexyl]methyl}-N²-(4-chloro-2-fluorobenzyl)-5-nitropyrimidine-2,4-diamine; N⁴-{[4-(aminomethyl)cyclohexyl]methyl}-N²-(2-bromobenzyl)-5-nitropyrimidine-2,4-diamine; N⁴-{[4-(aminomethyl-)cyclohexyl]methyl}-N²-(2,3-dimethylbenzyl)-5-nitropyrimidine-2,4-diamine; N⁴-{[4-(aminomethyl)cyclohexyl]methyl}-N²-[2-(methylthio)benzyl]-5-nitropyrimidine-2,4-diamine; N⁴-{[4-(aminomethyl)cyclohexyl]methyl}-5-nitro-N²-{2-[(trifluoromethyl)thio]benzyl}pyrimidine-2,4-diamine; N⁴-{[4-(aminomethyl)cyclohexyl]methyl}-N²-(3-fluorobenzyl)-5-nitropyrimidine-2,4-diamine; N⁴-{[4-(aminomethyl)cyclohexyl]methyl}-N²-(6-chloro-2-fluoro-3-methylbenzyl)-5-nitropyrimidine-2,4-diamine; N⁴-{[4-(aminomethyl)cyclohexyl]methyl}-N²-(2-chloro-6-fluoro-3-methylbenzyl)-5-nitropyrimidine-2,4-diamine; N⁴-{[4-(aminomethyl)cyclohexyl]methyl}-N²-2-naphthyl-5-nitropyrimidine-2,4-diamine; N⁴-{[4-(aminomethyl)cyclohexyl]methyl}-N²-(1-naphthylmethyl)-5-nitropyrimidine-2,4-diamine; N⁴-{[4-(aminomethyl)cyclohexyl]methyl}-N²-(4-chloro-2-methylbenzyl)-5-nitropyrimidine-2,4-diamine; N⁴-{[4-(aminomethyl)cyclohexyl]methyl}-N²-(5-chloro-2-methylbenzyl)-5-nitropyrimidine-2,4-diamine; N⁴-{[4-(aminomethyl)cyclohexyl]methyl}-N²-(3-chloro-2-methylbenzyl)-5-nitropyrimidine-2,4-diamine; N⁴-{[4-(aminomethyl)cyclohexyl]methyl}-N²-[5-fluoro-2-(trifluoromethyl)benzyl]-5-nitropyrimidine-2,4-diamine; N⁴-{[4-(aminomethyl)cyclohexyl]methyl}-N²-(5-chloro-2-fluorobenzyl)-5-nitropyrimidine-2,4-diamine; N⁴-{[4-(aminomethyl-)cyclohexyl]methyl}-N²-(2,3-difluoro-4-methylbenzyl)-5-nitropyrimidine-2,4-diamine; N⁴-{[4-(aminomethyl)cyclohexyl]methyl}-N²-(5-fluoro-2-methylbenzyl)-5-nitropyrimidine-2,4-diamine; N⁴-{[4-(aminomethyl)cyclohexyl]methyl}-5-bromo-N²-(2,-5-dichlorobenzyl)pyrimidine-2,4-diamine; N⁴-{[4-(aminomethyl)cyclohexyl]methyl}-5-bromo-N²-(2-bromobenzy-1)pyrimidine-2,4-diamine; N⁴-{[4-(aminomethyl)cyclohexyl]methyl}-N²-(cyclohexylmethyl)-5-nitropyrimidine-2,4-diamine; N⁴-{[4-(aminomethyl)cyclohexyl]methyl}-5-bromo-N²-[2-(trifluoromethyl)benzyl]pyrimidine-2,4-diamine; N⁴-{[4-(aminomethyl)cyclohexyl]methyl}-N²-[2-(difluoromethoxy)benzyl]-5-nitropyrimidine-2,4-diamine; N⁴-{[4-(aminomethyl)cyclohexyl]methyl}-N²-(2-chloro-4-fluorobenzyl)-5-nitropyrimidine-2,4-diamine; N⁴-{[4-(aminomethyl-)cyclohexyl]methyl}-N²-(2-chloro-3,6-difluorobenzyl)-5-nitropyrimidine-2,4-diamine; N⁴-{[4-(aminomethyl)cyclohexyl]methyl}-5-nitro-N²-(2,3,5-trifluorobenzyl)pyrimidine-2,4-diamine; N⁴-{[4-(aminomethyl)cyclohexyl]methyl}-N²-2,-3-dihydro-1H-inden-2-yl-5-nitropyrimidine-2,4-diamine; N⁴-{[4-(aminomethyl)cyclohexyl]methyl}-N²-(4-chloro-1-naphthyl)-5-nitropyrimidine-2,4-diamine;

N⁴-{[4-(aminomethyl)cyclohexyl]methyl}-N²-(4-methoxy-2-naphthyl)-5-nitropyrimidine-2,4-diamine; N⁴-{[4-(aminomethyl)cyclohexyl]methyl}-5-nitro-N²-quinolin-6-ylpyrimidine-2,4-diamine; N⁴-{[4-trans-(aminomethyl)cyclohexyl]methyl}-N²-(2,3-dichlorobenzyl)-5-nitropyrimidine-2,4-diamine; N⁴-{[4-(aminomethyl)cyclohexyl]methyl}-N²-[2-(2-chlorophenyl)ethyl]-5-nitropyrimidine-2,4-diamine; N⁴-{[4-(aminomethyl)cyclohexyl]methyl}-N²-[2-(3-chlorophenyl)ethyl]-5-nitropyrimidine-2,4-diamine; N⁴-{[4-(aminomethyl)cyclohexyl]methyl}-5-bromo-N²-2-naphthylpyrimidine-2,4-diamine; 4-({[4-(aminomethyl)cyclohexyl]methyl}amino)-2-[(2-chlorobenzyl)amino]pyrimidine-5-carbonitrile; N⁴-{[4-trans-(aminomethyl)cyclohexyl]methyl}-N²-(2-bromobenzyl)-5-nitropyrimidine-2,4-diamine; N⁴-(7-aminoheptyl)-N²-(2-bromobenzyl)-5-nitropyrimidine-2,4-diamine; N⁴-(7-aminoheptyl)-N²-(2,5-dichlorobenzyl)-5-nitropyrimidine-2,4-diamine; N-({4-[({2-[(2-chlorobenzyl)amino]-5-nitropyrimidin-4-yl}aminomethyl]cyclohexyl}methyl)guanidine; N⁴-{[4-(aminomethyl)cyclohexyl]methyl}-5-nitro-N²-(2-nitrobenzy-1)pyrimidine-2,4-diamine; N⁴-{[4-(aminomethyl)cyclohexyl]methyl}-N²-[2-(2-bromophenyl)ethyl]-5-nitropyrimidine-2,4-diamine; N⁴-{[4-(aminomethyl)cyclohexyl]methyl}-N²-(2-bromobenzyl)-5-chloropyrimidine-2,4-diamine; N-({3-[({2-[(2-chlorobenzyl)amino]-5-nitropyrimidin-4-yl}amino)methyl]cyclohexyl}methylguanidine 3-({[4-({[4-(aminomethyl)cyclohexyl]methyl}amino)-5-nitropyrimidin-2-yl]amino}methyl)phenol; N²-(2-chlorobenzyl)-N⁴-({4-cis-[(dimethylamino)methyl]cyclohexyl}methyl)-5-nitropyrimidine-2,4-diamine; N²-(2-chlorobenzyl)-5-nitro-N⁴-(piperidin-4-ylmethyl)pyrimidine-2,4-diamine; N⁴-{[4-(aminomethyl)cyclohexyl]methyl}-5-nitro-N²-(2-phenylethy-1)pyrimidine-2,4-diamine; N⁴-{[4-(aminomethyl)cyclohexyl]methyl}-5-nitro-N²-(4-phenylbutyl)pyrimidine-2,4-diamine; or N⁴-{[trans-4-(aminomethyl)cyclohexyl]methyl}-5-nitro-N²-[2-(trifluoromethoxy)-benzyl]pyrimidine-2,4-diamine.

In yet other embodiments, the pyrimidine derivative compounds of formula (XVIII) are selected from:

N⁴-({4-[(dimethylamino)methyl]cyclohexyl}methyl)-N²-(1-naphthylmethyl)-5-nitropyrimidine-2,4-diamine; N²-[2-(methylthio)benzyl]-5-nitro-N⁴-(piperidin-4-ylmethyl)pyrimidine-2,4-diamine; 5-nitro-N⁴-(piperidin-4-ylmethyl)-N²-{-2-[(trifluoromethyl)thio]benzyl}pyrimidine-2,4-diamine; N²-(1-naphthylmethyl)-5-nitro-N⁴-(piperidin-4-ylmethyl)pyrimidine-2,4-diamine; N⁴-({4-[(dimethylamino)methyl]cyclohexyl}methyl-)-N²-[2-(methylthio)benzyl]-5-nitropyrimidine-2,4-diamine; N⁴-({4-[(dimethylamino)methyl]cyclohexyl}methyl)-5-nitro-N²-{2-[(trifluoromethyl)thio]benzyl}pyrimidine-2,4-diamine; N⁴-({4-[(dimethylamino)methyl]cyclohexyl}methyl)-N²-(1-naphthyl-methyl)-5-nitropyrimidine-2,4-diamine; N⁴-{4-[(dimethylamino)methyl]benzyl}-N²-[2-(methylthio)benzyl]-5-nitropyrimidine-2,4-diamine; N⁴-{4-[(dimethylamino)methyl]benzyl}-5-nitro-N²-{2-[(trifluoromethyl)thio]benzyl}pyrimidine-2,4-diamine; N⁴-[(l-methylpiperidin-4-yl)methyl]-N²-[2-(methylthio)benzyl]-5-nitropyrimidine-2,4-diamine; N⁴-[(l-methylpiperidin-4-yl)methyl]-5-nitro-N²-{2-[(trifluoromethyl)thio]benzyl}pyrimidine-2,4-diamine; N⁴-{[4-(aminomethyl)cyclohexyl]methyl}-N²-(2-methoxybenzyl)-5-nitropyrimidine-2,4-diamine; N⁴-{[4-(aminomethyl)cyclohexyl]methyl}-5-nitro-N²-[2-(trifluoromethoxy)benzyl]pyrimidine-2,4-diamine; N⁴-{[4-(aminomethyl)cyclohexyl]-methyl}-N²-(2,3-dichlorobenzyl)-5-nitropyrimidine-2,4-diamine; N⁴-{[3-(aminomethyl)cyclohexyl]methyl}-N²-(2-chlorobenzy-1)-5-nitropyrimidine-2,4-diamine; N²-(2-chlorobenzyl)-N-⁴-({4-[(dimethylamino)methyl]cyclohexyl}methyl)-5-nitropyrimidine-2,4-diamine; N⁴-{[4-(aminomethyl)cyclohexyl]methyl}-N²-(2-bromobenzyl)-5-nitropyrimidine-2,4-diamine; N⁴-{[4-(aminomethyl)cyclohexyl]methyl}-N²-[2-(methylthio)benzyl-]-5-nitropyrimidine-2,4-diamine; N⁴-{[4-(aminomethyl)cyclohexyl]methyl}-5-nitro-N²-{2-[(trifluoromethyl)thio]benzyl}-pyrimidine-2,4-diamine; N⁴-{[4-(aminomethyl)cyclohexyl]methyl}-N²-(1-naphtylmethyl)-5-nitropyrimidine-2,4-diamine; N⁴-{[4-(aminomethyl)cyclohexyl]methyl}-N²-(2,3-dichlorobenzyl)-5-nitropyrimidine-2,4-diamine; N⁴-{[4-(aminomethyl)cyclohexyl]methyl}-N²-(2-bromobenzyl)-5-nitropyrimidine-2,4-diamine; N²-(2-chlorobenzyl)-5-nitro-N⁴-(piperidin-4-ylmethyl)pyrimidine-2,4-diamine; or N⁴-{[trans-4-(aminomethyl)cyclohexyl]methyl}-5-nitro-N²-[2-(trifluoromethoxy)-benzyl]pyrimidine-2,4-diamine.

Alternative PKC-6 inhibitor pyrimidine derivatives include the compounds described by Barbosa et al. in US Publication No. 2010/0318929, which is incorporated herein by reference in its entirety. These compounds are represented by formula (XIX):

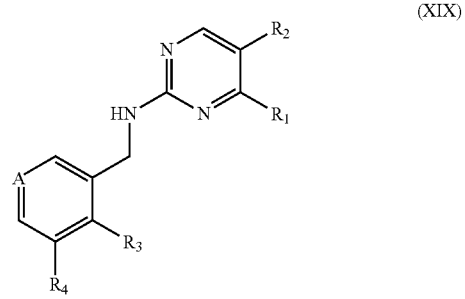

(XIX)

$R_1$ is selected from the following groups:

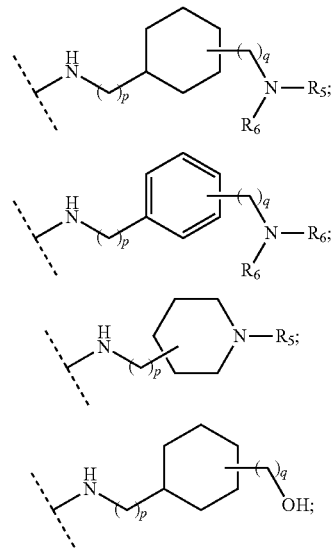

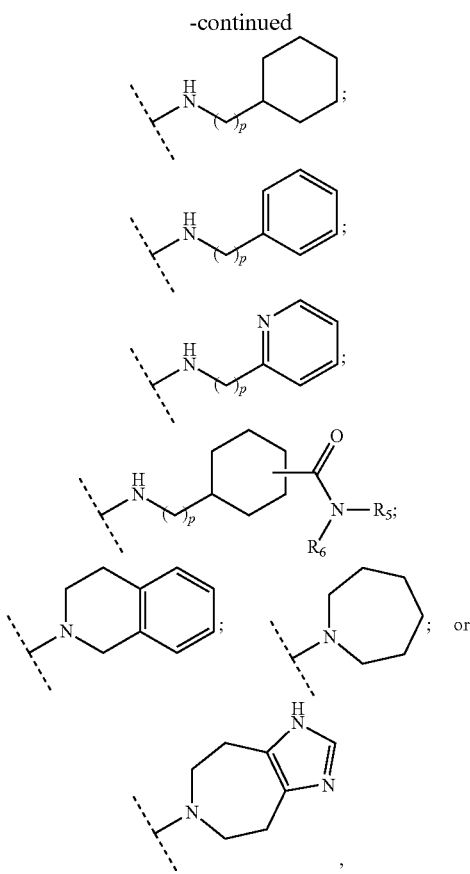

wherein: p is 1, 2 or 3; q is 0 or 1, $R_5$, $R_6$ are each independently selected from: (A) hydrogen, (B) $C_{1-6}$alkyl, or wherein $R_5$ and $R_6$ together constitute a methylene bridge which together with the nitrogen atom between them forms a four to six-membered ring wherein one of the methylene groups is optionally replaced by an oxygen or nitrogen atom, and which ring is optionally and independently substituted by one or more of the following groups: (i) $C_{1-6}$alkyl (ii) $COR_7$, wherein $R_7$ is: (a) $C_{1-6}$alkyl, (b) $C_{1-6}$alkyloxy, (C) $C_{1-6}$alkylcarbonyl, (D) $C_{1-6}$alkylsulfonyl, (E) —$CONR_8R_9$, wherein $R_8$ and $R_9$ are each independently selected from: (i) hydrogen (ii) $C_{1-6}$alkyl; $R_2$ is selected from the following groups: (F) $CF_3$, (G) cyano, (H) $CONH_2$ (I) halogen, or (J) nitro; $R_3$ is selected from the following groups: (A) hydrogen, (B) $C_{1-6}$alkyl, which is optionally substituted with halogen, (C) $C_{1-6}$alkyloxy, which is optionally substituted with halogen, (D) halogen, $R_4$ is selected from the following groups: (A) heteroaryl, which is optionally substituted with $C_{1-6}$alkyl; (B) aryl or heteroaryl, which is substituted with one or more of the following groups: (i) $C_{1-6}$alkyl, which is substituted with hydroxyl, oxo, or $NR_{10}R_{11}$, wherein $R_{10}$ and $R_{11}$ are each independently selected from the following groups: (a) hydrogen, (b) $C_{1-6}$alkyl, which is optionally substituted with hydroxyl or $CONH_2$, (c) $C_{1-6}$alkylcarbonyl, which is optionally substituted with one or more halogens, (d) $C_{1-6}$alkylsulfonyl, (e) or wherein $R_{10}$ and $R_{11}$ constitute a methylene bridge which together with the nitrogen atom between them forms a four to six-membered ring, (ii) $CONR_{12}R_{13}$, wherein $R_{12}$ and $R_{13}$ are each independently selected from hydrogen or $C_{1-6}$alkyl, (iii) $SO_2NR_{12}R_{13}$, wherein $R_{12}$ and $R_{13}$ are each independently selected from hydrogen or $C_{1-6}$alkyl, (C)—$NR_{14}R_{15}$, wherein $R_{14}$ and $R_{15}$ are each independently selected from: (i) $C_{1-6}$alkylcarbonyl, which is substituted with amino, (ii) or wherein $R_{14}$ and $R_{15}$ constitute a methylene bridge which together with the nitrogen atom between them forms a four to seven-membered ring, wherein one of the methylene groups is substituted with $C_{1-6}$alkyl, and wherein each $C_{1-6}$alkyl is optionally substituted with hydroxyl or $NR_{10}R_{11}$, wherein $R_{10}$ and $R_{11}$ are as defined previously, (D)-$CONR_{16}R_{17}$, wherein $R_{16}$ and $R_{17}$ are each independently selected from: (i) $C_{1-6}$alkyl, which is substituted with hydroxyl or $NR_{18}R_{19}$, wherein $R_{18}$ and $R_{19}$ are each independently selected from hydrogen or $C_{1-6}$alkyl, or wherein $R_{18}$ and $R_{19}$ constitute a methylene bridge which together with the nitrogen atom between them forms a four to six-membered ring, wherein one of the methylene groups is optionally replaced by an oxygen; (E) $C_6$alkynyl group optionally substituted by amino, $C_{1-3}$alkylamino, or di-($C_{1-3}$alkyl)amino; and A is independently selected from carbon or nitrogen; or a tautomer, pharmaceutically acceptable salt, solvate or amino-protected derivative thereof.

In illustrative examples of this type: $R_1$ is selected from the following groups:

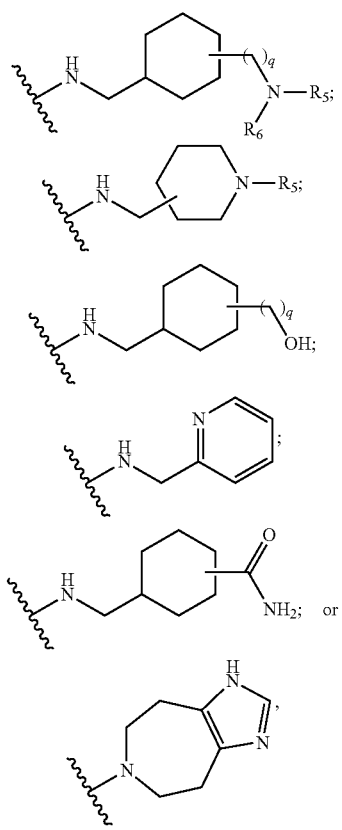

wherein: q is 0 or 1, $R_5$, $R_6$ are each independently selected from: (A) hydrogen, (B) or wherein $R_5$ and $R_6$ together constitute a methylene bridge which together with the nitrogen atom between them forms a five to six-membered ring wherein one of the methylene groups is optionally replaced by a nitrogen atom, and which ring is optionally and independently substituted by one or more of the following groups: (iv) $C_{1-6}$alkyl (v) $COR_7$, wherein $R_7$ is $C_{1-6}$alkyloxy, (C) $C_{1-6}$alkylcarbonyl (D) $C_{1-6}$alkylsulfonyl; $R_2$ is selected from the following groups: (A) cyano, or (B)

nitro; R₃ is selected from the following groups: (A) C₁₋₃alkyl, (B) C₁₋₃alkyloxy, which is optionally substituted with fluorine, (C) halogen; R₄ is selected from the following groups: (A) aryl, which is substituted with one or more of the following groups: (i) C₁₋₃alkyl, which is substituted with hydroxyl or NR₂₀R₂₁, wherein R₂₀ and R₂₁ are each independently selected from the following groups: (f) hydrogen, (g) C₁₋₃alkyl, which is optionally substituted with hydroxyl or CONH₂, (h) or wherein R₂₀ and R₂₁ constitute a methylene bridge which together with the nitrogen atom between them forms a five to six-membered ring, (ii) CONH₂ (iii) SO₂NH₂, (B) 3-pyridyl, which is optionally substituted with C₁₋₃alkyl, wherein each alkyl group is optionally substituted with amino, (C) —NR₂₂R₂₃, wherein R₂₂ and R₂₃ constitute a methylene bridge which together with the nitrogen atom between them forms a five to six-membered ring, wherein one of the methylene groups is substituted with C₁₋₃alkyl, and wherein each C₁₋₃alkyl is optionally substituted with OH or NR₂₀R₂₁, where R₂₀ and R₂₁ are as defined previously, (D) —CONR₂₄R₂₅, wherein R₂₄ and R₂₅ are each independently selected from: (i) C₁₋₃alkyl, which is substituted with C₁₋₃alkylamino; and A is independently selected from carbon or nitrogen; or a tautomer, pharmaceutically acceptable salt, solvate or amino-protected derivative thereof.

In other illustrative examples, the compounds of formula (XIX) are represented by formula (XIXa):

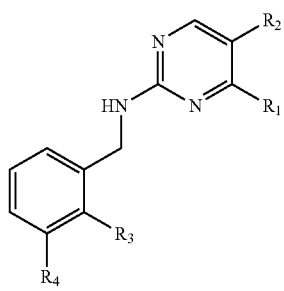

(XIXa)

wherein:

R₁ is selected from the following groups:

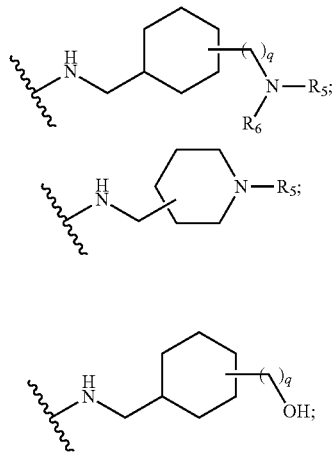

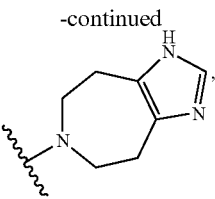

wherein: q is 0 or 1 R₅, R₆ are each independently selected from: (A) hydrogen, (B) C₁₋₆alkylcarbonyl, (C) C₁₋₆alkylsulfonyl; R₂ is selected from the following groups: (A) cyano, or (B) nitro; R₃ is selected from the following groups: (A) CH₃, (B) OCF₃, (C) Cl; R₄ is selected from the following groups:

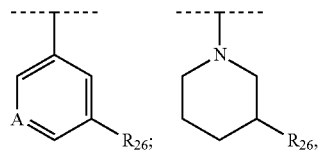

wherein: R₂₆ is selected from the following groups: (A) C₁₋₃alkyl, which is substituted with hydroxyl or NR₂₇R₂₅, wherein R₂₇ and R₂₅ are each independently selected from the following groups: (i) hydrogen, (ii) C₁₋₃alkyl, which is optionally substituted with hydroxyl or CONH₂, (B) CONH₂ (C) SO₂NH₂; and A is carbon or nitrogen; or a tautomer, pharmaceutically acceptable salt, solvate or amino-protected derivative thereof.

Also contemplated as small molecule PKC-θ inhibitors are aniline compounds as described for example by Ajioka et al. in US Publication No. 2010/0120869, which is incorporated herein by reference in its entirety. Representative compounds of this type are represented by formula (XX):

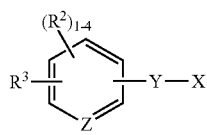

(XX)

wherein X of formula XX is aryl or heteroaryl, each substituted with 1-5 R¹ groups. Y of formula XX is —O—, —S(O)ₙ—, —N(R⁴)— and —C(R⁴)₂—, wherein subscript n is 0-2. Z of formula XX is —N= or —CH=. Each R¹ of formula XX is independently from the group consisting of H, halogen, C₁₋₆ alkyl, C₁₋₆ heteroalkyl, C₁₋₆ haloalkyl, C₂₋₆ alkenyl, C₂₋₆ alkynyl, C₁₋₆ haloalkoxy, —OR¹ᵃ, —C(O)R¹ᵃ, —C(O)OR¹ᵃ, —C(O)NR¹ᵃR¹ᵇ, —NR¹ᵃR¹ᵇ, —SR¹ᵃ, —N(R¹ᵃ)C(O)R¹ᵇ, —N(R¹ᵃ)C(O)OR¹ᵇ, —N(R¹ᵃ)C(O)NR¹ᵃR¹ᵇ, —OP(O)(OR¹ᵃ)₂, —S(O)₂OR¹ᵃ, —S(O)₂NR¹ᵃR¹ᵇ, —S(O)₂—C₁₋₆ haloalkyl, —CN, cycloalkyl, heterocycloalkyl, aryl or heteroaryl. Each of R¹ᵃ and R¹ᵇ of formula XX is independently H or C₁₋₆ alkyl. Each R² of formula XX is independently H, halogen, C₁₋₆ alkyl, C₁₋₆ haloalkyl, C₂₋₆ alkenyl, C₂₋₆ alkynyl, —NR¹ᵃR¹ᵇ, —NR¹ᵃC(O)—C₁₋₆ alkyl, —NR¹ᵃC(O)—C₁₋₆ is haloalkyl, —NR¹ᵃ—(CH₂)—NR¹ᵃR¹ᵇ, —NR¹ᵃ—C(O)—NR¹ᵃR¹ᵇ, or —NR¹ᵃ—C(O)OR¹ᵃ, alternatively, adjacent R¹ groups and adjacent R² groups can be combined to form a cycloalkyl, heterocycloalkyl, aryl or heteroaryl. R³ of formula XX is —NR³ᵃR³ᵇ or —NCO. Each of R³ᵃ and R³ᵇ of formula XX are independently H, $C_{1-6}$ alkyl, —C(O)—$C_{1-6}$ alkyl, —C(O)—$C_{1-6}$ haloalkyl, —(CH$_2$)—NR$^{1a}$R$^{1b}$, —C(O)—NR$^{1a}$R$^{1b}$, —C(O)OR$^{1a}$, —C(S)CN, an amino acid residue, a peptide or an oligopeptide. Each R$^4$ of formula XX is independently H or $C_{1-6}$ alkyl, or when more than one R$^4$ group is attached to the same atom, the R$^4$ groups are optionally combined to form a $C_{5-8}$ cycloalkyl. The compounds of formula XX also include the salts, hydrates and prodrugs thereof.

In some embodiments, the aniline compounds of formula XX are represented by formula XXa:

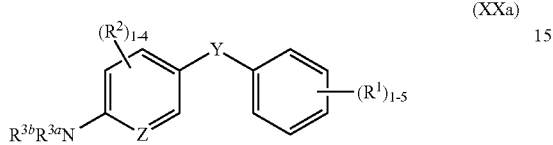

(XXa)

wherein each R$^1$ of formula XXa is independently H, halogen, $C_{1-8}$ alkyl, $C_{1-6}$ heteroalkyl, $C_{1-6}$ haloalkyl, $C_{2-6}$ alkenyl, $C_{2-6}$ alkynyl, $C_{1-6}$ haloalkoxy, —OR$^{1a}$, —CN, cycloalkyl, heterocycloalkyl, aryl or heteroaryl, and each of R$^{3a}$ and R$^{3b}$ of formula XXa are independently H, —C(O)—$C_{1-6}$ alkyl, an amino acid residue, a peptide or an oligopeptide.

In still other embodiments, each R$^1$ of formula XXa is independently H, halogen, $C_{1-6}$ alkyl, $C_{1-6}$ haloalkyl, $C_{1-6}$ haloalkoxy, —C(O)OR$^{1a}$, cycloalkyl, or heteroaryl. Furthermore, each R$^2$ of formula XXa is independently H, halogen, or —NR$^{1a}$C(O)—$C_{1-6}$, alkyl. In yet other embodiments, each R$^1$ of formula XXa is independently H, methyl, n-propyl, isopropyl, t-butyl, t-pentyl, Cl, Br, CF$_3$, OCF$_3$, cyclopentyl, pyrrolyl, or CO$_2$H, and each R$^2$ is independently H or Cl. In other embodiments, R$^{3a}$ of formula XX is an amino acid residue, and R$^{3b}$ is H. Suitably, the amino acid residue is an arginine residue.

In still other embodiments, the aniline compounds of formula XX have the formula XXb:

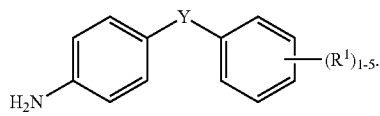

In some other embodiments, Y of formula XXb is S. In still other embodiments, Y of formula XXb is O. In some embodiments, each R$^1$ of formula XXb is independently H, methyl, n-propyl, isopropyl, t-butyl, t-pentyl, Cl, Br, CF$_3$, OCF$_3$, cyclopentyl, pyrrolyl, or CO$_2$H. In yet other embodiments, each R$^1$ of formula XXb is independently $C_{1-8}$ alkyl or cycloalkyl. In still yet other embodiments, each R$^1$ of formula XXb is independently 4-t-butyl, 4-cyclopentyl or 4-t-pentyl.

In other embodiments, small molecule PKC-θ inhibitors are selected from rottlerin (also known as mallotoxin or 1-[6-[(3-acetyl-2,4,6-trihydroxy-5-methylphenyl)methyl]-5,7-dihydroxy-2,2-dimethyl-2H-1-benzopyran-8-yl]-3-phenyl-2-propen-1-one, available from Calbiochem, San Diego, Calif.) having formula (XXI), or a derivative or analogue thereof.

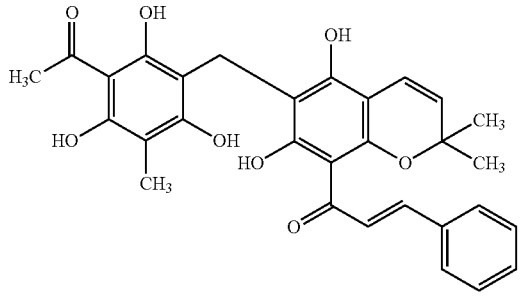

(XXI)

In still other embodiments, small molecule PKC-θ inhibitors include substituted diaminopyrimidines as disclosed for example by Baudler in US Patent Application Publication US 2005/0222186 A1, which is incorporated herein by reference in its entirety. These compounds are represented by formula (XXII):

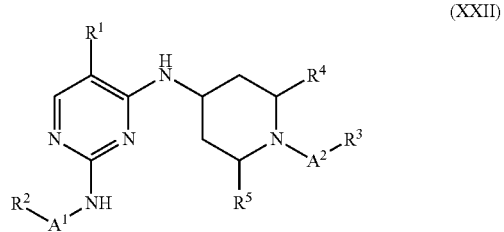

(XXII)

wherein R$^1$, R$^2$ and R$^3$ are independently selected from the group consisting of substituted or unsubstituted phenyl, naphthyl, pyrrolyl, pyrazolyl, imidazolyl, 1,2,3-triazolyl, indolyl, benzimidazolyl, furanyl(furyl), benzofuranyl(benzofuryl), thiophenyl(thienyl), benzothiophenyl(benzothienyl), thiazolyl, isoxazolyl, pyridinyl, pyrimidinyl, quinolinyl and isoquinolinyl; R$^4$ is hydrogen or methyl; R$^5$ is hydrogen or methyl; A$^1$ is $C_{1-3}$ alkylene or ethyleneoxy (—CH$_2$—CH$_2$—O—); and A$^2$ is $C_{1-3}$ alkylene or ethyleneoxy (—CH$_2$—CH$_2$—O—); and hydrates, solvates, salts, or esters thereof.

Non-limiting examples of such compounds include [1-benzyl(4-piperidyl)]{2-[(2-pyridylmethyl)amino]-5-(3-thienyl)pyrimidin-4-yl}amine; (5-(4-methoxyphenyl)-2-[(4-pyridylmethyl)amino)pyrimidin-4-yl}[1-benzyl-(-4-piperidyl)]amine; {5-phenyl-2-[(4-pyridylmethyl)amino)pyrimidin-4-yl}[1-benzyl(4-piperidy-1-)]amine; {5-(4-chlorophenyl)-2-[(4-pyridylmethyl)amino)pyrimidin-4-yl}[1-benzyl(4-piperidyl)]amine; {5-(4-(N,N-dimethylamino)phenyl)-2-[(4-pyridylmethyl)amino)pyrimidin-4-yl-}[1-benzyl(4-piperidyl)]amine; (5-(phenyl-4-carboxamido)-2-[(4-pyridylmethyl)amino)pyrimidin-4-yl) [1-benzyl(4-piperidyl)]-amine; (5-(4-carboxyphenyl)-2-[(4-pyridylmethyl)amino)pyrimidin-4-yl) [1-benzyl-(-4-piperidyl)]amine; {5-(2-thienyl)-2-[(4-pyridylmethyl)amino)pyrimidin-4-yl}[1-benzyl(4-piperidyl)]amine; {5-(2-furanyl)-2-[(4-pyridylmethyl)amino)pyrimidin-4-yl}[1-benzyl(4-piperidyl)]amine; {5-(3-furanyl)-2-[(4-pyridylmethyl)amino)pyrimidin-4-yl}[1-benzyl(4-piperidyl)]amine; N(4)-(1-benzyl-piperidin-4-yl)-5-(3-chloro-4-fluoro-phenyl)-N(2)-pyridin-2-ylmethyl-pyrimidine-2,4-diamine; N-(3-[4-(1-benzyl-piperidin-4-ylamino)-2-[(pyridin-2-ylmethyl)-amino]-pyrimidin-5- yl}phenyl)-acetamide; 3-[4-(1-benzyl-piperidin-4-ylamino)-2-[(pyridin-2-ylmethyl)-amino]-pyrimidin-5-yl]-phenol; and 4-{4-(1-benzyl piperidin-4-ylamino)-2-[(pyridin-2-ylmethyl)-amino]-pyrimidin-5-yl}N,N-dimethyl-benzamide.

In still other embodiments, small molecule PKC-θ inhibitors are selected from substituted pyridine compounds as disclosed for example by Brunette in US Patent Application Publication US 2006/0217417, which is incorporated herein by reference in its entirety. These compounds are represented by formula (XXIII):

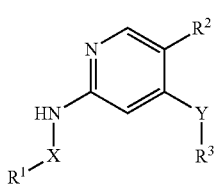
(XXIII)

wherein X is a bond or C1-6 substituted or unsubstituted alkyl wherein one or two of the methylene units can be replaced by an oxygen or sulfur atom; Y is —NH—, —O— or —S—; $R^1$ is a C34 substituted or unsubstituted cycloalkyl, substituted or unsubstituted aryl or substituted or unsubstituted heteroaryl; $R^2$ is selected from the following group consisting of trifluoromethyl, cyano, —$CONH_2$, halogen, and nitro; and $R^3$ is

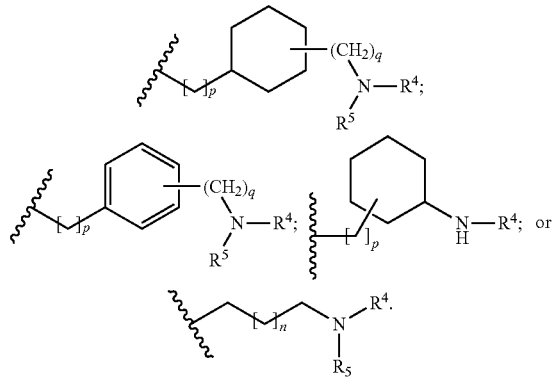

wherein p is an integer from 1 to 3, inclusive; q is an integer from 0 to 3, inclusive; n is an integer from 0 to 5, inclusive; $R^4$ and $R^5$ are each independently selected from the group consisting of hydrogen, $C_{1-6}$ substituted or unsubstituted alkyl, or wherein $R^4$ and $R^5$ together constitute methylene bridges which together with the nitrogen atom between them form a four to six-membered substituted or unsubstituted ring wherein one of the methylene groups is optionally replaced by an oxygen, sulfur or NR group, wherein R is hydrogen or C1-6 substituted or unsubstituted alkyl; tautomers; and pharmaceutically acceptable salts, solvates or amino-protected derivatives thereof.

Non-limiting examples of the compounds having formula (XXIII) include 5-nitro-N4-piperidin-4-ylmethyl-N2-(2-trifluoromethoxy-benzyl)-pyridine-2-,4-diamine; N2-(2,3-dichloro-benzyl)-5-nitro-N4-piperidin-4-ylmethyl-pyridine-2,4-diamine; N2-[2-(3-chloro-phenyl)-ethyl]-5-nitro-N4-piperidin-4-ylmethyl-pyridine-2,4-diamine; 5-nitro-N2-phenethyl-N4-piperidin-4-ylmethyl-pyridine-2,4-diamine; N4-(4-aminomethyl-cyclohexylmethyl)-5-nitro-N2-(2-trifluoromethoxy-benzyl-)-pyridine-2,4-diamine; N4-(4-aminomethyl-cyclohexylmethyl)-N2-(2,3-dichloro-benzyl)-5-nitro-pyri-dine-2,4-diamine; N4-(4-aminomethyl-cyclohexylmethyl)-5-nitro-N2-phenethyl-pyridine-2,4-diamine; N4-(4-aminomethyl-cyclohexylmethyl)-N2-[2-(3-chloro-phenyl)-ethyl]-5-nitro-1-pyridine-2,4-diamine; N4-(4-aminomethyl-cyclohexylmethyl)-5-nitro-N2-(2-chloro-benzyl)-pyridine-2,4-diamine; N4-(4-trans-aminomethyl-cyclohexylmethyl)-5-nitro-N-2-(2-trifluoromethoxy-benzyl)-pyridine-2,4-diamine; N4-(4-trans-amino-cyclohexylmethyl)-5-nitro-N2-(2-trifluoromethoxy-benzyl-)-pyridine-2,4-diamine; 4-[(4-aminomethyl-cyclohexylmethyl)-amino]-6-(2-chloro-benzylamino)-nicotinamide; and 4-[(4-aminomethyl-cyclohexylmethyl)-amino]-6-(2-chloro-benzylamino)-nicotinonitrile.

In still other embodiments, small molecule PKC-θ inhibitors are selected from indolyl-pyrroledione derivatives as disclosed for example by Auberson in US Patent Application Publication US 2007/0142401, which is incorporated herein by reference in its entirety. These compounds are represented by formula (XXIV):

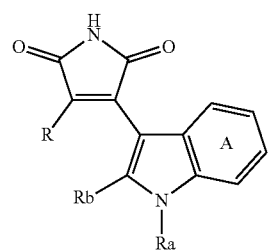
(XXIV)

wherein $R_a$ is H; $C_{1-4}$alkyl; or $C_{1-4}$alkyl substituted by OH, $NH_2$, $NHC_{1-4}$alkyl or $N(di-C_{1-4}alkyl)_2$;

$R_b$ is H; or $C_{1-4}$alkyl;

R is a radical of formula (a), (b), (c), (d), (e) or (f)

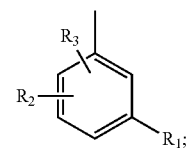
(a)

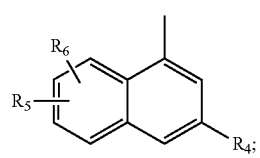
(b)

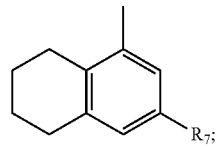
(c)

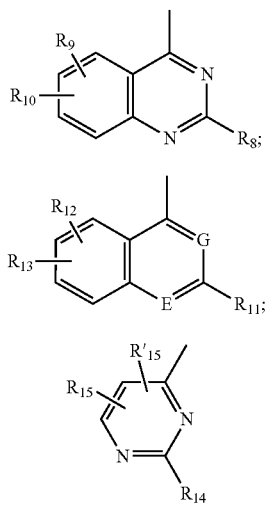

wherein each of $R_1$, $R_4$, $R_7$, $R_8$, $R_{11}$ and $R_{14}$ is OH; SH; a heterocyclic residue; $NR_{16}R_{17}$ wherein each of $R_{16}$ and $R_{17}$, independently, is H or $C_{1-4}$alkyl or $R_{16}$ and $R_{17}$ form together with the nitrogen atom to which they are bound a heterocyclic residue; or a radical of formula α-X—$R_c$—Y (α) wherein X is a direct bond, O, S or $NR_{18}$ wherein $R_{18}$ is H or $C_{1-4}$alkyl, $R_c$ is $C_{1-4}$alkylene or $C_{1-4}$alkylene wherein one $CH_2$ is replaced by $CR_xR_y$ wherein one of $R_x$ and $R_y$ is H and the other is $CH_3$, each of $R_x$ and $R_y$ is $CH_3$ or $R_x$ and $R_y$ form together —$CH_2$—$CH_2$—, and Y is bound to the terminal carbon atom and is selected from OH, a heterocyclic residue and —$NR_{19}R_{20}$ wherein each of $R_{19}$ and $R_{20}$ independently is H, $C_{3-6}$cycloalkyl, $C_{3-6}$cycloalkyl-$C_{1-4}$alkyl, aryl-$C_{1-4}$alkyl or $C_{1-4}$alkyl optionally substituted on the terminal carbon atom by OH, or $R_{19}$ and $R_{20}$ form together with the nitrogen atom to which they are bound a heterocyclic residue;

each of $R_2$, $R_3$, $R_5$, $R_6$, $R_9$, $R_{10}$, $R_{12}$, $R_{13}$, $R_{15}$ and $R'_{15}$, independently, is H, halogen, $C_{1-4}$alkyl, $CF_3$, OH, SH, $NH_2$, $C_{1-4}$alkoxy, $C_{1-4}$alkylthio, $NHC_{1-4}$alkyl, $N(di-C_{1-4}alkyl)_2$ or CN;

either E is —N═ and G is —CH═ or E is —CH═ and G is —N═; and ring A is optionally substituted, or a salt thereof.

In illustrative examples, the heterocyclic residue as $R_1$, $R_4$, $R_7$, $R_8$, $R_{11}$, $R_{14}$ or Y or formed, respectively, by $NR_{16}R_{17}$ or $NR_{19}R_{20}$, is a three to eight membered saturated, unsaturated or aromatic heterocyclic ring comprising 1 or 2 heteroatoms, and optionally substituted on one or more ring carbon atoms and/or on a ring nitrogen atom when present.

In specific embodiments, the heterocyclic residue is $R_1$, $R_4$, $R_7$, $R_8$, $R_{11}$, $R_{14}$ or Y or formed, respectively, by $NR_{16}R_{17}$ or $NR_{19}R_{20}$, is a residue of formula (γ).

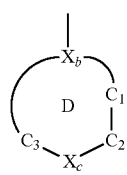

(γ)

wherein the ring D is a 5, 6 or 7 membered saturated, unsaturated or aromatic ring;

$X_b$ is —N—, —C— or —CH—;

$X_c$ is —N═, —$NR_f$—, —$CR_f$═ or —$CHR_f$— wherein $R_f$ is a substituent for a ring nitrogen atom and is selected from $C_{1-6}$alkyl; acyl; $C_{3-6}$cycloalkyl; $C_{3-6}$cycloalkyl-$C_{1-4}$alkyl; phenyl; phenyl-$C_{1-4}$alkyl;

a heterocyclic residue; and a residue of formula β-$R_{21}$—Y' (β)

wherein $R_{21}$ is $C_{1-4}$alkylene or $C_{2-4}$alkylene interrupted by O and Y' is OH, $NH_2$, $NH(C_{1-4}alkyl)$ or $N(C_{1-4}alkyl)_2$; and $R_{f'}$ is a substituent for a ring carbon atom and is selected from $C_{1-4}$alkyl;

$C_3$-cycloalkyl optionally further substituted by $C_{1-4}$alkyl;

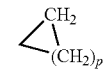

wherein p is 1, 2 or 3; $CF_3$;

halogen; OH; $NH_2$; —$CH_2$—$NH_2$; —$CH_2$—OH; piperidin-1-yl; and pyrrolidinyl;

the bond between $C_1$ and $C_2$ is either saturated or unsaturated;

each of $C_1$ and $C_2$, independently, is a carbon atom which is optionally substituted by one or two substituents selected among those indicated above for a ring carbon atom; and the line between $C_3$ and $X_b$ and between $C_1$ and $X_b$, respectively, represents the number of carbon atoms as required to obtain a 5, 6 or 7 membered ring D.

In other non-limiting examples of compounds according to formula (XXIV)

Ra is H; $CH_3$; $CH_2$—$CH_3$; or isopropyl,

Rb is H; halogen; $C_{1-6}$alkoxy; or $C_{1-6}$alkyl, and either

I. R is a radical of formula (a)

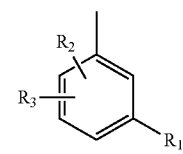

(a)

wherein $R_1$ is piperazin-1-yl optionally substituted by $CH_3$ in position 3 or 4; or 4,7-diaza-spiro [2.5] oct-7-yl; $R_2$ is Cl; Br; $CF_3$; or $CH_3$; and $R_3$ is H; $CH_3$; or $CF_3$; $R_3$ being other than H when Ra is H or $CH_3$, $R_b$ is H and $R_1$ is 4-methyl-1-piperazinyl; or II. R is a radical of formula (b)

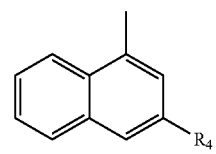

(b)

wherein R4 is piperazin-1-yl substituted in positions 3 and/or 4 by $CH_3$; or 4,7-diaza-spiro [2.5] oct-7-yl; Ra being other than H or $CH_3$ when $R_4$ is 4-methyl-1-piperazinyl; or III. R is a residue of formula (c)

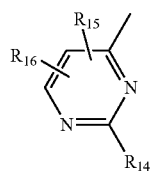

wherein R14 is piperazin-1-yl optionally substituted by $CH_3$ in position 3 and/or 4 or in position 3 by ethyl, phenyl-$C_{1-4}$alkyl, $C_{1-4}$alkoxy-$C_{1-4}$alkyl or halogeno-$C_{1-4}$alkyl; or 4,7-diaza-spiro [2.5] oct-7-yl; $R_{15}$ is halogen; $CF_3$; or $CH_3$; $R_{15}$ being other than $CH_3$ when Ra is H or $CH_3$, $R_b$ is H and $R_{14}$ is 4-methyl-1-piperazinyl; and R16 is H; $CH_3$; or $CF_3$; $R_{16}$ being other than H when $R_{15}$ is Cl, Ra is H or $CH_3$, $R_b$ is H and $R_{14}$ is 4-methyl-1-piperazinyl; or IV. R is a radical of formula (d)

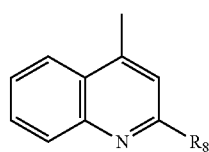

wherein $R_8$ is piperazin-1-yl, 3-methyl-piperazin-1-yl or 4-benzyl-piperazin-1-yl; or V. R is a radical of formula (e)

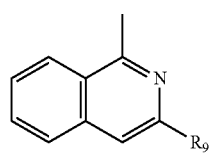

wherein $R_9$ is 4,7-diaza-spiro [2.5] oct-7-yl; or piperazin-1-yl substituted in position 3 by methyl or ethyl and optionally in position 4 by methyl.

In some embodiments of compounds according to formula (XXIV)

when R is of formula (a)

$R_1$ is -(4-methyl-piperazin-1-yl), 1-piperazinyl, 3-methyl-piperazin-1-yl or -(4,7-diaza-spiro[2.5]oct-7-yl)

$R_2$ is 2-Cl or 2-$CH_3$ $R_3$ is 3-$CH_3$, 3-$CF_3$ or H $R_a$ is H or $CH_3$ and when, R is of formula (b)

$R_4$ is -(4,7-diaza-spiro[2.5]oct-7-yl), 3-methyl-piperazin-1-yl or 4-methyl-3-methyl-piperazin-1-yl $R_a$ is H or $CH_3$ and when R is of formula (c)

$R_{14}$ is -4-methyl-piperazin-1-yl, 3-methyl-piperazin-1-yl, -4,7-diaza-spiro[2.5]oct-7-yl, 1-piperazinyl, 4-methyl-3-methyl-piperazin-yl, 3-methoxyethyl-piperazin-1-yl, 3-ethyl-piperazin-1-yl, 3-benzyl-piperazin-1-yl or 3-$CH_2$F-piperazin-1-yl $R_{15}$ is Cl, Br, $CF_3$, F $R_{16}$ is $CH_3$, H, $CH_2$—$CH_3$ $R_a$ is H or $CH_3$ $R_b$ is H, $CH_2$—$CH_2$—$CH_3$, F, $CH(CH_3)_2$, Cl, $OCH_3$, $CH_3$ or $CH_2$—$CH_3$ and when R is of formula (d)

$R_a$ is 3-methyl-piperazin-1-yl, 4-benzyl-1-piperazinyl or 1-piperazinyl $R_a$ is $CH_3$ or H and when R is of formula (e)

$R_9$ is -4,7-diaza-spiro[2.5]oct-7-yl, 3-ethyl-piperazin-1-yl, 3-methyl-piperazin-1-yl, 4-methyl-3-methyl-piperazin-1-yl or 3-ethyl-piperazin-1-yl $R_a$ is H, $CH_2$—$CH_3$ or $CH(CH_3)_2$ $R_b$ is $CH_3$, F, $CH(CH_3)_2$, $OCH_3$, $CH_2$—$CH_3$ or Cl.

Specific embodiments of compounds according to formula (XXIV) include 3-[2-Chloro-5-(4-methyl-piperazin-1-yl)-3-trifluoromethyl-phenyl]-4-(1H-indol-3-yl)-pyrrole-2,5-dione having the formula

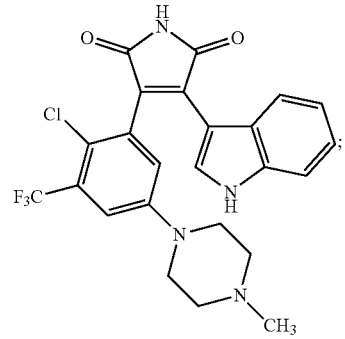 [SMILES: CN1CCN(c2cc(C3=C(c4c[nH]c5ccccc45)C(=O)NC3=O)c(Cl)c(C(F)(F)F)c2)CC1]

3-(1H-Indol-3-yl)-4-[2-(4-methyl-piperazin-1-yl)-quinazolin-4-yl]-pyrrole-2,5-dione having the formula

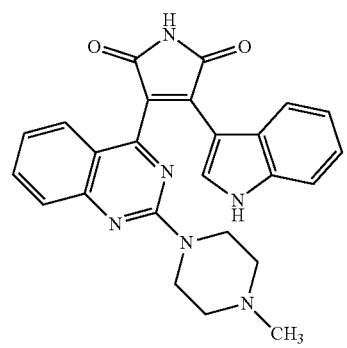 [SMILES: CN1CCN(c2nc(C3=C(c4c[nH]c5ccccc45)C(=O)NC3=O)c3ccccc3n2)CC1]

In other embodiments, PKC-θ inhibitors are selected from selective PKC-θ small molecule compounds disclosed by Ajioka in US Patent Application Publication US 2013/0225687, which is incorporated herein by reference in its entirety. These compounds are represented by formula (XXV):

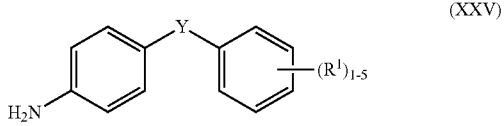

(XXV)

wherein:

Y is selected from the group consisting of —O—, and —S—; and each $R^1$ is independently selected from the group consisting of n-propyl, isopropyl, t-butyl, t-pentyl, $CF_3$, $OCF_3$, cyclopentyl, pyrrolyl, and $CO_2H$ and salts, hydrates and prodrugs thereof, thereby selectively inhibiting PKC-θ.

The invention not only encompasses known PKC-θ inhibitors but PKC-θ inhibitors identified by any suitable screening assay. Accordingly, the present invention extends to methods of screening for modulatory agents that are useful for inhibiting a PKC-θ and, in turn, for altering at least one of: (i) formation; (ii) proliferation; (iii) maintenance; (iv) EMT; or (v) MET of a PKC-θ-overexpressing cell (e.g., a CSC), or for treating or preventing a cancer (e.g., a metastatic cancer). In some embodiments, the screening methods comprise (1) contacting a preparation with a test agent, wherein the preparation comprises (i) a polypeptide comprising an amino acid sequence corresponding to at least a biologically active fragment of a PKC-θ, or to a variant or derivative thereof; or (ii) a polynucleotide comprising a nucleotide sequence from which a transcript of a PKC-θ gene or portion thereof is producible, or (iii) a polynucleotide comprising at least a portion of a genetic sequence (e.g., a transcriptional element) that regulates the expression of a PKC-θ gene, which is operably linked to a reporter gene; and (2) detecting a change in the level or functional activity of the polypeptide, the polynucleotide or an expression product of the reporter gene, relative to a reference level or functional activity in the absence of the test agent. A detected reduction in the level and/or functional activity of the polypeptide, transcript or transcript portion or an expression product of the reporter gene, relative to a normal or reference level and/or functional activity in the absence of the test agent, indicates that the agent is useful for altering at least one of: (i) formation; (ii) proliferation; (iii) maintenance; (iv) EMT; or (v) MET of a PKC-θ-overexpressing cell (e.g., a CSC), or for treating or preventing a cancer (e.g., a metastatic cancer). Suitably, this is confirmed by analyzing or determining whether the test agent alters at least one of: (i) formation; (ii) proliferation; (iii) maintenance; (iv) EMT; or (v) MET of a PKC-θ-overexpressing cell, or treats or prevents the cancer.

Modulators falling within the scope of the present invention include inhibitors of the level or functional activity of a PKC-θ, including antagonistic antigen-binding molecules, and inhibitor peptide fragments, antisense molecules, ribozymes, RNAi molecules and co-suppression molecules as well as polysaccharide and lipopolysaccharide inhibitors of a PKC-θ.

Candidate agents encompass numerous chemical classes, though typically they are organic molecules, preferably small organic compounds having a molecular weight of more than 50 and less than about 2,500 Dalton. Candidate agents comprise functional groups necessary for structural interaction with proteins, particularly hydrogen bonding, and typically include at least an amine, carbonyl, hydroxyl or carboxyl group, desirably at least two of the functional chemical groups. The candidate agent often comprises cyclical carbon or heterocyclic structures or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogues or combinations thereof.

Small (non-peptide) molecule modulators of a PKC-θ are particularly advantageous. In this regard, small molecules are desirable because such molecules are more readily absorbed after oral administration, have fewer potential antigenic determinants, or are more likely to cross the cell membrane than larger, protein-based pharmaceuticals. Small organic molecules may also have the ability to gain entry into an appropriate cell and affect the expression of a gene (e.g., by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogues.

Screening may also be directed to known pharmacologically active compounds and chemical analogues thereof.

Screening for modulatory agents according to the invention can be achieved by any suitable method. For example, the method may include contacting a cell expressing a polynucleotide corresponding to a gene that encodes a PKC-θ with an agent suspected of having the modulatory activity and screening for the modulation of the level or functional activity of the PKC-θ, or the modulation of the level of a transcript encoded by the polynucleotide, or the modulation of the activity or expression of a downstream cellular target of the polypeptide or of the transcript (hereafter referred to as target molecules). Detecting such modulation can be achieved utilizing techniques including, but not restricted to, ELISA, cell-based ELISA, inhibition ELISA, Western blots, immunoprecipitation, slot or dot blot assays, immunostaining, RIA, scintillation proximity assays, fluorescent immunoassays using antigen-binding molecule conjugates or antigen conjugates of fluorescent substances such as fluorescein or rhodamine, Ouchterlony double diffusion analysis, immunoassays employing an avidin-biotin or a streptavidin-biotin detection system, and nucleic acid detection assays including reverse transcriptase polymerase chain reaction (RT-PCR).

It will be understood that a polynucleotide from which a PKC-θ is regulated or expressed may be naturally occurring in the cell which is the subject of testing or it may have been introduced into the host cell for the purpose of testing. In addition, the naturally-occurring or introduced polynucleotide may be constitutively expressed—thereby providing a model useful in screening for agents which down-regulate expression of an encoded product of the sequence wherein the down regulation can be at the nucleic acid or expression product level. Further, to the extent that a polynucleotide is introduced into a cell, that polynucleotide may comprise the entire coding sequence that codes for the PKC-θ or it may comprise a portion of that coding sequence (e.g., the active site of the PKC-θ) or a portion that regulates expression of the corresponding gene that encodes the PKC-θ (e.g., a PKC-θ promoter). For example, the promoter that is naturally associated with the polynucleotide may be introduced into the cell that is the subject of testing. In this instance, where only the promoter is utilized, detecting modulation of the promoter activity can be achieved, for example, by operably linking the promoter to a suitable reporter polynucleotide including, but not restricted to, green fluorescent protein (GFP), luciferase, β-galactosidase and catecholamine acetyl transferase (CAT). Modulation of expression may be determined by measuring the activity associated with the reporter polynucleotide.

These methods provide a mechanism for performing high throughput screening of putative modulatory agents such as proteinaceous or non-proteinaceous agents comprising synthetic, combinatorial, chemical and natural libraries. These methods will also facilitate the detection of agents which bind either the polynucleotide encoding the target molecule or which modulate the expression of an upstream molecule, which subsequently modulates the expression of the polynucleotide encoding the target molecule. Accordingly, these methods provide a mechanism of detecting agents that either directly or indirectly modulate the expression or activity of a target molecule according to the invention.

In alternative embodiments, test agents are screened using commercially available PKC-θ assays, illustrative examples of which include ADP-Glo™ PKC-θ Kinase Assay (Promega Corporation, Madison, Wis.), the PKC Theta KinEASE™ FP Fluorescein Green Assay (EMD Millipore, Billerica, Mass.) and or using the PKC-θ assay disclosed in US Patent Application Publication US2008/0318929.

Compounds may be further tested in the animal models to identify those compounds having the most potent in vivo effects. These molecules may serve as "lead compounds" for the further development of pharmaceuticals by, for example, subjecting the compounds to sequential modifications, molecular modeling, and other routine procedures employed in rational drug design.

3. Therapeutic and Prophylactic Uses

In accordance with the present invention, it is proposed that agents that inhibits PKC-θ function are useful as actives for altering at least one of: (i) formation; (ii) proliferation; or (iii) maintenance of a PKC-θ-overexpressing cell (e.g., a CSC or a non-CSC tumor cell); (iv) EMT of a PKC-θ-overexpressing cell (e.g., a CSC); or (v) MET of a PKC-θ-overexpressing cell (e.g., a CSC), or for treating or preventing a cancer (e.g., a metastatic cancer). Thus, PKC-θ inhibitor compounds, in accordance with the present invention, are useful, suitably in pharmaceutical compositions, for treating or preventing cancers, including metastatic cancers. As such the present invention contemplates pharmaceutical compositions for treating, preventing and/or relieving the symptoms of a malignancy, particularly a metastatic cancer, wherein the compositions comprise an effective amount of a PKC-θ inhibitor and a pharmaceutically acceptable carrier and/or diluent.

Any PKC-θ inhibitor can be used in the compositions and methods of the present invention, provided that the inhibitor is pharmaceutically active. In some embodiments, the PKC-θ inhibitor is a non-selective PKC-θ inhibitor. In specific embodiments, the PKC-θ inhibitor is a selective PKC-θ inhibitor. A "pharmaceutically active" PKC-θ inhibitor is in a form that results in a reduction, impairment, abrogation or prevention the (i) formation; (ii) proliferation; or (iii) maintenance of a PKC-θ-overexpressing cell (e.g., a CSC or non-CSC tumor cell); or (iv) EMT of a PKC-θ-overexpressing cell (e.g., a CSC), and/or in the enhancement of (v) MET of a PKC-θ-overexpressing cell (e.g., a CSC), and/or in the treatment and/or prevention of a malignancy, particularly a metastatic cancer, including the prevention of incurring a symptom, holding in check such symptoms or treating existing symptoms associated with the metastatic cancer, when administered to an individual in need thereof.

Modes of administration, amounts of PKC-θ inhibitor administered, and PKC-θ inhibitor formulations, for use in the methods of the present invention, are routine and within the skill of practitioners in the art. Whether a malignancy, particularly a metastatic cancer, has been treated is determined by measuring one or more diagnostic parameters indicative of the course of the disease, compared to a suitable control. In the case of an animal experiment, a "suitable control" is an animal not treated with the PKC-θ inhibitor, or treated with the pharmaceutical composition without the PKC-θ inhibitor. In the case of a human subject, a "suitable control" may be the individual before treatment, or may be a human (e.g., an age-matched or similar control) treated with a placebo. In accordance with the present invention, the treatment of a metastatic cancer includes and encompasses without limitation: (1) impairing, abrogating, reducing, preventing, or arresting the development of, the (i) formation; (ii) proliferation; (iii) maintenance; or (iv) EMT of a PKC-θ-overexpressing cell (e.g., a CSC), or enhancing MET of a PKC-θ-overexpressing cell (e.g., a CSC), in a patient; (2) treating a cancer (e.g., a metastatic cancer) in a subject; (3) preventing a cancer (e.g., a metastatic cancer) in a subject that has a predisposition to the cancer but has not yet been diagnosed with the cancer and, accordingly, the treatment constitutes prophylactic treatment of the cancer; or (iii) causing regression of a cancer (e.g., a metastatic cancer).

The compositions and methods of the present invention are thus suitable for treating an individual who has been diagnosed with a cancer (e.g., a metastatic cancer), who is suspected of having a cancer (e.g., a metastatic cancer), who is known to be susceptible and who is considered likely to develop a cancer (e.g., a metastatic cancer), or who is considered likely to develop a recurrence of a previously treated cancer (e.g., a metastatic cancer). The cancer (e.g., a metastatic cancer) may be hormone receptor positive or hormone receptor negative. In some embodiments, the cancer (e.g., a metastatic cancer) is hormone receptor negative and is thus resistant to hormone or endocrine therapy. In some embodiments in which the cancer is breast cancer, the breast cancer (e.g., the non-breast CMC tumor cells) is hormone receptor negative (e.g., estrogen receptor (ER) negative and/or progesterone receptor (PR) negative).

In some embodiments, and dependent on the intended mode of administration, the PKC-θ inhibitor-containing compositions will generally contain about 0.000001% to 90%, about 0.0001% to 50%, or about 0.01% to about 25%, by weight of PKC-θ inhibitor, the remainder being suitable pharmaceutical carriers or diluents etc. The dosage of the PKC-θ inhibitor can depend on a variety of factors, such as mode of administration, the species of the affected subject, age, sex, weight and general health condition, and can be easily determined by a person of skill in the art using standard protocols. The dosages will also take into consideration the binding affinity of the PKC-θ inhibitor to its target molecule, its bioavailability and its in vivo and pharmacokinetic properties. In this regard, precise amounts of the agents for administration can also depend on the judgment of the practitioner. In determining the effective amount of the agents to be administered in the treatment or prevention of a cancer (e.g., a metastatic cancer), the physician or veterinarian may evaluate the progression of the disease or condition over time. In any event, those of skill in the art may readily determine suitable dosages of the PKC-θ inhibitor without undue experimentation. The dosage of the actives administered to a patient should be sufficient to effect a beneficial response in the patient over time such as reduction, impairment, abrogation or prevention in the (i) formation; (ii) proliferation; (iii) maintenance; or (iv) EMT of a PKC-θ-overexpressing cell (e.g., a CSC), and/or in the enhancement of (v) MET of a PKC-θ-overexpressing cell (e.g., a CSC), and/or in the treatment and/or prevention of a cancer (e.g., a metastatic cancer). The dosages may be administered at suitable intervals to ameliorating the symptoms of the hematologic malignancy. Such intervals can be ascertained using routine procedures known to persons of skill in the art and can vary depending on the type of active agent employed and its formulation. For example, the interval may be daily, every other day, weekly, fortnightly, monthly, bimonthly, quarterly, half-yearly or yearly.

Dosage amount and interval may be adjusted individually to provide plasma levels of the active agent, which are sufficient to maintain PKC-θ-inhibitory effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

In specific embodiments of the present invention, inhibition of PKC-θ by the PKC-θ inhibitor will result in reduced formation, proliferation, maintenance or EMT of CSC (e.g., breast cancer CSC), or in enhanced MET of CSC (e.g., breast cancer CSC), which will in turn result in fewer non-CSC tumor cells differentiating from the CSC and in more effective treatment of non-CSC tumor cells with a cancer therapy or agent. Thus, the present invention further contemplates administering a PKC-θ inhibitor concurrently with at least one cancer therapy that inhibits the proliferation, survival or viability of non-CMC tumor cells. The PKC-θ inhibitor may be used therapeutically after the cancer therapy or may be used before the therapy is administered or together with the therapy. Accordingly, the present invention contemplates combination therapies, which employ a PKC-θ inhibitor and concurrent administration of an cancer therapy, non-limiting examples of which include radiotherapy, surgery, chemotherapy, hormone ablation therapy, pro-apoptosis therapy and immunotherapy.

3.1 Radiotherapy

Radiotherapies include radiation and waves that induce DNA damage for example, γ-irradiation, X-rays, UV irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half life of the isotope, the strength and type of radiation emitted, and the uptake by the neoplastic cells.

Non-limiting examples of radiotherapies include conformal external beam radiotherapy (50-100 Grey given as fractions over 4-8 weeks), either single shot or fractionated, high dose rate brachytherapy, permanent interstitial brachytherapy, systemic radio-isotopes (e.g., Strontium 89). In some embodiments the radiotherapy may be administered in combination with a radiosensitizing agent. Illustrative examples of radiosensitizing agents include but are not limited to efaproxiral, etanidazole, fluosol, misonidazole, nimorazole, temoporfin and tirapazamine.

3.2 Chemotherapy

Chemotherapeutic agents may be selected from any one or more of the following categories:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyridines like 5-fluorouracil and tegafur, raltitrexed, methotrexate, cytosine arabinoside and hydroxyurea; anti-tumor antibiotics (for example anthracyclines like adriamycin, bleomycin, doxorubicin, daunomycin, epirubicin, idarubicin, mitomycin-C, dactinomycin and mithramycin); antimitotic agents (for example *Vinca* alkaloids like vincristine, vinblastine, vindesine and vinorelbine and taxoids like paclitaxel and docetaxel; and topoisomerase inhibitors (for example epipodophyllotoxins like etoposide and teniposide, amsacrine, topotecan and camptothecin);

(ii) cytostatic agents such as antiestrogens (for example tamoxifen, toremifene, raloxifene, droloxifene and idoxifene), oestrogen receptor down regulators (for example fulvestrant), antiandrogens (for example bicalutamide, flutamide, nilutamide and cyproterone acetate), UH antagonists or LHRH agonists (for example goserelin, leuprorelin and buserelin), progestogens (for example megestrol acetate), aromatase inhibitors (for example as anastrozole, letrozole, vorozole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody Cetuximab [C225]), farnesyl transferase inhibitors, MEK inhibitors, tyrosine kinase inhibitors and serine/threonine kinase inhibitors, for example other inhibitors of the epidermal growth factor family (for example other EGFR family tyrosine kinase inhibitors such as N-(3-chloro-4-fluorophenyl)-7-methoxy-6-(3-morpholinopropoxy)quinazolin-4-amine (Gefitinib, AZD 1839), N-(3-ethynylphenyl)-6,7-bis (2-methoxyethoxy)quinazolin-4-amine (Erlotinib, OSI-774) and 6-acrylamido-N-(3-chloro-4-fluorophenyl)-7-(3-morpholinopropoxy)quinazoli-n-4-amine (CI 1033)), for example inhibitors of the platelet-derived growth factor family and for example inhibitors of the hepatocyte growth factor family;

(v) anti-angiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense; and (viii) gene therapy approaches, including for example approaches to replace aberrant genes such as aberrant p53 or aberrant GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

3.3 Immunotherapy

Immunotherapy approaches, include for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies. These approaches generally rely on the use of immune effector cells and molecules to target and destroy cancer cells. The immune effector may be, for example, an antibody specific for some marker on the surface of a malignant cell. The antibody alone may serve as an effector of therapy or it may recruit other cells to actually facilitate cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a malignant cell target. Various effector cells include cytotoxic T cells and NK cells.

3.4 Other Therapies

Examples of other cancer therapies include phototherapy, cryotherapy, toxin therapy or pro-apoptosis therapy. One of skill in the art would know that this list is not exhaustive of the types of treatment modalities available for cancer and other hyperplastic lesions.

It is well known that chemotherapy and radiation therapy target rapidly dividing cells and/or disrupt the cell cycle or cell division. These treatments are offered as part of the treating several forms of cancer, aiming either at slowing their progression or reversing the symptoms of disease by means of a curative treatment. However, these cancer treatments may lead to an immunocompromised state and ensuing pathogenic infections and thus the present invention also extends to combination therapies, which employ both a PKC-θ inhibitor, a cancer therapy and an anti-infective agent that is effective against an infection that develops or that has an increased risk of developing from an immunocompromised condition resulting from the cancer therapy. The anti-infective drug is suitably selected from antimicrobials, which include without limitation compounds that kill or inhibit the growth of microorganisms such as viruses, bacteria, yeast, fungi, protozoa, etc. and thus include antibiotics, amebicides, antifungals, antiprotozoals, antimalarials, antituberculotics and antivirals. Anti-infective drugs also include within their scope anthelmintics and nematocides. Illustrative antibiotics include quinolones (e.g., amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin; and garenoxacin), tetracyclines, glycylcyclines and oxazolidinones (e.g., chlortetracycline, demeclocycline, doxycycline, lymecycline, methacycline, minocycline, oxytetracycline, tetracycline, tigecycline; linezolide, eperezolid), glycopeptides, aminoglycosides (e.g., amikacin, arbekacin, butirosin, dibekacin, fortimicins, gentamicin, kanamycin, menomycin, netilmicin, ribostamycin, sisomicin, spectinomycin, streptomycin, tobramycin), β-lactams (e.g., imipenem, meropenemrn, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephacetrile, cephalexin, cephaloglycin, cephaloridine, cephalothin, cephapirin, cephradine, cefinetazole, cefoxitin, cefotetan, azthreonam, carumonam, flomoxef, moxalactam, amdinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), rifamycins, macrolides (e.g., azithromycin, clarithromycin, erythromycin, oleandomycin, rokitamycin, rosaramicin, roxithromycin, troleandomycin), ketolides (e.g., telithromycin, cethromycin), coumermycins, lincosamides (e.g., clindamycin, lincomycin) and chloramphenicol.

Illustrative antivirals include abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine.

Non-limiting examples of amebicides or antiprotozoals include atovaquone, chloroquine hydrochloride, chloroquine phosphate, metronidazole, metronidazole hydrochloride, and pentamidine isethionate. Anthelmintics can be at least one selected from mebendazole, pyrantel pamoate, albendazole, ivermectin and thiabendazole. Illustrative antifungals can be selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. Non-limiting examples of antimalarials include chloroquine hydrochloride, chloroquine phosphate, doxycycline, hydroxychloroquine sulfate, mefloquine hydrochloride, primaquine phosphate, pyrimethamine, and pyrimethamine with sulfadoxine. Antituberculotics include but are not restricted to clofazimine, cycloserine, dapsone, ethambutol hydrochloride, isoniazid, pyrazinamide, rifabutin, rifampin, rifapentine, and streptomycin sulfate.

As noted above, the present invention encompasses co-administration of an PKC-θ inhibitor in concert with an additional agent. It will be understood that, in embodiments comprising administration of the PKC-θ inhibitor with other agents, the dosages of the actives in the combination may on their own comprise an effective amount and the additional agent(s) may further augment the therapeutic or prophylactic benefit to the patient. Alternatively, the PKC-θ inhibitor and the additional agent(s) may together comprise an effective amount for preventing or treating the cancer (e.g., metastatic cancer). It will also be understood that effective amounts may be defined in the context of particular treatment regimens, including, e.g., timing and number of administrations, modes of administrations, formulations, etc. In some embodiments, the PKC-θ inhibitor and optionally the cancer therapy are administered on a routine schedule. Alternatively, the cancer therapy may be administered as symptoms arise. A "routine schedule" as used herein, refers to a predetermined designated period of time. The routine schedule may encompass periods of time which are identical or which differ in length, as long as the schedule is predetermined. For instance, the routine schedule may involve administration of the PKC-θ inhibitor on a daily basis, every two days, every three days, every four days, every five days, every six days, a weekly basis, a monthly basis or any set number of days or weeks there-between, every two months, three months, four months, five months, six months, seven months, eight months, nine months, ten months, eleven months, twelve months, etc. Alternatively, the predetermined routine schedule may involve concurrent administration of the PKC-θ inhibitor and the cancer therapy on a daily basis for the first week, followed by a monthly basis for several months, and then every three months after that. Any particular combination would be covered by the routine schedule as long as it is determined ahead of time that the appropriate schedule involves administration on a certain day.

Additionally, the present invention provides pharmaceutical compositions for reducing, impairing, abrogating or preventing the (i) formation; (ii) proliferation; (iii) maintenance; or (iv) EMT of a PKC-θ-overexpressing cell (e.g., a CSC), and/or for enhancing (v) MET of a PKC-θ-overexpressing cell (e.g., a CSC), and for preventing or treating malignancies, particularly metastatic cancers, which comprise a PKC-θ inhibitor and optionally a cancer therapy agent useful for treating malignancies. The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. Depending on the specific conditions being treated, the formulations may be administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the active agents or drugs of the invention may be formulated in aqueous solutions, suitably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

The drugs can be formulated readily using pharmaceutically acceptable carriers well known in the art into dosages suitable for oral administration. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more drugs as described above with the carrier, which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments may be added to the tablets or dragee coatings for identification or to characterize different combinations of active compound doses.

Pharmaceutical which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dosage forms of the drugs of the invention may also include injecting or implanting controlled releasing devices designed specifically for this purpose or other forms of implants modified to act additionally in this fashion. Controlled release of an agent of the invention may be achieved by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be achieved by using other polymer matrices, liposomes or microspheres.

The drugs of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

For any compound used in the method of the invention, the therapeutically effective dose can be estimated initially from cell culture assays. For example, a dose can be formulated in animal models to achieve a circulating concentration range that includes the IC50 as determined in cell culture (e.g., the concentration of an active agent, which achieves a half-maximal inhibition in activity of a PKC-θ polypeptide). Such information can be used to more accurately determine useful doses in humans.

Toxicity and therapeutic efficacy of such drugs can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See for example Fingl et al., 1975, in "The Pharmacological Basis of Therapeutics", Ch. 1 p1).

Alternately, one may administer the compound in a local rather than systemic manner, for example, via injection of the compound directly into a tissue, which is preferably subcutaneous or omental tissue, often in a depot or sustained release formulation.

Furthermore, one may administer the drug in a targeted drug delivery system, for example, in a particle, which is suitably targeted to and taken up selectively by a cell or tissue. In some embodiments, the PKC-θ inhibitor is contained or otherwise associated with a vehicle selected from the group consisting of liposomes, micelles, dendrimers, biodegradable particles, artificial DNA nanostructure, lipid-based nanoparticles, and carbon or gold nanoparticles. In illustrative examples of this type, the vehicle selected from the group consisting of Poly(lactic acid) (PLA), Poly(glycolic acid) (PGA); polymer poly(lactic-co-glycolic acid) (PLGA); poly(ethylene glycol) (PEG), and PLA-PEG copolymers, or any combinations thereof.

In cases of local administration or selective uptake, the effective local concentration of the agent may not be related to plasma concentration.

In order that the invention may be readily understood and put into practical effect, particular preferred embodiments will now be described by way of the following non-limiting examples.

EXAMPLES

Example 1

PKC Pathway: EMT and CSC

Figure 1:
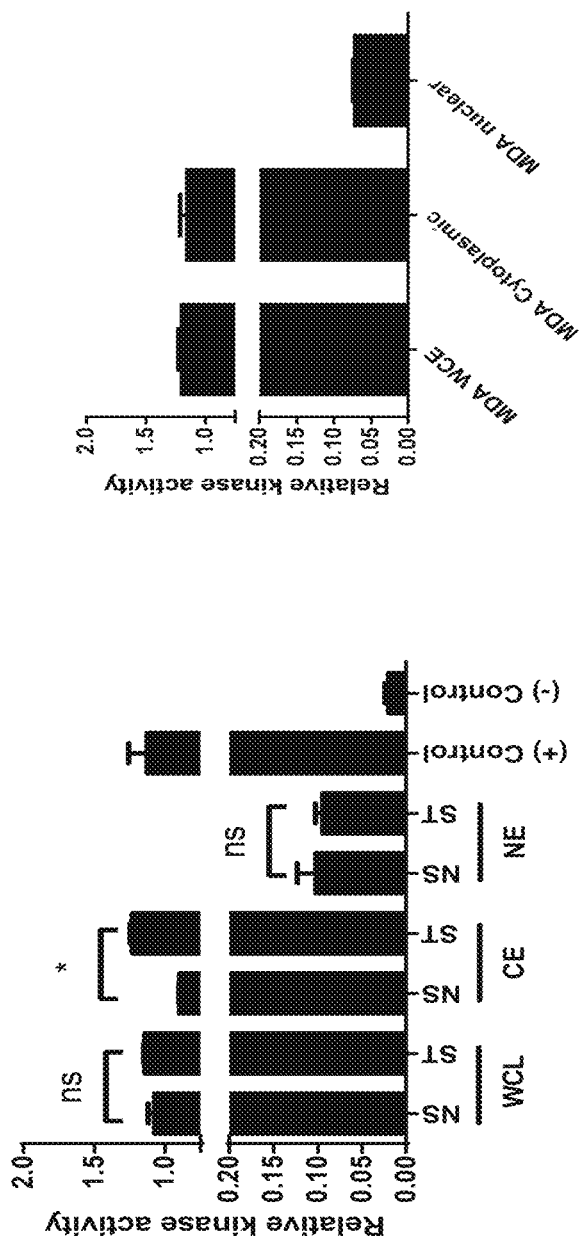
FIG. 1D is a graphical representation showing higher PKC kinase activity in a MCF-IM and basal/metastatic model. MCF-7 cells were either non-stimulated (NS) or stimulated (ST) with PMA (0.65 ng/mL). PKC ELISA-based kinase assays were performed either on whole cell lysate (WCL), cytoplasmic extract (CE) or nuclear extract (NE) from both NS and ST treated MCF-7 cells and MDA-MD 231 cells. Absorbance was measured at 450 nm. Data are plotted as relative kinase activity compared to the negative control. Data are representative of the mean±SE of three independent experiments and statistical significance was determined by a two-tailed paired t-test using GraphPad Prism 5.03.
FIG. 1E is a graphical representation showing FACS gating strategies for sorting of $CD44^{high}/CD24^{low}$-cancer stem-like cell (CSC) sub-population in a MCF-IM model. MCF-7 cells were either left untreated, non-stimulated (NS) or stimulated (ST) with PMA (0.65 ng/mL) for 60 hr. Cells were subsequently stained with Hoechst, APC-anti-CD44 and PE-anti-CD24 cocktail prior to FACS sorting. Cancer stem-like cell (CSC) population was defined by $CD44^{high}/CD24^{low}$ stain. Gates for CSC-like and NCSC sub-populations were first made on PMA stimulated populations and these gates were copied to non-stimulated population to confirm that the CSC-like population was below 0.1% in non-stimulated cells. Representative FACS plot of 10 independent experiments has been shown for highlighting the gating strategy.
FIG. 1F is a graphical representation showing that the MCF-IM model results in a high percentage of $CD44^{high}/CD24^{low}$ or CSC-like sub-population. MCF-7 cells were either left untreated, non-stimulated (NS) or stimulated (ST) with PMA (0.65 ng/mL) for 60 hr. FACS analysis was carried out using gating strategies described in FIG. 1E and subsequently, the mean % CSC-like subpopulation was plotted (error bars are standard errors) from ten independent experiments.
FIG. 1G is a photographic and graphical representation showing that the MCF-IM model leads to the generation of mammospheres. Mammosphere assay was performed with $4\times10^4$ MCF-7 cells/well in ultra low attachment 6 well plates. Cells were either (A) non-stimulated (NS), or stimulated with (B) PMA (0.65 ng/mL) or (C) TNF-α (10 ng/mL). Images were captured using phase contrast microscopy for mammosphere assay after 6 days of assay commencement and a graph was plotted. Experiment was performed in duplicate and mammospheres in each well were counted for average. Data represent the average±SE of two independent experiments.
FIG. 1H is a graphical representation showing that induced CSC-like sub-populations have distinct transcriptional profile in the MCF-IM model. Transcript analysis was carried out on MCF-7 cells, either non-stimulated (NS), or PMA stimulated (0.65 ng/mL for 60 hrs) and FACS sorted sub-population-cancer stem-like cells (CSC-like) and non-cancer stem like cells (NCSC), for genes CD44, laminin-5, uPAR, Fibronectin and Integrin-3. TaqMan® real time PCR was performed on cDNA synthesized from total RNA isolated from above said three populations. Threshold cycle (Ct) values generated for each time points were converted to arbitrary copy number and normalized to Cyclophilin A reference levels. mRNA levels are expressed in arbitrary copy numbers and fold change in comparison to non-stimulated cells is shown above the error bars. Data represent the mean±standard error (SE) of three independent experiments.
FIG. 1I is a graphical representation showing that induced CSC-like and NCSC sub-populations results in reduced expression of miR200 family members in the MCF-IM model. MicroRNA cDNA levels for miR 200b and miR 200c were measured by TaqMan® microRNA real-time analysis from either MCF-7 cells left untreated, non-stimulated (NS), or PMA stimulated (0.65 ng/mL for 60 hrs.) FACS sorted sub-populations-cancer stem-like cells (CSC-like) and non-cancer stem like cells (NCSC). Threshold cycle (Ct) values generated for each time points were converted to arbitrary copy number and normalized to RNU6B reference levels. MicroRNA levels are expressed in arbitrary copy and data represent the mean±standard error (SE) of three independent experiments.
Figure 1:
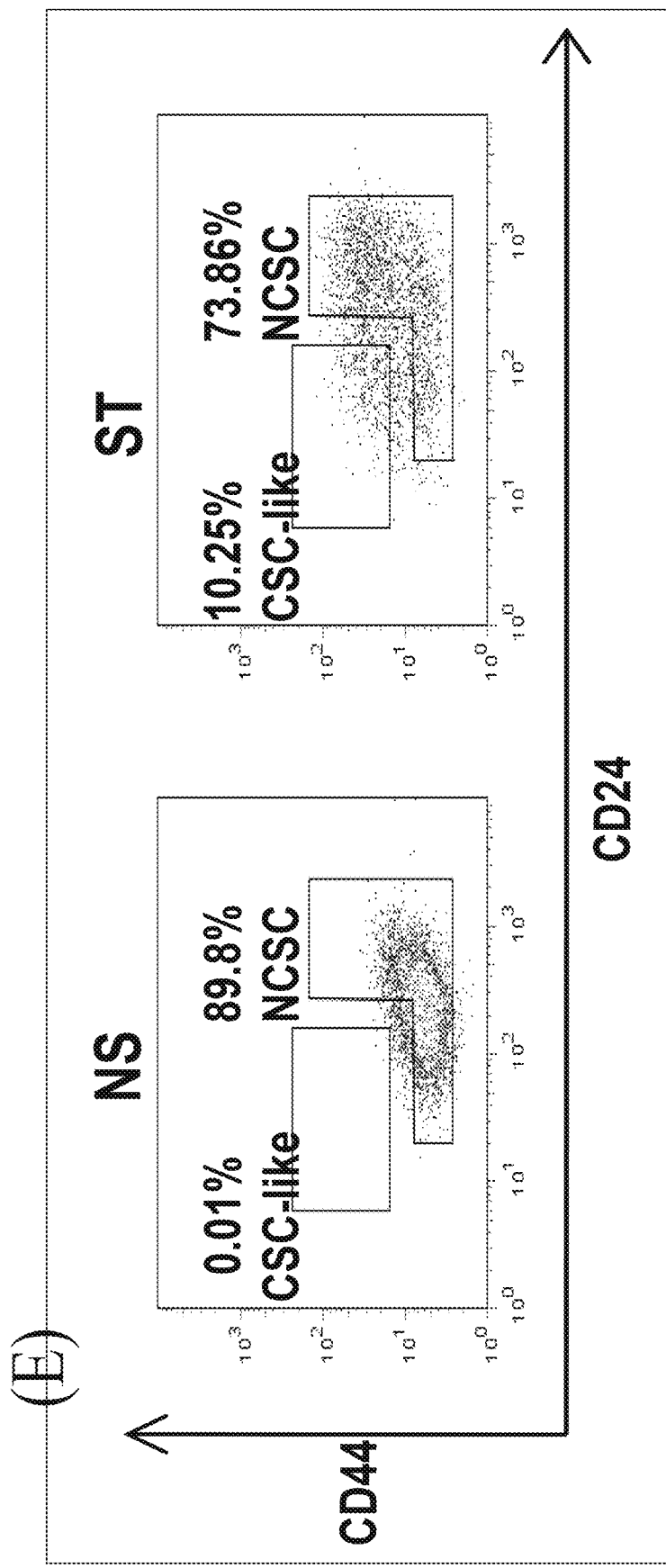
Figure 1:
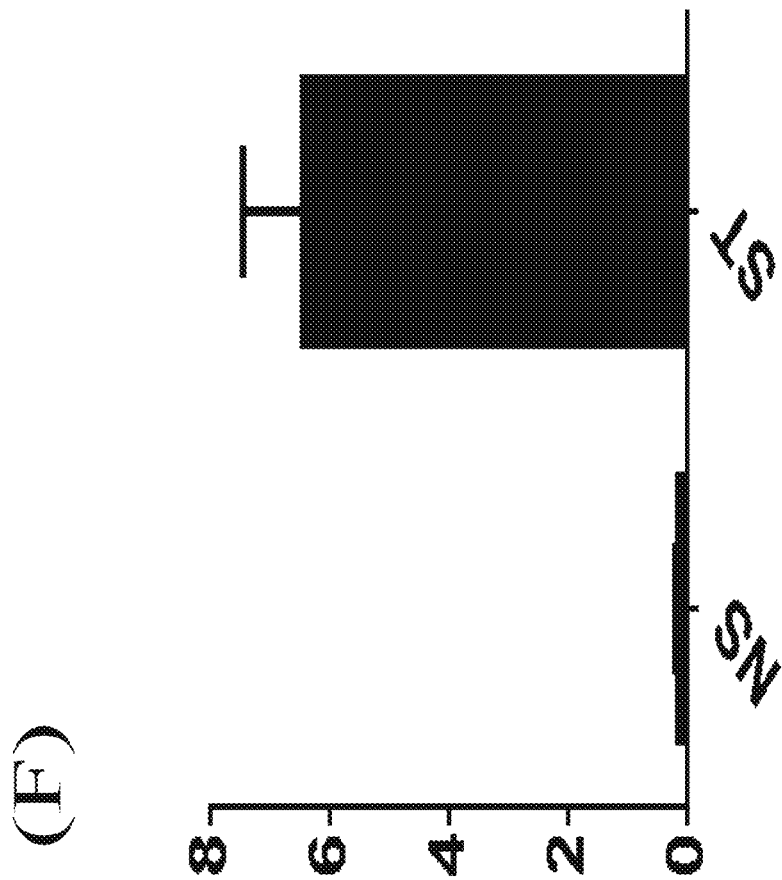
Figure 1:
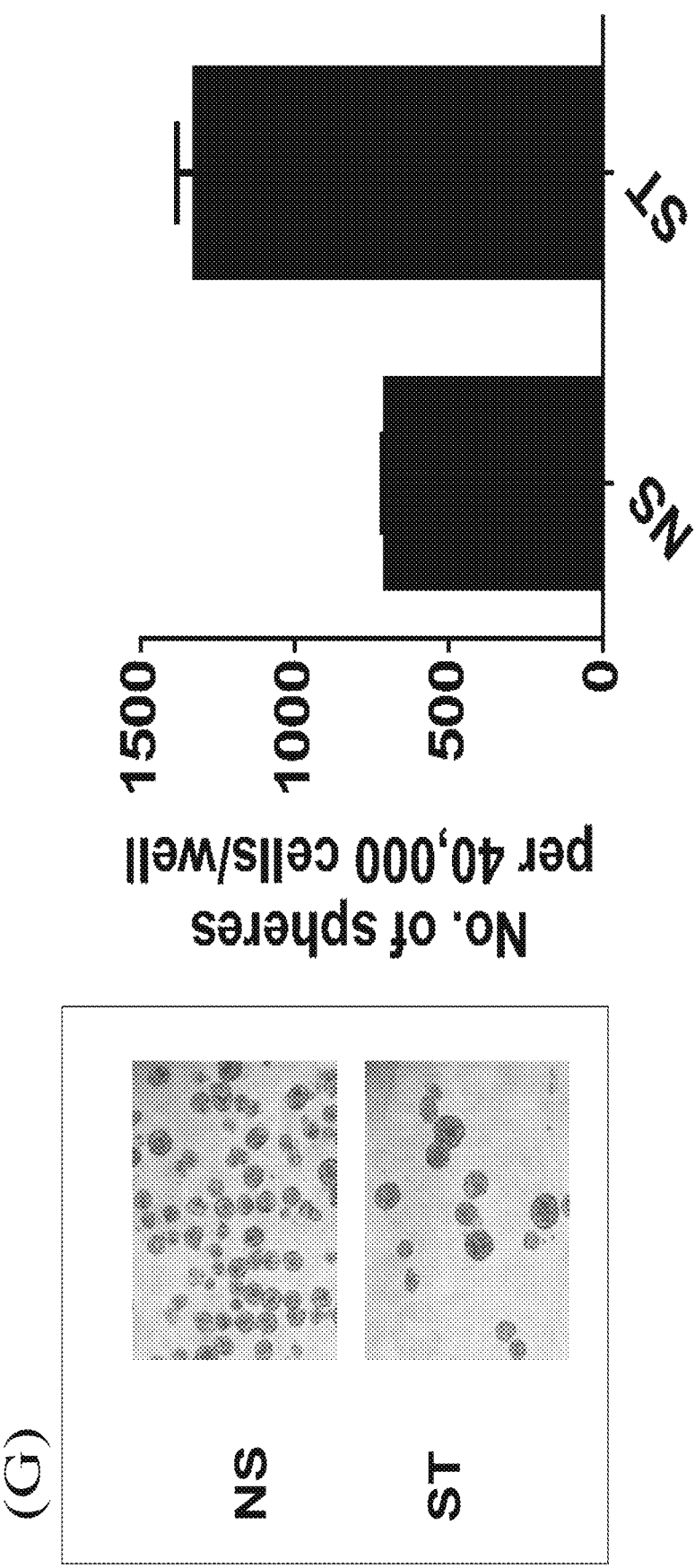
Figure 1H:
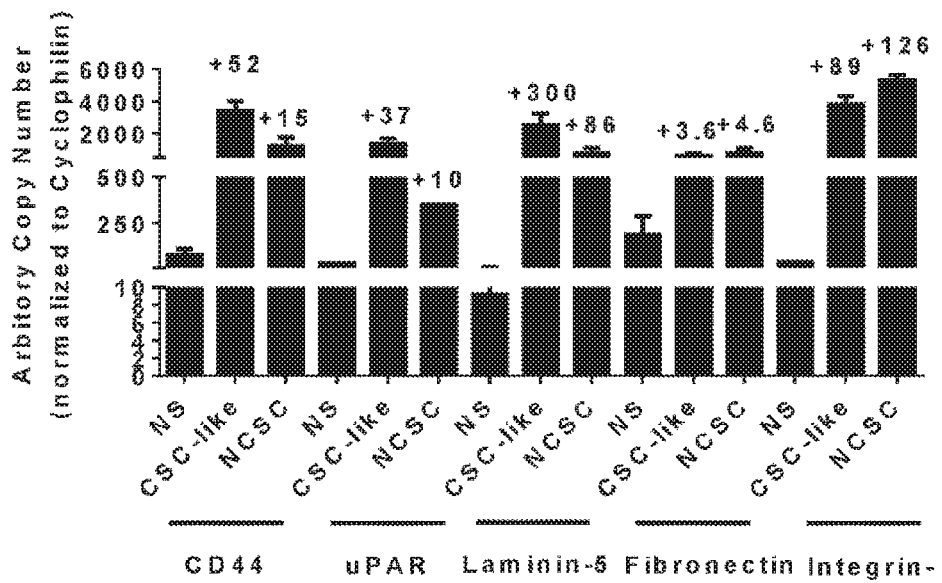
Figure 1I:
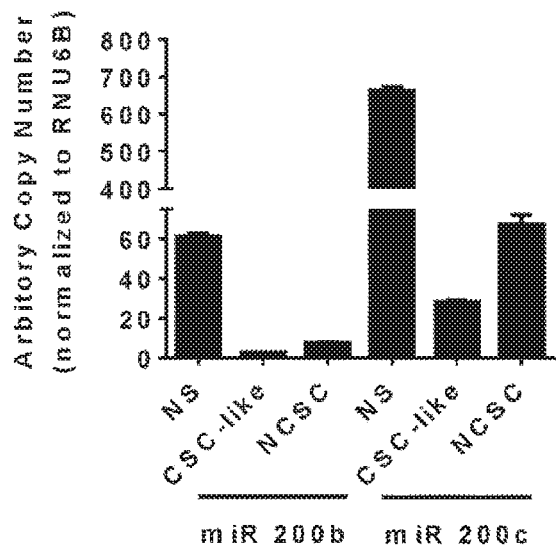

PKC pathway is associated by EMT and CSC utilizing a variety of cellular assays. First, PKC pathway inducer, PMA caused highest EMT changes as observed by morphological changes (FIGS. 1 A and B), EMT marker-Laminin-5's intracellular staining (FIG. 1 B) and wound healing (Migration assays) (FIG. 1 C) in MCF-IM model. Second, PKC is active in both cytoplasm and nuclei in the MCF-IM and basal/metastatic model (FIG. 1 D). Third, induction of PKC pathway by PMA results in the generation of $CD44^{high}/CD24^{low}$-CSC like cells as observed by flow cytometry (FACS) analysis (FIGS. 1 E and F), mammosphere assay (FIG. 1 G) and transcript analysis of CSC-inducible genes (FIG. 1 H) and microRNAs (FIG. 1 I).

Overall these results show that PKC pathway is important for EMT and CSC formation.

Example 2

Inhibition of PKC Activity Reduces EMT and CSC Formation

Figure 2:
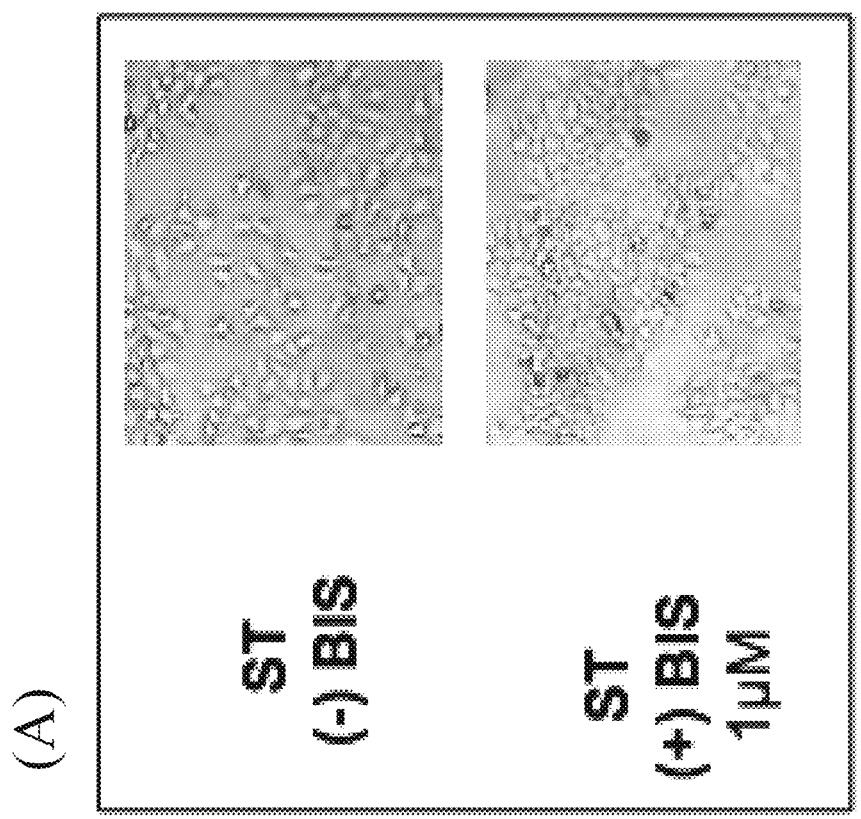
FIG. 2A is a photographic representation showing that the broad spectrum PKC inhibitor, bisindolylmaleimide-I inhibits EMT in the MCF-IM model. Phase contrast microscopy images of non-stimulated (NS) and PMA (0.65 ng/μL for 60 hrs.) stimulated (ST) MCF-7 cells were captured either without pre-treatment of PKC specific inhibitor (ST-BIS), with 1 hr. pre-treatment of bisindolylmaleimide (1 μM) before PMA stimulation (ST+BIS).
FIG. 2B is a graphical representation showing that only very high concentration of bisindolylmaleimide-I but not Go 6976 inhibits CD44 high CD24 low-CSC-like subpopulation in the MCF-IM model. MCF-7 cells were either pre-incubated with vehicle alone or with bisindolylmaleimide-I (100 nm and 1 μM) or Go6976 (1 μM), prior to PMA (0.65 ng/μL for 60 hrs.) stimulation (ST) or. Cells were subsequently stained with Hoechst 33528, APC-anti-CD44 and PE-anti-CD24 for 20 minutes on ice and subjected to FACS analysis. Circles on FACS plot indicate appropriate gating of $CD44^{high}/CD24^{low}$ CSC-like subpopulation and % CSC-like subpopulation is shown above the gates respectively.
FIG. 2C is an alternate graphical representation of the data presented in FIG. 2B. Data represent the mean±standard error (SE) of two independent experiments.
FIG. 2D is a photographic representation showing that 1 μM Bisindolylmaleimide-I reduce mammosphere formation in the MCF-IM model. Mammosphere assay was performed with $4\times10^4$ MCF-7 cells/well in an ultra low attachment 6 well plates. MCF-7 cells were pre-incubated either with vehicle alone or bisindolylmaleimide-I (1 μM for 1 hr.) prior to PMA stimulation (0.65 ng/mL for 6 days) (ST) or left non-stimulated (NS). Phase contrast microscopic images of mammospheres were taken after 6 days of assay and only mammospheres larger than 60 μm were counted.
FIG. 2E is an alternate graphical representation of the data presented in FIG. 2B. Data represent the mean±standard error (SE) of two independent experiments.
FIG. 2F is a graphical representation showing that 100 nM bisindolylmaleimide-I treatment cannot inhibit transcription of key inducible EMT/CSC genes in the MCF-IM model. MCF-7 cells were either left untreated, non-stimulated (NS) or pre-treated with either bisindolylmaleimide-I (100 nM) for 1 hour prior to PMA (0.65 ng/L for 60 hrs.) stimulation (ST). TaqMan® real time PCR analysis for EMT/CSC genes-laminin-5, uPAR and CD44 was performed on cDNA synthesized from total RNA. Threshold cycle (Ct) values generated for each time point were converted to arbitrary copy number and normalized to Cyclophilin A reference levels. mRNA levels are expressed in fold change in comparison to non-stimulated cells. Data represent the mean±standard error (SE) of two independent experiments.
FIG. 2G is a graphical representation showing that 1 μM bisindolylmaleimide-I treatment inhibits transcription of key inducible EMT/CSC genes in thae MCF-IM model. MCF-7 cells were either left untreated, non-stimulated (NS) or pre-treated with either bisindolylmaleimide-I (1 μM) for 1 hour prior to PMA (0.65 ng/μl for 60 hrs.) stimulation (ST). TaqMan® real time PCR analysis for EMT/CSC genes-laminin-5, uPAR and CD44 was performed on cDNA synthesized from total RNA. Threshold cycle (Ct) values generated for each time point were converted to arbitrary copy number and normalized to Cyclophilin A reference levels. mRNA levels are expressed in fold change in comparison to non-stimulated cells. Data represent the mean±standard error (SE) of two independent experiments.
FIG. 2H is a graphical representation showing that 1 μM Go6976 treatment failed to inhibit transcription of key inducible EMT/CSC genes in the MCF-IM model. MCF-7 cells were either left untreated, non-stimulated (NS) or pre-treated with either Go6976 (1 μM) for 1 hour prior to PMA (0.65 ng/μL for 60 hrs.) stimulation (ST). TaqMan® real time PCR analysis for EMT/CSC genes-laminin-5, uPAR and CD44 was performed on cDNA synthesized from total RNA. Threshold cycle (Ct) values generated for each time point were converted to arbitrary copy number and normalized to Cyclophilin A reference levels. mRNA levels are expressed in fold change in comparison to non-stimulated cells. Data represent the mean±standard error (SE) of two independent experiments.
FIG. 2I is a photographic representation showing that the broad spectrum PKC inhibitor, bisindolylmaleimide-I inhibits EMT in a basal/metastatic model. Phase contrast microscopy images of MDA-MB 231 cells were captured either without pre-treatment of PKC specific inhibitor (−BIS) or with treatment of Bisindolylmaleimide (4 μM) (+BIS).
FIG. 2J is a graphical representation showing that bisindolylmaleimide-I inhibits CD44 high CD24 low-CSC-like subpopulation in Basal/metastatic model. MDA-MB 231 cells were either incubated with vehicle alone or with bisindolylmaleimide-I (4 μM). Cells were subsequently stained with Hoechst 33528, APC-anti-CD44 and PE-anti-CD24 for 20 minutes on ice and subjected to FACS analysis. Percent CSC-like subpopulation is shown in the bar graph. Data represent the mean±standard error (SE) of two independent experiments.
FIG. 2K is a graphical representation showing that bisindolylmaleimide-I treatment inhibits transcription of key inducible EMT/CSC genes in a basal/metastatic model. MDA-MB 231 cells were either incubated with vehicle alone or with bisindolylmaleimide-I (4 μM). TaqMan® real time PCR analysis for EMT/CSC genes-laminin-5, uPAR and CD44 was performed on cDNA synthesized from total RNA. Threshold cycle (Ct) values generated for each time point were converted to arbitrary copy number and normalized to Cyclophilin A reference levels. mRNA levels are expressed in fold change in comparison to non-stimulated cells. Data represent the mean±standard error (SE) of two independent experiments.
Figure 2:
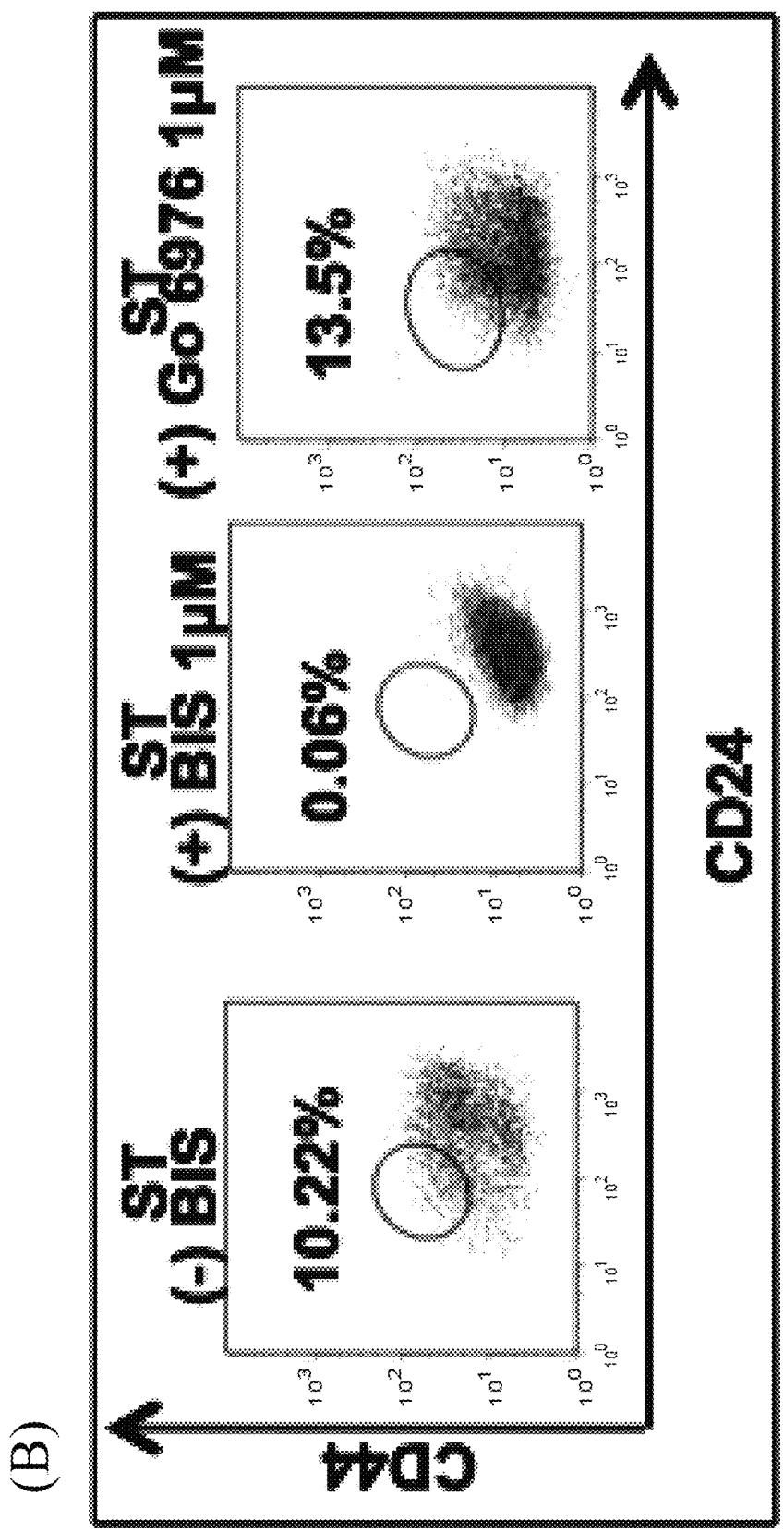
Figure 2:
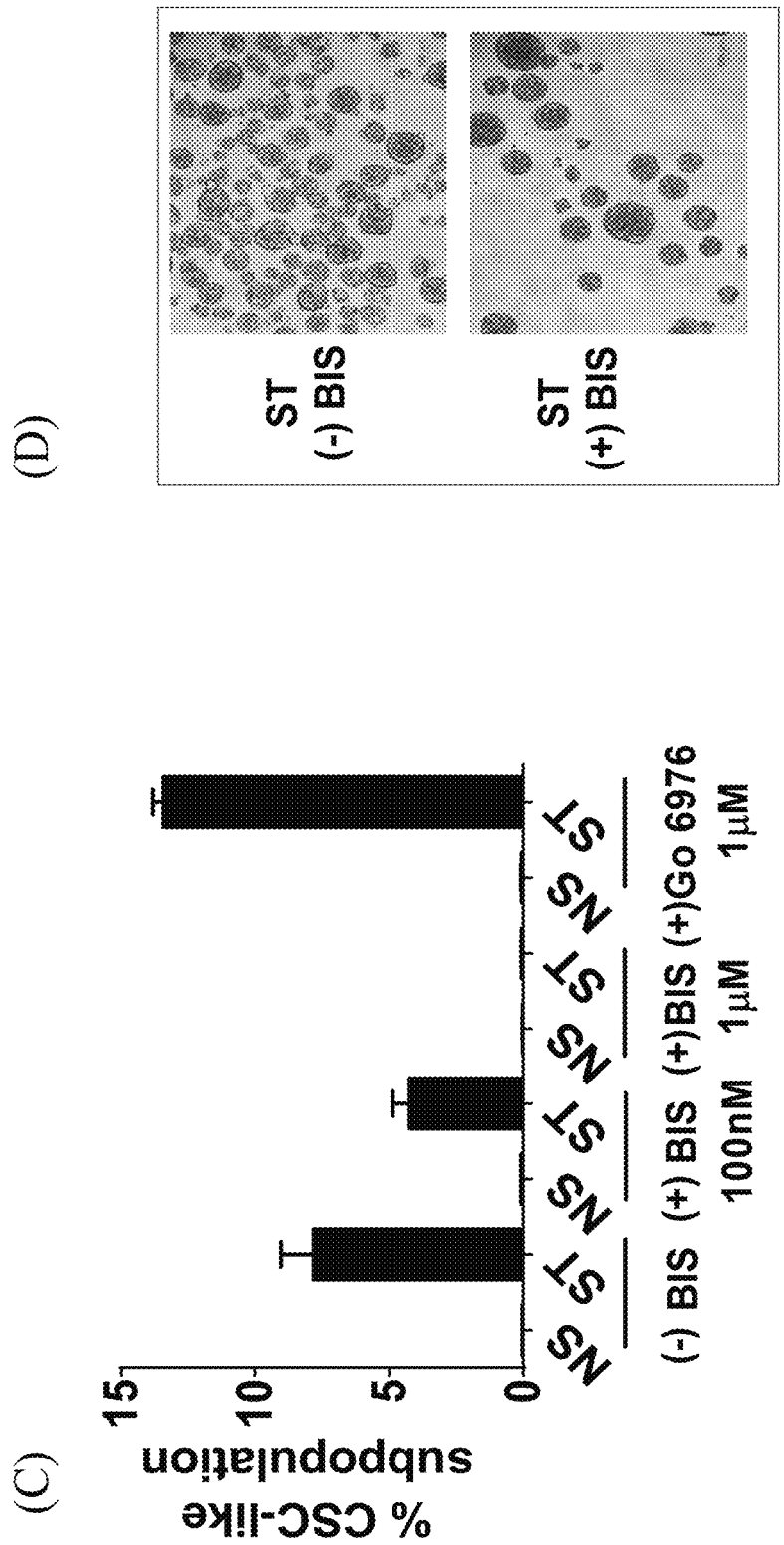
Figure 2E:
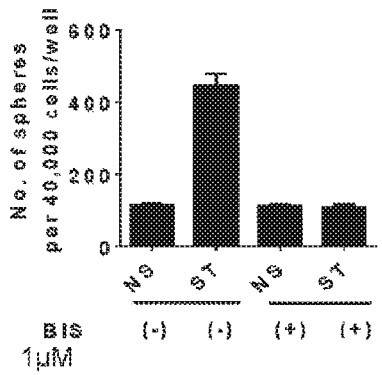
Figure 2F:
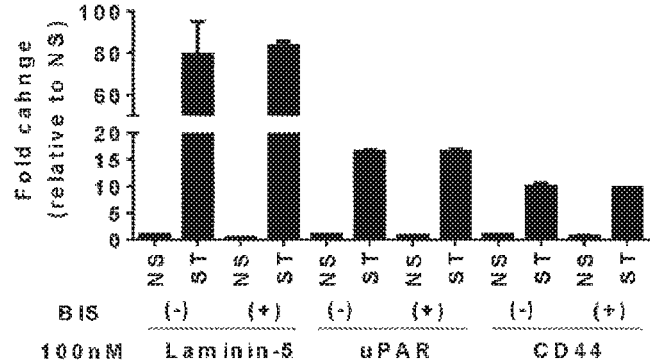
Figure 2G:
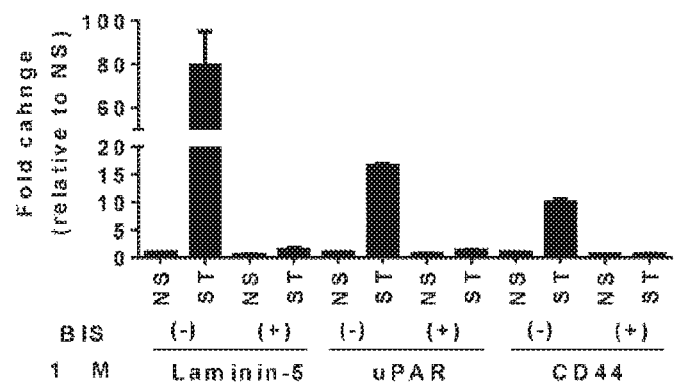
Figure 2H:
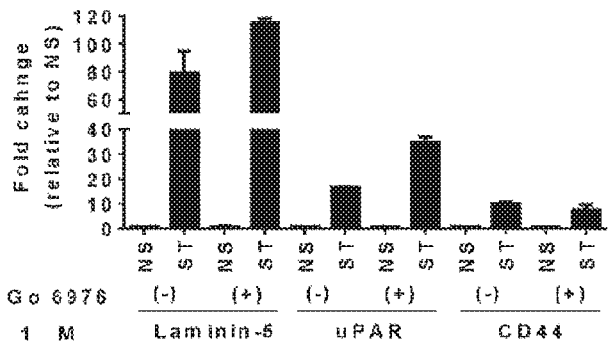
Figure 2I:
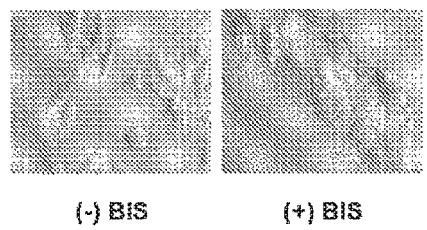
Figure 2J:
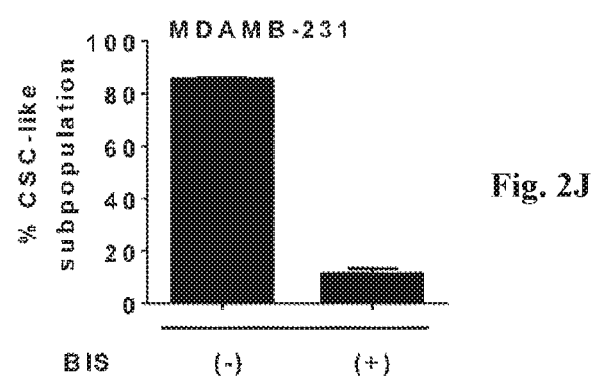
Figure 2K:
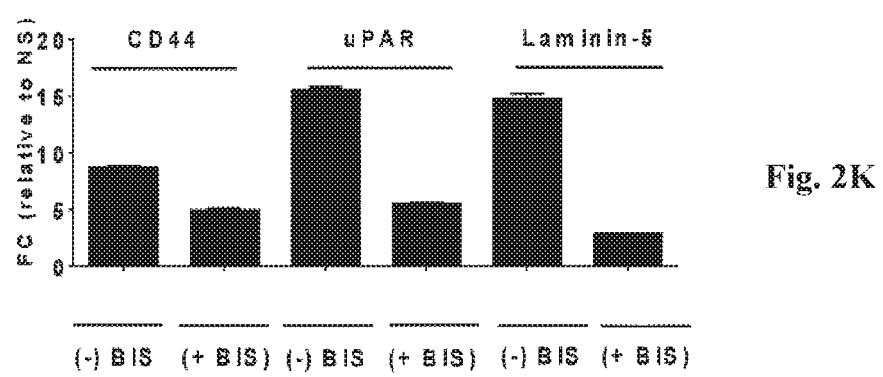
Figure 3A:
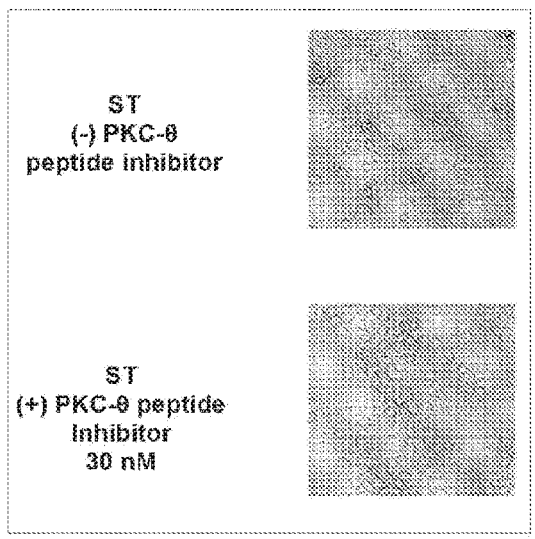
FIG. 3A is a photographic representation showing that a very low concentration of a PKC-θ peptide inhibitor abolishes EMT in the MCF-IM model. Phase contrast microscopy images of non-stimulated (NS) and PMA (0.65 ng/L for 60 hrs.) stimulated (ST) MCF-7 cells were captured either without pre-treatment of inhibitor or with 24 hrs. pre-treatment of PKC-θ specific peptide (30 μM) before PMA stimulation.
Figure 3B:
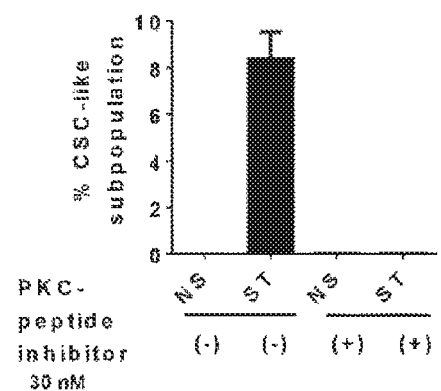
FIG. 3B is a graphical representation showing that a PKC-θ peptide inhibitor inhibits CD44 high CD24 low-CSC-like subpopulation in the MCF-IM model. MCF-7 cells were either pre-incubated with vehicle alone or with PKC-θ specific peptide (30 μM), prior to PMA (0.65 ng/μL for 60 hrs.) stimulation (ST). Cells were subsequently stained with Hoechst 33528, APC-anti-CD44 and PE-anti-CD24 for 20 minutes on ice and subjected to FACS analysis. Appropriate gating of $CD44^{high}/CD24^{low}$ CSC-like subpopulation was done and a bar graph was plotted. Data represent the mean±standard error (SE) of two independent experiments.
Figure 3C:
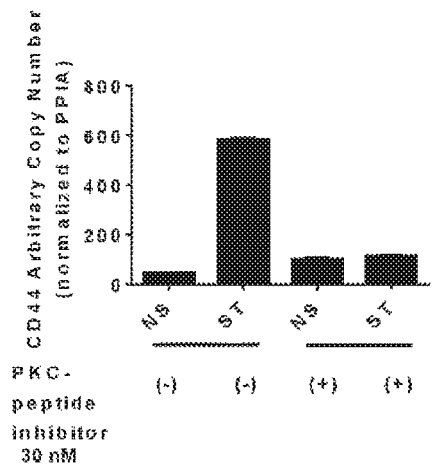
FIG. 3C is a graphical representation showing that a PKC-θ peptide inhibitor treatment reduces transcription of key inducible EMT/CSC genes in the MCF-IM model. MCF-7 cells were either pre-incubated with vehicle alone or with PKC-θ specific peptide (30 μM), prior to PMA (0.65 ng/μL for 60 hrs.) stimulation (ST). TaqMan® real time PCR analysis for EMT/CSC gene-CD44 was performed on cDNA synthesized from total RNA. Threshold cycle (Ct) values generated for each time point were converted to arbitrary copy number and normalized to Cyclophilin A reference levels. mRNA levels are expressed in fold change in comparison to non-stimulated cells. Data represent the mean±standard error (SE) of two independent experiments.
Figure 3D:
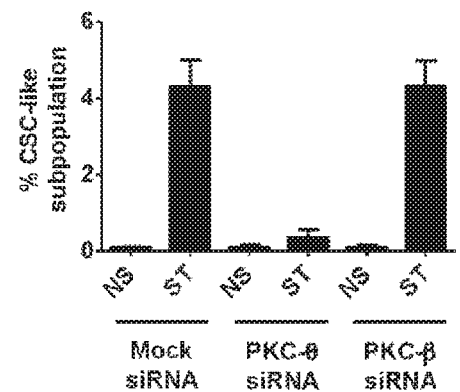
FIG. 3D is a graphical representation showing that PKC-θ knockdown results in abolishment of PMA-induced CSC-like subpopulation while PKC-β knockdown enhances PMA-induced CSC-like subpopulation in MCF-IM model. MCF-7 cells were transfected with either mock siRNA (mock), PKC-θ siRNA or PKC-β siRNA for 48 hr and followed by either left untreated, non-stimulation (NS) or PMA stimulation (ST) (0.65 ng/mL for 60 hrs.). FACS analysis was subsequently carried out by staining cells with Hoechst, APC-anti-CD44 and PE-anti-CD24 antibodies stain cocktail. Appropriate gating of CSC-like subpopulation was done and % CSC-like subpopulation is shown in a bar graph. Data represent the mean±standard error (SE) of two independent experiments.
Figure 4A:
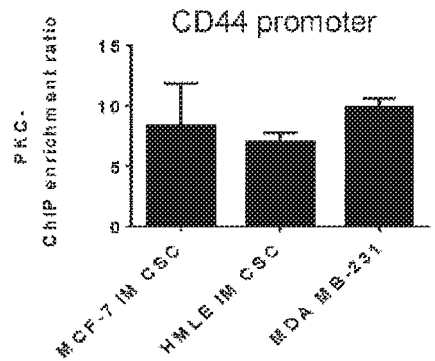
FIG. 4A is a graphical representation showing that PKC-θ is associated with chromatin at the promoter region of the CD44 gene in cancer stem cells. ChIP assays were performed on immuno-precipitated DNA with antibodies anti-PKC-θ antibody in MCF-IM, HMLE-IM and basal metastatic model. Real time PCR analysis was carried out on these immuno-precipitated DNA using CD44 promoter primers. The data are shown graphically as ChIP enrichment ratio of immuno-precipitated DNA relative to the nil antibody control and normalized against the total input DNA. The results represent the ChIP enrichment ratio from one of the three independent experiments.
Figure 4B:
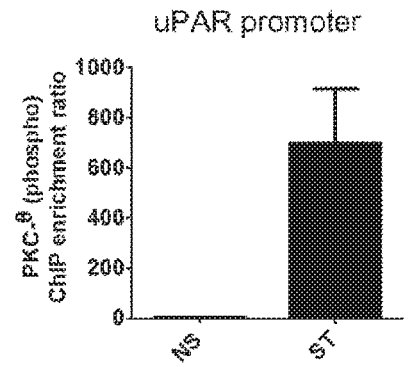
FIGS. 4B and C are graphical representations showing that the active form of PKC-θ, PKC-θ (phospho) is highly enriched with chromatin at the promoter region of CSC inducible genes in the MCF-IM model. MCF-7 cells were either non-stimulated (NS) or stimulated with PMA (ST) (0.65 ng/L for 60 hrs.). ChIP assays were subsequently performed on immuno-precipitated DNA with antibodies anti-PKC-θ (phospho). Real time PCR analysis was carried out on these immuno-precipitated DNA using (B) uPAR and (C) CD44 promoter primers. The data are shown graphically as ChIP enrichment ratio of immuno-precipitated DNA relative to the nil antibody control and normalized against the total input DNA. The results represent the ChIP enrichment ratio from one of the three independent experiments.
Figure 4C:
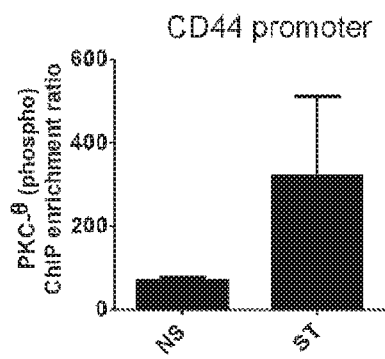
FIG. 4D is a graphical representation showing that PKC-θ physically interacts with Pol II on CSC inducible gene uPAR in the MCF-IM model. Sequential ChIP was performed on either non-stimulated (NS) or PMA stimulated (ST) (0.65 ng/mL for 60 hours) MCF-7 cells. First primary chromatin immunoprecipitation was carried out, and then secondary chromatin immunoprecipitation was performed on chromatin recovered from the primary immunoprecipitation. The antibodies used were: Primary ChIP with anti Pol II antibody and secondary ChIP with anti-PKC-θ antibody. Real time PCR analysis was performed on the immuno-precipitated DNA using uPAR promoter directed primers. The data are shown graphically as ChIP enrichment ratio of immuno-precipitated DNA relative to the nil antibody control and normalized against the total input DNA. "Nil antibody" refers to the sample where no antibody (neither of primary or secondary) have been added to the cross-linked DNA. The results represent the ChIP enrichment ratio from one of three independent experiments.
FIG. 4E is a graphical representation showing that pharmacological inhibition or knockdown of PKC-θ reduces its chromatin association across the uPAR promoter in the MCF-IM model. MCF-7 cells that were first pre-incubated for 1 hr. with vehicle alone or with bisindolylmaleimide-I (1 μM) and subsequently stimulated (ST) with PMA (0.65 ng/μl for 60 hours). In a separate experiment cells were transfected with either mock siRNA (mock) or PKC-θ siRNA followed by PMA stimulation (ST) (0.65 ng/mL for 60 hrs.) 48 hrs. post-transfection. ChIP assays were subsequently performed on immuno-precipitated DNA with anti-PKC-θ antibodies. Real time PCR analysis was performed on these immuno-precipitated DNA by using uPAR promoter primer. The data are shown graphically as ChIP enrichment ratio of immuno-precipitated DNA relative to the nil antibody control and normalized against the total input DNA. The results represent the ChIP enrichment ratio from one of the three independent experiments.
Figure 4D:
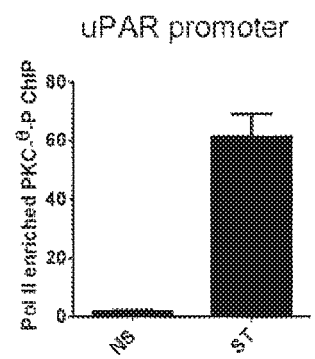
Figure 4E:
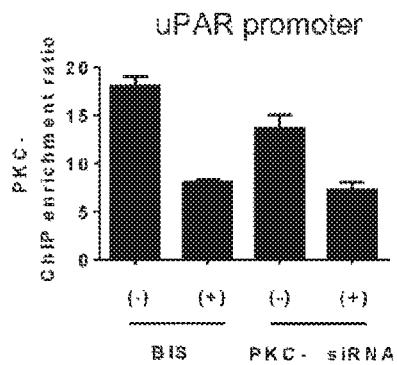

Broad spectrum PKC pathway inhibitor results in inhibition of EMT and CSC formation in MCF-IM model as monitored by morphology (FIG. 2 A), FACS (FIGS. 2 B & C), mammosphere assay (FIGS. 2 D & E) and transcript analysis of CSC-inducible genes (FIGS. 2 F & G) and also in basal metastatic model (FIGS. 2 I, J & K). In contrast, pre-incubation with Go6976, a conventional PKC inhibitor did not prevent PMA-induced EMT-like morphological changes or CSC formation (FIGS. 2 C & H).

Overall these results show that PKC activity is essential for EMT and CSC formation.

Example 3

Inhibition of PKC-θ Signaling and Nuclear Effect Results in Abolishment of EMT and CSC PKC-θ specific peptide inhibitor abolishes EMT and CSC as monitored by morphology (FIG. 3 A), FACS (FIG. 3 B) and transcript analysis (FIG. 3 C) in MCF-IM model. Knockdown of PKC-θ but not PKC-β results in inhibition of EMT and CSC in MCF-IM model (FIGS. 3 D, E & F). Over-expression of PKC-θ NLS (Nuclear Localization Signal) mutation reduces entry of PKC-θ in nucleus and therefore results in reduction of EMT and CSC effects in comparison to effect of PKC-θ Wild type vector in MCF-IM model (FIGS. 3 G, H and I).

Overall these results show that PKC-θ is the master-regulator of EMT and CSC formation. In addition, nuclear PKC-θ is important for EMT and CSC formation.

Example 4

Direct Binding of Nuclear PKC-θ on Inducible Gene Promoters in CSC

Chromatin immune-precipitation assay (ChIP) PKC-θ showed that PKC-θ directly tethers to the promoter of CSC inducible genes CD44 in various CSC models (FIG. 4 A). Active form of PKC-θ (PKC-θ-phospho) associates with chromatin on CSC inducible genes-uPAR and CD44 in MCF-IM model (FIGS. 4 B & C) and this active form is present in the active transcription mark RNA Polymerase-II (Pol II) (FIG. 4 D). PKC inhibitor and knockdown of PKC-θ results in reduction of binding of PKC-θ on the CD44 gene promoter.

Overall these results show that active PKC-θ is the epigenetic regulator of EMT and CSC formation.

Example 5

Nuclear Active PKC-Θ: A Marker of Invasive Breast Cancer

Figure 5:
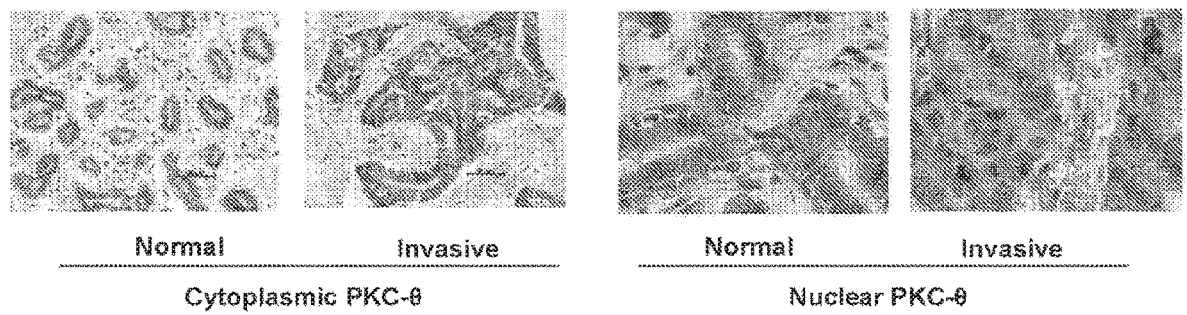
FIG. 5 is a photographic representation showing nuclear staining of active PKC-θ in human normal and invasive breast cancer tissue. Nuclear staining of normal and human breast cancer tissue was carried out using anti-PKC-θ (phosphor) antibody and photomicrographs were taken.

Clinical relevance of PKC-θ in breast cancer progression was analysed by investigating PKC-θ protein expression in normal breast tissue and invasive breast cancers from patients. Strong cytoplasmic expression of PKC-θ in ER/PR/I Her-2 invasive cancer subtype was observed when compared to breast tissue from healthy individuals. Additionally, ER/PR$^+$/Her-2$^-$ invasive cancer subtype had faint nuclear staining of active-PKC-θ (FIG. 5). All breast cancer types showed weak cytoplasmic immune-reactivity for active-PKC-θ with strong nuclear staining seen in the breast cancer cells undergoing mitosis regardless of receptor status.

Overall these results show that active PKC-θ in nuclei is a diagnostic marker of aggressive/invasive breast cancer.

Example 6

Figure 6:
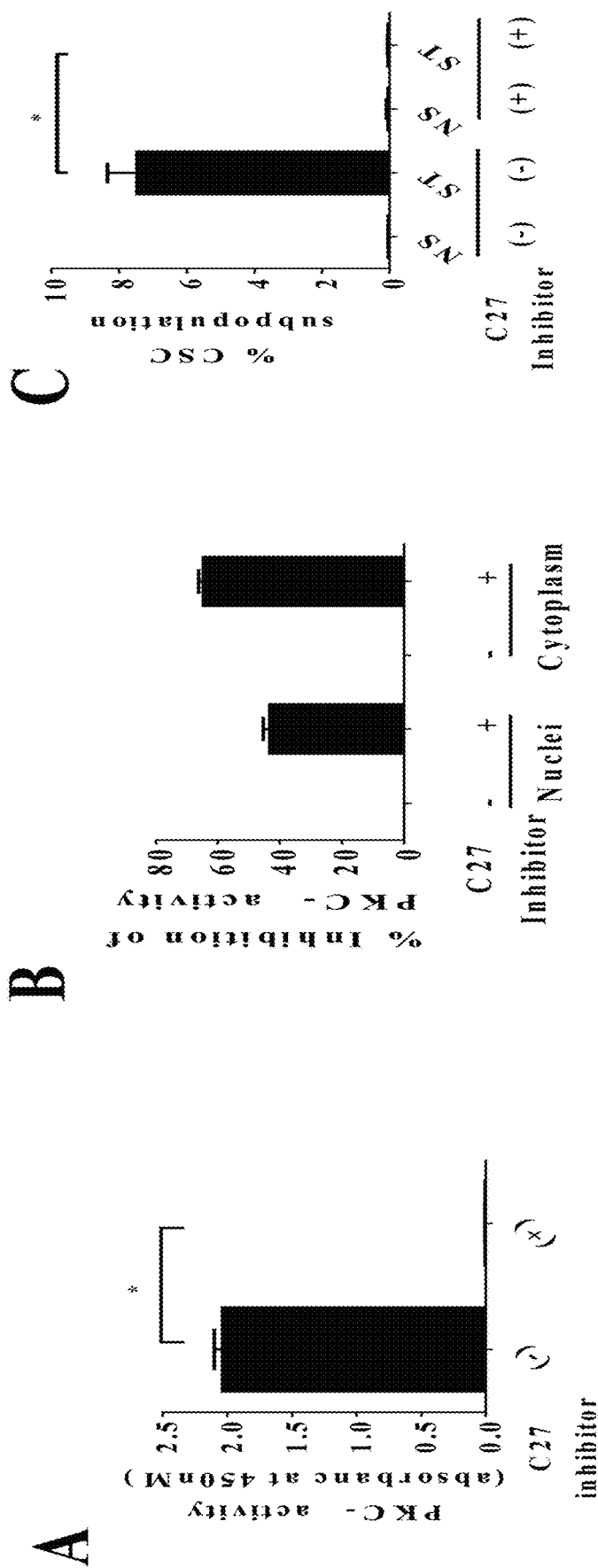
FIG. 6A is a graphical representation showing PKC ELISA-based kinase assays for PKC-θ specific activity inhibitor compound 27 (C27). Kinase activity was calculated after subtracting blank wells.
FIG. 6B is a graphical representation showing PKC ELISA-based kinase assays of nuclear extract—or cytoplasmic extract—from MCF-IM without (−) or with (+) C27 inhibitor. Assays were performed without specific immuno-precipitates for global PKC activity.
FIG. 6C is a graphical representation showing FACS analysis of $CD44^{high}/CD24^{low}$ CSC subpopulation in MCF-IM model. MCF-7 cells were stimulated with PMA (0.65 ng/ml for 60 h) either without pre-treatment of PKC-θ specific activity inhibitor compound 27 (−C27) or with pre-treatment with compound 27 (+C27) (1 uM for 24 hours).
FIG. 6D is a graphical representation showing mRNA expression by real-time PCR with samples.
FIGS. 6E and F is a graphical representation showing nuclear p50 or nuclear p65 activity after treatment of MCF-IM either with vehicle alone or with PKC-θ specific inhibitor, compound 27 (C27).
FIG. 6G is a photographic and graphical representation showing immunoblotting of MCF-IM nuclear extracts for phosphorylated NF-κB p65 at serine 468 (p468) after with (+) or without (−) compound 27 treatment. 15 μg of the protein was used for western blots and histone H3 antibody was used as a nuclear control.
FIG. 6H is a photographic and graphical representation showing immunoblotting of MCF-IM nuclear fraction for global NF-κB p65 after with (+) or without (−) compound 27 treatment. Densitometric analyses were carried out using Image J software provided below western blots.
FIG. 6I is a photographic and graphical representation showing immunoblotting of MCF-IM cytoplasmic fraction for global NF-κB p65 after with (+) or without (−) compound 27 treatment. Densitometric analyses were carried out using Image J software provided below western blots.
FIG. 6J is a photographic representation showing halfway ChIP analysis of stimulated MCF-IM cells with anti-PKC-θ antibody. (WCL) is the whole cell lysate utilized for the immunoprecipitation (IP) experiments. WCL is immunoblotted with anti-PKC-θ antibody. (−Ab) is the absence of antibody. Immunoblot with either anti-RNA Pol II, anti-p65 antibodies or anti-PKC-θ antibody. All results represent either the mean±the standard error of three independent experiments or a representative experiment from three replicates (N=3) **, $P<0.01$, *, $P<0.05$ and ns, not significant.
Figure 6:
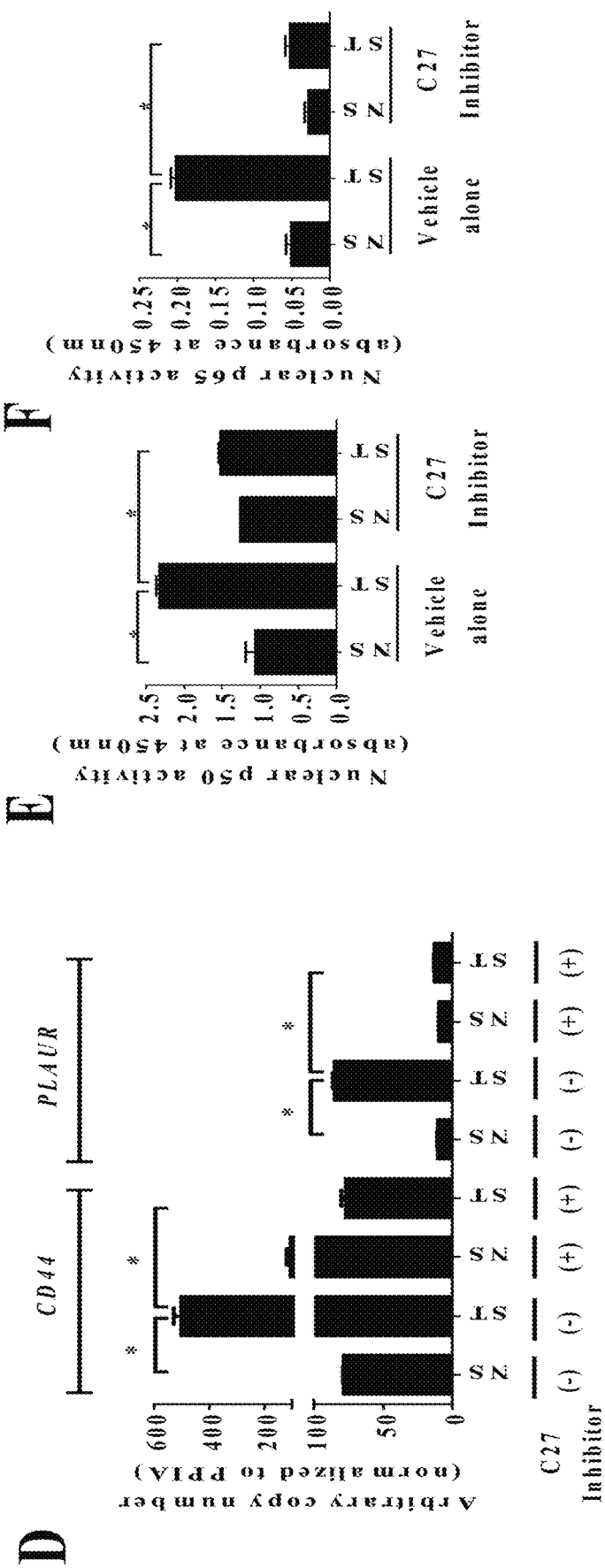
Figure 6:
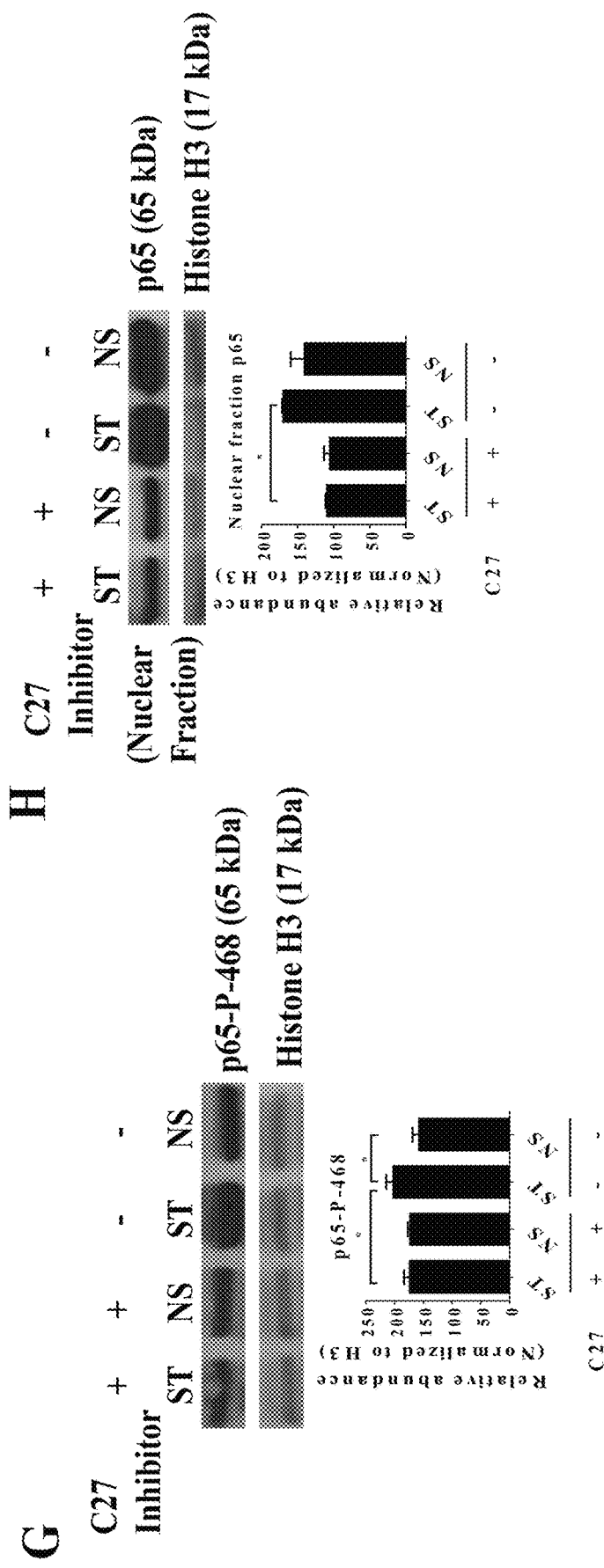
Figure 6:
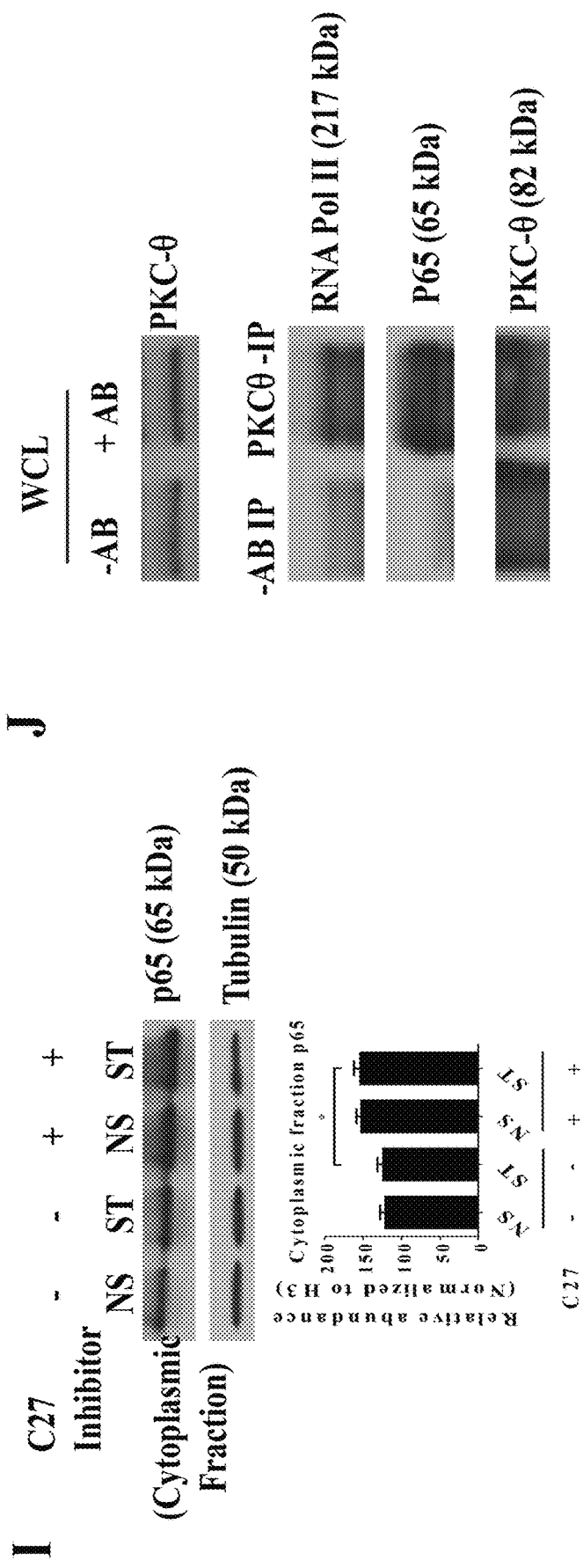

ATP-Competitive PKC-θ Specific Inhibitor, Compound 27 Prevents CSC Formation in MCF-IM and Signaling Via PKC-θ is a Pre-Requisite for NF-κB Activity A novel, highly selective ATP-competitive PKC-θ specific inhibitor, compound 27 (C27) (Jimenez, J.-M. et al., 2013. Design and optimization of selective protein kinase C theta (PKCtheta) inhibitors for the treatment of autoimmune diseases. Journal of Medicinal Chemistry 56:1799-1810.) abrogated PKC-θ activity both in in-vitro PKC-θ activity assay (FIG. 6A) and in nuclear and cellular extracts generated from MCF-IM pre-treated with C27 (FIGS. 6B and C). C27 also abolished CSC formation as measured by FACS (FIG. 6C) and transcription of CSC inducible genes (FIG. 6D). Furthermore, C27 significantly decreased p50 and p65 nuclear activity (FIGS. 6E and F), suggesting that PKC-θ also signals to NF-κB proteins in the mesenchymal state.

Immunoblotting analysis of nuclear extracts from MCF-IM was carried out with anti-phospho p65 (serine-468) antibodies. p65-phosphorylated at serine 468 (p65-P-468) was induced following stimulation and this phosphorylation was inhibited in the presence of C27 (FIG. 6G). However, immunoblotting with pan-p65 antibody revealed that C27 also inhibited p65 abundance in the nuclei of both epithelial and mesenchymal state (FIG. 6H). On the other hand, global accumulation of p65 was observed in the cytoplasmic fraction of C27 treated epithelial and mesenchymal cells derived from the MCF-IM (FIG. 6I). Collectively, this suggests that PKC-θ activity is possibly required globally for both maintaining p65 in the nucleus and also for its phosphorylation at a key active site (serine 468) of this transcription factor.

PKC-θ halfway ChIP on MCF-IM nuclear extracts showed an association between endogenous PKC-θ and p65 or RNA Pol II (FIG. 5J). Hence, nuclear PKC-θ exists in the proximity of NF-κB and the active transcription complex in a mesenchymal state.

Overall, these data suggest that ATP-Competitive PKC-θ specific inhibitor, compound 27 prevents CSC formation and active PKC-θ collaborates with active NF-κB family members.

Experimental Procedures

Cell Culture and Separation of CSC from NCSC

The adherent human mammary adenocarcinoma MCF-7 and MDA-MB-231 cells were cultured in low glucose DMEM (Gibco) and both supplemented with 10% FCS, 2 mM L-glutamine and 0.1% PSN antibiotics. Cells were stimulated with 0.65 ng/ml of phorbol 12-myristate 13-acetate (PMA) (Sigma-Aldrich) or 20 ng/ml of TGF-β (R&D systems) for the times indicated. For Bisindolylmaleimide-I (Calbiochem) or PKC-θ peptide inhibitor (Calbiochem) studies, cells were pre-treated with 1 μM or 30 μM of inhibitor respectively for 1 h prior to stimulation in MCF-7 cells. In case of MDA-MB-231, cells were treated with 4 μM or 30 JAM Bisindolylmaleimide-I or PKC-θ peptide inhibitor respectively.

To separate CSC from non-CSC (NCSC), florescence activated cell sorting (FACS) was performed on single-cell suspensions that were stained with anti-CD44-APC (559942, BD Biosciences) and anti-CD24-PE antibodies (555428, BD Biosciences) along with Hoechst 33258 to monitor cell viability. As used throughout this work, CSC are defined by minority $CD44^{high}/CD24^{low}$, whereas NCSC are defined by rest of the cell populations.

Mammosphere culture media components were purchased from StemCell Technologies and mammosphere assays were performed as recommended by the manufacturer's guidelines. Briefly, 40,000 cells/2 ml cell dilutions were then prepared and 2 ml of cells were seeded in the 6 well-ultralow adherent, flat bottom plates (Costar). Mammospheres larger than 60 μm were counted per well on day 7 and pictures were taken.

Phase Contrast Microscopy phase contrast microscopy was performed where cells were viewed at ×4 magnification (wound healing assay) or ×10 magnification (EMT) using an Olympus fluorescence IX71 microscope (Olympus) and images were captured using DPController software (2002 Olympus Optical Co. LTD) and analysed using Photoshop CS3 (Adobe Systems Inc.). Scans were taken with a 10 μm scale bar.

Wound-Healing Assay

MCF-7 cell monolayer was wounded with a sterile plastic tip. Cells were washed twice with PBS and once with DMEM. Reference marks were created on the dish for each well and a time zero image was acquired by microscopy. Cells were treated with PMA (0.65 ng/ml) for 60 hr and a second image was taken in the matched region. The edges of two sides of wound monolayer were drawn and overlapped using Photoshop CS3 (Adobe Systems Inc.).

Plasmids

Within the full length PKC-θ wild type gene sequence the nuclear localization site (NLS) was mutated and were cloned into the pTracer-CMV vector in frame with a C-terminal HA-tag as described before (Sutcliffe et al., 2012. Front Immunol. 3:260).

Primers

Human TaqMan™ primer sets used were: CD44, Hs00153304, CD24, Hs00273561, uPAR, Hs00182181, Laminin-5, Hs00194333, Zeb-1, Hs00611018, Fibronectin, Hs00415006 and Integrin-β, Hs00168458 (Applied Biosystems). Primers used for SYBR Green real-time PCR are: Zeb (sense: 5'-GTGCTGTAAGTGCCATTTCTCAGTA-3' and antisense: 5'-CAAGAGACAAATCAACAAATGCTAGTT-3') and Cyclophilin A (sense: 5'-CTCCTTTGAGCTGTTT-GCAG-3' and antisense: 5'-CACCACATGCTFGCCATCC-3').

Transfection Conditions

Human PKC-θ siRNA (sc-36252), p50 siRNA (sc-44211) and p65 siRNA (sc-44212) were purchased from Santa Cruz Biotechnologies and forward transfections with 10 nM siRNA were performed by using Lipofectamine 2000 (Invitrogen).

Total RNA Isolation and Quantitative Real-Time PCR Analysis

Total RNA was extracted using TRIzol® Reagent (Invitrogen) and first strand cDNA was synthesized using the Superscript™ III RNase H-reverse transcriptase kit (Invitrogen). TaqMan® Gene Expression Assays and SYBR Green real-time PCR were performed as previously described (Sutcliffe et al., 2009. Molecular and Cellular Biology. 29: 1972-86). MicroRNA assays were performed with the TaqMan® MicroRNA Reverse Transcription Kit (ABI 4366596) and the data were normalized to RNU6B as previously described in Sutcliffe et al. (2010, Molecular Cell. 41: 704-719).

Chip and Sequential Chip Assays

ChIP buffers were purchased from Upstate Biotechnology and ChIP assays were performed according to the protocol supplied by Upstate Biotechnology as previously described (Sutcliffe et al., 2011. Molecular Cell. 41: 704-719). Antibody used were: Anti-PKC-θ (Santa Cruz, sc-212), Anti-PKC-θ Phospho s695 (Abcam, ab76568) and Pol II c-21 (Abcam, ab817). Promoter primers used for RT-PCR were human CD44 (Fwd: TGAGCTCTCCCTCTTTCCAC, Rev: TTGGATATCCTGGGAGAGGA), uPAR (Fwd: GGGAAGCAAAGCAAGGGTA, Rev: GTTTTGTCAG-GAGGGATACTGG) and IL-6 (Fwd: CTCACCCTC-CAACAAAGATTT, Rev: CAGAATGAGCCTCAGA-CATC). Sequential ChIP assays performed as described previously by Sutcliffe et al. (2011. Molecular Cell. 41: 704-719).

PKC Activity Assay

PKC activity assay were purchased from Enzo Life Sciences (DI-EKS-420A) and assays were performed according to the manufacture's protocol as previously described (Sutcliffe, 2012. supra).

Immunofluorescence

The immunohistochemistry was performed on Bond automated system (Vision Biosystems), following a standard protocol. In brief, 5 μM tissue sections were dewaxed, rehydrated though graded alcohol, and stained separately with anti-PKC-θ or anti-PKC-θ phospho antibodies (as described in 0539). Heat retrieval for 28 min at pH 8 was used. The Chromogen Fast Red (Leica Biosystems) and DAKO Envision kit were used to visualize the signals. Haematoxylin counterstain was used to visualize the nuclei. In each run a positive and a negative isotype-matched controls were included on each slide to ensure that there is no false-positive staining.

Intracellular staining was performed as described previously in Sutcliffe et al., 2011. Molecular Cell. 41: 704-719.

Data Analysis

Data was analyzed using Microsoft Excel (Microsoft) and graphs were generated using Prism (version 5.0, GraphPad software).

PKC Activity Assay for Example 6

PKC-θ and PKC-β activity assays (Enzo Life Sciences; DI-EKS-420A) were performed according to the manufacturer's protocol and as previously described (Sutcliffe et. Al., 2012. Chromatinized Protein Kinase C-theta: Can It Escape the Clutches of NF-kappaB? Front Immunol 3:260.).

NF-κB Activity Assay for Example 6

TransAM NF-κB Family kit was used for NF-κB activity assays (43296, Active Motif). Assays were performed according to the manufacturer's guidelines. 5 μg protein from MDA-MB231 or MCF-IM derived whole cell, nuclear and cytoplasmic extracts were used in triplicate for the assays. Raji nuclear extract was used as a positive control. Wild-type and mutated consensus oligonucleotides were also used as a negative and positive controls respectively.

Immunoblot Analysis for Example 6

Immunoblot analysis was performed according to the manufacturer's protocol and as previously described (Rao et. al., 2003. c-Rel is required for chromatin remodeling across the IL-2 gene promoter. Journal of immunology 170:3724-3731.) with anti-PKC-θ (sc-212, SantaCruz), anti-p65 (ab7970, Abcam), anti-p65 phospho (ser-468) (3039, Cell Signaling), anti-p65 phospho (ser-536) (3031, Cell Signaling) and RNA Pol II(c-21) (ab817, Abcam) antibodies.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method for treating a metastatic cancer in a subject, wherein the cancer comprises a cancer stem cell (CSC) and a non-CSC tumor cell, the method comprising concurrently administering to the subject a selective protein kinase C theta (PKC-θ) inhibitor in an effective amount to inhibit formation, proliferation, maintenance or epithelial to mesenchymal transition (EMT) of the CSC or to stimulate or induce mesenchymal to epithelial transition (MET) of the CSC, and a cancer therapy agent that inhibits proliferation, survival or viability of the non-CSC tumor cell, to thereby treat the metastatic cancer.

2. A method according to claim 1, wherein the cancer therapy agent targets rapidly dividing cells or disrupts the cell cycle or cell division.

3. A method according to claim 1, wherein the cancer therapy agent is a chemotherapeutic agent.

4. A method according to claim 3, wherein the chemotherapeutic agent is a taxoid.

5. A method according to claim 3, wherein the chemotherapeutic agent is paclitaxel or docetaxel.

6. A method according to claim 1, wherein the cancer therapy agent is an antibody.

7. A method according to claim 1, wherein the metastatic cancer is metastatic breast cancer.

8. A method for treating a metastatic cancer in a subject, wherein the cancer comprises a cancer stem cell (CSC) and a non-CSC tumor cell, the method comprising concurrently administering to the subject an effective amount of a selective protein kinase C theta (PKC-θ) inhibitor and an effective amount of chemotherapeutic agent, to thereby treat the metastatic cancer.

9. A method according to claim 8, wherein the chemotherapeutic agent is a taxoid.

10. A method according to claim 9, wherein the taxoid is paclitaxel or docetaxel.

11. A method according to claim 8, wherein the metastatic cancer is metastatic breast cancer.

* * * * *

SEQUENCE LISTING

<160> NUMBER OF SEQ ID NOS: 17

<210> SEQ ID NO 1
<211> LENGTH: 8
<212> TYPE: PRT
<213> ORGANISM: Artificial
<220> FEATURE:
<223> OTHER INFORMATION: Theta V1 derived peptide (PKC-theta residues
      8-15)

<400> SEQUENCE: 1

Gly Leu Ser Asn Phe Asp Cys Gly
1               5

<210> SEQ ID NO 2
<211> LENGTH: 11
<212> TYPE: PRT
<213> ORGANISM: Artificial
<220> FEATURE:
<223> OTHER INFORMATION: Theta V1 derived peptide (PKC-theta residues
      36-46)

<400> SEQUENCE: 2

Tyr Val Glu Ser Glu Asn Gly Gln Met Tyr Ile
1               5                   10

<210> SEQ ID NO 3
<211> LENGTH: 8
<212> TYPE: PRT
<213> ORGANISM: Artificial
<220> FEATURE:
<223> OTHER INFORMATION: ThetaV5 derived peptide (PKC-theta residues
      655-662)

<400> SEQUENCE: 3

Val Lys Ser Pro Phe Asp Cys Ser
1               5

<210> SEQ ID NO 4
<211> LENGTH: 7
<212> TYPE: PRT
<213> ORGANISM: Artificial
<220> FEATURE:
<223> OTHER INFORMATION: Theta V5 derived peptide

<400> SEQUENCE: 4

Asp Arg Ala Leu Ile Asn Ser
1               5

<210> SEQ ID NO 5
<211> LENGTH: 8
<212> TYPE: PRT
<213> ORGANISM: Artificial
<220> FEATURE:
<223> OTHER INFORMATION: Theta V5 derived peptide

<400> SEQUENCE: 5

Val Arg Ser Pro Phe Asp Cys Ser
1               5

<210> SEQ ID NO 6
<211> LENGTH: 8
<212> TYPE: PRT
<213> ORGANISM: Artificial
<220> FEATURE:
<223> OTHER INFORMATION: PsiTheta RACK derived peptide

<400> SEQUENCE: 6

```
Lys Gly Asp Asn Val Asp Leu Ile
1               5

<210> SEQ ID NO 7
<211> LENGTH: 8
<212> TYPE: PRT
<213> ORGANISM: Artificial
<220> FEATURE:
<223> OTHER INFORMATION: PsiTheta RACK derived peptide

<400> SEQUENCE: 7

Lys Gly Glu Asn Val Asp Leu Ile
1               5

<210> SEQ ID NO 8
<211> LENGTH: 8
<212> TYPE: PRT
<213> ORGANISM: Artificial
<220> FEATURE:
<223> OTHER INFORMATION: PsiTheta RACK derived peptide

<400> SEQUENCE: 8

Lys Gly Lys Glu Val Asp Leu Ile
1               5

<210> SEQ ID NO 9
<211> LENGTH: 8
<212> TYPE: PRT
<213> ORGANISM: Artificial
<220> FEATURE:
<223> OTHER INFORMATION: PsiTheta RACK derived peptide

<400> SEQUENCE: 9

Lys Gly Lys Asn Val Asp Leu Ile
1               5

<210> SEQ ID NO 10
<211> LENGTH: 8
<212> TYPE: PRT
<213> ORGANISM: Artificial
<220> FEATURE:
<223> OTHER INFORMATION: PsiTheta RACK derived peptide

<400> SEQUENCE: 10

Arg Gly Lys Asn Val Glu Leu Ala
1               5

<210> SEQ ID NO 11
<211> LENGTH: 8
<212> TYPE: PRT
<213> ORGANISM: Artificial
<220> FEATURE:
<223> OTHER INFORMATION: PsiTheta RACK derived peptide

<400> SEQUENCE: 11

Arg Gly Glu Asn Val Glu Leu Ala
1               5

<210> SEQ ID NO 12
<211> LENGTH: 8
<212> TYPE: PRT
<213> ORGANISM: Artificial
<220> FEATURE:
<223> OTHER INFORMATION: PsiTheta RACK derived peptide

<400> SEQUENCE: 12
```

```
Lys Gly Lys Gln Val Asn Leu Ile
1               5
```

<210> SEQ ID NO 13
<211> LENGTH: 8
<212> TYPE: PRT
<213> ORGANISM: Artificial
<220> FEATURE:
<223> OTHER INFORMATION: PsiTheta RACK derived peptide

<400> SEQUENCE: 13

```
Lys Gly Lys Gln Val Asn Leu Ile
1               5
```

<210> SEQ ID NO 14
<211> LENGTH: 8
<212> TYPE: PRT
<213> ORGANISM: Artificial
<220> FEATURE:
<223> OTHER INFORMATION: PsiTheta RACK derived peptide

<400> SEQUENCE: 14

```
Lys Gly Glu Gln Val Asn Leu Ile
1               5
```

<210> SEQ ID NO 15
<211> LENGTH: 8
<212> TYPE: PRT
<213> ORGANISM: Artificial
<220> FEATURE:
<223> OTHER INFORMATION: PsiTheta RACK derived peptide

<400> SEQUENCE: 15

```
Lys Gly Glu Gln Val Asn Leu Ile
1               5
```

<210> SEQ ID NO 16
<211> LENGTH: 17
<212> TYPE: PRT
<213> ORGANISM: Artificial
<220> FEATURE:
<223> OTHER INFORMATION: Drosophila Antennapedia homeodomain-derived
      sequence

<400> SEQUENCE: 16

```
Cys Arg Gln Ile Lys Ile Trp Phe Gln Asn Arg Arg Met Lys Trp Lys
1               5                   10                  15

Lys
```

<210> SEQ ID NO 17
<211> LENGTH: 11
<212> TYPE: PRT
<213> ORGANISM: Artificial
<220> FEATURE:
<223> OTHER INFORMATION: Tat-derived transport polypeptide

<400> SEQUENCE: 17

```
Tyr Gly Arg Lys Lys Arg Arg Gln Arg Arg Arg
1               5                   10
```